United States Patent
Lee et al.

(10) Patent No.: US 10,957,863 B2
(45) Date of Patent: Mar. 23, 2021

(54) CONDENSED CYCLIC COMPOUND AND ORGANIC LIGHT-EMITTING DEVICE INCLUDING THE SAME

(71) Applicant: Samsung Electronics Co., Ltd., Suwon-si (KR)

(72) Inventors: Saeyoun Lee, Suwon-si (KR); Masaki Numata, Hwaseong-si (KR); Hiroshi Miyazaki, Hwaseong-si (KR); Myungsun Sim, Suwon-si (KR); Hasup Lee, Seoul (KR); Sooghang Ihn, Hwaseong-si (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 327 days.

(21) Appl. No.: 15/906,502

(22) Filed: Feb. 27, 2018

(65) Prior Publication Data
US 2018/0248127 A1 Aug. 30, 2018

(30) Foreign Application Priority Data

Feb. 27, 2017 (KR) .................. 10-2017-0025404

(51) Int. Cl.
*H01L 51/50* (2006.01)
*H01L 51/00* (2006.01)
(Continued)

(52) U.S. Cl.
CPC ........ *H01L 51/0072* (2013.01); *C07D 403/14* (2013.01); *C07D 487/04* (2013.01);
(Continued)

(58) Field of Classification Search
None
See application file for complete search history.

(56) References Cited

U.S. PATENT DOCUMENTS 9,166,175 B2   10/2015  Xia et al.
9,882,144 B2    1/2018  Kawamura et al.
(Continued)

FOREIGN PATENT DOCUMENTS

KR    2010/0131939 A  † 12/2010
KR   10-2015-0034333 A   4/2015
(Continued)

OTHER PUBLICATIONS

Dong Ryun Lee et al. "Design Strategy for 25% External Quantum Efficiency in Green and Blue Thermally Activated Delayed Fluorescent Devices", Adv. Mater. 2015, 27(39), 5861-5867.

(Continued)

*Primary Examiner* — Gregory D Clark
(74) *Attorney, Agent, or Firm* — Cantor Colburn LLP

(57) ABSTRACT

A condensed cyclic compound represented by Formula 1:

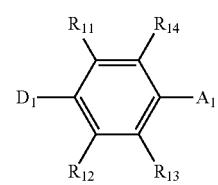

Formula 1

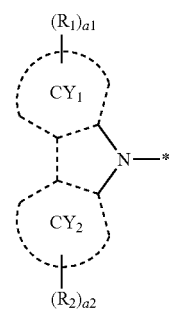

Formula 1-1

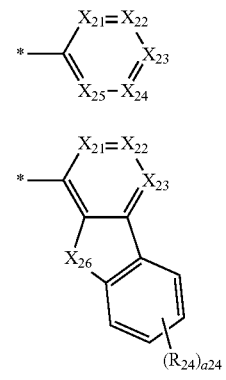

Formula 1-2

Formula 1-3

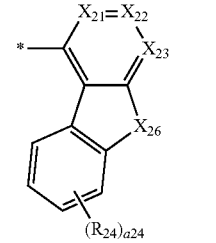

Formula 1-4 wherein $D_1$ in Formula 1 is a group represented by Formula 1-1, $A_1$ in Formula 1 is a group represented by Formula 1-2, 1-3, or 1-4, wherein in Formulae 1-1, 1-2, 1-3, and 1-4, groups and variables are the same as described in the specification.

18 Claims, 1 Drawing Sheet

(51) Int. Cl.
    *C07D 487/04*     (2006.01)
    *C09K 11/06*     (2006.01)
    *C07D 403/14*     (2006.01)

(52) U.S. Cl.
    CPC .......... C09K 11/06 (2013.01); H01L 51/0067 (2013.01); *C09K 2211/1018* (2013.01); *H01L 51/5004* (2013.01); *H01L 51/5012* (2013.01); *H01L 51/5016* (2013.01); *H01L 51/5024* (2013.01); *H01L 51/5056* (2013.01); *H01L 51/5072* (2013.01); *H01L 51/5088* (2013.01); *H01L 51/5092* (2013.01); *H01L 51/5096* (2013.01); *H01L 2251/308* (2013.01); *H01L 2251/552* (2013.01)

(56) References Cited

U.S. PATENT DOCUMENTS

| | | |
|---|---|---|
| 2012/0241732 A1† | 9/2012 | Endo |
| 2016/0093823 A1 | 3/2016 | Seo et al. |
| 2016/0197286 A1* | 7/2016 | Kawamura .......... C09K 11/025 257/40 |

FOREIGN PATENT DOCUMENTS

| | | |
|---|---|---|
| KR | 10-2015-0099762 A | 9/2015 |
| WO | 2015-175678 A1 | 11/2015 |

\* cited by examiner
† cited by third party

10

| 19 |
|----|
| 15 |
| 11 |

CONDENSED CYCLIC COMPOUND AND ORGANIC LIGHT-EMITTING DEVICE INCLUDING THE SAME

CROSS-REFERENCE TO RELATED APPLICATION

This application claims priority to Korean Patent Application No. 10-2017-0025404, filed on Feb. 27, 2017, in the Korean Intellectual Property Office, and all the benefits accruing therefrom under 35 U.S.C. § 119, the content of which is incorporated herein in its entirety by reference.

BACKGROUND

1. Field

The present disclosure relates to a condensed cyclic compound and an organic light-emitting device including the same.

2. Description of the Related Art

Organic light-emitting devices (OLEDs) are self-emission devices that produce full-color images, and also have wide viewing angles, high contrast ratios, short response times, and excellent characteristics in terms of brightness, driving voltage, and response speed, compared to devices in the art.

An example of such organic light-emitting devices may include an anode, a cathode, and an organic layer disposed between the anode and the cathode, wherein the organic layer includes an emission layer. A hole transport region may be disposed between the anode and the emission layer, and an electron transport region may be disposed between the emission layer and the cathode. Holes provided from the anode may move toward the emission layer through the hole transport region, and electrons provided from the cathode may move toward the emission layer through the electron transport region. Carriers, such as holes and electrons, recombine in an emission layer region to produce excitons. These excitons transit from an excited state to a ground state, thereby generating light.

Various types of organic light emitting devices are known. However, there still remains a need in OLEDs having low driving voltage, high efficiency, high brightness, and long lifespan.

SUMMARY

Provided is a condensed cyclic compound having excellent delayed fluorescence-emission characteristics.

Provided is an organic light-emitting device exhibiting high efficiency and/or long lifespan by including the condensed cyclic compound.

Additional aspects will be set forth in part in the description which follows and, in part, will be apparent from the description, or may be learned by practice of the presented embodiments.

According to an aspect of an embodiment, there is provided a condensed cyclic compound is represented by Formula 1 below:

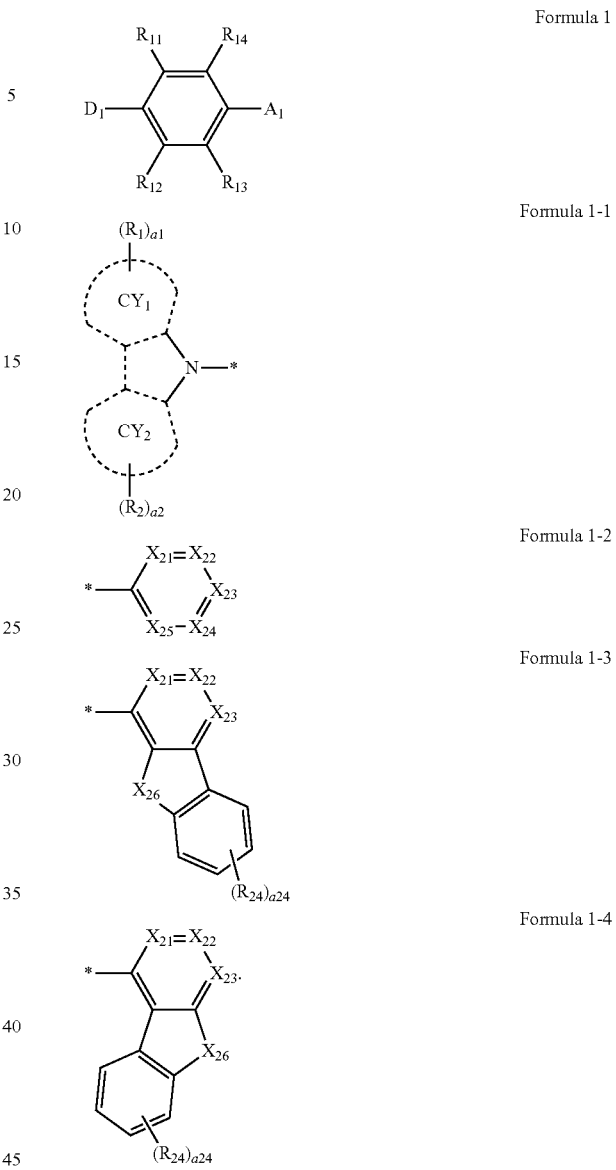

In Formula 1, $D_1$ is a group represented by Formula 1-1, $A_1$ in Formula 1 is a group represented by Formula 1-2, 1-3, or 1-4, ring $CY_1$ and ring $CY_2$ in Formula 1-1 are each independently a benzene group, a fluorene group, a carbazole group, a dibenzofuran group, or a dibenzothiophene group, in Formulae 1-2 to 1-4, $X_{21}$ is N or $C(R_{21})$, $X_{22}$ is N or $C(R_{22})$, $X_{23}$ is N or $C(R_{23})$, $X_{24}$ is N or $C(R_{24})$, $X_{25}$ is N or $C(R_{25})$, and $X_{26}$ is O or S, wherein at least one of $X_{21}$ to $X_{25}$ in Formula 1-2 is N or C(CN) and at least one of $X_{21}$ to $X_{23}$ in Formulae 1-3 and 1-4 is N or C(CN), in Formulae 1 and 1-1 to 1-4, $R_1$, $R_2$, $R_{11}$ to $R_{14}$, and $R_{21}$ to $R_{25}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_4$)($Q_5$), and —B($Q_6$)($Q_7$), wherein at least one of $R_{11}$ to $R_{14}$ is each independently selected from a cyano group, a substituted or unsubstituted $C_3$-$C_{10}$ cycloalkyl group, a substituted or unsubstituted $C_3$-$C_{10}$ cycloalkenyl group, a substituted or unsubstituted $C_6$-$C_{60}$ aryl group, and a substituted or unsubstituted monovalent non-aromatic condensed polycyclic group, a1 and a2 in Formula 1-1 may each independently be an integer from 0 to 8, a24 in Formulae 1-3 to 1-4 may be an integer from 0 to 4,

* indicates a binding site to a neighboring atom, at least one substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, and the substituted monovalent non-aromatic condensed polycyclic group and substituted monovalent non-aromatic condensed heteropolycyclic group is selected from:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{14}$)($Q_{15}$), and —B($Q_{16}$)($Q_{17}$), a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{24}$)($Q_{25}$), and —B($Q_{26}$)($Q_{27}$); and —Si($Q_{31}$)($Q_{32}$)($Q_{33}$), —N($Q_{34}$)($Q_{35}$), and —B($Q_{36}$)($Q_{37}$), and $Q_1$ to $Q_7$, $Q_{11}$ to $Q_{17}$, $Q_{21}$ to $Q_{27}$, and $Q_{31}$ to $Q_{37}$ are each independently selected from hydrogen, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

According to another aspect of an embodiment, there is provided an organic light-emitting device including:
a first electrode,
a second electrode, and
an organic layer disposed between the first electrode and the second electrode, wherein the organic layer includes an emission layer, and
wherein the organic layer includes at least one condensed compound described above.

BRIEF DESCRIPTION OF THE DRAWING

These and/or other aspects will become apparent and more readily appreciated from the following description of the embodiments, taken in conjunction with the FIGURE which is a schematic view of an organic light-emitting device according to an embodiment.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the FIGURES, to explain aspects of the present disclosure. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

The term "or" means "and/or." It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the FIGURES are schematic in nature and their shapes are not intended to illustrate the precise shape of a region and are not intended to limit the scope of the present claims.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

In an embodiment, a condensed cyclic compound is provided. The condensed cyclic compound according to an embodiment may be represented by Formula 1, wherein $D_1$ in Formula 1 may be a group represented by Formula 1-1, and $A_1$ in Formula 1 may be a group represented by Formula 1-2, 1-3, or 1-4:

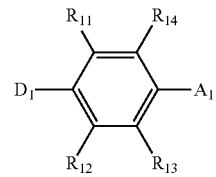

Formula 1

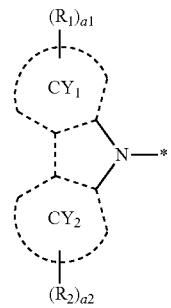

Formula 1-1

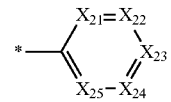

Formula 1-2

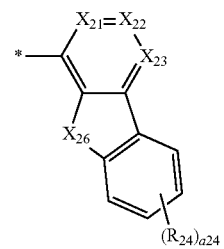

Formula 1-3

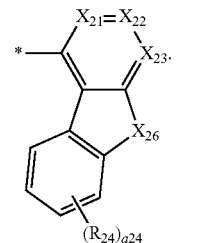

Formula 1-4

Hereinafter, Formulae 1 and 1-1 to 1-4 will be described in detail.

In Formula 1-1, ring $CY_1$ and ring $CY_2$ may each independently be a benzene group, a fluorene group, a carbazole group, a dibenzofuran group, or a dibenzothiophene group.

In one or more embodiments, in Formula 1-1, ring $CY_1$ may be a benzene group, and ring $CY_2$ may be a benzene group, a fluorene group, a carbazole group, a dibenzofuran group, or a dibenzothiophene group.

In one or more embodiments, in Formula 1-1, ring $CY_1$ may be a benzene group, and ring $CY_2$ may be a fluorene group, a carbazole group, a dibenzofuran group, or a dibenzothiophene group, but embodiments of the present disclosure are not limited thereto.

In Formulae 1-2 to 1-4, $X_{21}$ may be N or $C(R_{21})$, $X_{22}$ may be N or $C(R_{22})$, $X_{23}$ may be N or $C(R_{23})$, $X_{24}$ may be N or $C(R_{24})$, $X_{25}$ may be N or $C(R_{25})$, and $X_{26}$ may be O or S, wherein at least one of $X_{21}$ to $X_{25}$ in Formula 1-2 may be N or C(CN), and at least one of $X_{21}$ to $X_{23}$ in Formulae 1-3 and 1-4 may be N or C(CN).

For example, two or three of $X_{21}$ to $X_{25}$ in Formula 1-2 may each be N, two or three of $X_{21}$ to $X_{25}$ in Formula 1-2 may each be C(CN), and two of $X_{21}$ to $X_{23}$ in Formulae 1-3 and 1-4 may each be N, but embodiments of the present disclosure are not limited thereto.

In Formulae 1 and 1-1 to 1-4, $R_1$, $R_2$, $R_{11}$ to $R_{14}$, and $R_{21}$ to $R_{25}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted heterocycloalkyl group, a substituted or unsubstituted $C_3$-$C_{10}$ cycloalkenyl group, a substituted or unsubstituted heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_4$)($Q_5$), and —B($Q_6$)($Q_7$), wherein at least one of $R_{11}$ to $R_{14}$ may each independently be selected from a cyano group, a substituted or unsubstituted $C_3$-$C_{10}$ cycloalkyl group, a substituted or unsubstituted $C_3$-$C_{10}$ cycloalkenyl group, a substituted or unsubstituted $C_6$-$C_{60}$ aryl group, and a substituted or unsubstituted monovalent non-aromatic condensed polycyclic group.

For example, $R_1$ and $R_2$ in Formula 1-1 may each independently be selected from:

hydrogen, deuterium, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a furanyl group, a thiophenyl group, an indolyl group, a benzofuranyl group, a benzothiophenyl group, a carbazolyl group, a dibenzofuranyl group, a dibenzothiophenyl group, a benzocarbazolyl group, a naphthobenzofuranyl group, a naphthobenzothiophenyl group, a dibenzocarbazolyl group, a dinaphthofuranyl group, a dinaphthothiophenyl group, an indolocarbazolyl group, an indolodibenzofuranyl group, and an indolodibenzothiophenyl group; and a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a furanyl group, a thiophenyl group, an indolyl group, a benzofuranyl group, a benzothiophenyl group, a carbazolyl group, a dibenzofuranyl group, a dibenzothiophenyl group, a benzocarbazolyl group, a naphthobenzofuranyl group, a naphthobenzothiophenyl group, a dibenzocarbazolyl group, a dinaphthofuranyl group, a dinaphthothiophenyl group, an indolocarbazolyl group, an indolodibenzofuranyl group, and an indolodibenzothiophenyl group, each substituted with at least one selected from deuterium, a $C_1$-$C_{20}$ alkyl group, a $C_1$-$C_{20}$ alkoxy group, a phenyl group, a biphenyl group, a terphenyl group, a naphthyl group, a fluorenyl group, a dimethylfluorenyl group, a diphenylfluorenyl group, a carbazolyl group, a phenylcarbazolyl group, a biphenylcarbazolyl group, a dibenzofuranyl group, and a dibenzothiophenyl group.

In one or more embodiments, $R_1$ and $R_2$ in Formula 1-1 may each independently be selected from hydrogen, deuterium, a $C_1$-$C_{20}$ alkyl group, a $C_1$-$C_{20}$ alkoxy group, a phenyl group, a biphenyl group, a terphenyl group, a naphthyl group, a fluorenyl group, a dimethylfluorenyl group, a diphenylfluorenyl group, a carbazolyl group, a phenylcarbazolyl group, a biphenylcarbazolyl group, a dibenzofuranyl group, and a dibenzothiophenyl group, but embodiments of the present disclosure are not limited thereto.

In Formula 1-1, a1 and a2 respectively indicate the numbers of $R_1$ and $R_2$, and may each independently be an integer from 0 to 8. When a1 is two or more, two or more of groups $R_1$ may be identical to or different from each other, and when a2 is two or more, two or more of groups $R_2$ may be identical to or different from each other. For example, a1 and a2 may each independently be 0, 1, 2, 3, or 4, or in some embodiments, may each independently be 0, 1, or 2, but the embodiments are not limited thereto.

In Formulae 1-3 and 1-4, a24 indicates the number of groups $R_{24}$, and may be an integer from 0 to 4. When a24 is two or more, two or more of groups $R_{24}$ may be identical to or different from each other. For example, a24 may be 0, 1, or 2, but embodiments of the present disclosure are not limited thereto.

In Formulae 1 and 1-2 to 1-4, $R_{11}$ to $R_{14}$ and $R_{21}$ to $R_{25}$ may each independently be selected from:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a pyridinyl group, a pyrimidinyl group, a pyrazinyl group, a pyridazinyl group, and a triazinyl group;

a cyclopentyl group, a cyclohexyl group, a cyclopentenyl group, a cyclohexenyl group, a cycloheptenyl group, a phenyl group, a pentalenyl group, an indenyl group, a naphthyl group, an azulenyl group, a heptalenyl group, an indacenyl group, an acenaphthyl group, a fluorenyl group, a spiro-bifluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzoxazolyl group, a benzimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, an imidazopyridimidinyl group, and an imidazopyridinyl group; and a cyclopentyl group, a cyclohexyl group, a cyclopentenyl group, a cyclohexenyl group, a cycloheptenyl group, a phenyl group, a pentalenyl group, an indenyl group, a naphthyl group, an azulenyl group, a heptalenyl group, an indacenyl group, an acenaphthyl group, a fluorenyl group, a spiro-bifluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzoxazolyl group, a benzimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, an imidazopyridimidinyl group, and an imidazopyridinyl group, each substituted with at least one selected from deuterium, —F, —Cl, —Br, —I, a hydroxyl group, a cyano group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a naphthyl group, an anthracenyl group, a pyrenyl group, a phenanthrenyl group, a fluorenyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group.

In one or more embodiments, at least one of $R_{11}$ to $R_{14}$ in Formula 1 may be selected from:

a cyano group;

a phenyl group; and a phenyl group substituted with at least one selected from deuterium, a $C_1$-$C_{20}$ alkyl group, and a phenyl group, but embodiments of the present disclosure are not limited thereto.

In one or more embodiments, at least one of $R_{11}$ to $R_{14}$ in Formula 1 may be selected from:

a cyano group;

a cyclopentyl group, a cyclohexyl group, a cyclopentenyl group, a cyclohexenyl group, a cycloheptenyl group, a phenyl group, a pentalenyl group, an indenyl group, a naphthyl group, an azulenyl group, a heptalenyl group, an indacenyl group, an acenaphthyl group, a fluorenyl group, a spiro-bifluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, and a hexacenyl group; and a cyclopentyl group, a cyclohexyl group, a cyclopentenyl group, a cyclohexenyl group, a cycloheptenyl group, a phenyl group, a pentalenyl group, an indenyl group, a naphthyl group, an azulenyl group, a heptalenyl group, an indacenyl group, an acenaphthyl group, a fluorenyl group, a spiro-bifluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, and a hexacenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a naphthyl group, an anthracenyl group, a pyrenyl group, a phenanthrenyl group, a fluorenyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group.

In one or more embodiments, at least one of $R_{11}$ to $R_{14}$ in Formula 1 may be selected from:

a cyano group;

a phenyl group; and a phenyl group substituted with at least one selected from deuterium, a $C_1$-$C_{20}$ alkyl group, and a phenyl group, but embodiments of the present disclosure are not limited thereto.

In one or more embodiments, one or two of $R_{11}$ to $R_{14}$ in Formula 1 may each independently be selected from a cyano group, a substituted or unsubstituted $C_3$-$C_{10}$ cycloalkyl group, a substituted or unsubstituted $C_3$-$C_{10}$ cycloalkenyl group, a substituted or unsubstituted $C_6$-$C_{60}$ aryl group, and a substituted or unsubstituted monovalent non-aromatic condensed polycyclic group, and the others may each independently be selected from hydrogen, deuterium, a $C_1$-$C_{20}$ alkyl group, and a $C_1$-$C_{20}$ alkoxy group, but embodiments of the present disclosure are not limited thereto.

For example, $D_1$ in Formula 1 may be selected from groups represented by Formulae 2-1 to 2-7, but embodiments of the present disclosure are not limited thereto:

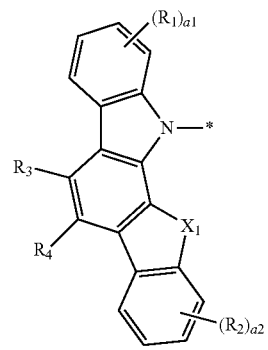

Formula 2-1

-continued

Formula 2-2
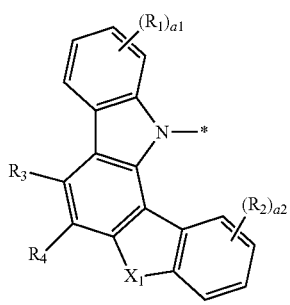

Formula 2-3
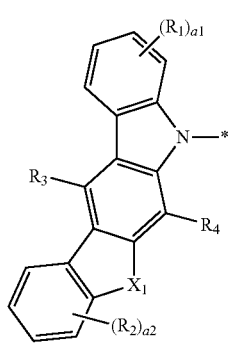

Formula 2-4
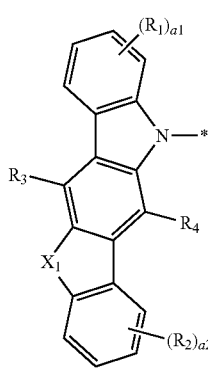

Formula 2-5
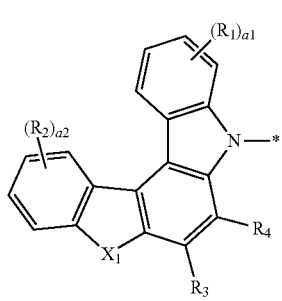

Formula 2-6
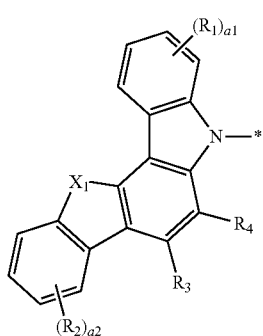

Formula 2-7
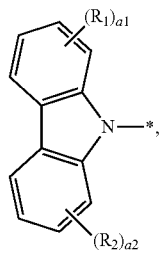

wherein, in Formulae 2-1 to 2-7, $X_1$ may be $C(R_5)(R_6)$, $N(R_7)$, O, or S, $R_1$ and $R_2$ may be the same as described above.

$R_3$ to $R_7$ may be understood by referring to the description provided herein in connection with $R_1$, a1 and a2 may each independently be an integer from 0 to 4, and

* indicates a binding site to a neighboring atom.

In one or more embodiments, $D_1$ in Formula 1 may be selected from groups represented by Formulae 2(1) to 2(9), but embodiments of the present disclosure are not limited thereto:

Formula 2(1)
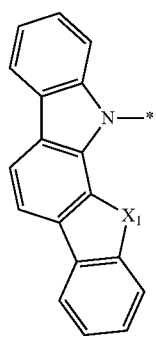

Formula 2(2)
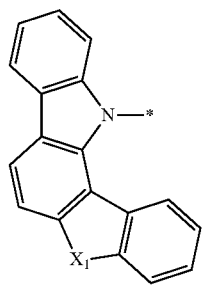

Formula 2(3)
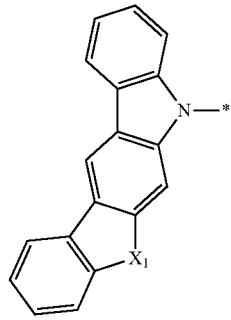

-continued
Formula 2(4)
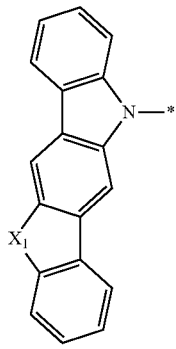
Formula 2(5)
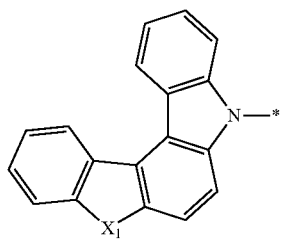
Formula 2(6)
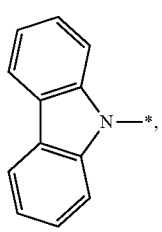
Formula 2(7)
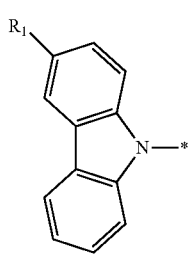
Formula 2(8)
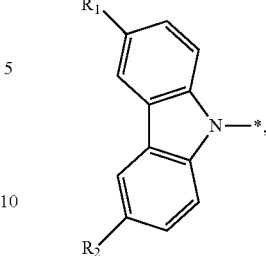
Formula 2(9)
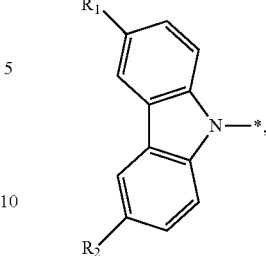
wherein, in Formulae 2(1) to 2(9), $X_1$, $R_1$, $R_2$, and * are the same as described above.
In one or more embodiments, $A_1$ in Formula 1 may be selected from groups represented by Formulae 3-1 to 3-8, but embodiments of the present disclosure are not limited thereto:
Formula 3-1
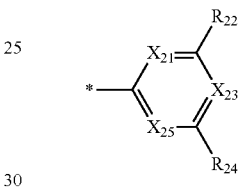
Formula 3-2
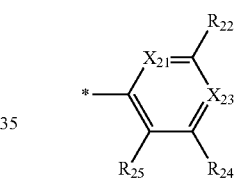
Formula 3-3
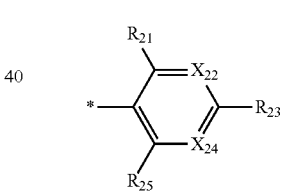
Formula 3-4
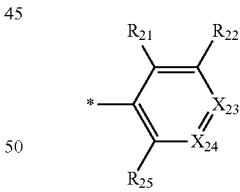
Formula 3-5
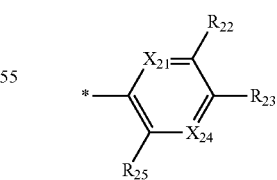
Formula 3-6
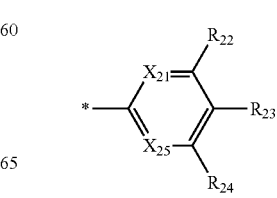

-continued

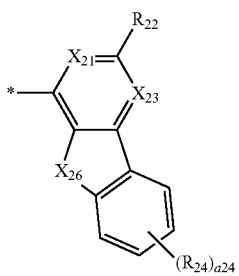
Formula 3-7

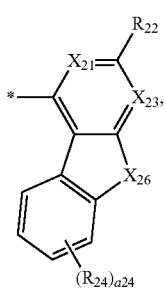
Formula 3-8 wherein, in Formulae 3-1 to 3-8, $X_{21}$ to $X_{25}$ may each independently be N or C(CN), $X_{26}$, $R_{21}$ to $R_{25}$, and a24 are the same as described above, and

* indicates a binding site to a neighboring atom.

For example, $R_{21}$ to $R_{25}$ in Formulae 3-1 to 3-8 may each independently be hydrogen, deuterium, a $C_1$-$C_{20}$ alkyl group, a phenyl group, or a biphenyl group, but embodiments of the present disclosure are not limited thereto.

In one or more embodiments, the condensed cyclic compound represented by Formula 1 may be represented by one of Formulae 1A to 1E:

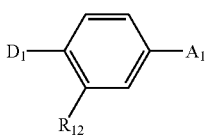
Formula 1A

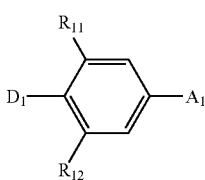
Formula 1B

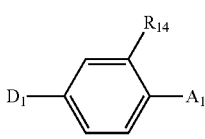
Formula 1C

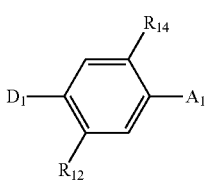
Formula 1D

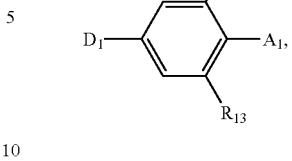
Formula 1E wherein $D_1$ and $A_1$ in Formulae 1A to 1E are the same as described above, and $R_{11}$ to $R_{14}$ may each independently be selected from a cyano group, a substituted or unsubstituted $C_3$-$C_{10}$ cycloalkyl group, a substituted or unsubstituted $C_3$-$C_{10}$ cycloalkenyl group, a substituted or unsubstituted $C_6$-$C_{60}$ aryl group, and a substituted or unsubstituted monovalent non-aromatic condensed polycyclic group.

In one or more embodiments, $R_{11}$ to $R_{14}$ in Formulae 1A to 1E may each independently be selected from:

a cyano group;

a phenyl group; and a phenyl group substituted with at least one selected from deuterium, a $C_1$-$C_{20}$ alkyl group, and a phenyl group.

For example, the condensed cyclic compound may be one of Compounds 1 to 307, but embodiments of the present disclosure are not limited thereto:

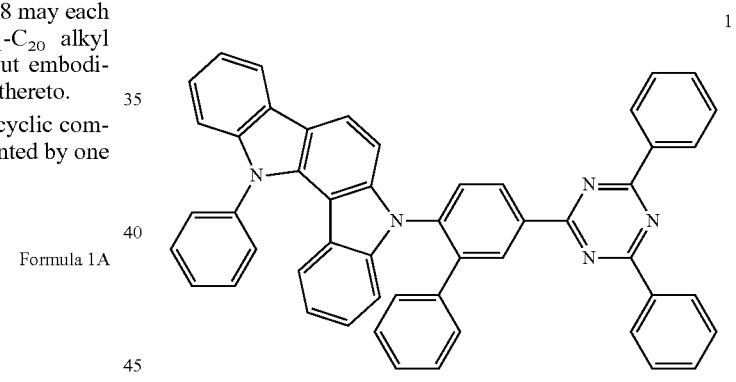

1

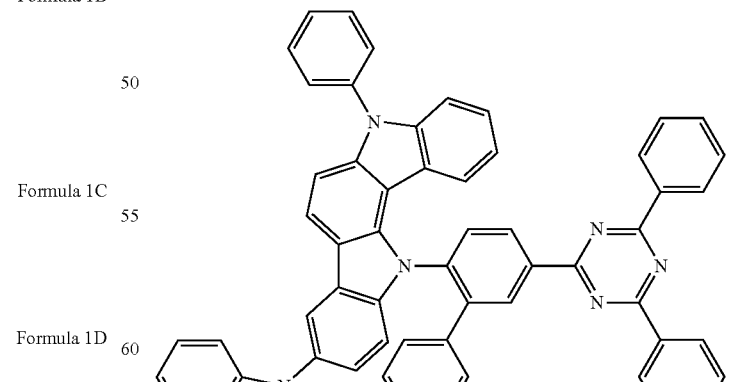

2

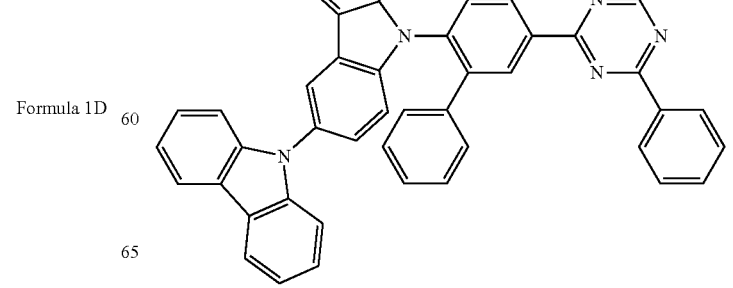

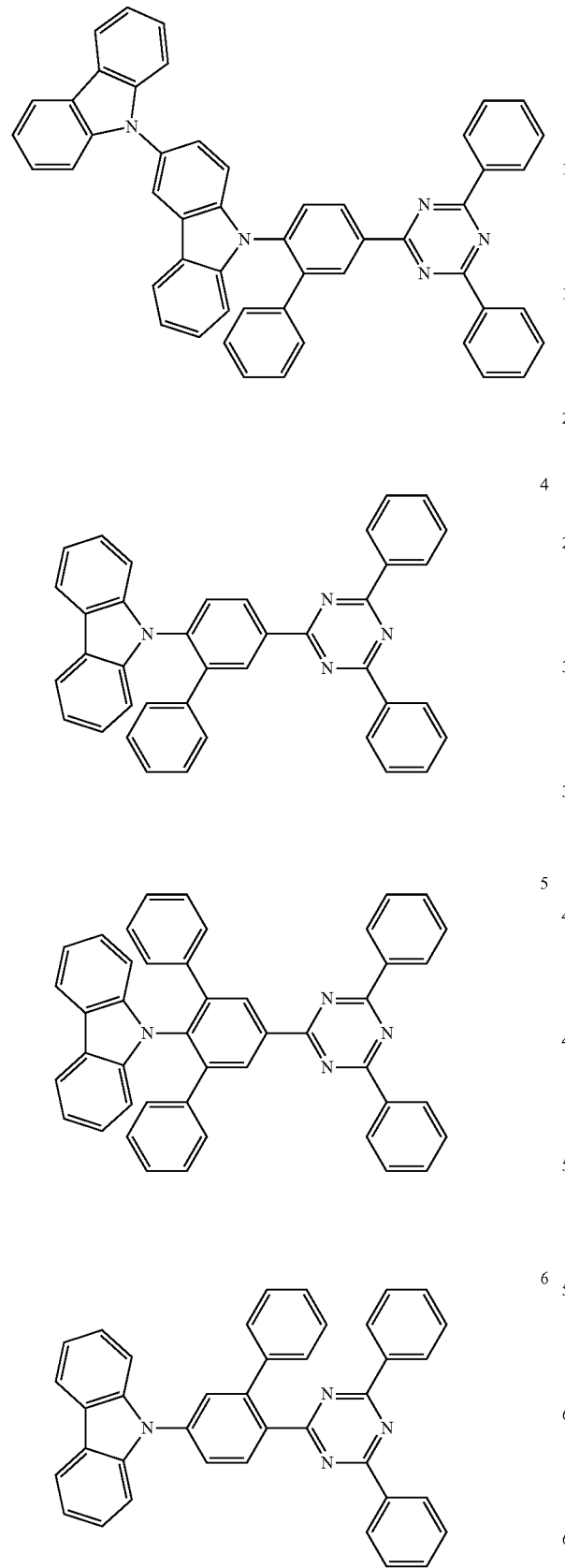
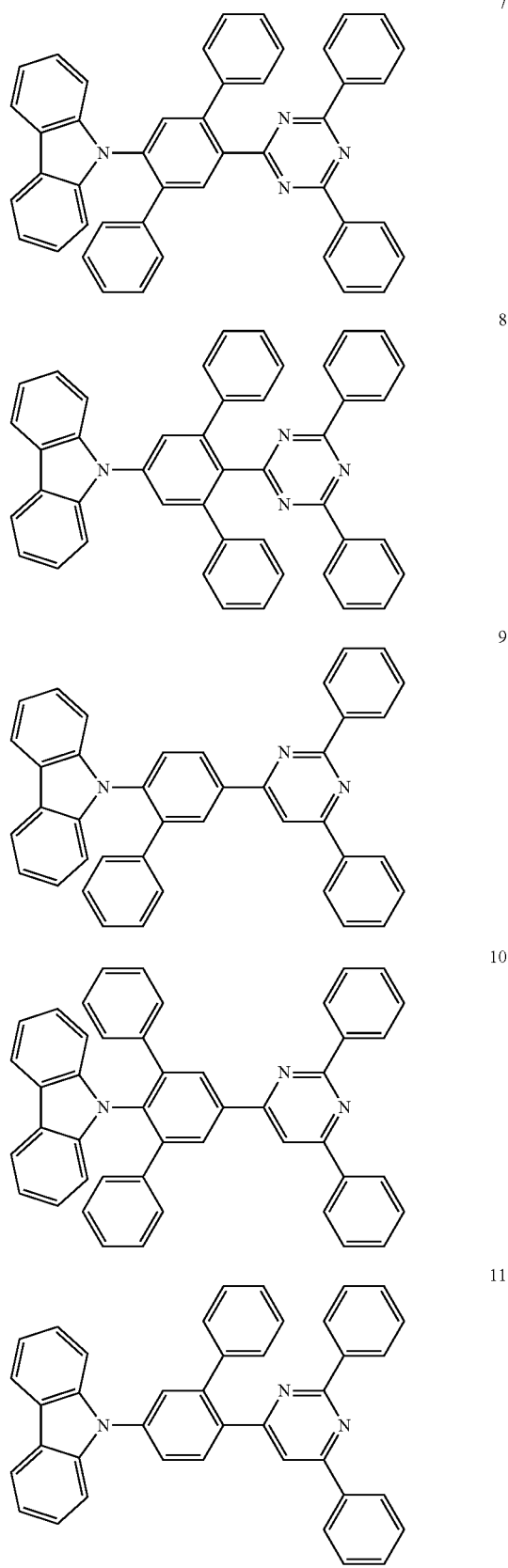

12
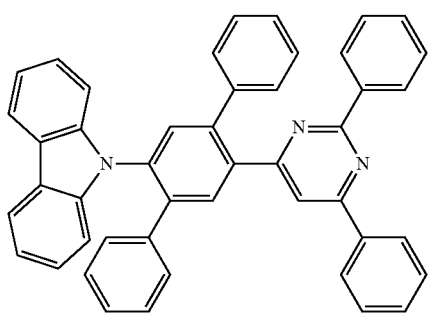
13
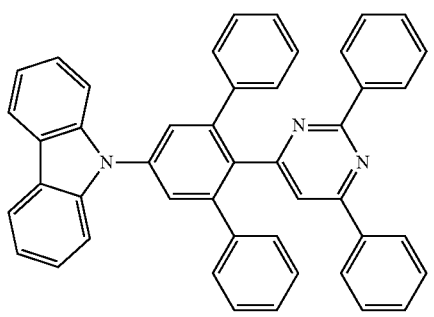
14
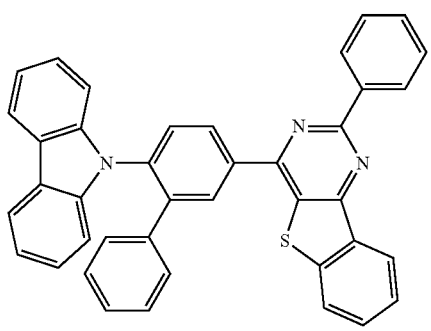
15
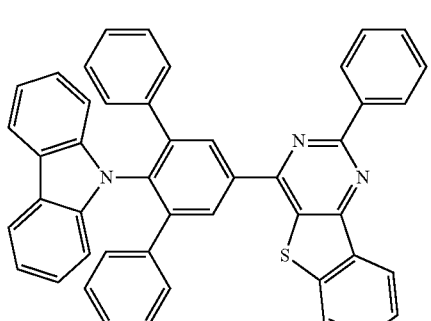
16
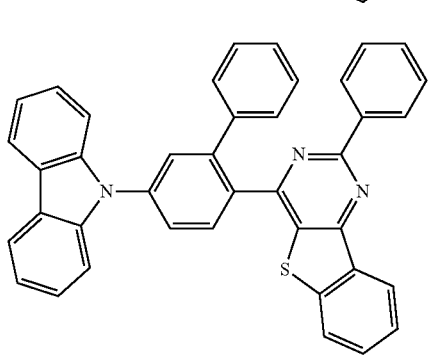
17
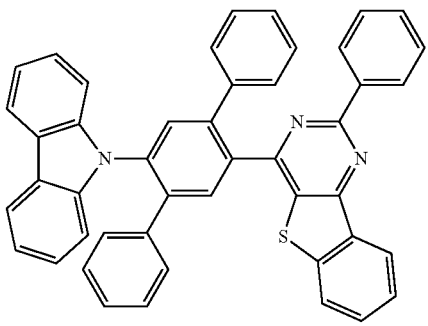
18
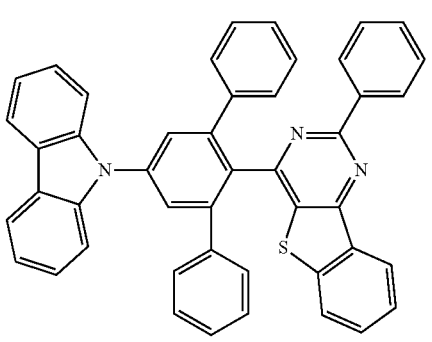
19
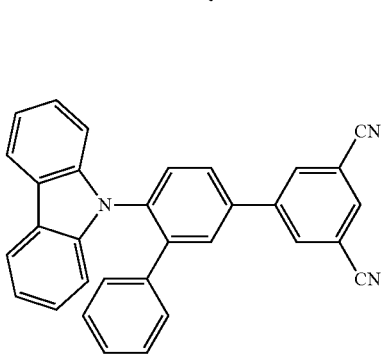
20
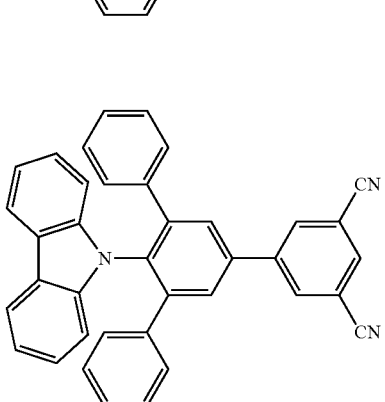
21
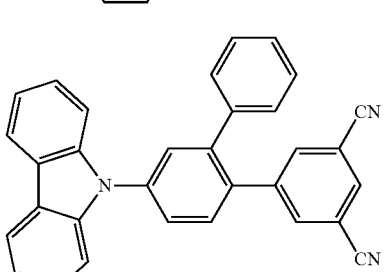

22
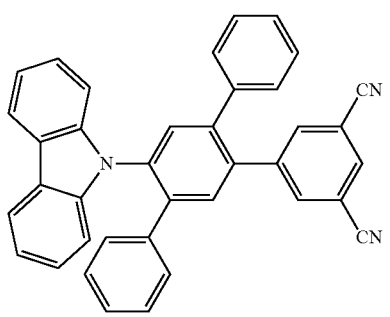
23
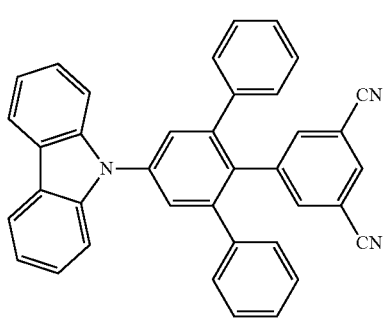
24
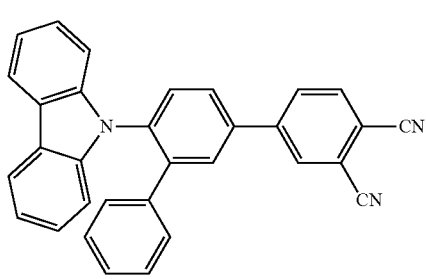
25
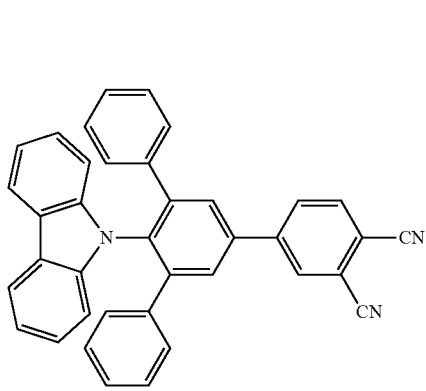
26
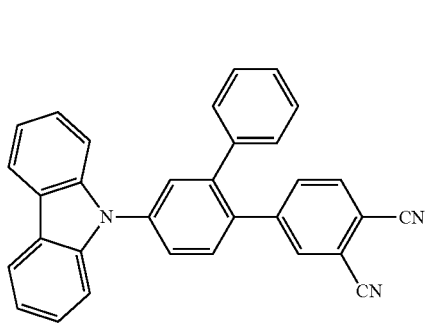
27
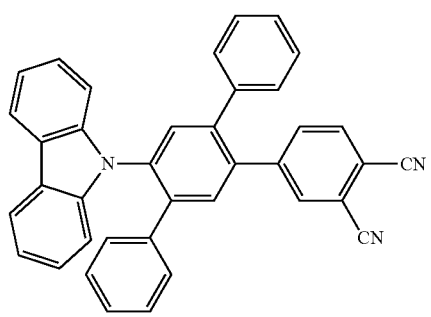
28
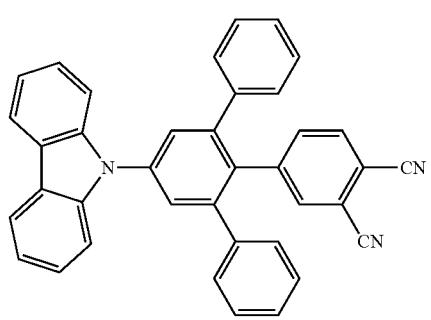
29
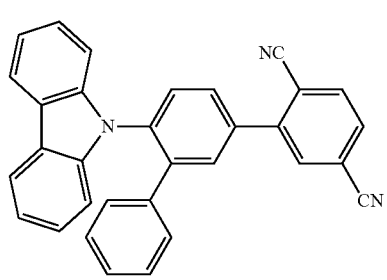
30
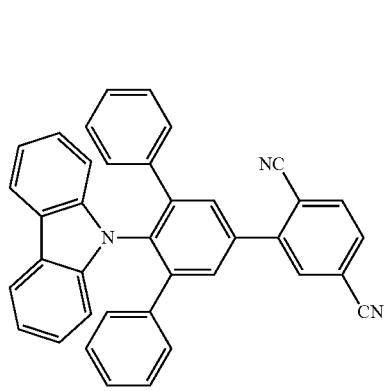
31
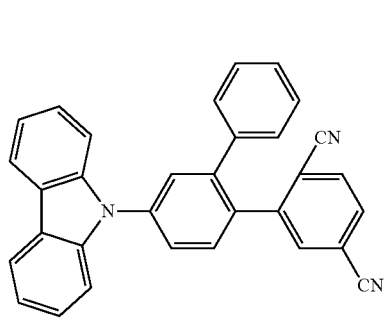

32
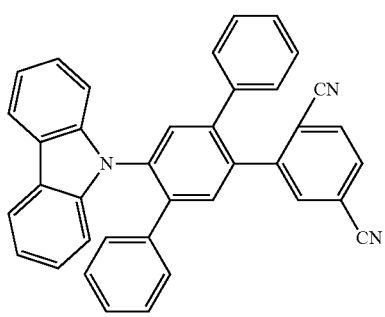
33
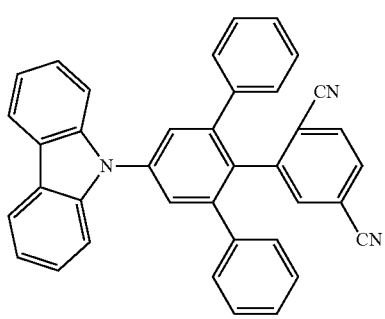
34
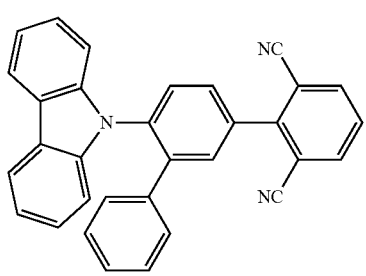
35
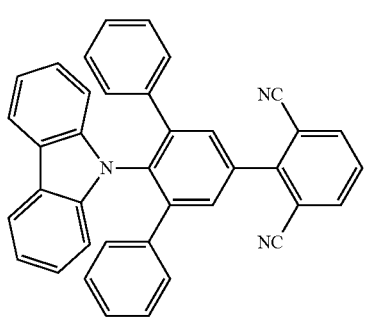
36
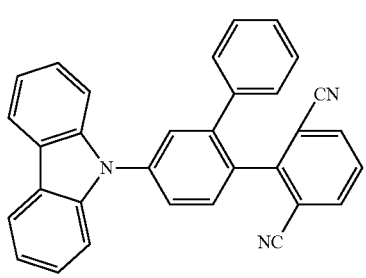
37
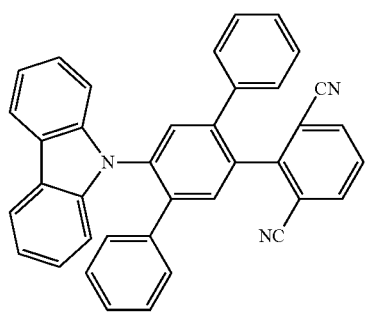
38
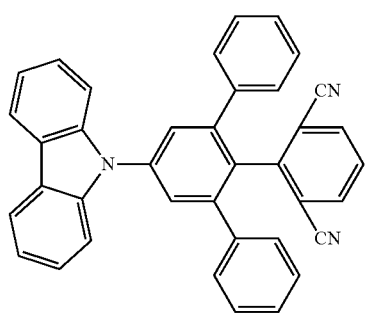
39
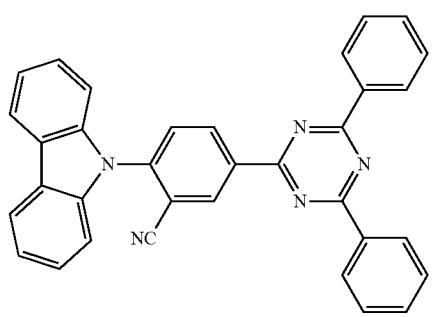
40
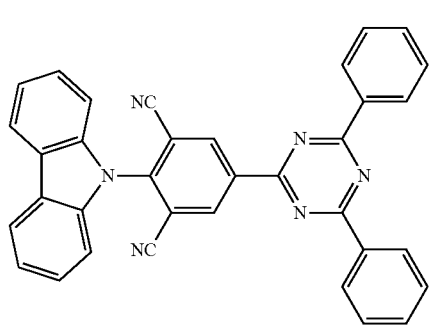
41
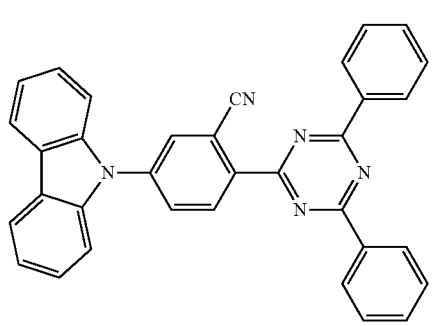

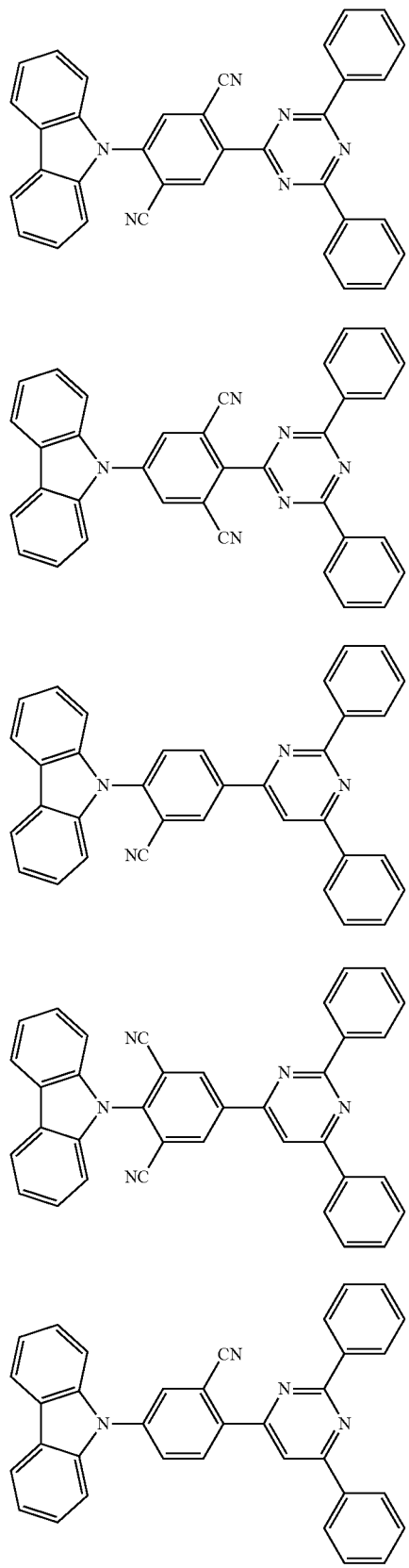
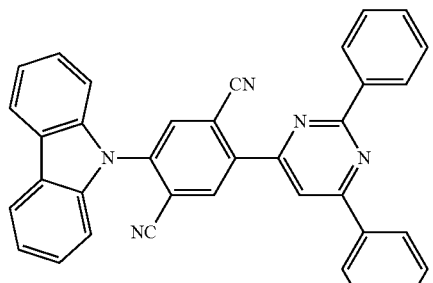
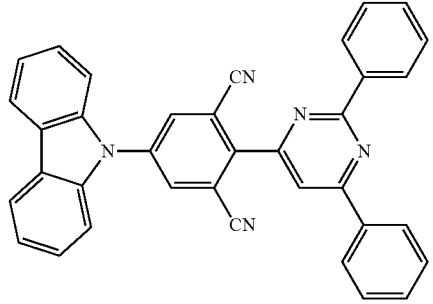
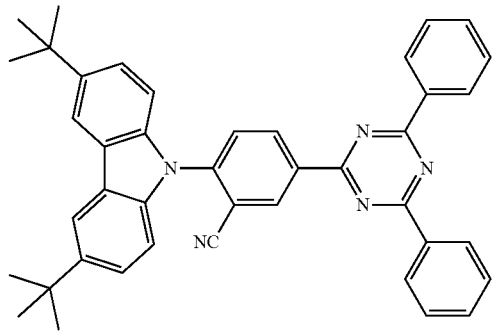
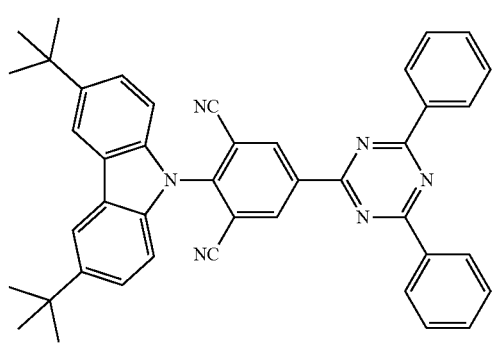
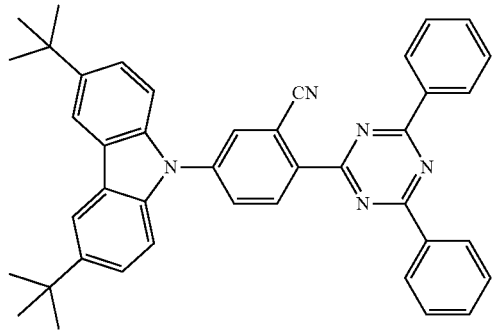

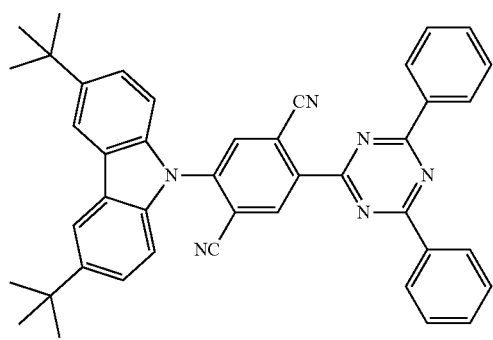
52
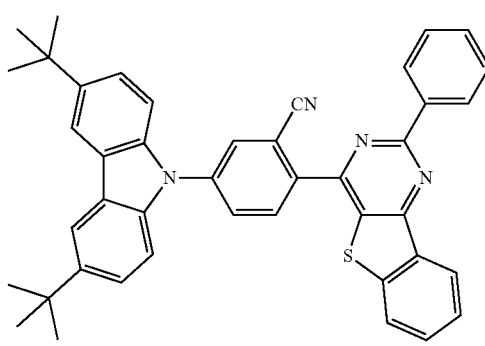
56
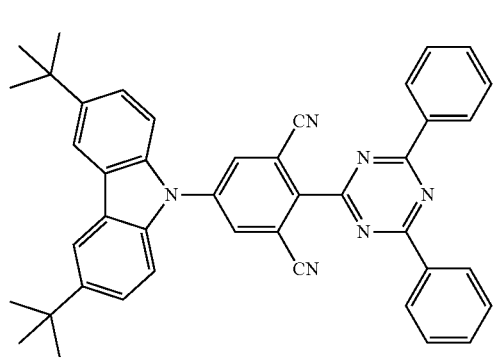
53
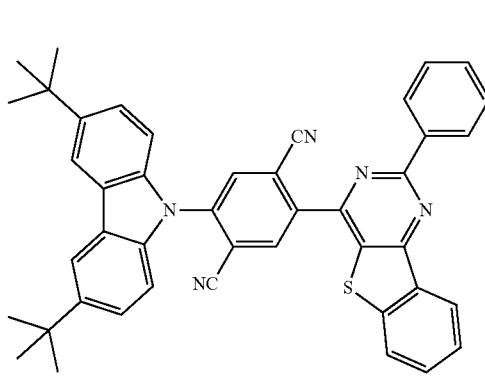
57
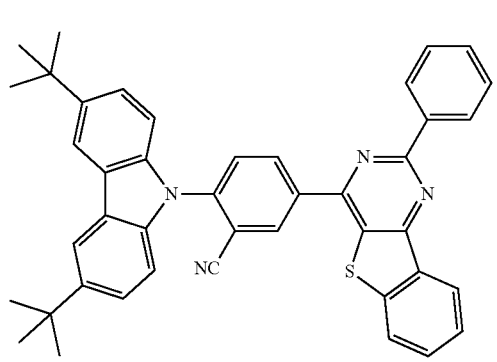
54
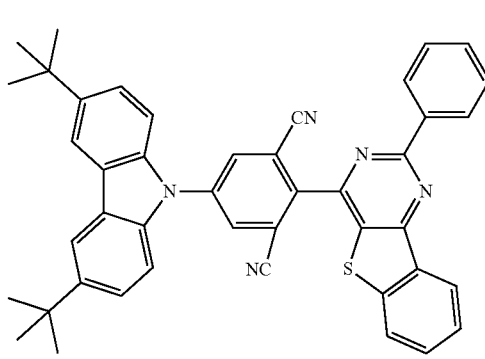
58
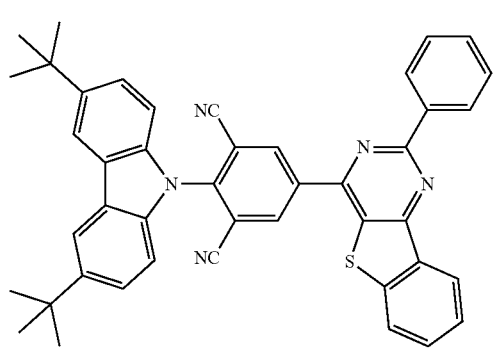
55
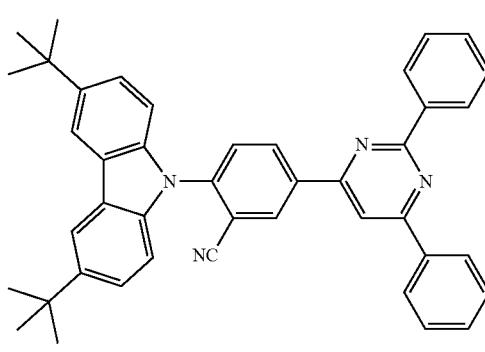
59

-continued
60
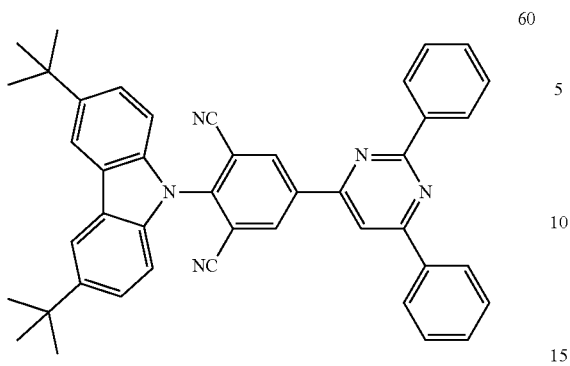
61
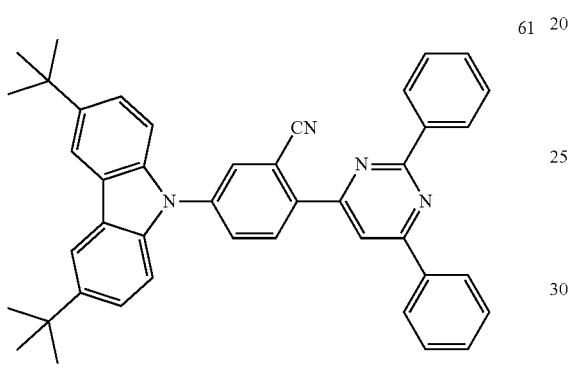
62
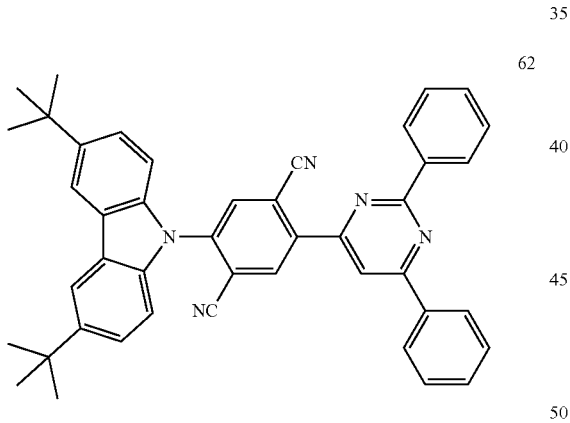
63
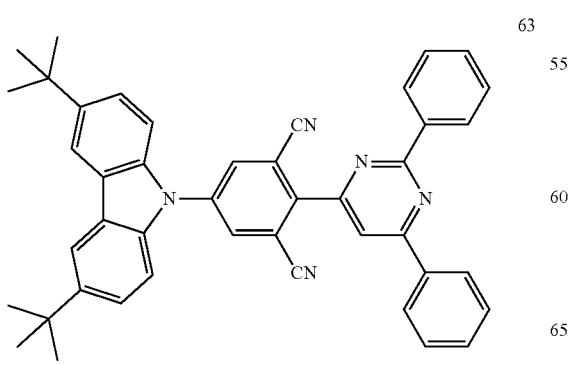
-continued
64
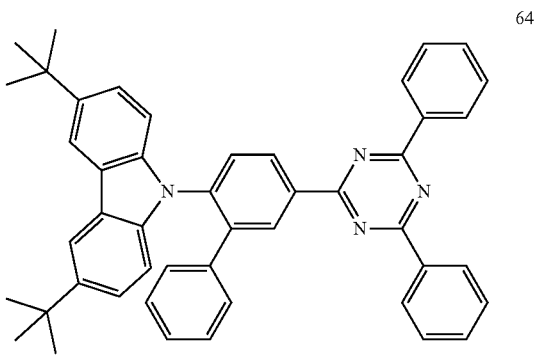
65
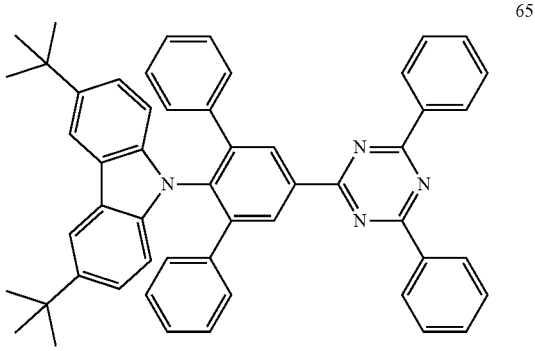
66
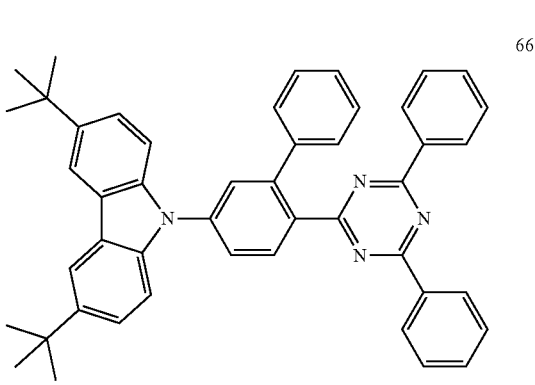
67
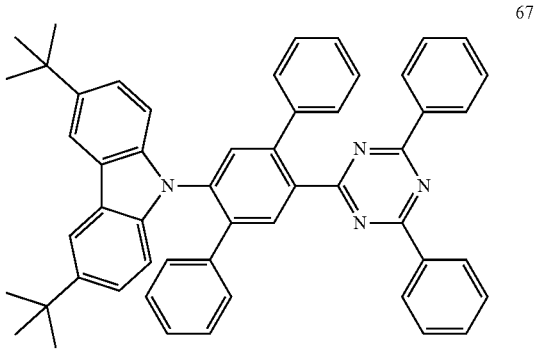

68
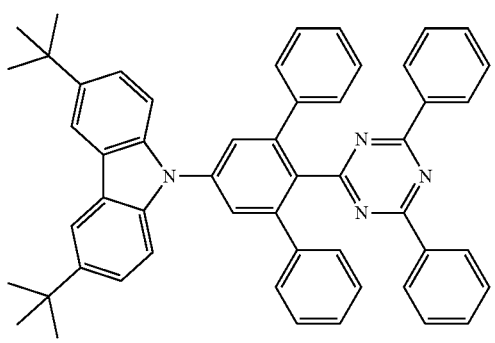
69
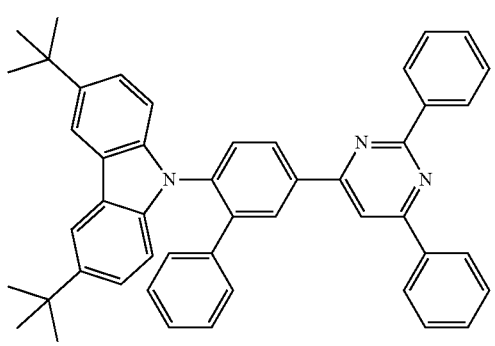
70
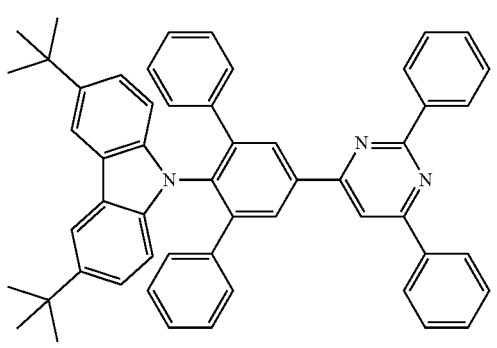
71
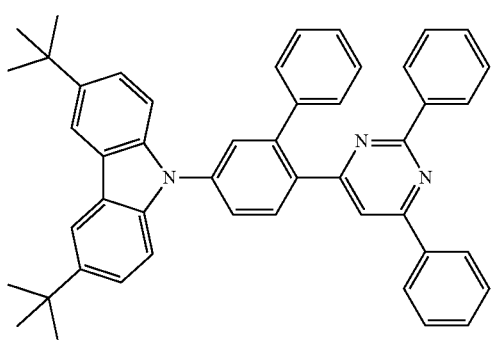
72
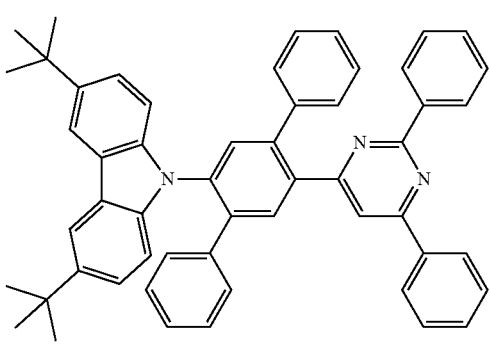
73
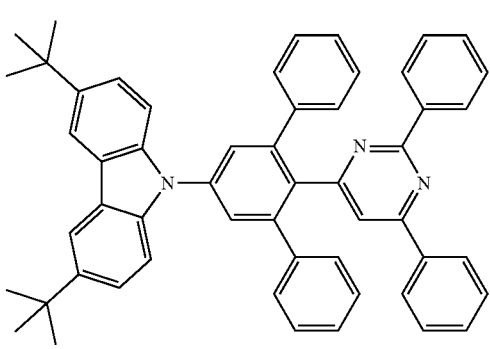
74
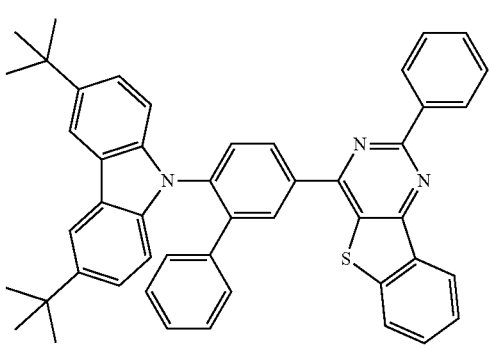
75
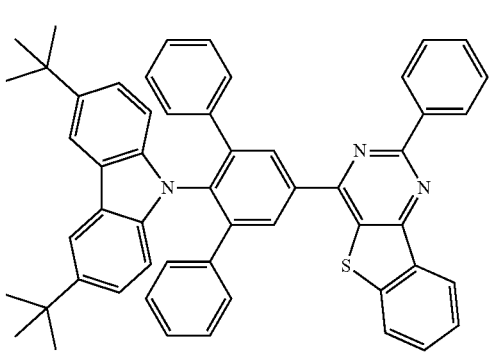

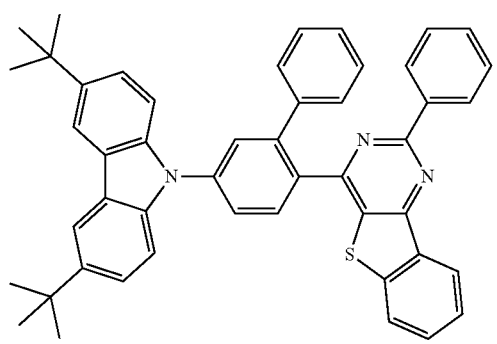
76
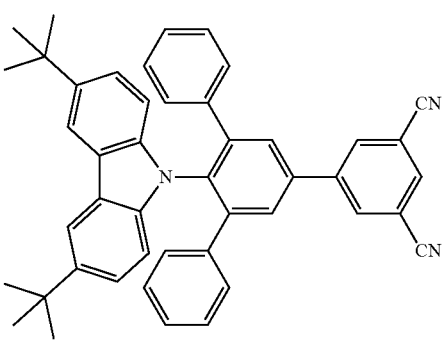
80
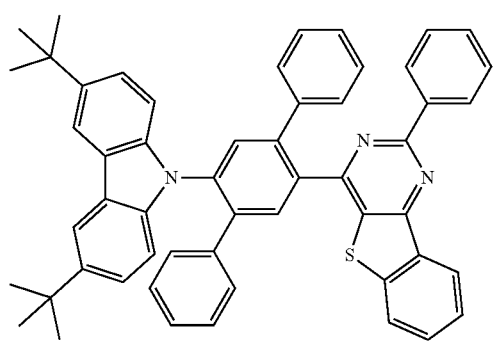
77
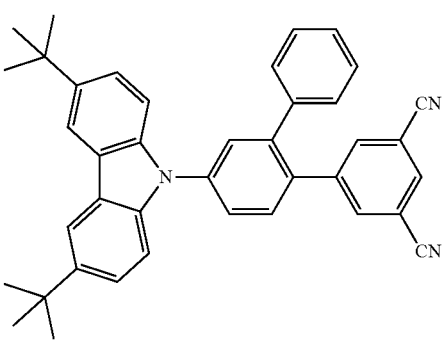
81
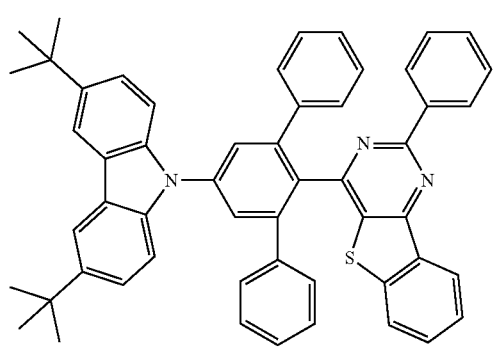
78
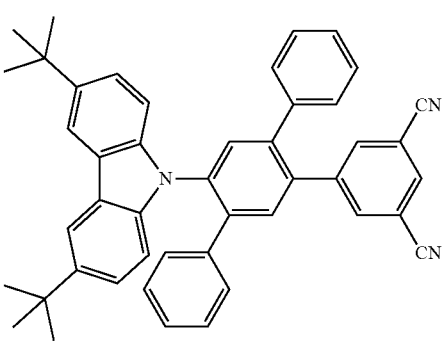
82
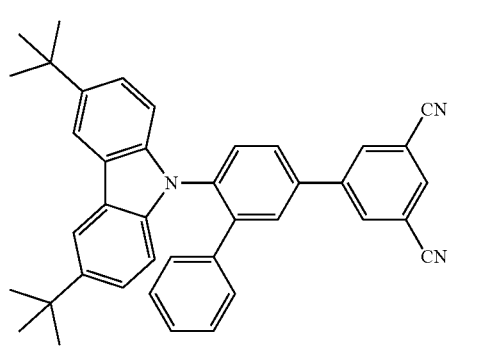
79
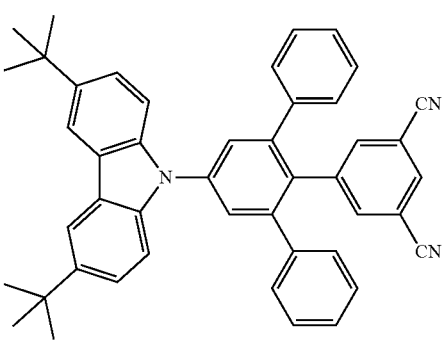
83

84
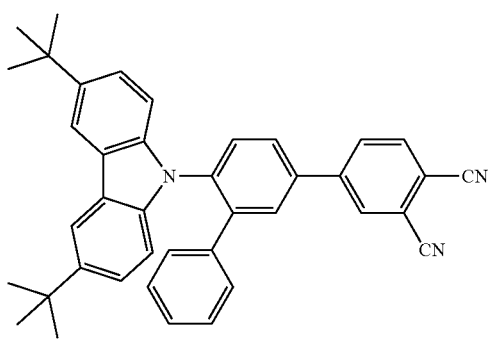
85
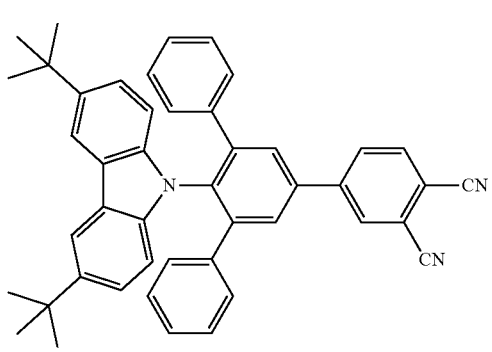
86
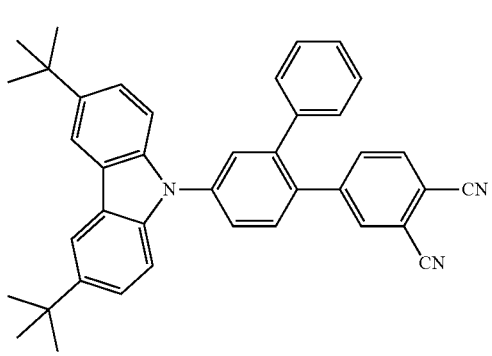
87
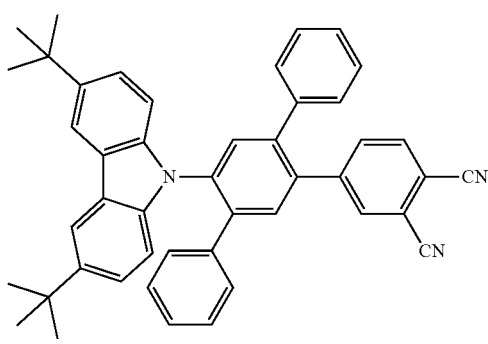
88
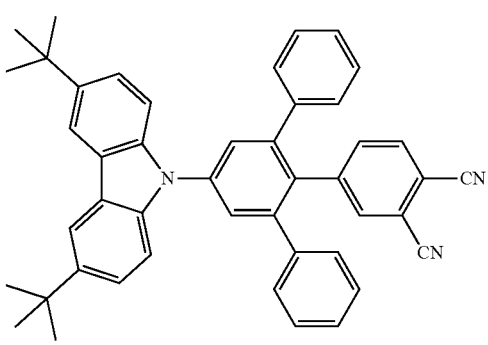
89
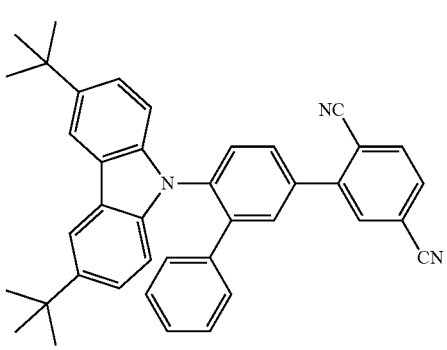
90
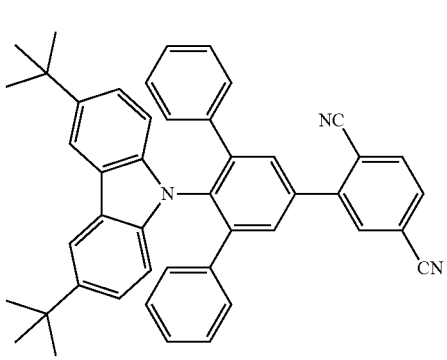
91
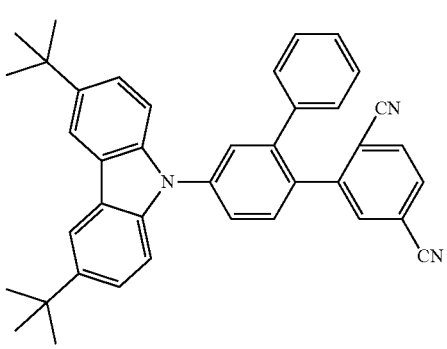

92
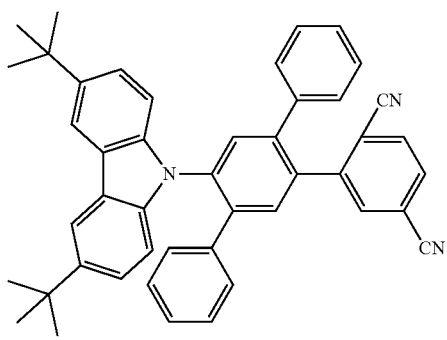
93
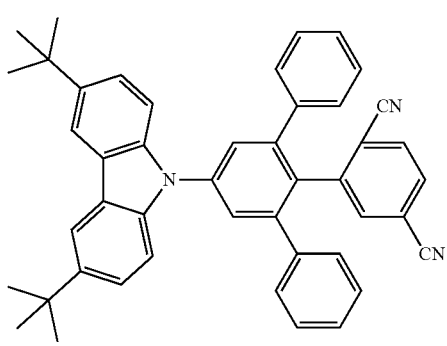
94
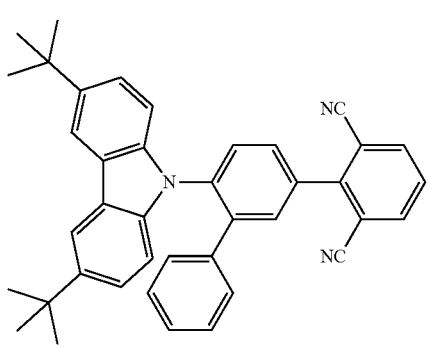
95
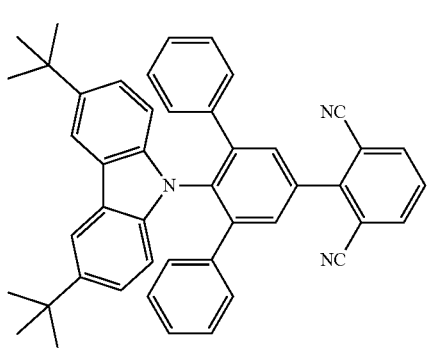
96
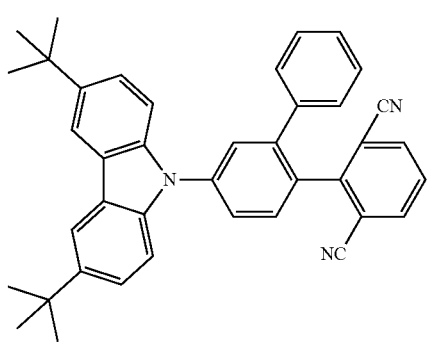
97
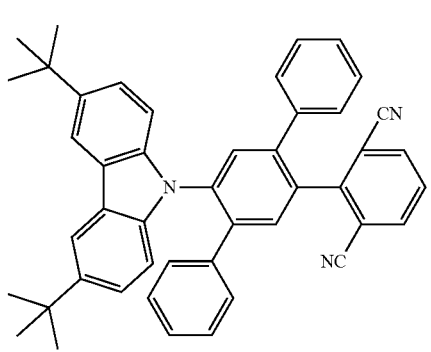
98
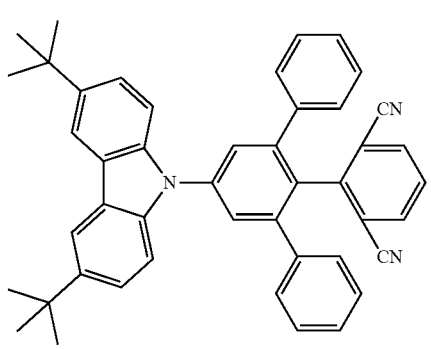
99
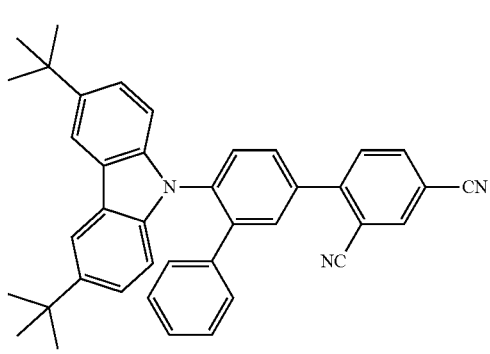

100
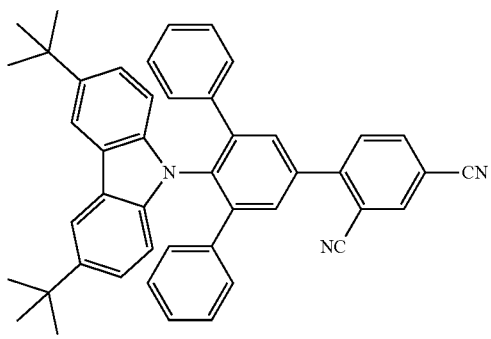
101
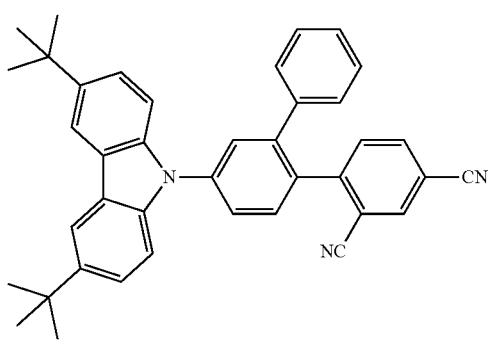
102
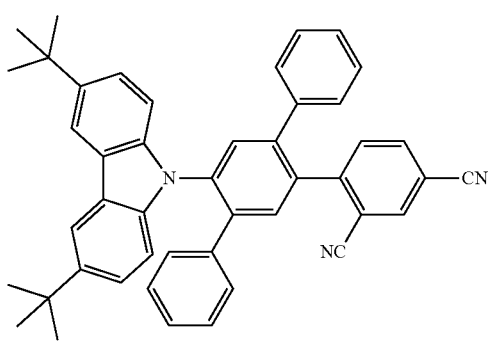
103
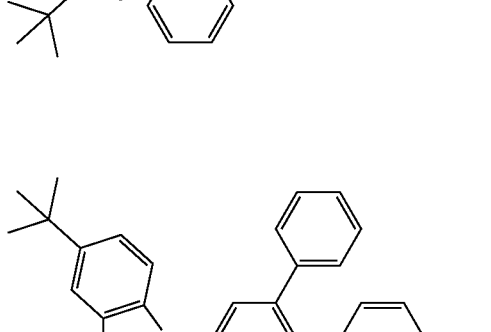
104
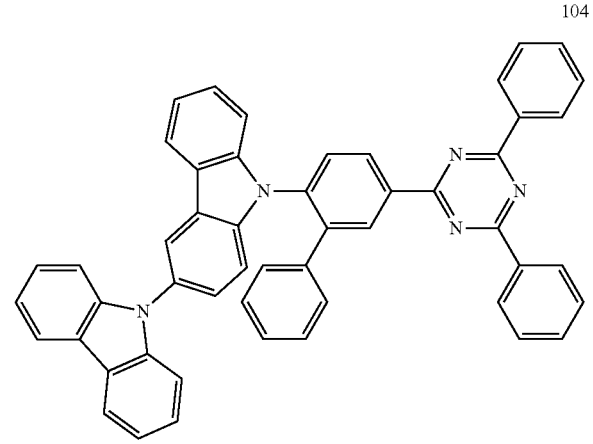
105
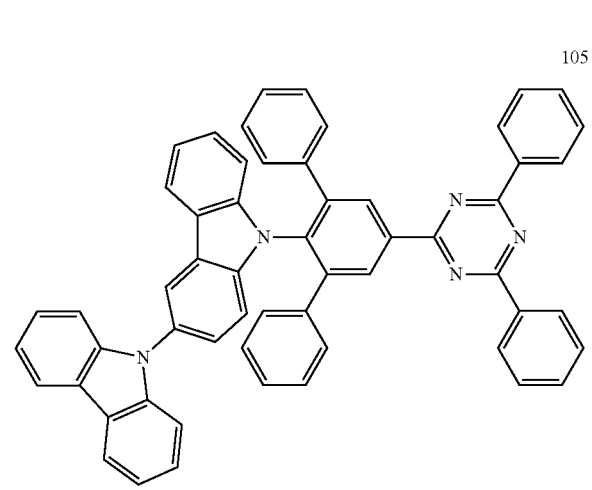
106
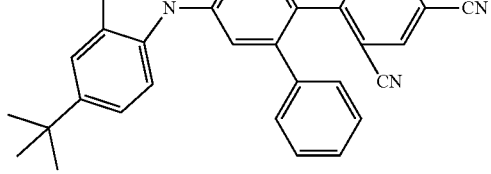

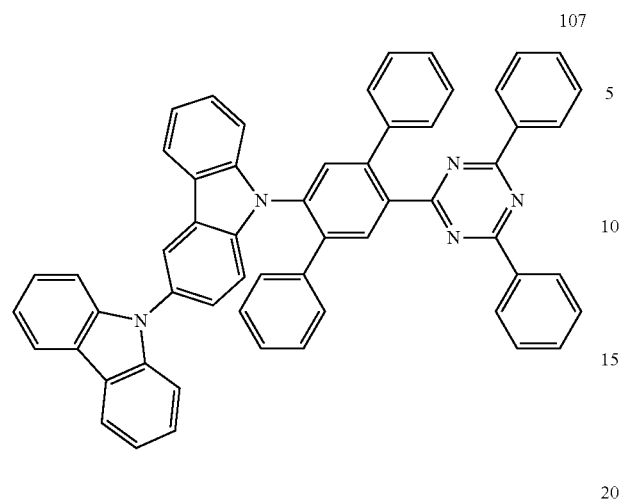
107
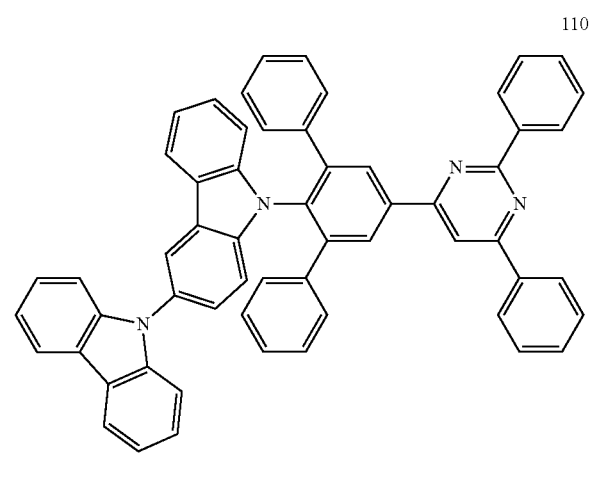
110
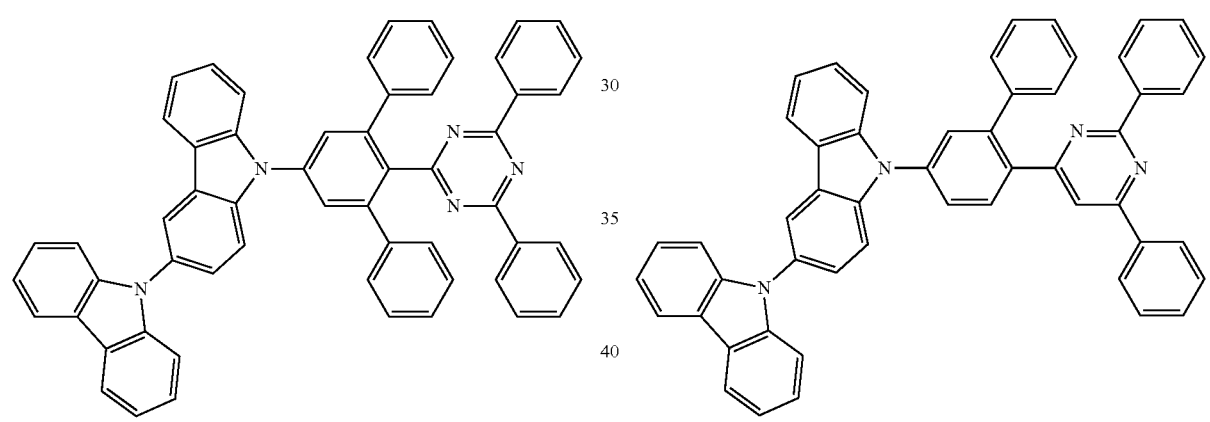
108
111
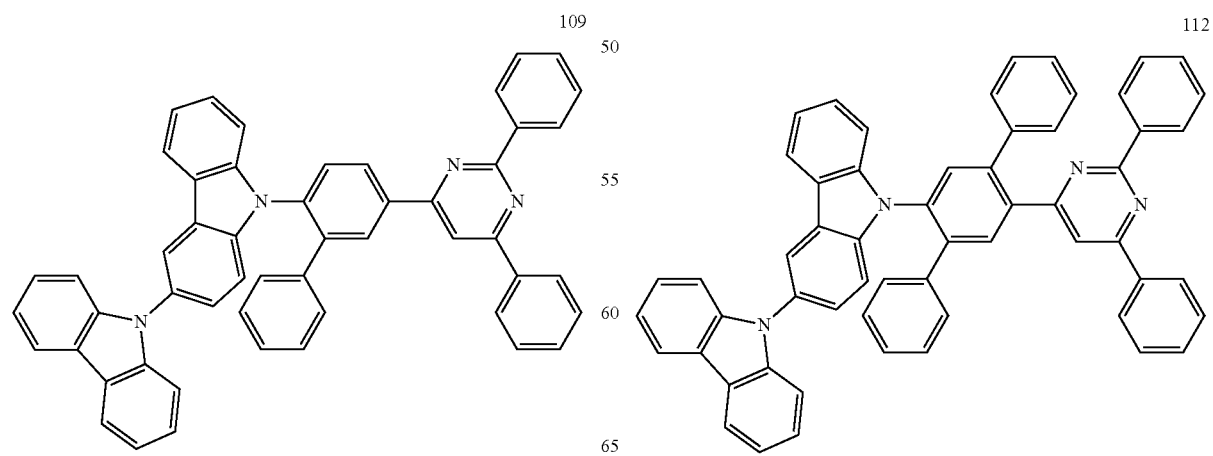
109
112

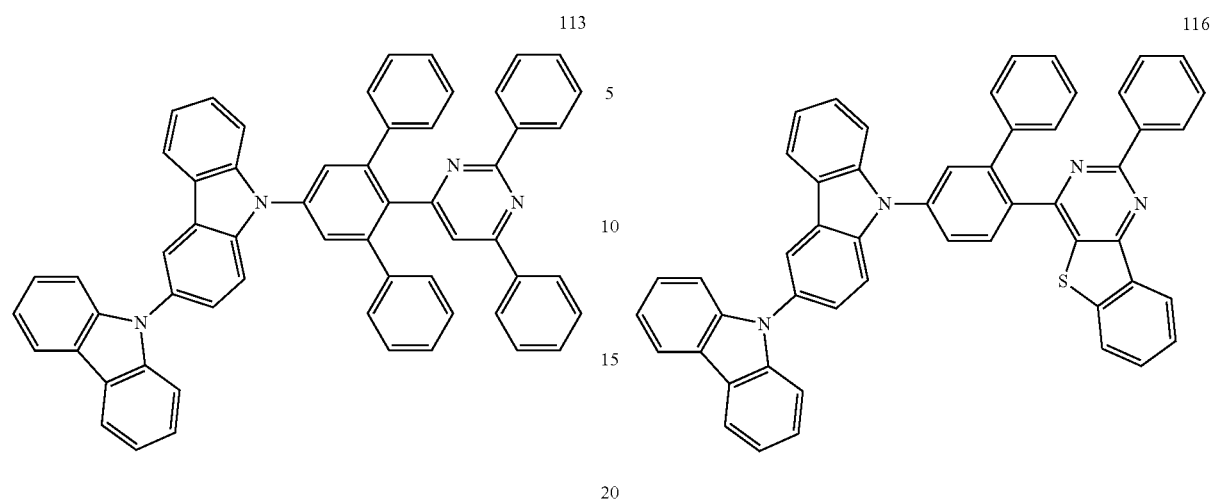
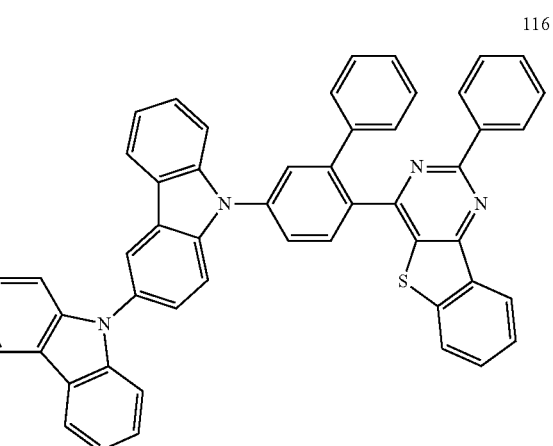
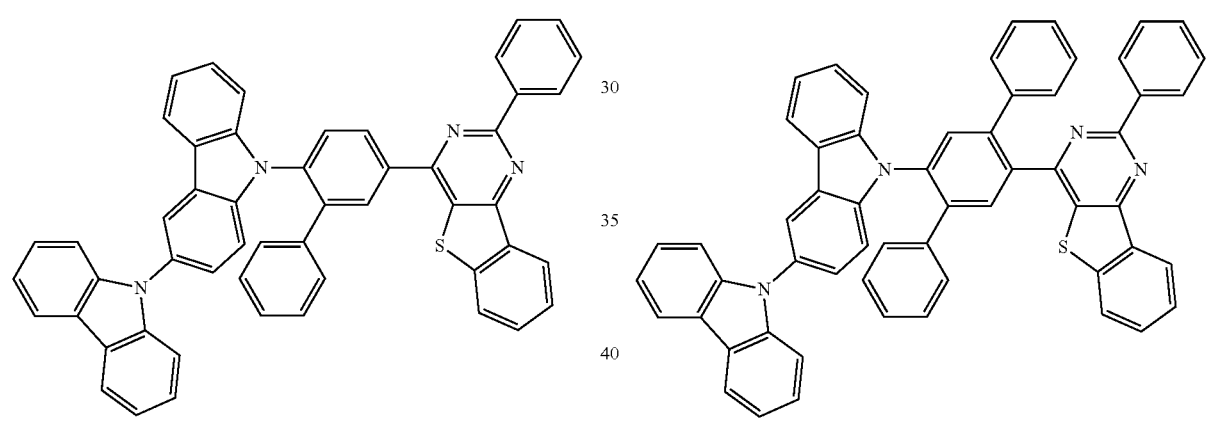
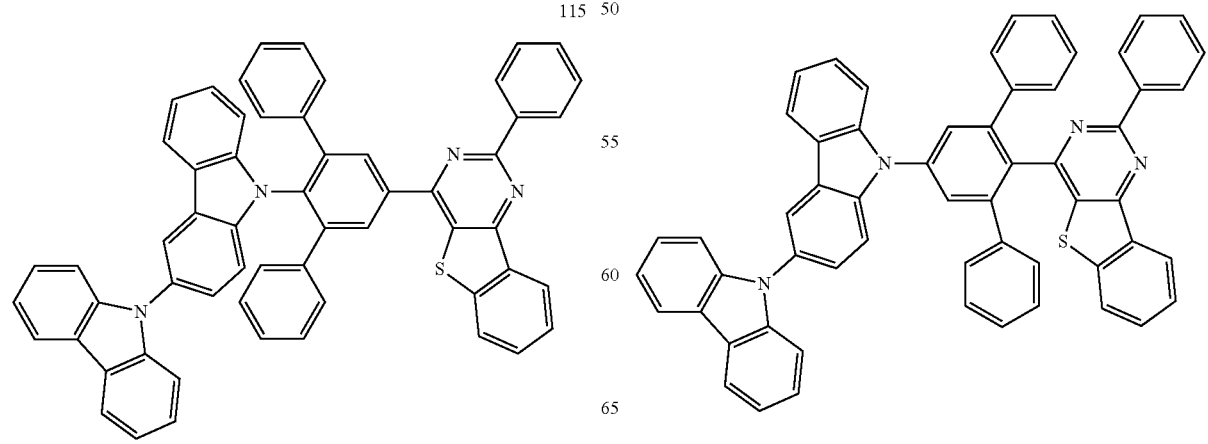

119
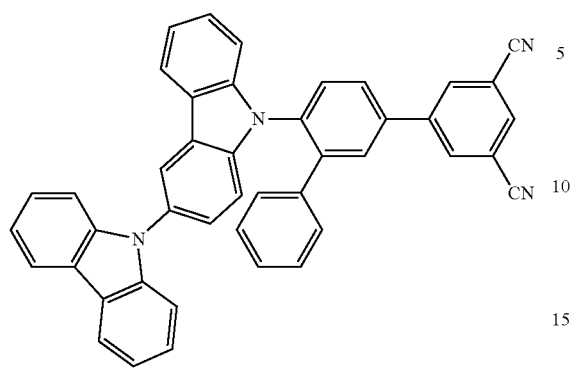
120
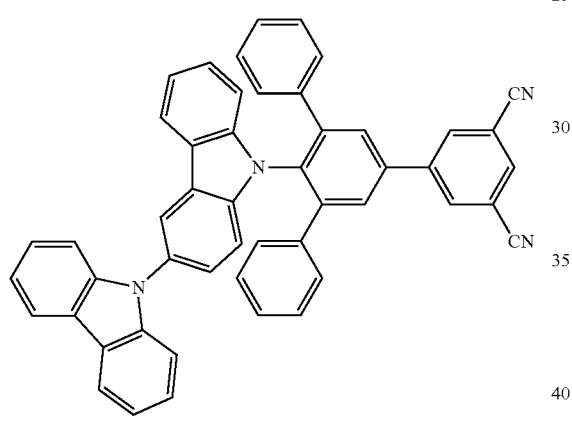
121
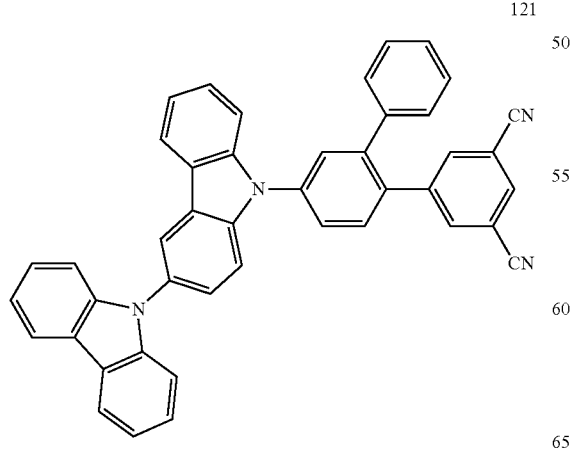
122
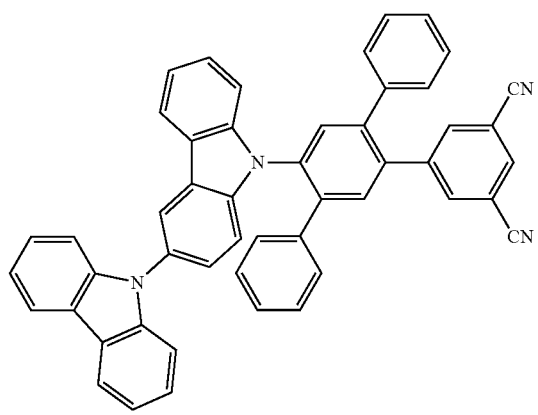
123
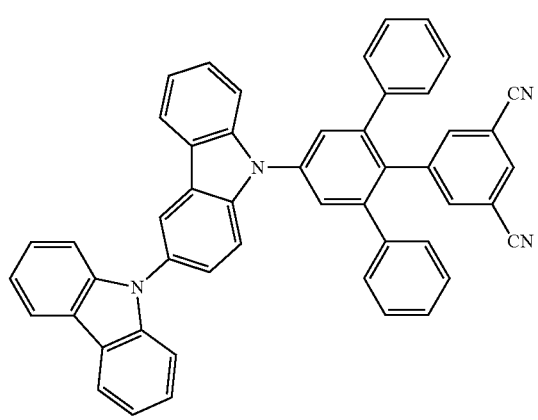
124

125
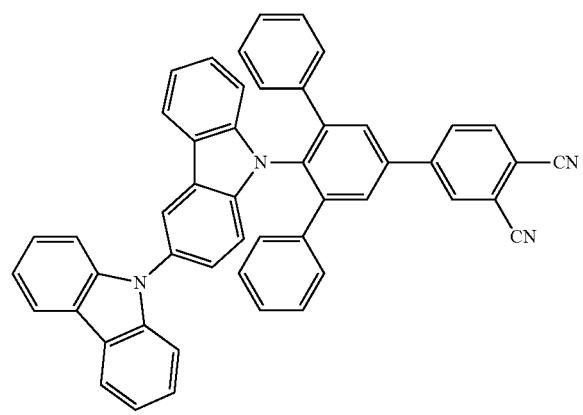
126
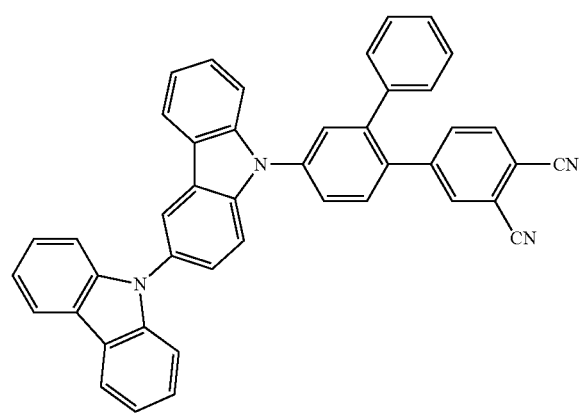
127
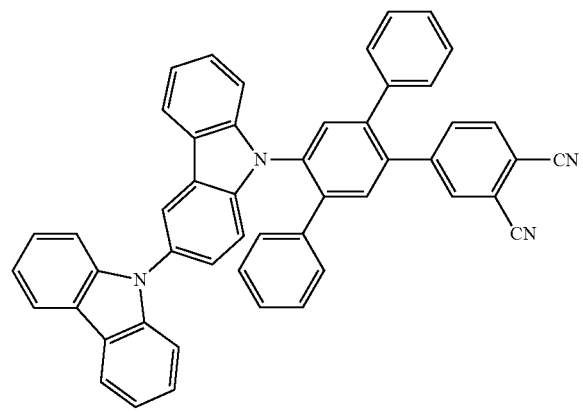
128
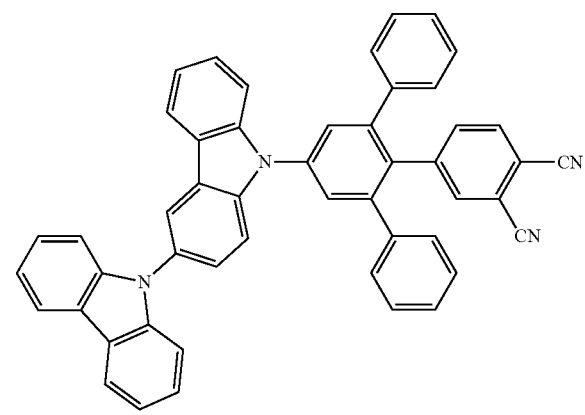
129
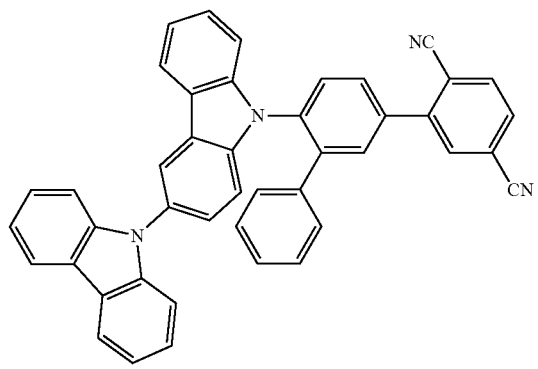
130
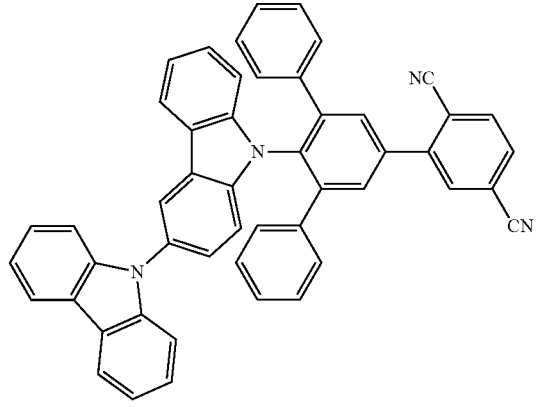

131
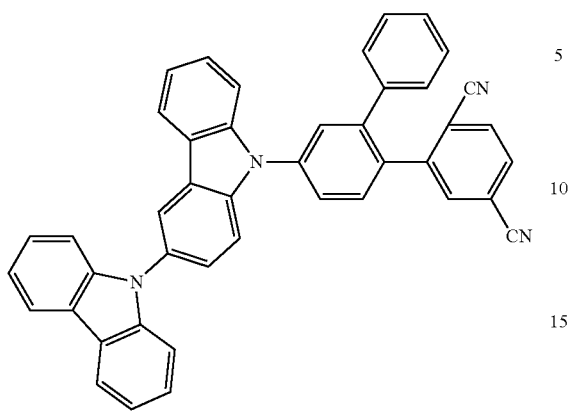
132
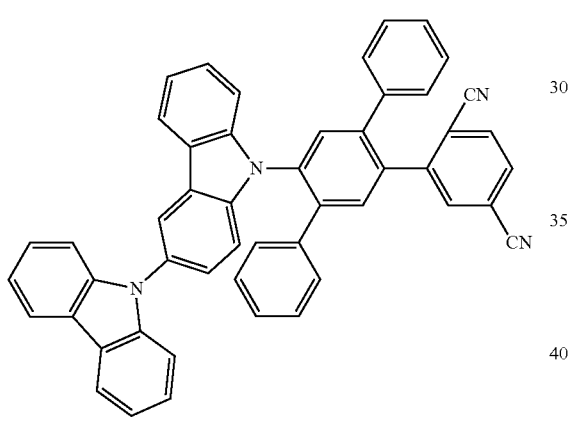
134
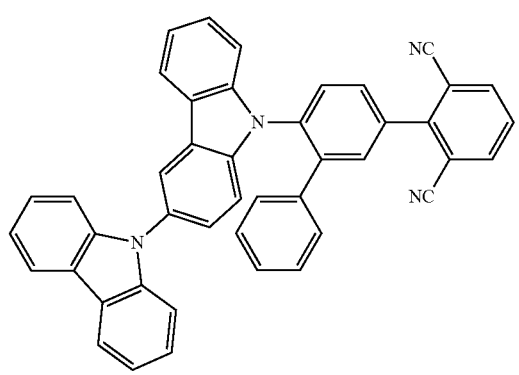
135
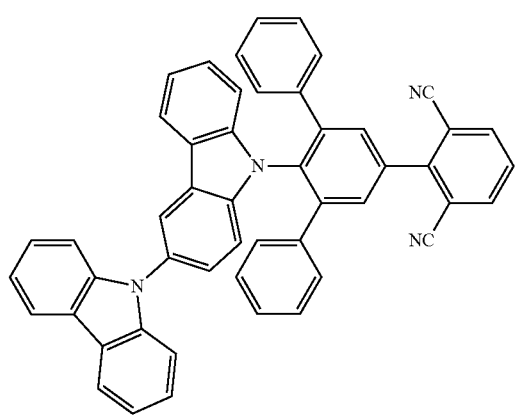
136
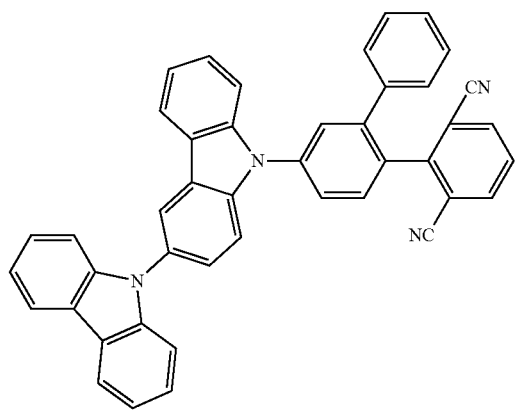

137
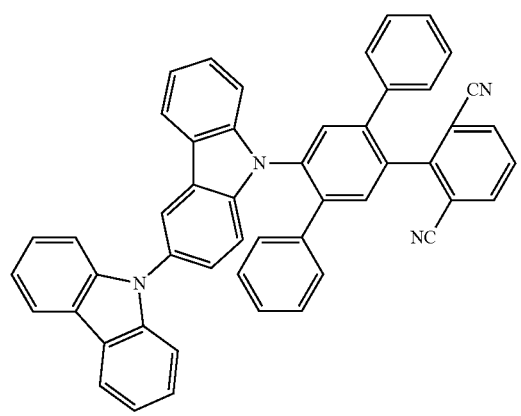
138
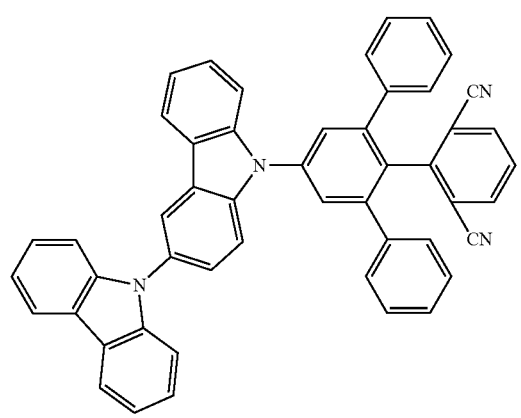
140
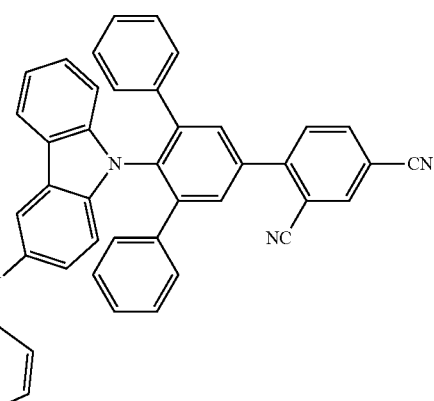
141
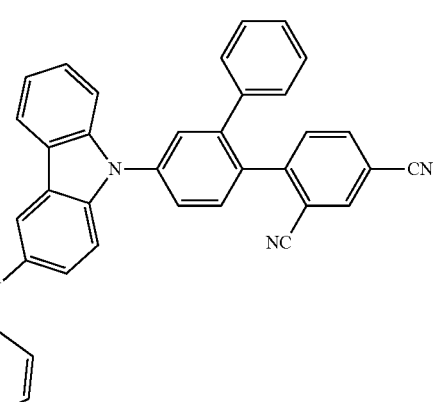
142
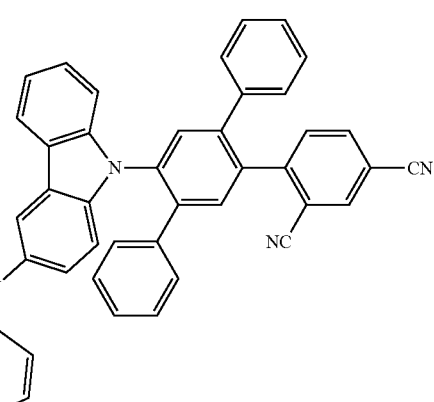

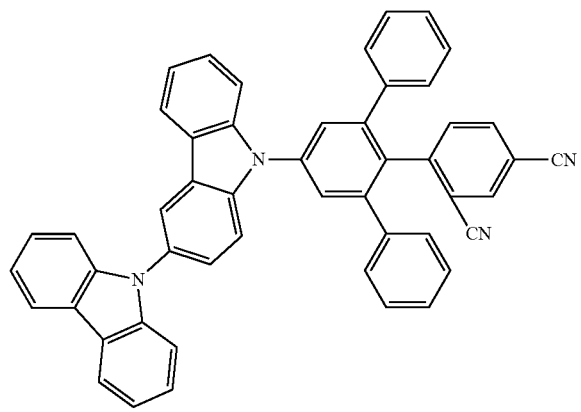
143
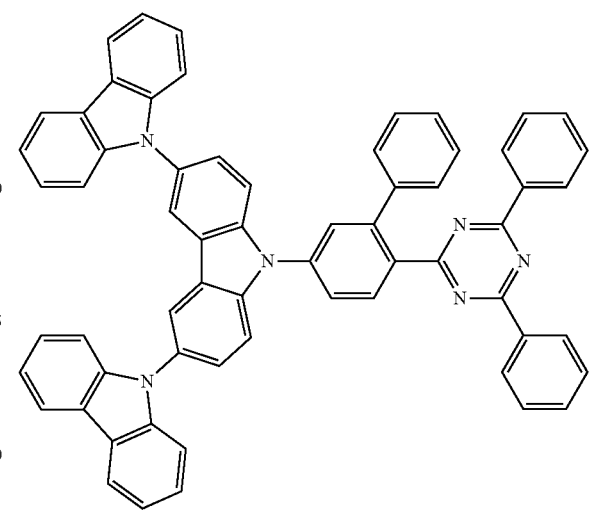
146
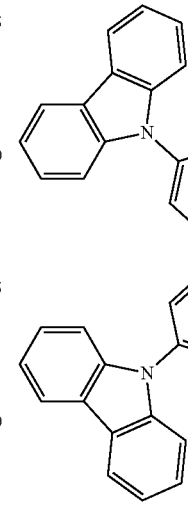
144
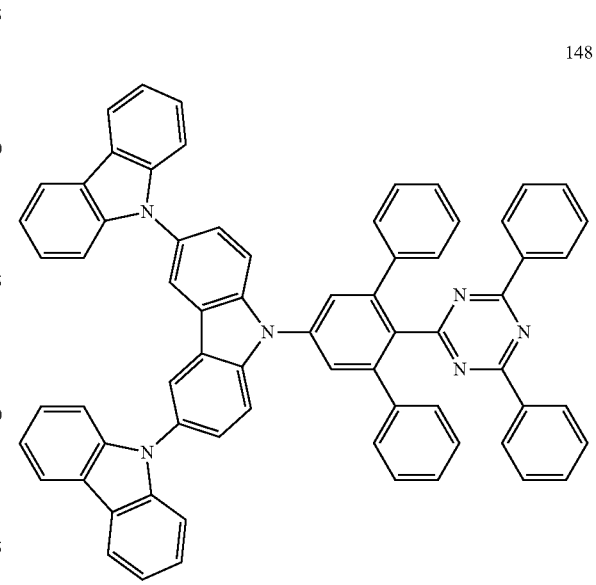
147
145
148

149
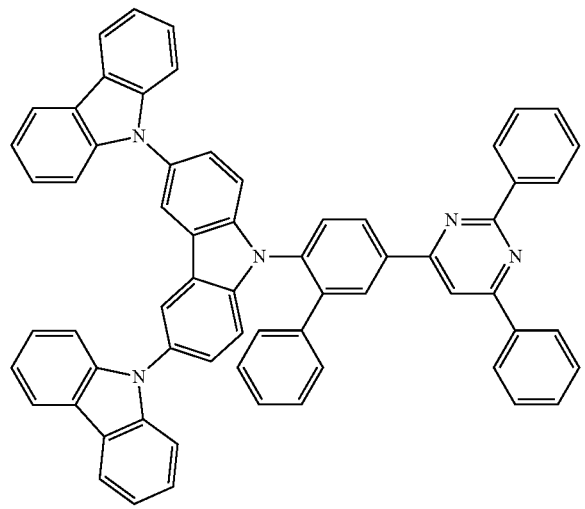
150
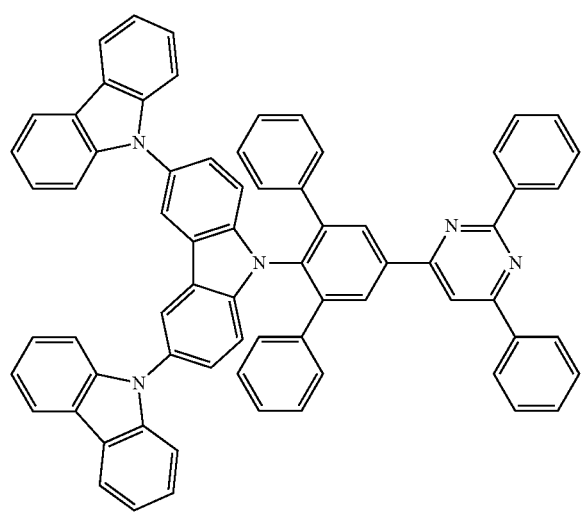
151
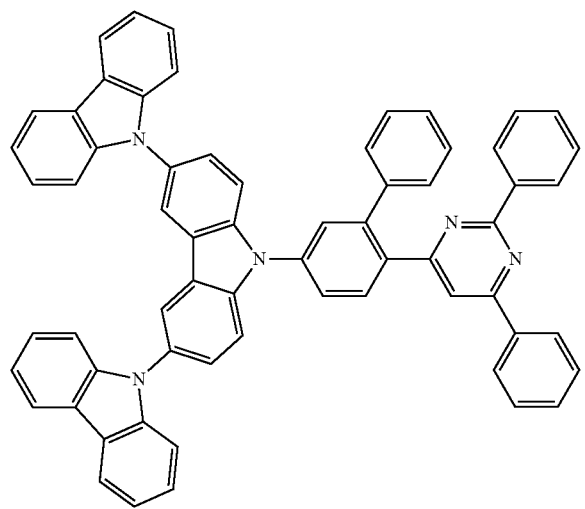
152
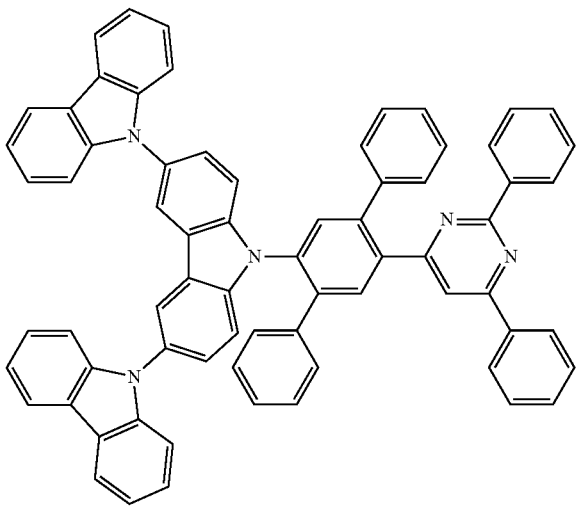
153
154
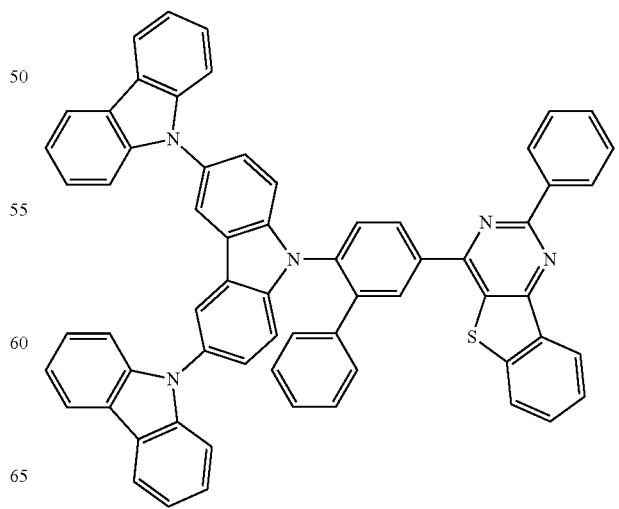

155
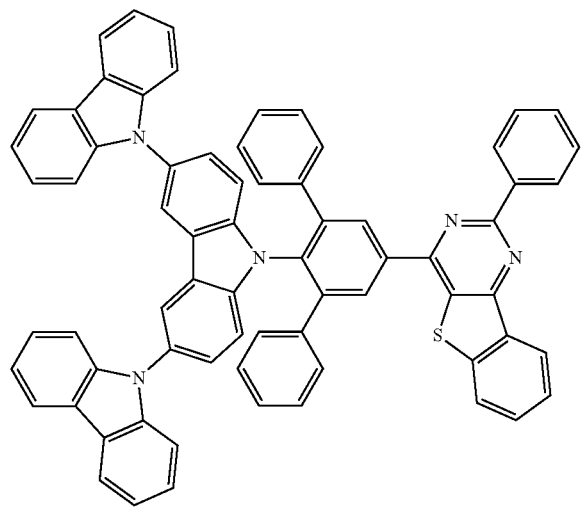
156
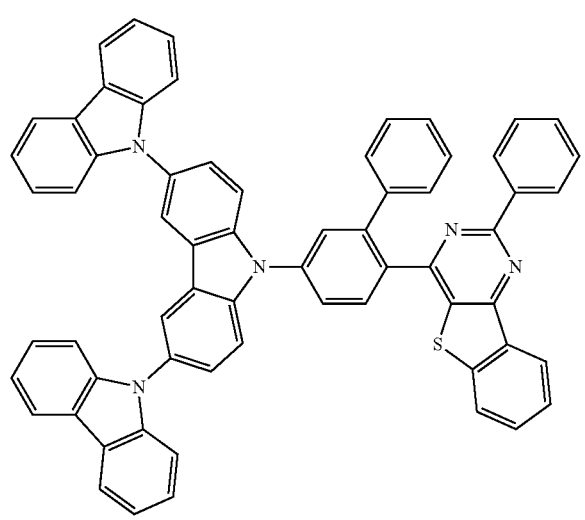
157
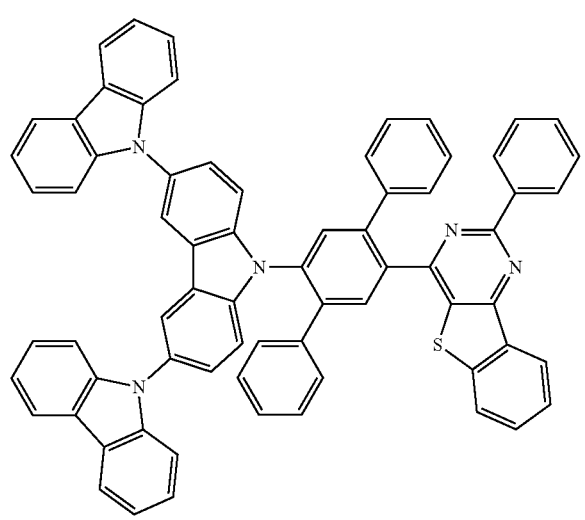
158
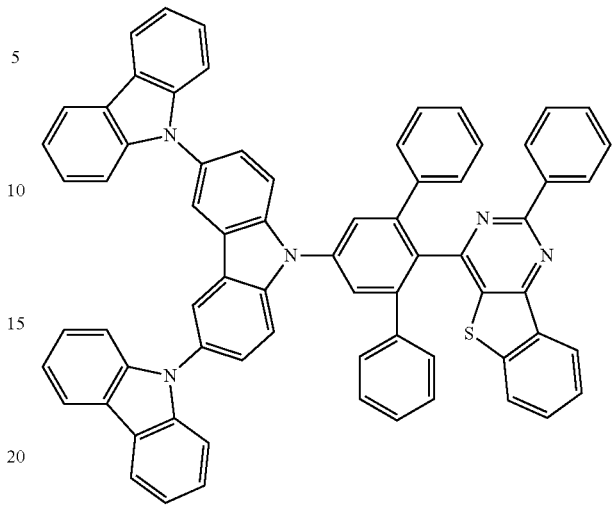
159
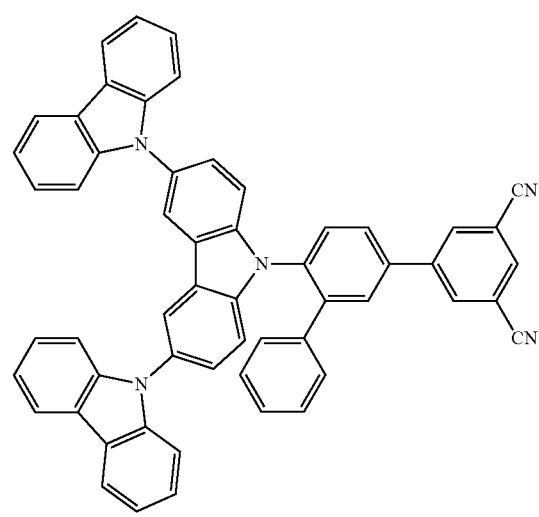
160
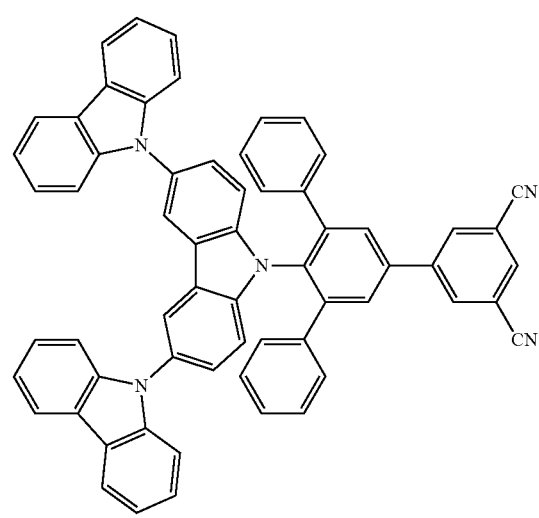

161
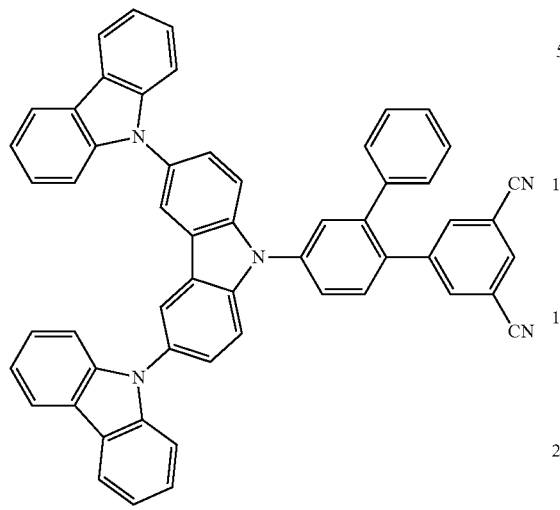
162
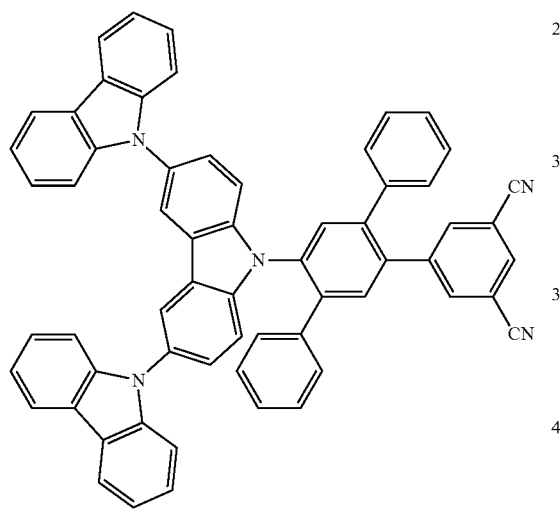
163
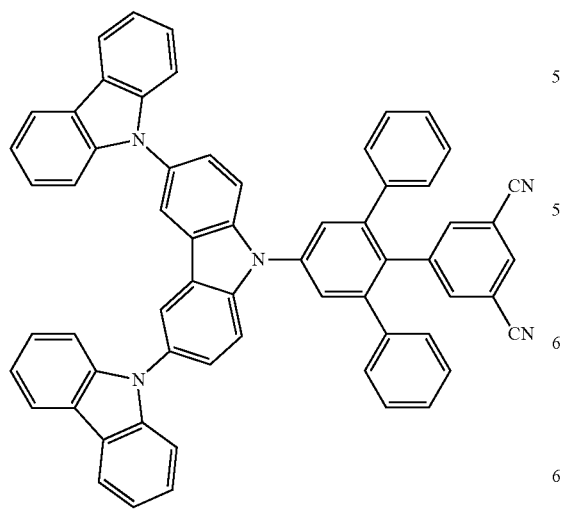
164

165
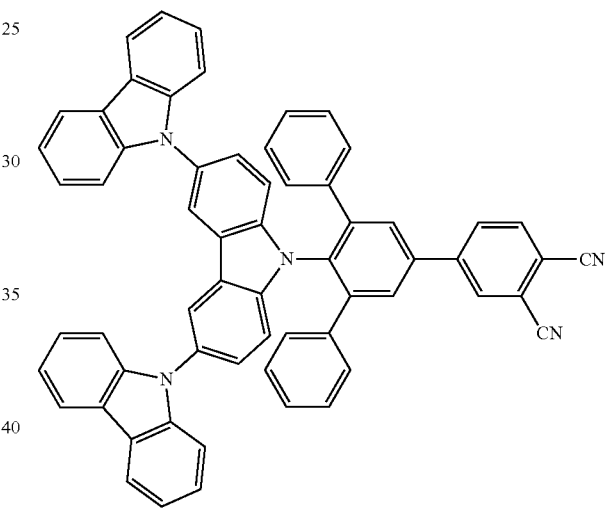
166
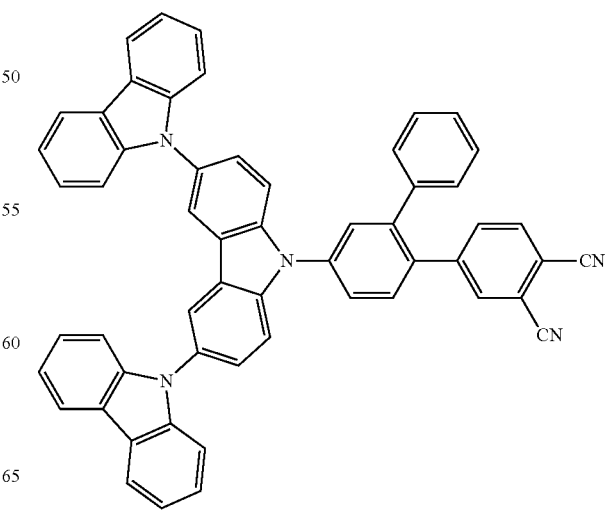

167
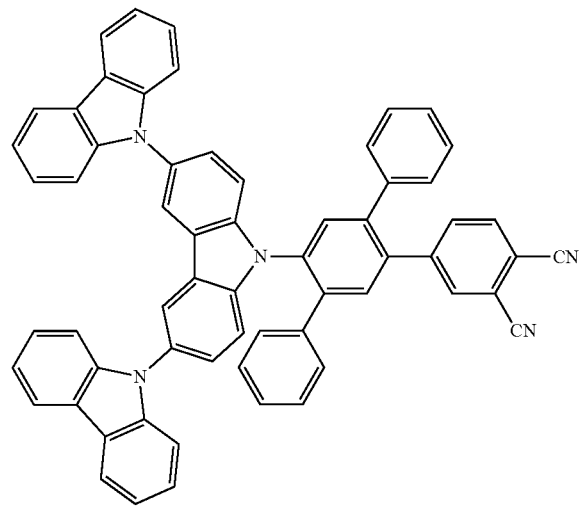
168
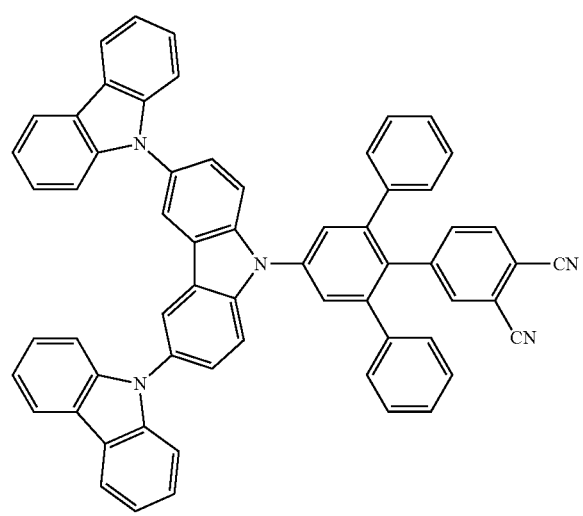
169
170
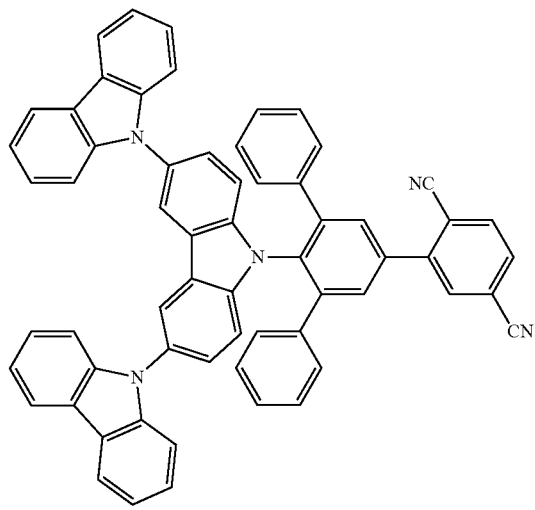
171
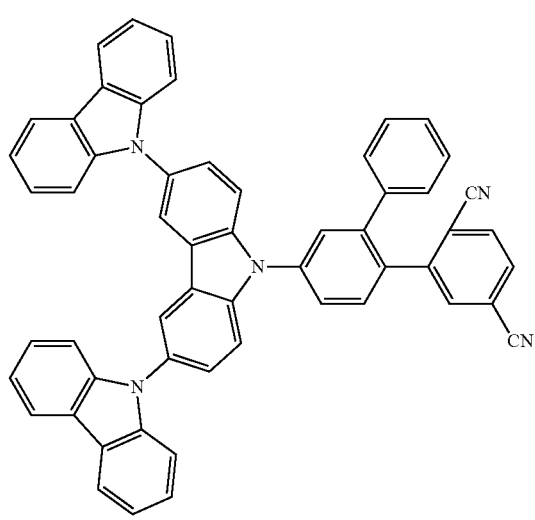
172
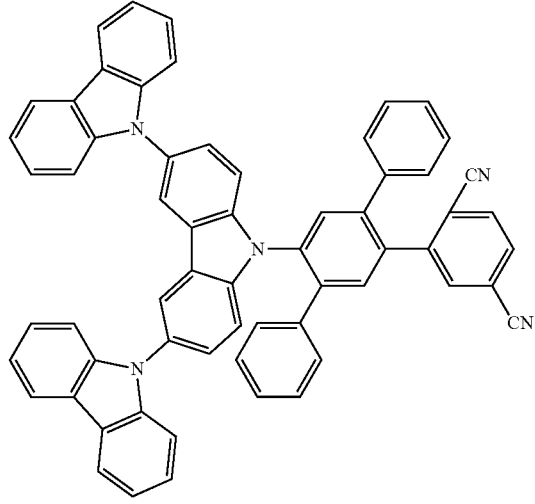

173
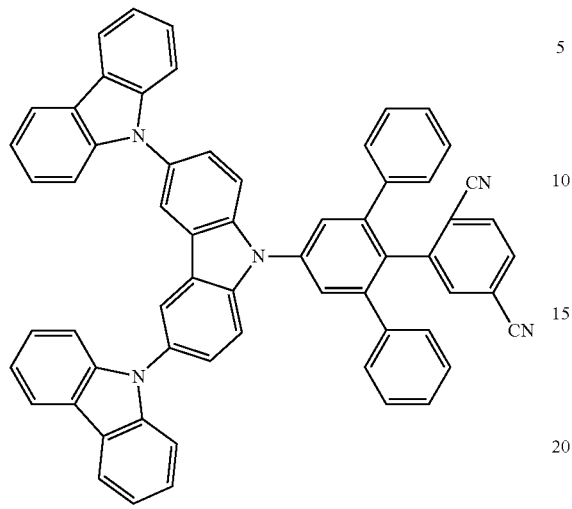
174
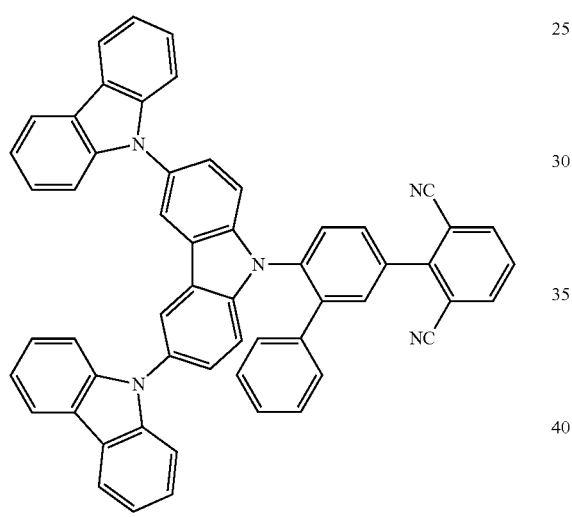
175
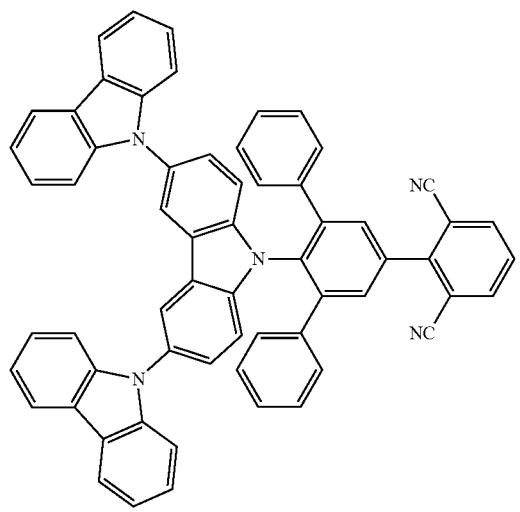
176
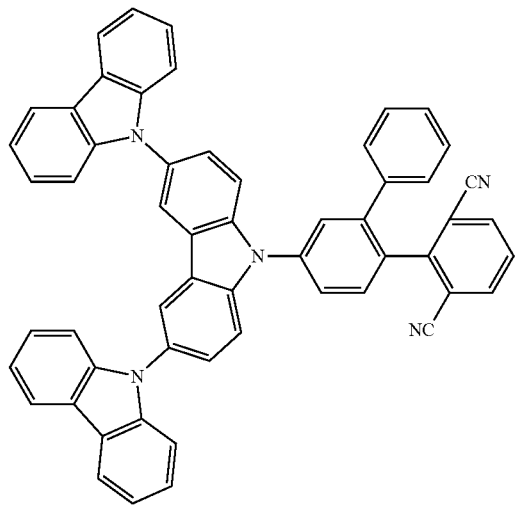
177
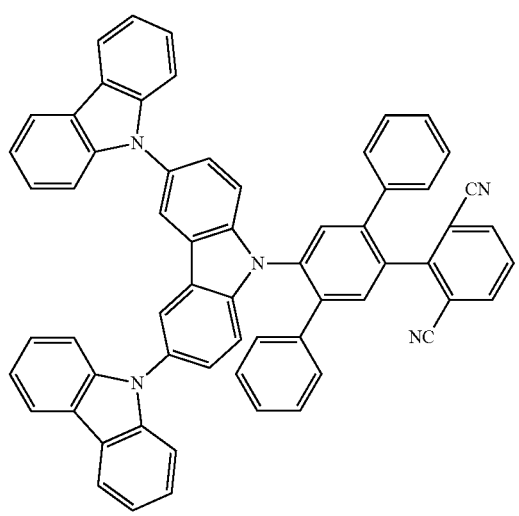
178
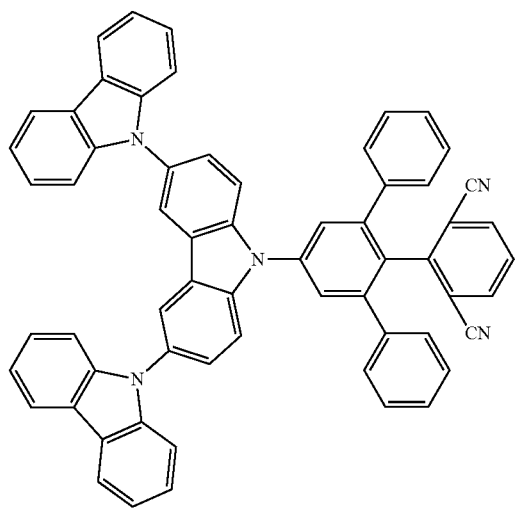

179
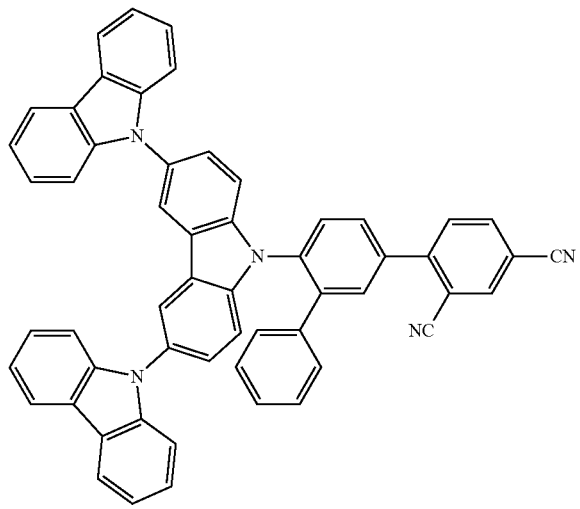
180
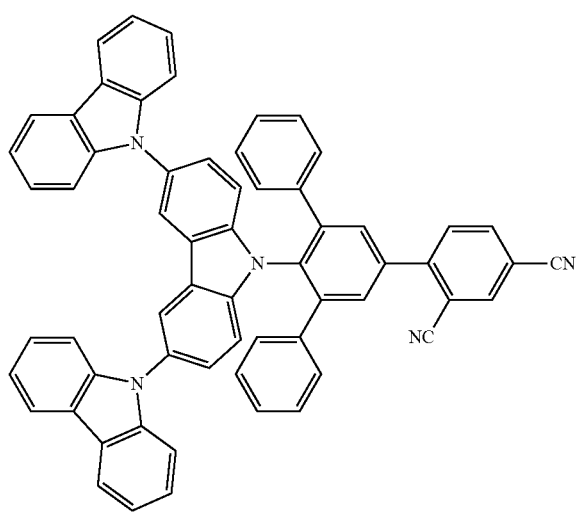
181
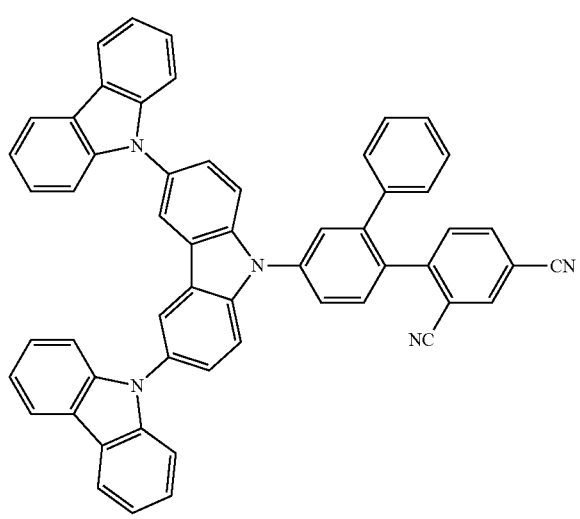
182
183
184
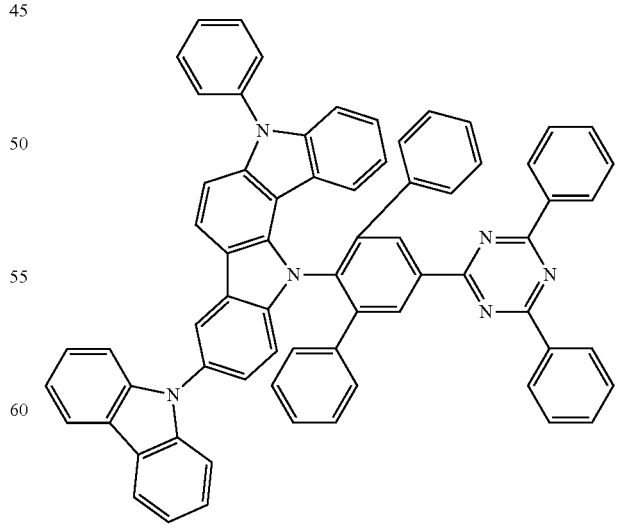

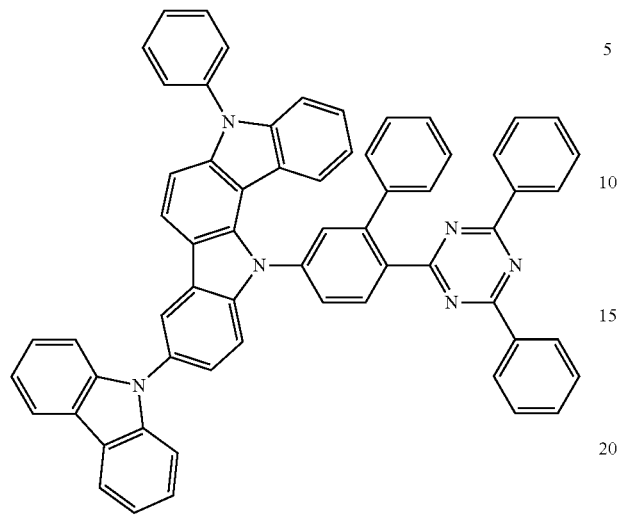
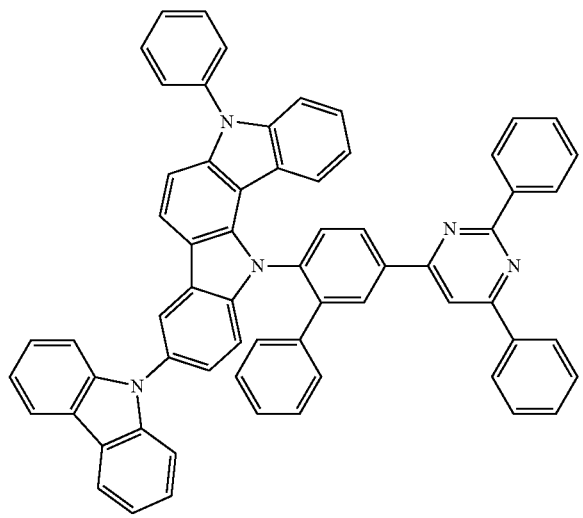

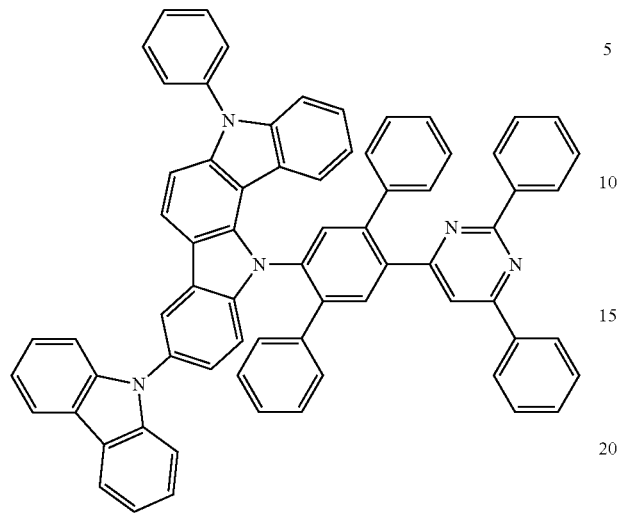
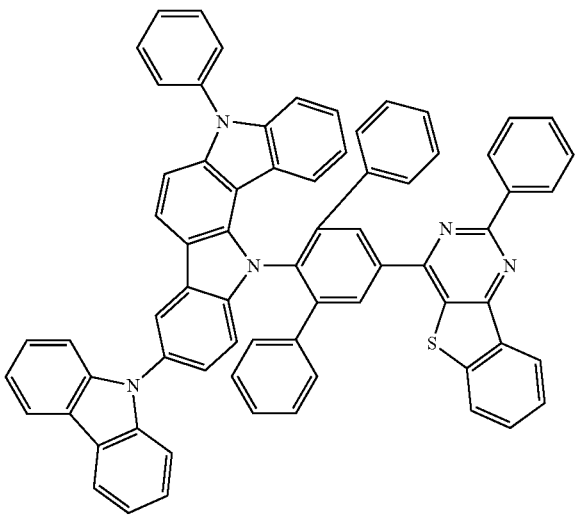

197
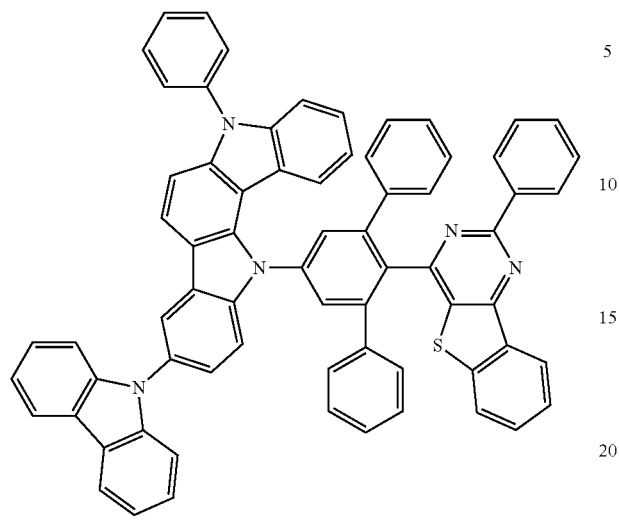
198
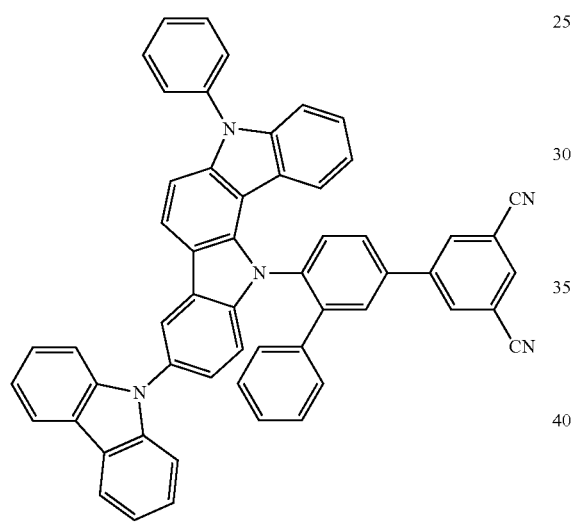
200
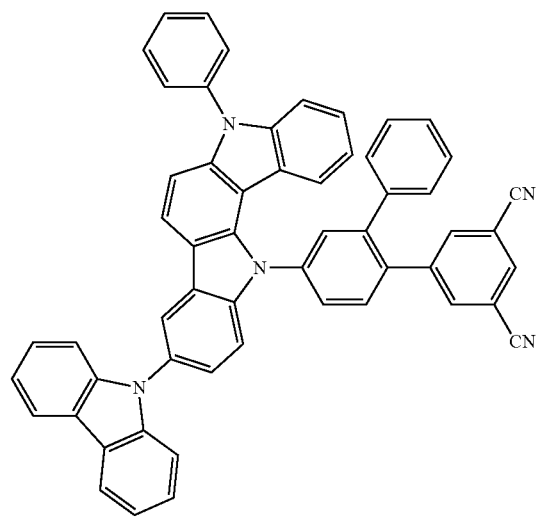
201
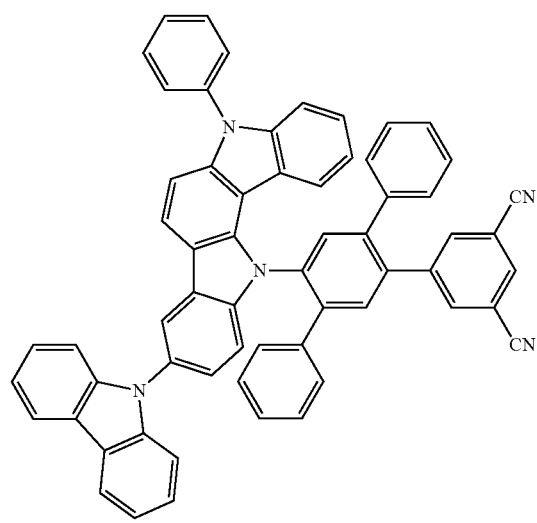
199
202
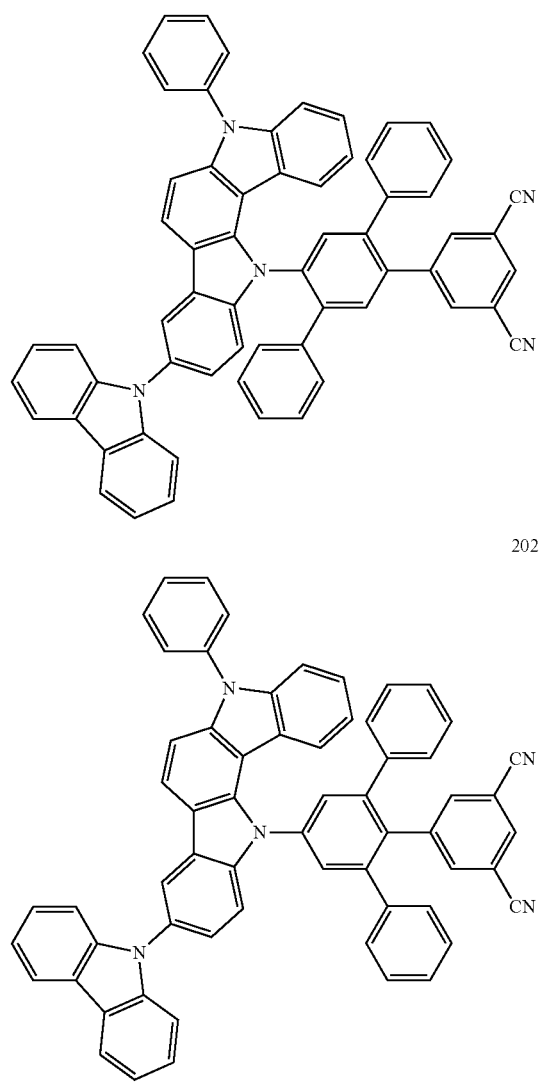

203
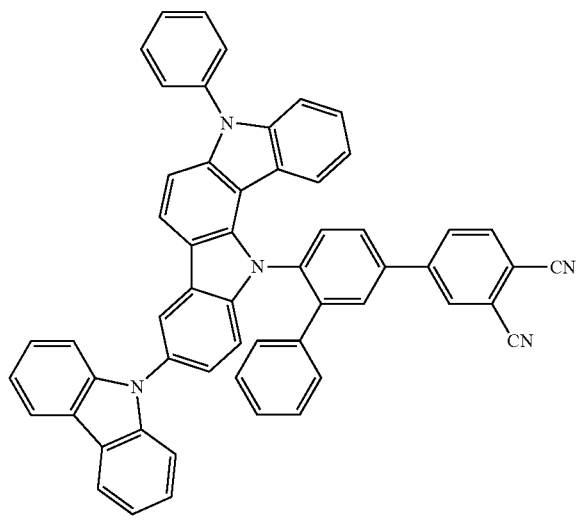
204
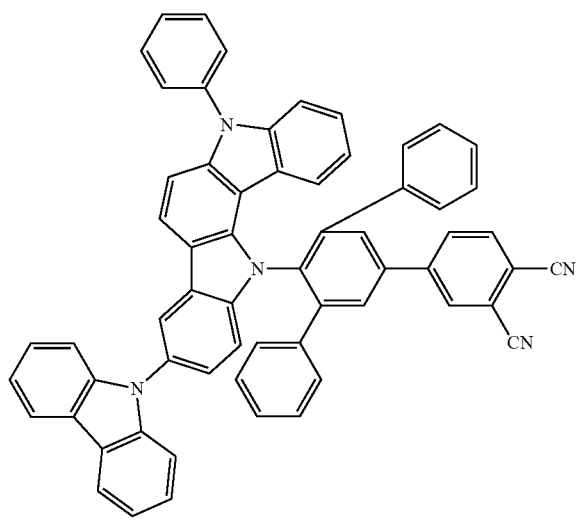
205
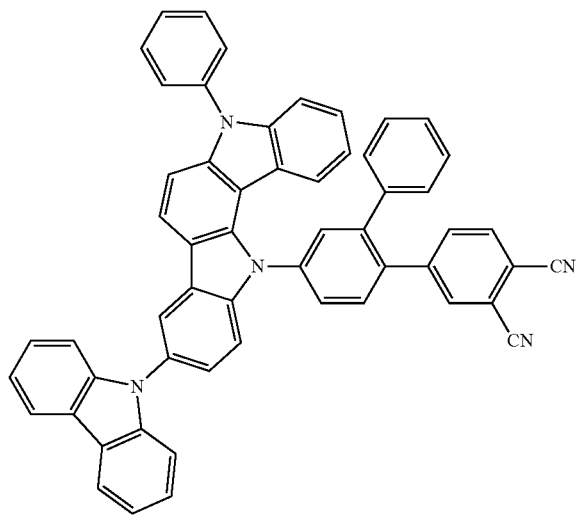
206
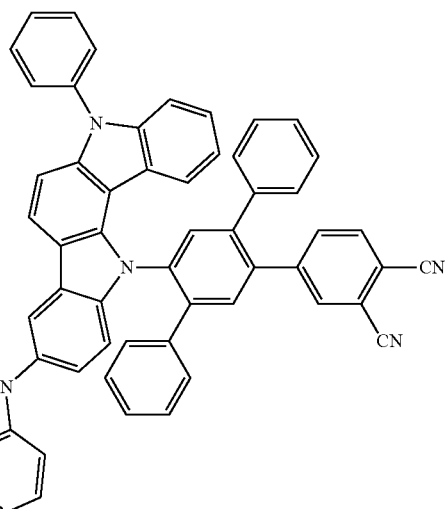
207
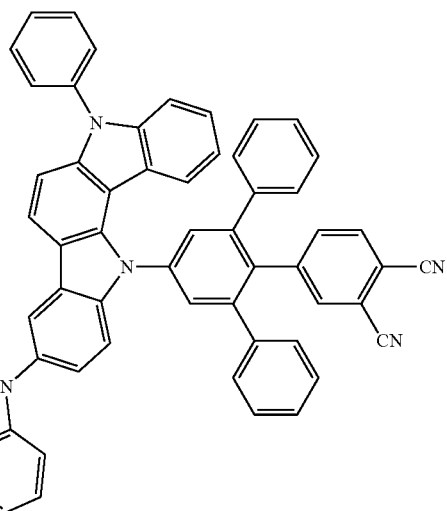
208
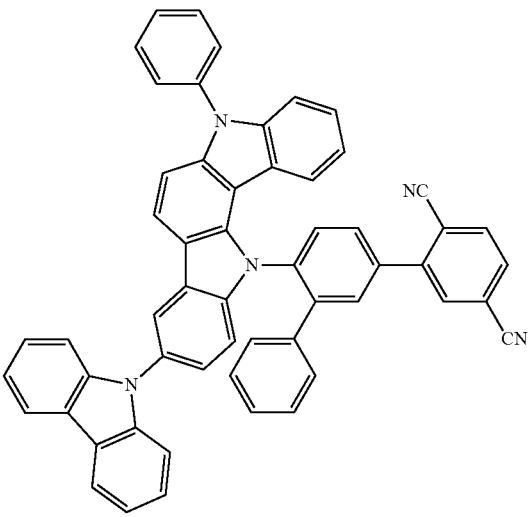

209
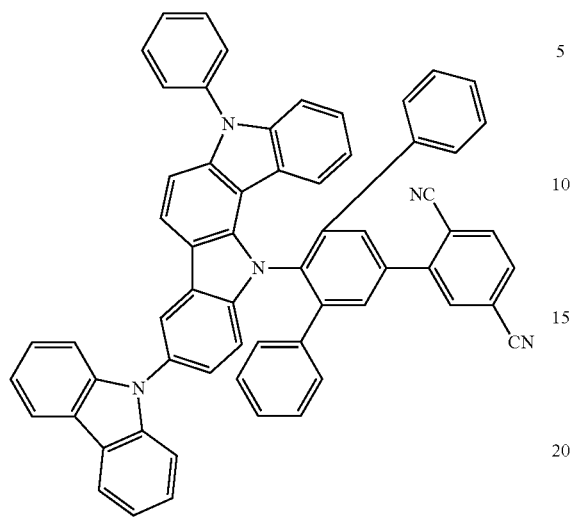
210
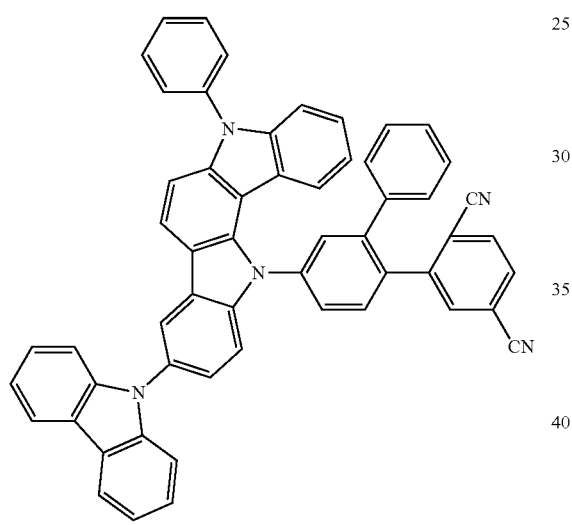
211
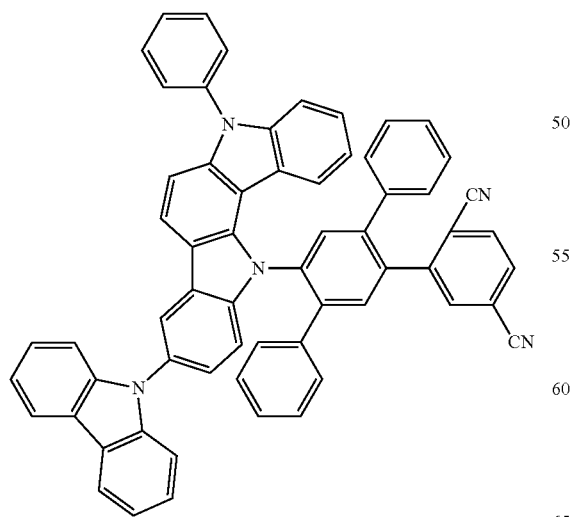
212
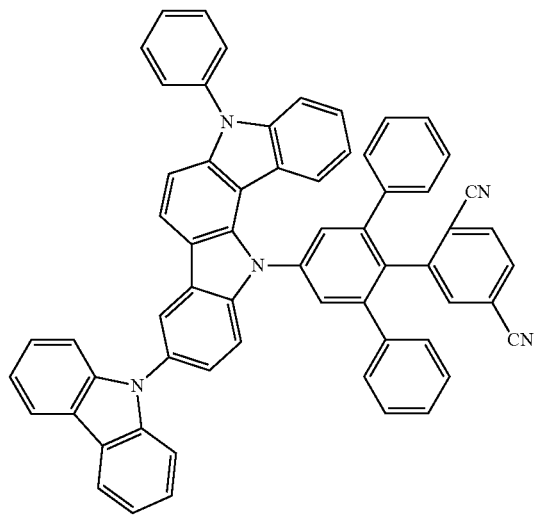
213
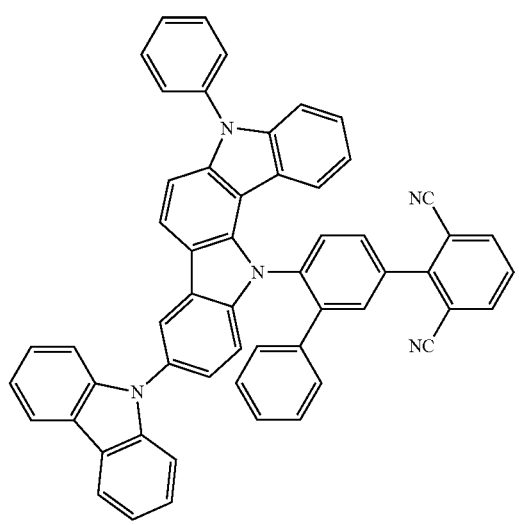
214
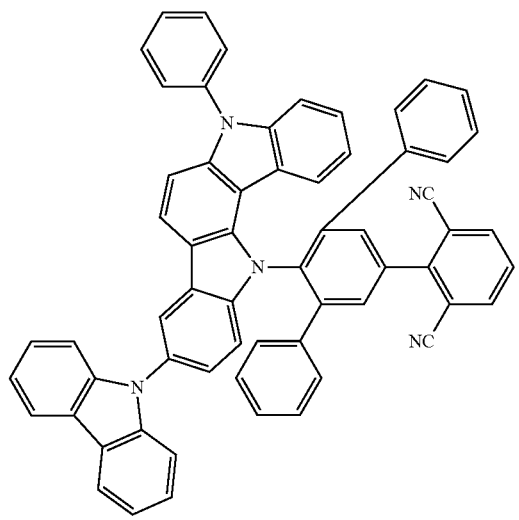

215
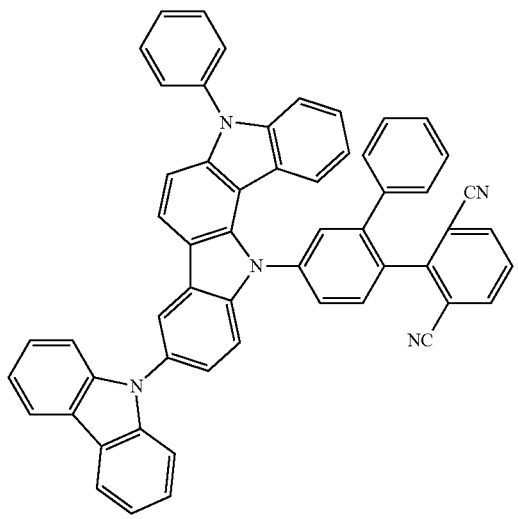
216
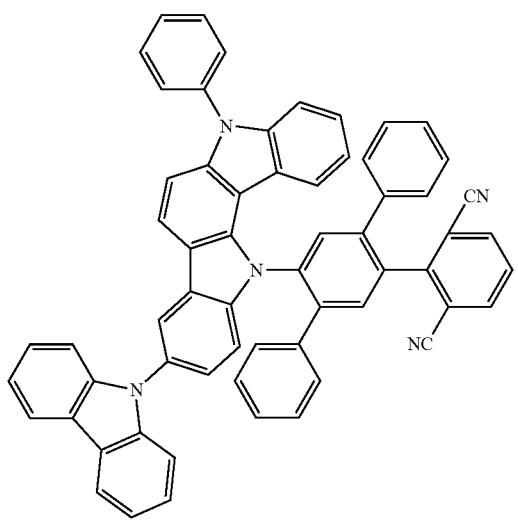
217
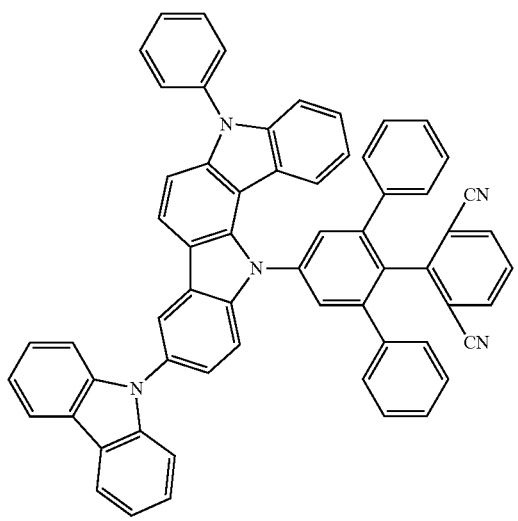
218
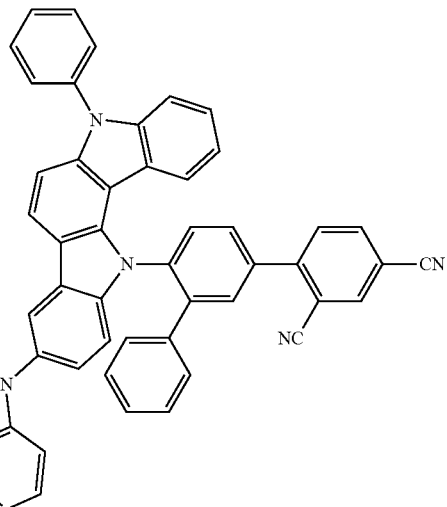
219
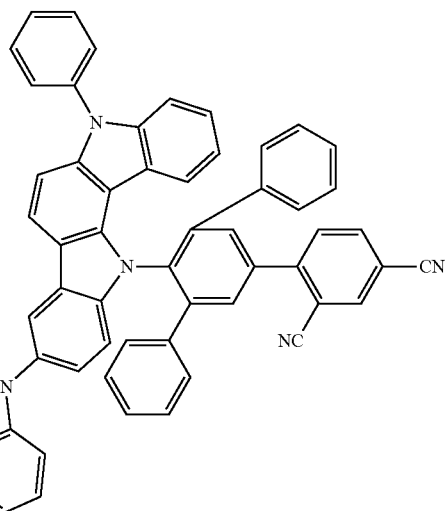
220
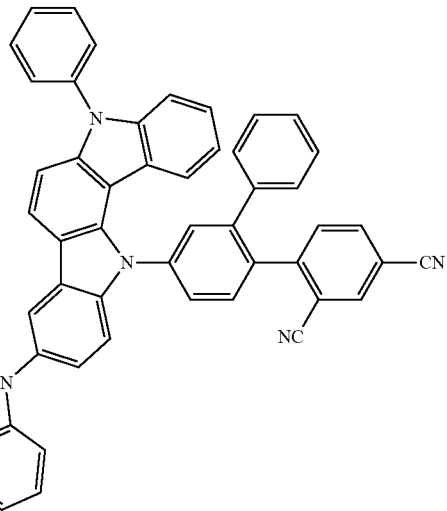

221
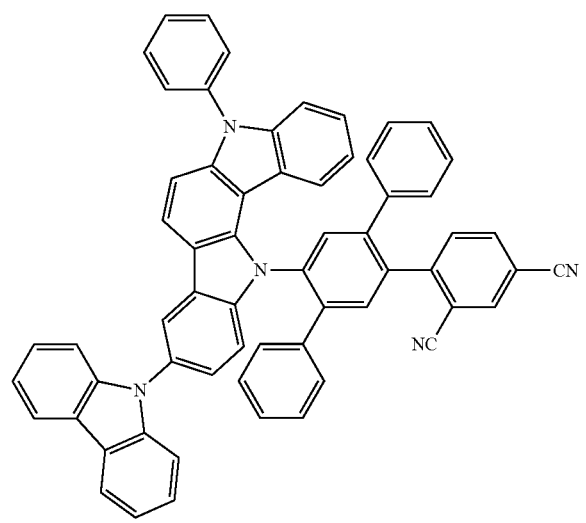
222
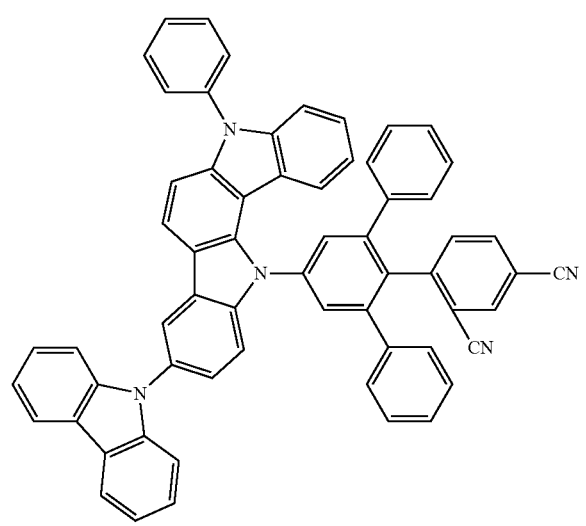
223
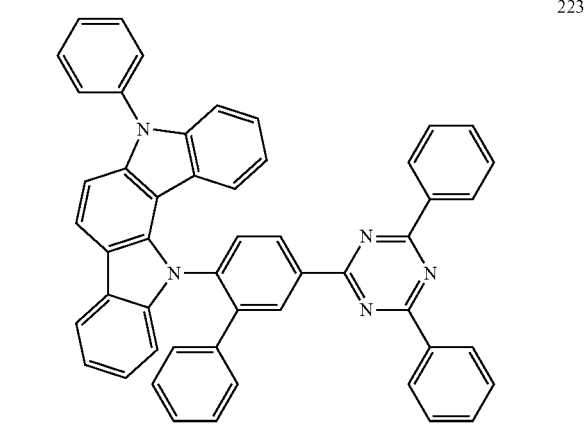
224
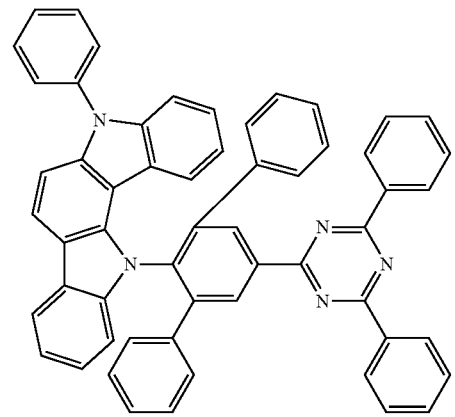
225
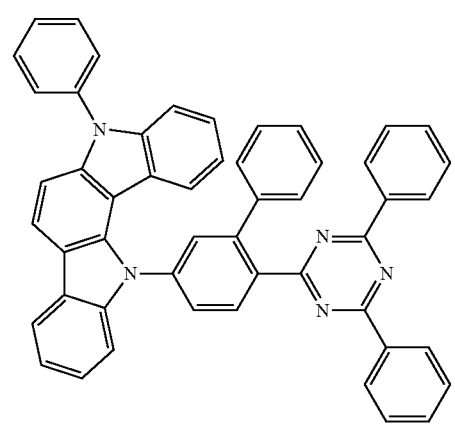
226
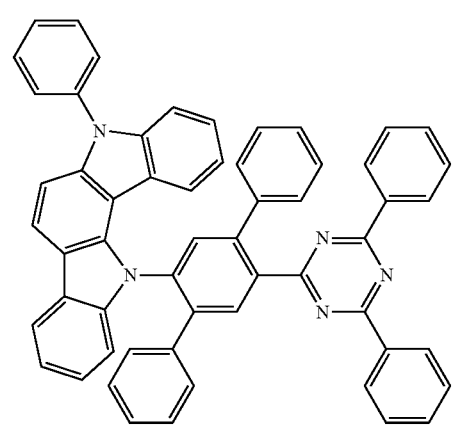
227
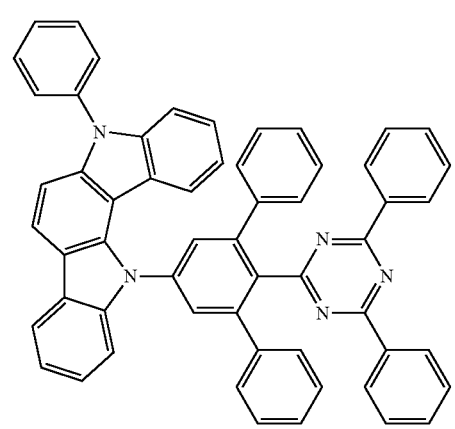

228
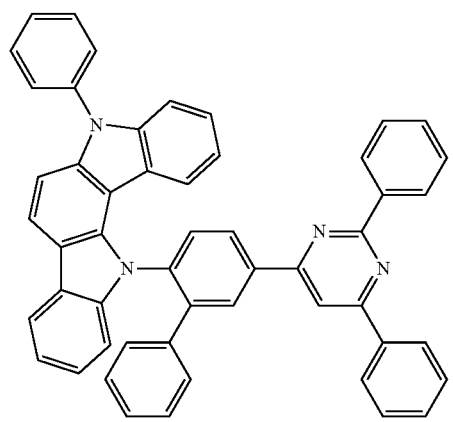
229
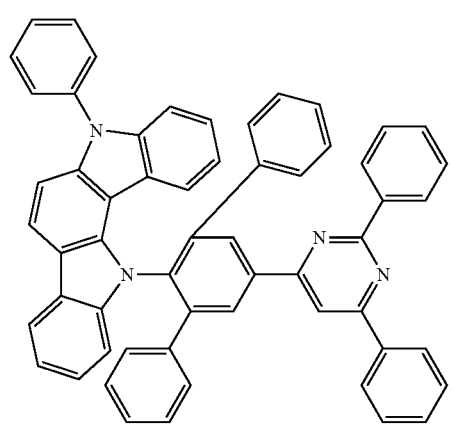
230
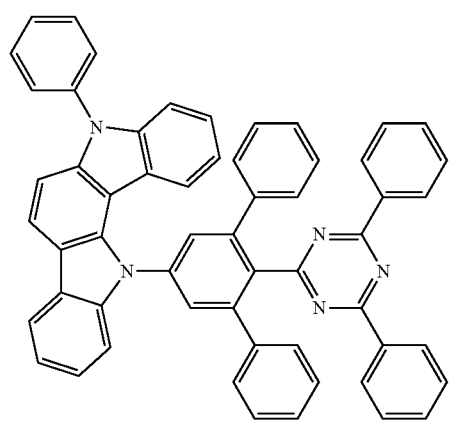
231
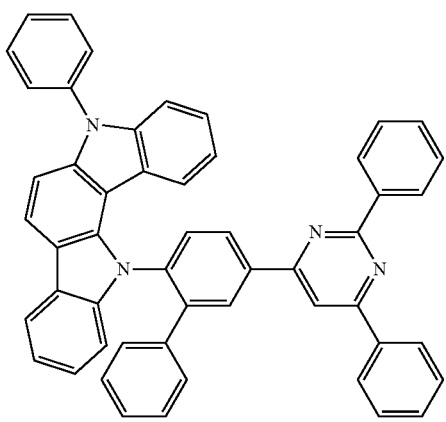
232
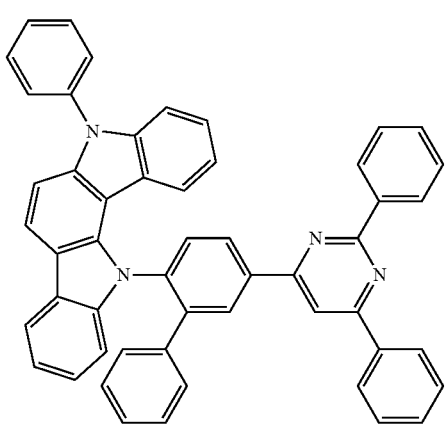
233
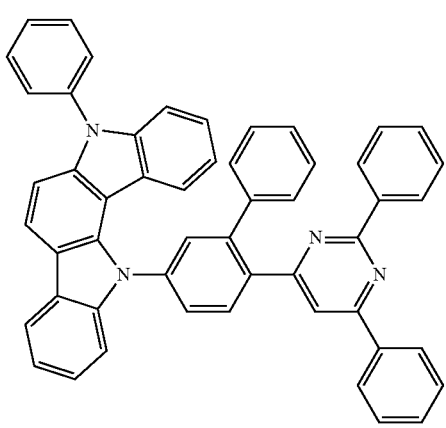

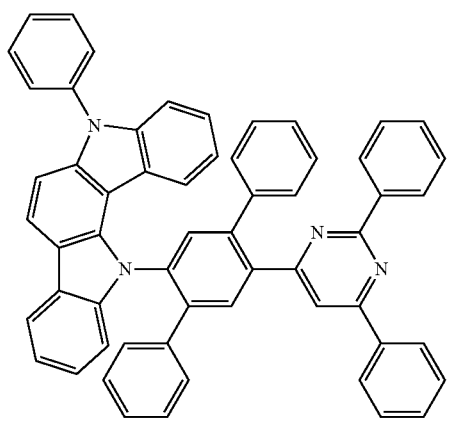
234
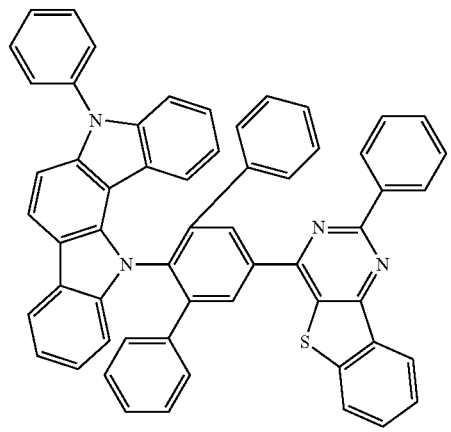
237
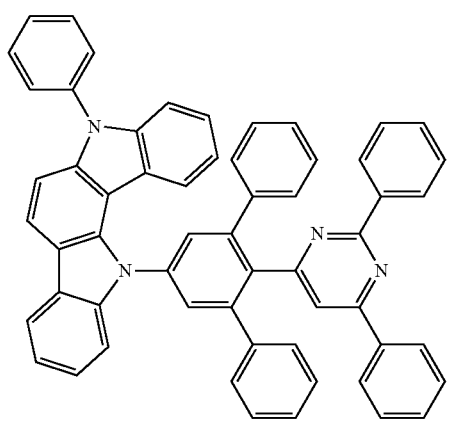
235
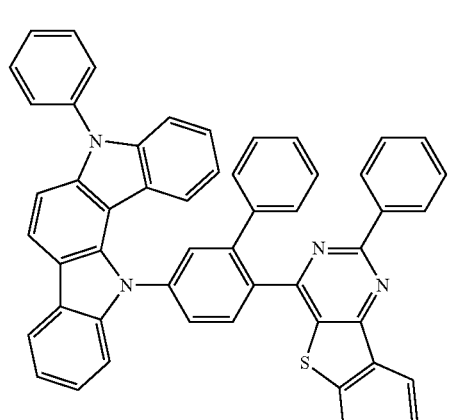
238
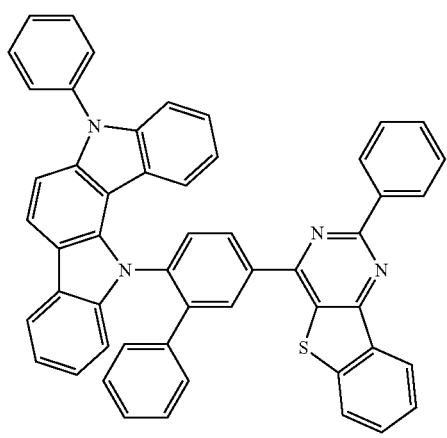
236
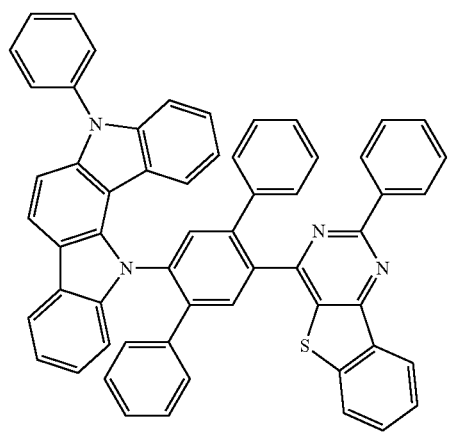
239

240
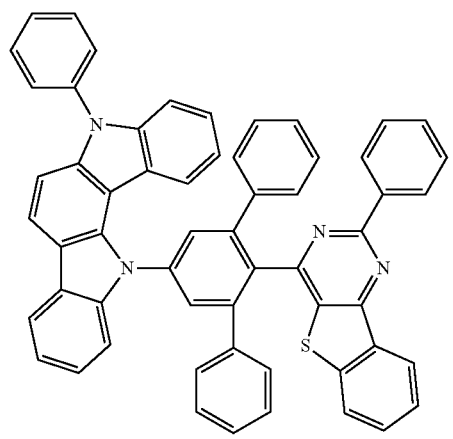
241
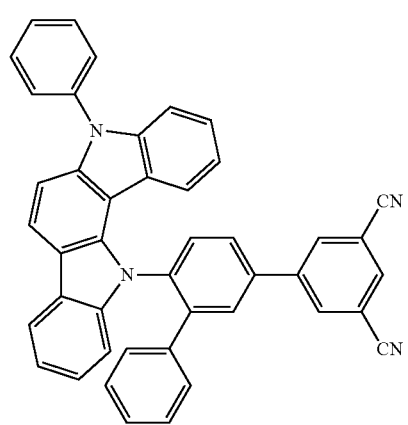
242
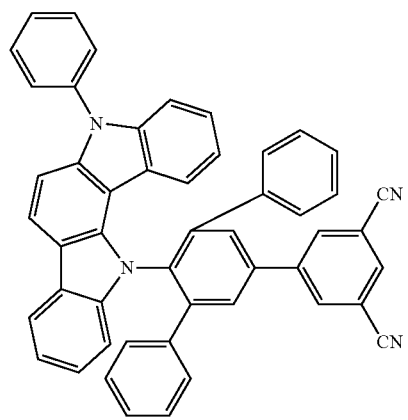
243
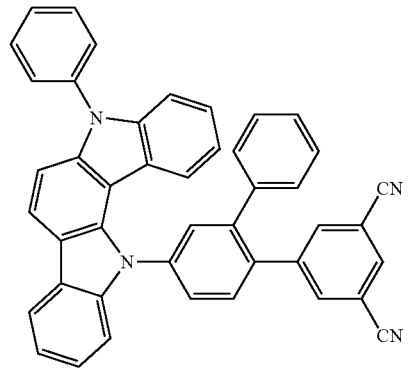
244
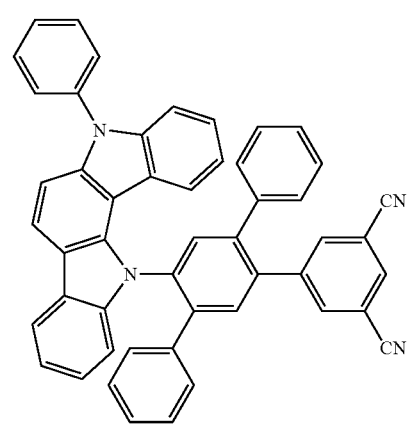
245
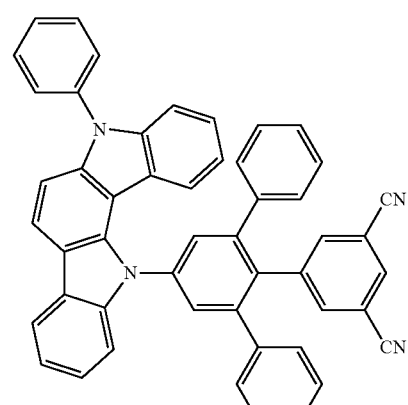
246
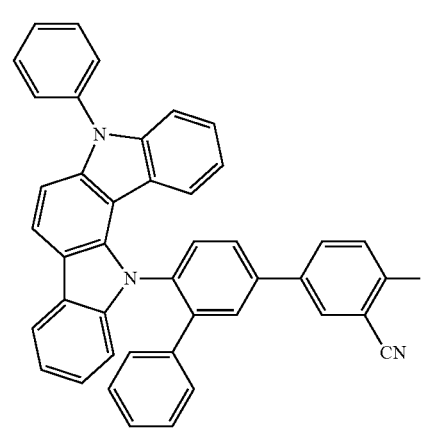

247
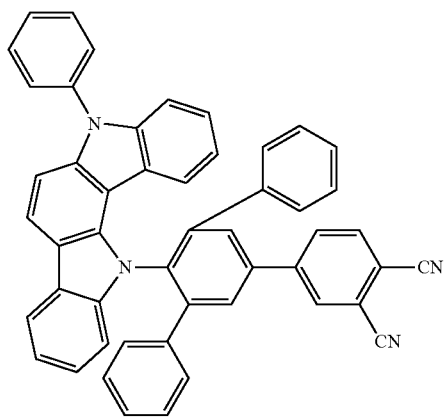
248
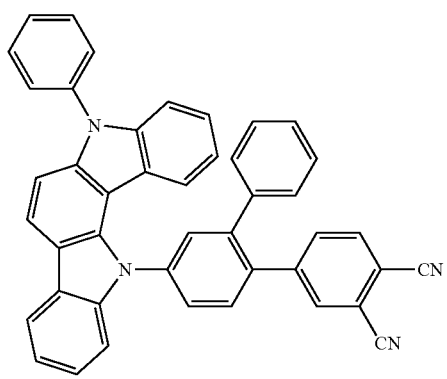
249
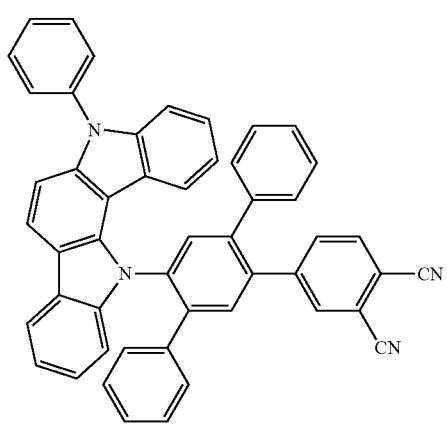
250
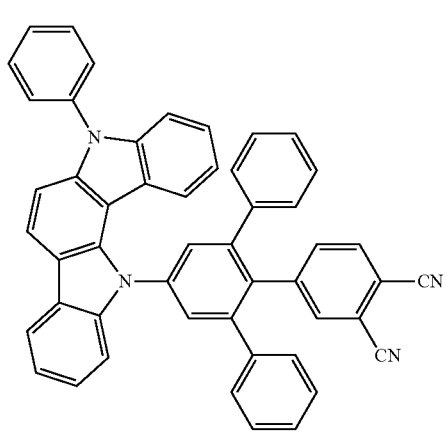
251
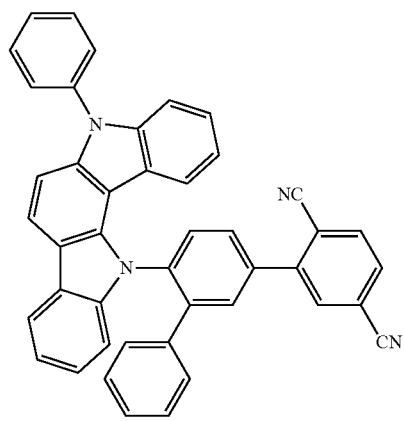
252
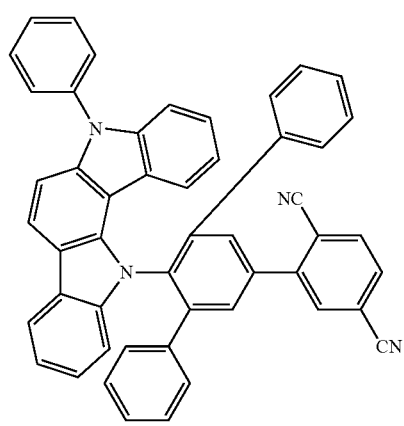
253
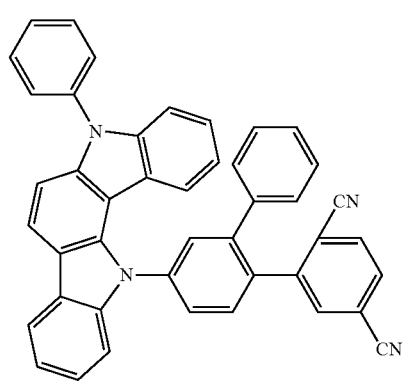
254
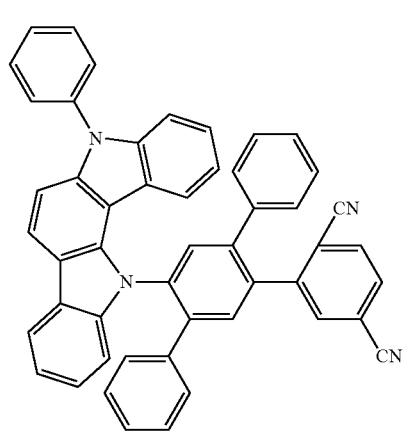

255 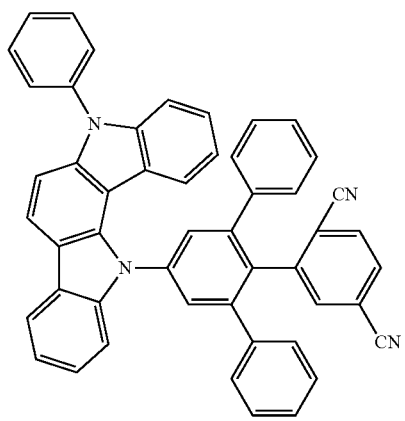
256 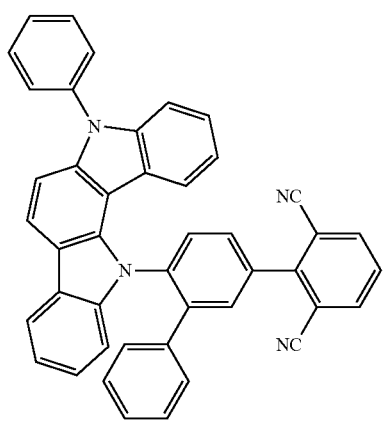
257 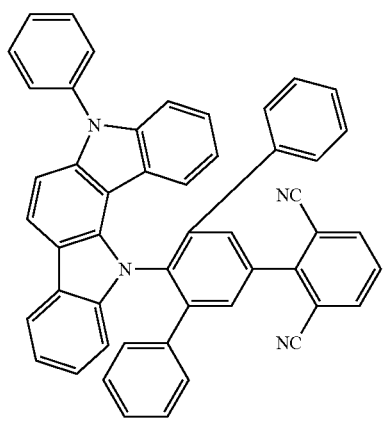
258 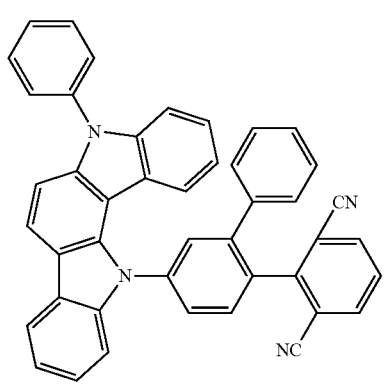
259 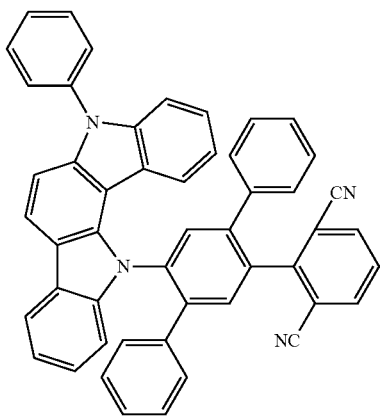
260 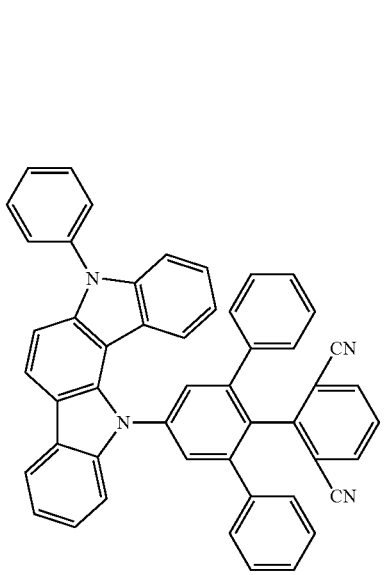
261 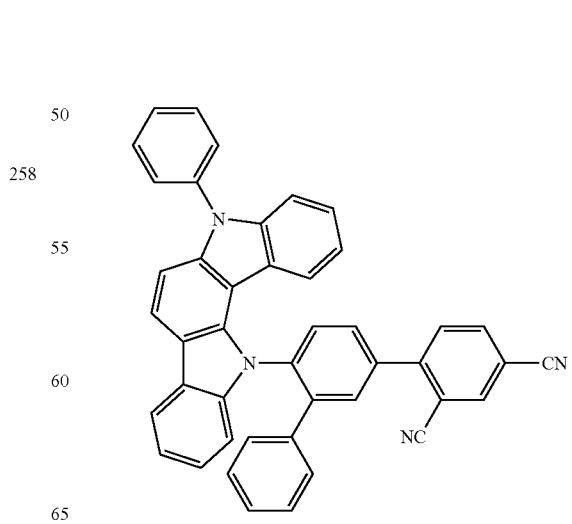

262
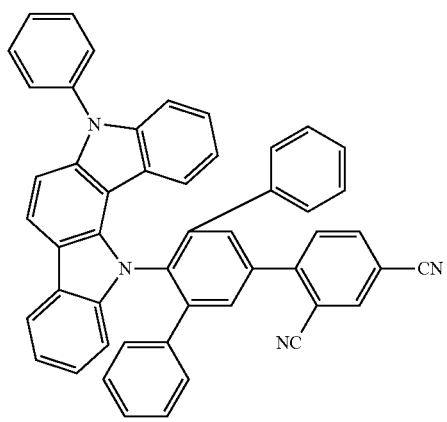
263
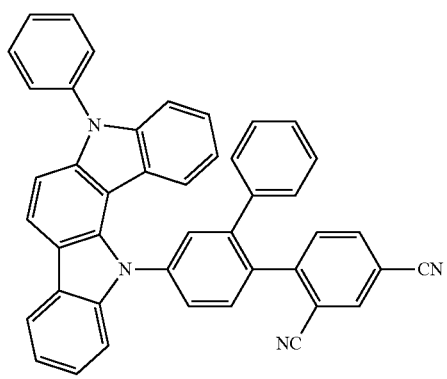
264
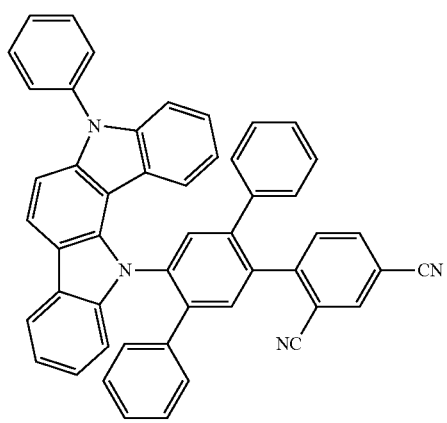
265
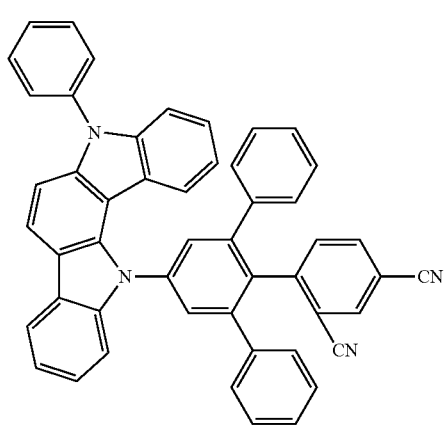
266
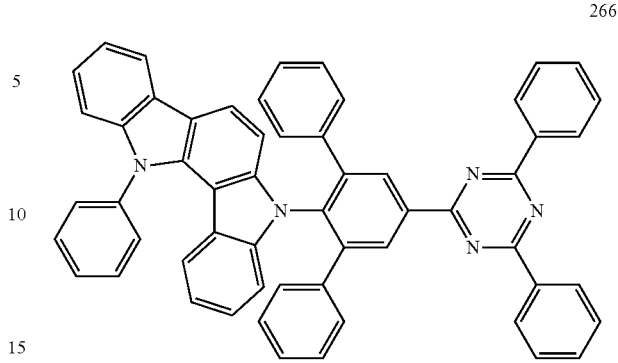
267
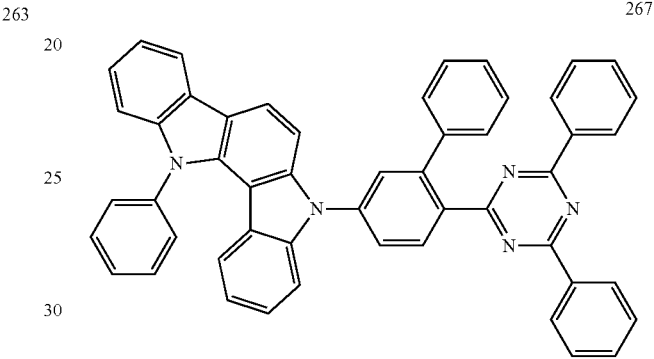
268
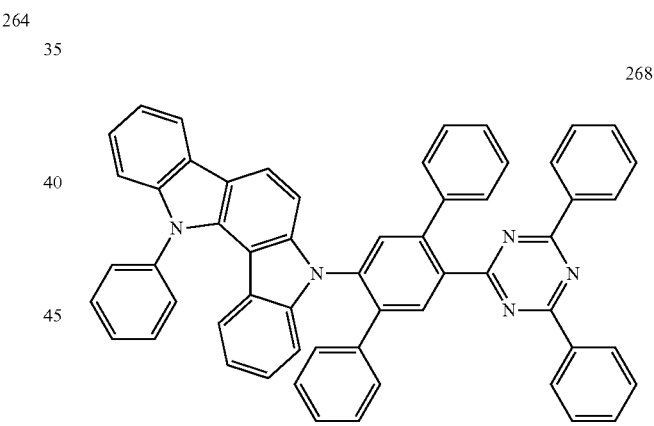
269
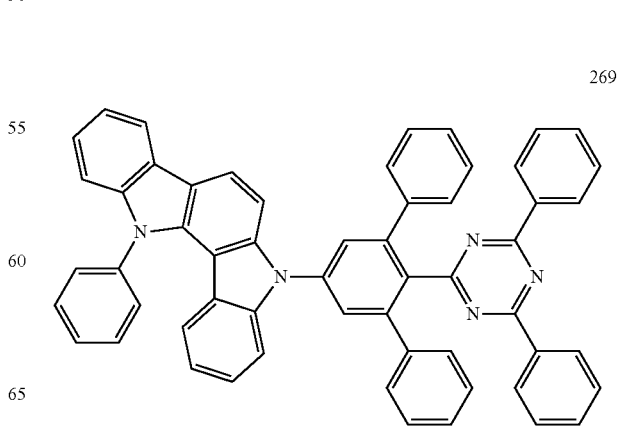

270
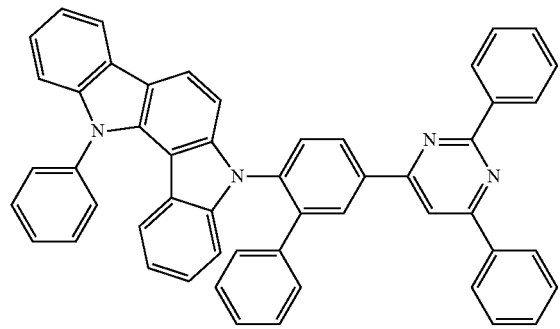
271
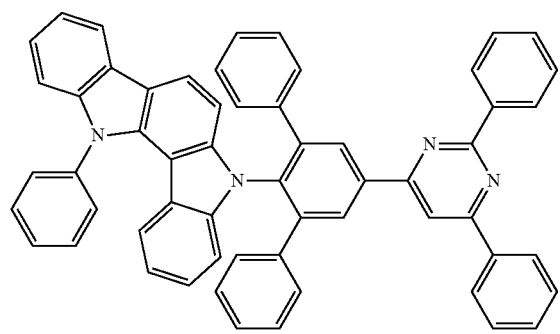
272
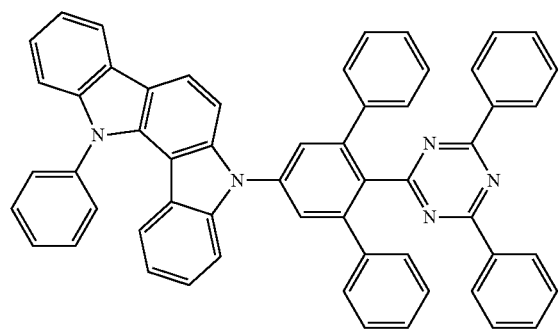
273
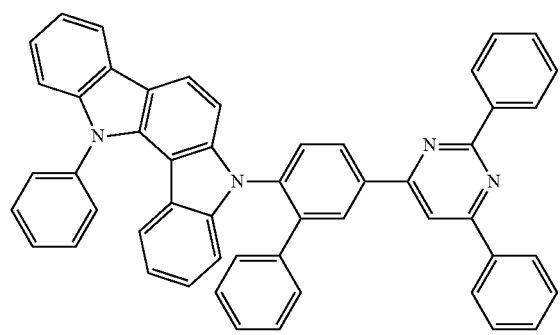
274
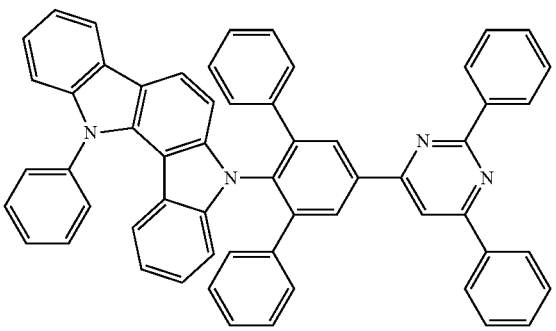
275
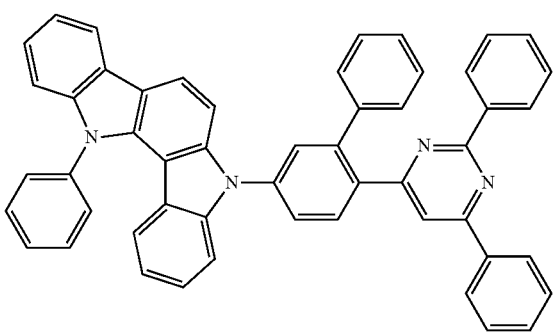
276
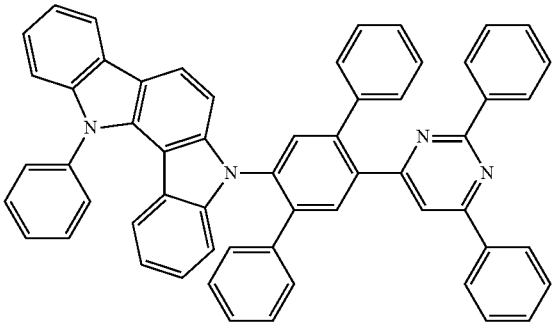
277
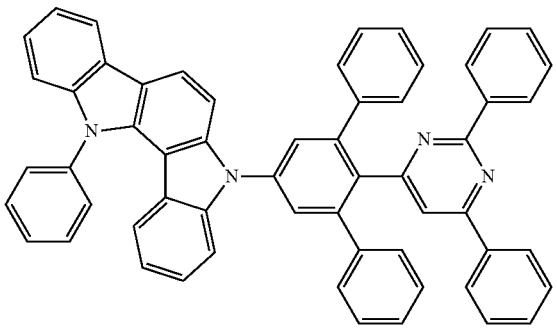

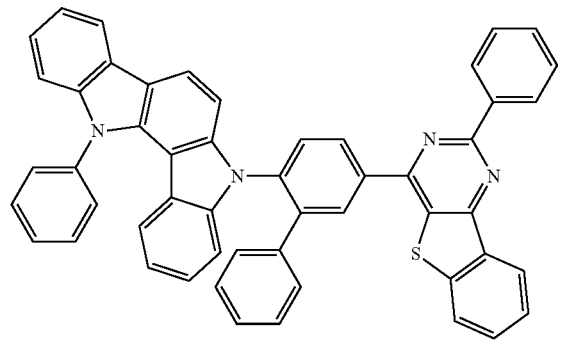
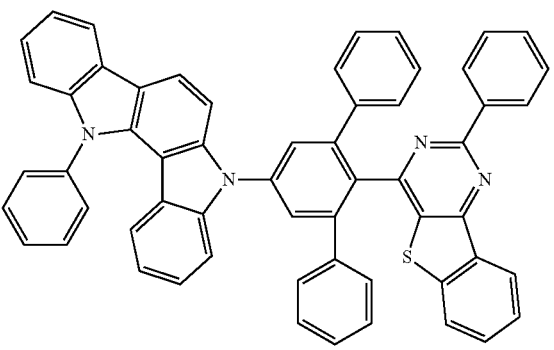
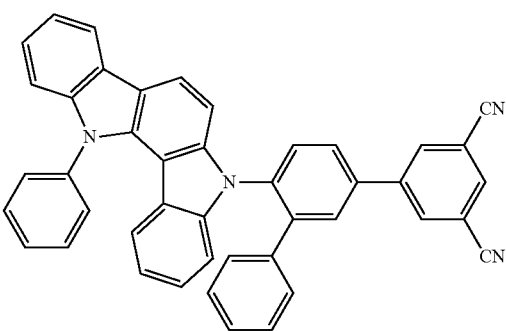
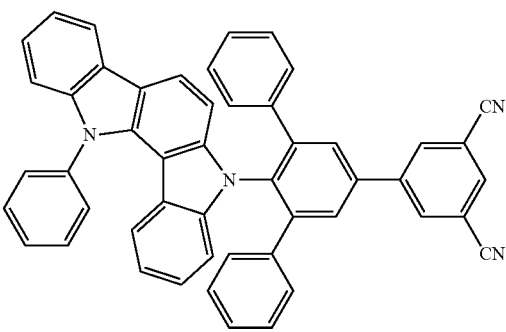
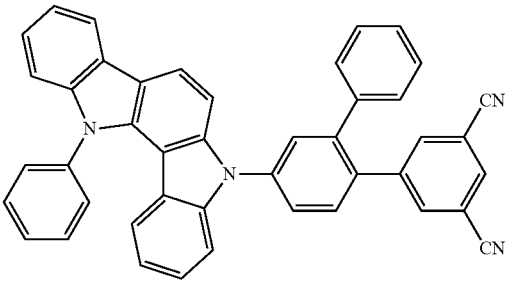

286
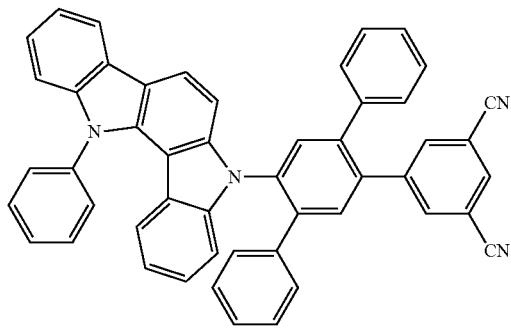
287
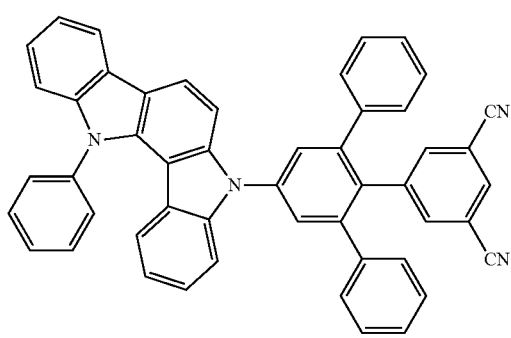
288
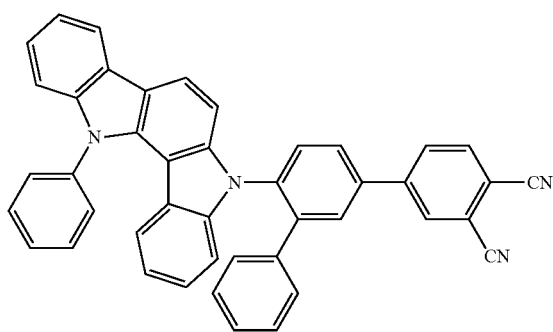
289
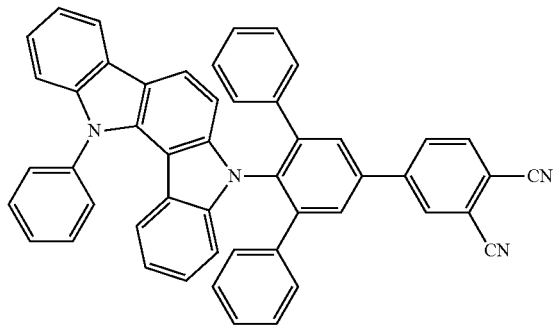
290
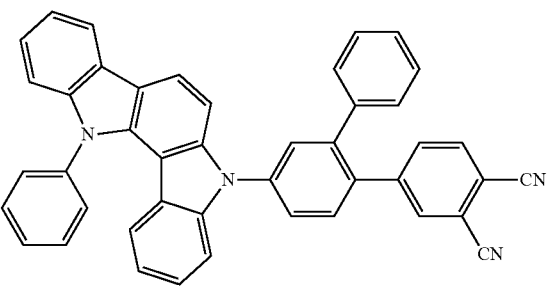
291
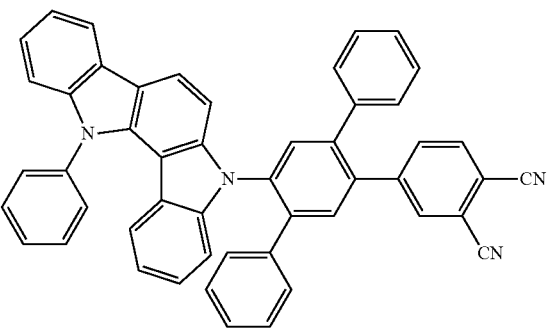
292
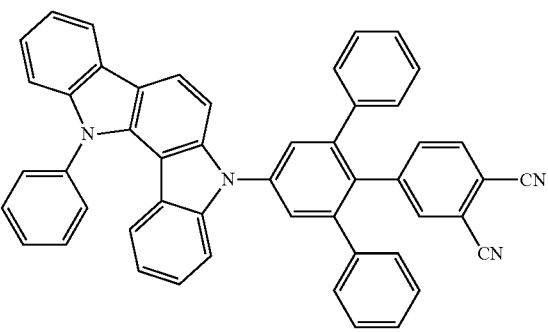
293
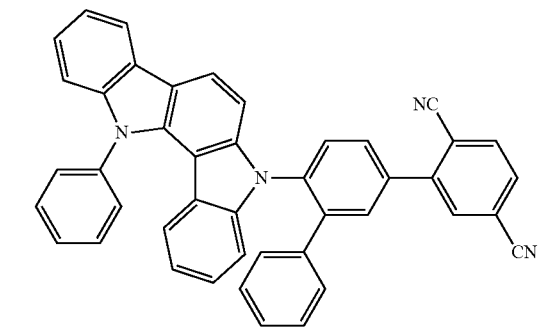

-continued
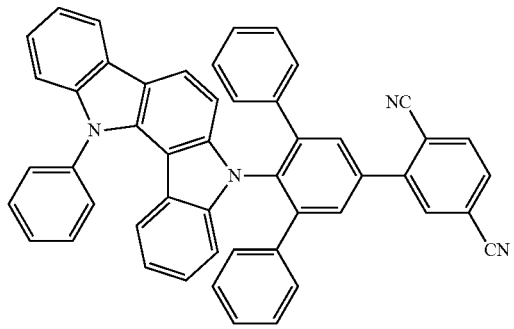
294
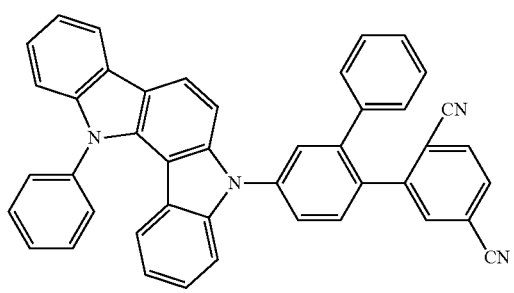
295
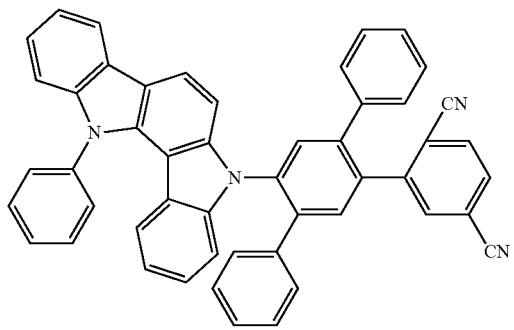
296
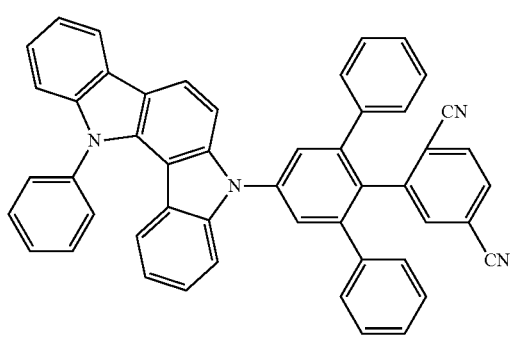
297
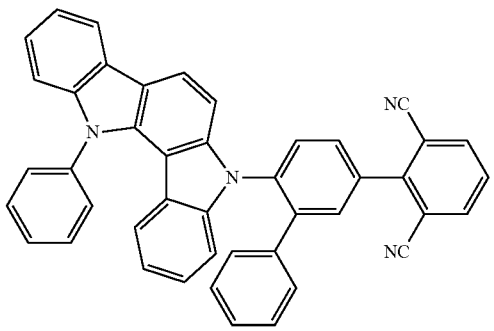
298
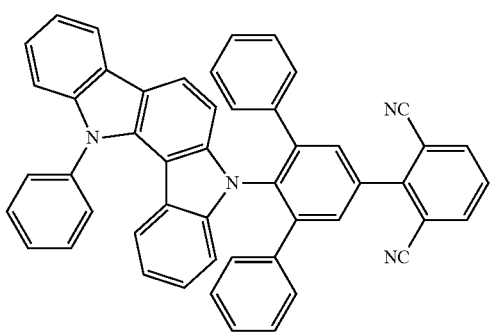
299
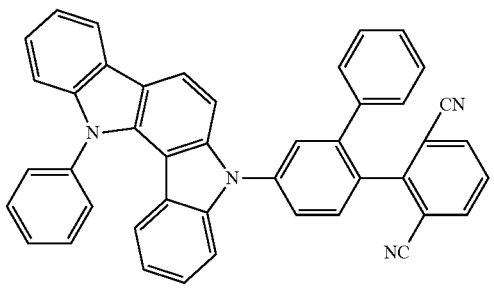
300
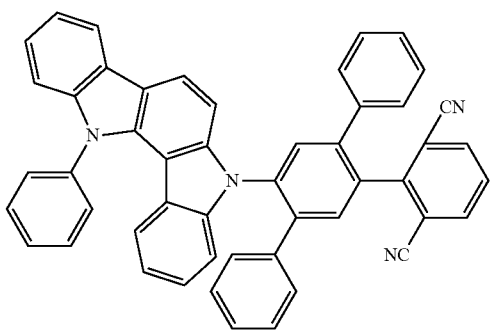
301

-continued

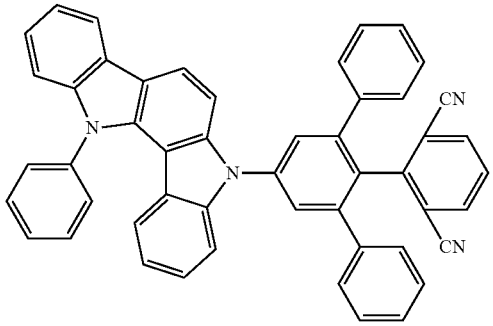
302

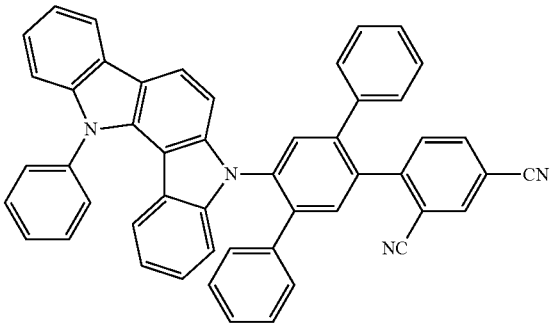
306

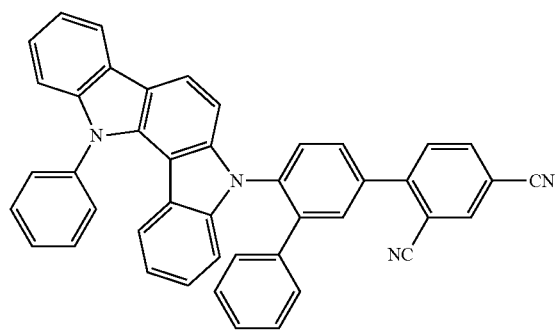
303

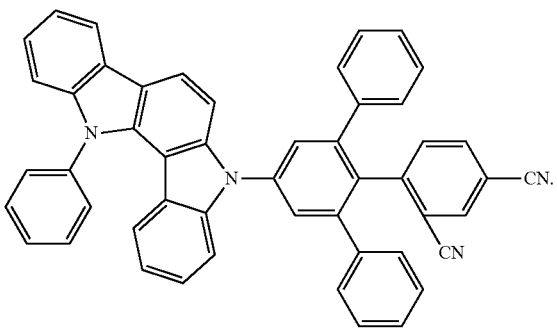
307

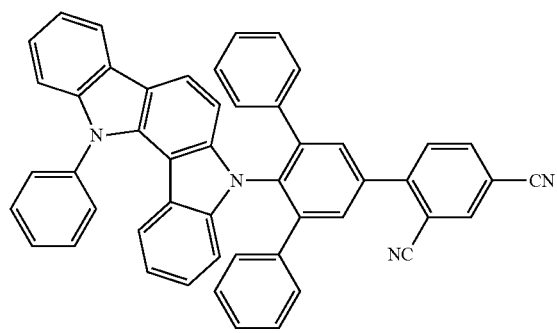
304

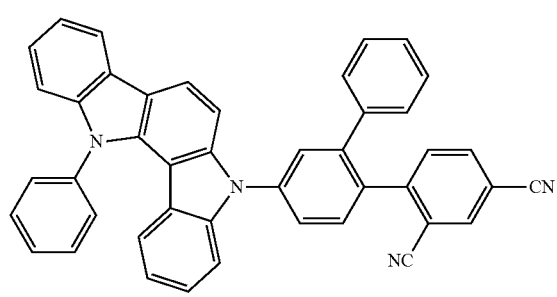
305

In Formula 1, at least one of $R_{11}$ to $R_{14}$ may be selected from a cyano group, a substituted or unsubstituted $C_3$-$C_{10}$ cycloalkyl group, a substituted or unsubstituted $C_3$-$C_{10}$ cycloalkenyl group, a substituted or unsubstituted $C_6$-$C_{60}$ aryl group, and a substituted or unsubstituted monovalent non-aromatic condensed polycyclic group. Accordingly, as an angle between a plane including $D_1$ in Formula 1 and a plane including $A_1$ in Formula 1 increases (i.e., a plane including $D_1$ and a plane including $A_1$ are twisted together), a difference between a singlet energy level and a triplet energy level of the condensed cyclic compound represented by Formula 1 may be reduced. Therefore, the condensed cyclic compound represented by Formula 1 may have efficient high reverse intersystem crossing (RISC), and thus, an electronic device, for example, an organic light-emitting device, which includes the condensed cyclic compound, may also have high luminescent efficiency and/or long lifespan. For example, a difference between a singlet excitation energy level and a triplet excitation energy level of the condensed cyclic compound represented by Formula 1 may be greater than 0 electron volts (eV) and less than or equal to 0.5 eV, and in some embodiments, may be greater than 0.01 eV and less than or equal to 0.3 eV, but embodiments of the present disclosure are not limited thereto.

In addition, in the condensed cyclic compound represented by Formula 1, $D_1$ and $A_1$ may be combined together at the para position of the phenylene group. In this regard, the condensed cyclic compound represented by Formula 1 may have a high oscillator strength such that an electronic device including the condensed cyclic compound, e.g., an organic light-emitting device, may also have high luminescent efficiency.

For example, calculations of highest occupied molecular orbital (HOMO) levels, lowest unoccupied molecular orbital (LUMO) levels, triplet state ($T_1$) energy levels, singlet state ($S_1$) energy levels, and oscillator strengths of Compounds 1 to 3 were carried out according to a density functional theory (DFT) method of a Gaussian program (structurally optimized at B3LYP, 6-31G(d,p)), and the results are shown in Table 1:

TABLE 2

| Compound No. | HOMO (eV) | LUMO (eV) | $T_1$ (eV) | $S_1$ (eV) | $S_1 - T_1$ (eV) | Oscillator strength (f) |
|---|---|---|---|---|---|---|
| Compound 1 | −5.051 | −1.991 | 2.523 | 2.604 | 0.081 | 0.080 |
| Compound 2 | −5.039 | −2.050 | 2.597 | 2.645 | 0.048 | 0.028 |
| Compound 3 | −5.139 | −2.082 | 2.660 | 2.733 | 0.073 | 0.055 |

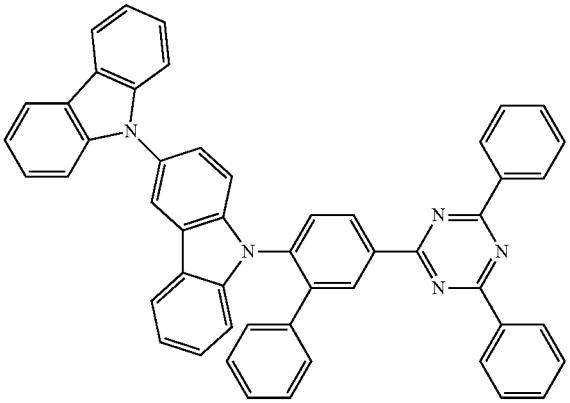

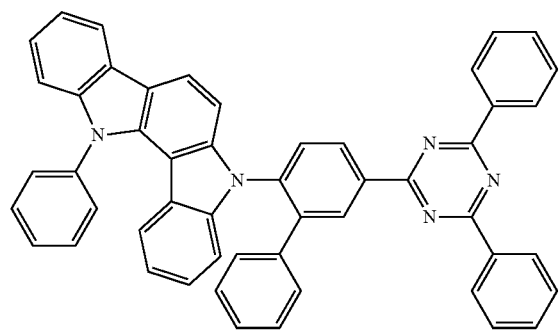

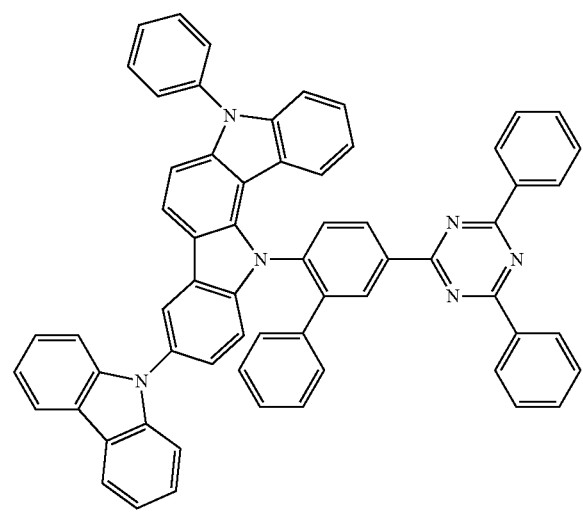

Referring to Table 1, it was confirmed that Compounds 1 to 3 had a relatively small difference between the $S_1$ energy level and the $T_1$ energy level, and a high oscillator strength. In this regard, an electronic device, for example, an organic light-emitting device, which includes Compounds 1 to 3, may accordingly have high light-emission efficiency.

Synthesis methods of the condensed cyclic compound represented by Formula 1 may be recognizable by those of ordinary skill in the art by referring to Examples provided below.

The condensed cyclic compound represented by Formula 1 may be used as a material for an electronic device, for example, an organic light-emitting device. Therefore, in one or more embodiments, there is provided an organic light-emitting device including:

a first electrode;

a second electrode; and an organic layer disposed between the first electrode and the second electrode, wherein the organic layer includes an emission layer, and wherein the organic layer includes at least one condensed cyclic compound represented by Formula 1.

The organic light-emitting device includes the organic layer including the condensed cyclic compound represented by Formula 1, and accordingly, may have low driving voltage, high efficiency, high brightness, high quantum efficiency, and/or a long lifespan.

The condensed cyclic compound of Formula 1 may be used between a pair of electrodes of an organic light-emitting device. For example, the condensed cyclic compound may be included in at least one selected from an emission layer, a hole transport region (including, for example, at least one of a hole injection layer, a hole transport layer, a buffer layer, and an electron blocking layer) disposed between the first electrode and the emission layer, and an electron transport region (including, for example, at least one selected from a hole blocking layer, an electron transport layer, and an electron injection layer) disposed between the emission layer and the second electrode.

In one or more embodiments, the emission layer may include the condensed cyclic compound. Here, a ratio of a fluorescent emission component among all emission components emitted from the emission layer may be at least 90%, for example, at least 95% (in some embodiments, at least 98%). In addition, the emission layer may include the condensed cyclic compound represented by Formula 1, but may not include a phosphorescent compound (for example, an organometallic compound including a heavy metal). Therefore, the emission layer may be, as described above, distinctly distinguished from a phosphorescent emission layer, which includes a phosphorescent dopant, in which a ratio of a phosphorescent emission component among all of the emission components is, for example, at least 80%.

Depending on use of the condensed cyclic compound represented by Formula 1, the emission layer of the organic light-emitting device may be embodied in accordance with Embodiments 1, 2, and 3 below.

Embodiment 1

In Embodiment 1, the condensed cyclic compound included in the emission layer serves as a fluorescent emitter, that is, the present embodiments provides a case in which the condensed cyclic compound is used as a fluorescent emitter.

Therefore, according to Embodiment 1, among all emission components emitted from the emission layer, a ratio of an emission component emitted from the condensed cyclic compound may be at least 80%, for example, at least 90%. For example, among all emission components emitted from the emission layer, a ratio of an emission component emitted from the condensed cyclic compound may be at least 95%. Here, the emission component of the condensed cyclic compound is the sum of a prompt emission component of the condensed cyclic compound and a delayed fluorescent emission component emitted by reverse intersystem crossing of the condensed cyclic compound.

According to Embodiment 1, the emission layer may consist of the condensed cyclic compound only; or the emission layer may further include a host (wherein the host may not be the same as the condensed cyclic compound).

In Embodiment 1, when the emission layer further includes a host in addition to the condensed cyclic compound, an amount of the condensed cyclic compound may be less than or equal to 50 parts by weight, for example, less than or equal to 30 parts by weight, per 100 parts by weight of the emission layer, and an amount of the host in the emission layer may be greater than or equal to 50 parts by weight, for example, greater than or equal to 70 parts by weight, per 100 parts by weight of the emission layer, but embodiments of the present disclosure are not limited thereto.

The host used in Embodiment 1 will be described in detail.

Embodiment 2

In Embodiment 2, the condensed cyclic compound included in the emission layer serves as a fluorescent host.

Therefore, according to Embodiment 2, the emission layer may include a host and a fluorescent dopant, wherein the host includes the condensed cyclic compound, and a ratio of an emission component emitted from the fluorescent dopant among all emission components emitted from the emission layer may be at least 80%, for example, at least 90% (in some embodiment, at least 95%).

In Embodiment 2, an amount of the fluorescent dopant in the emission layer may be less than or equal to 50 parts by weight, for example, less than or equal to 30 parts by weight, per 100 parts by weight of the emission layer, and an amount of the host in the emission layer may be greater than or equal to 50 parts by weight, for example, greater than or equal to 70 parts by weight, per 100 parts by weight of the emission layer, but embodiments of the present disclosure are not limited thereto.

The fluorescent dopant used in Embodiment 2 will be described in detail.

The host used in Embodiment 2 may consist of the condensed cyclic compound only, or may further include other hosts known in the art. The other hosts known in the art will be described in detail.

Embodiment 3

In Embodiment 3, the condensed cyclic compound included in the emission layer serves as an auxiliary dopant.

Therefore, according to Embodiment 3, the emission layer may include a host, an auxiliary dopant, and a fluorescent dopant, wherein the auxiliary dopant includes the condensed cyclic compound, and the emission layer satisfies Equations 1 and 2:

$$E_{T1(HOST)} - E_{T1(AD)} > 0.05 \text{ eV} \qquad \text{Equation 1}$$

$$E_{S1(FD)} - E_{S1(AD)} < 0 \text{ eV}, \qquad \text{Equation 2}$$

wherein, in Equation 1, $E_{T1(HOST)}$ indicates a triplet energy level (eV) of the host, and $E_{T1(AD)}$ indicates a triplet energy level (eV) of the auxiliary dopant, in Equation 2, $E_{S1(FD)}$ indicates a singlet energy level (eV) of the fluorescent dopant, and $E_{S1(AD)}$ indicates a singlet energy level (eV) of the auxiliary dopant, and $E_{T1(HOST)}$, $E_{T1(AD)}$, and $E_{S1(FD)}$ are calculated for evaluation according to the DFT method of a Gaussian program structurally optimized at B3LYP/6-31G(d,p).

In Embodiment 3, as the emission layer satisfies Equation 1 (for example, the calculation of $E_{T1(HOST)} - E_{T1(AD)}$ satisfies a range from 0.10 eV to 0.65 eV), the triplet excitation energy generated by the auxiliary dopant in the emission layer may not be transferred into the host in the emission layer. Thus, the probability that the triplet excitons are lost in a path other than an emission path may be decreased, such that the organic light-emitting device may have high luminescent efficiency.

In addition, in Embodiment 3, as the emission layer satisfies Equation 2 (for example, the calculation of $E_{S1(FD)} - E_{S1(AD)}$ satisfies a range from −0.4 eV to −0.05 eV), the singlet exciton energy generated by the auxiliary dopant in the emission layer may be rapidly transferred into the fluorescent dopant in the emission layer. Thus, emission occurs substantially only in the fluorescent dopant in the emission layer of the organic light-emitting device, thereby realizing a fluorescence emission spectrum of excellent color purity based on the fluorescent dopant. In addition, fluorescence emission having a relatively short exciton lifespan may be achieved, and accordingly, a luminescent efficiency decrease phenomenon under a high luminance (also referred to as a roll-off phenomenon) that may be caused by interaction of a plurality of excitons (exciton-exciton interaction) or interaction between an exciton and a charge (e.g., a hole or an electron) (exciton-polaron interaction) is suppressed, thereby implementing the organic light-emitting device having high luminescent efficiency. Furthermore, since the auxiliary dopant has a short exciton lifespan, the probability of chemical or physical deterioration that may occur in the exciton state of the auxiliary dopant may be reduced, and thus, the organic light-emitting device satisfying Equation 2 may have improved durability.

In Embodiment 3, an amount of the fluorescent dopant in the emission layer may be less than or equal to 50 parts by weight, for example, less than or equal to 30 parts by weight, per 100 parts by weight of the emission layer, and an amount of the host in the emission layer may be greater than or equal to 50 parts by weight, for example, greater than or equal to 70 parts by weight, per 100 parts by weight of the emission layer, but embodiments of the present disclosure are not limited thereto.

The host and the fluorescent dopant used in Embodiment 3 will be described in detail.

The emission layer used in Embodiment 2 may include i) the condensed cyclic compound (as a host) defined in the present specification and ii) a fluorescent dopant (as a fluorescent emitter). The emission layer used in Embodiment 3 may include i) a host, ii) a fluorescent dopant (as a fluorescent emitter), and iii) the condensed cyclic compound (as an auxiliary dopant) defined in the present specification. In this regard, the emission layer used in the second and third embodiments may achieve energy transfer from the condensed cyclic compound to the fluorescent dopant (as a fluorescent emitter) according to a Förster energy transfer mechanism.

The host used in the first and third embodiments may be selected from fluorescent hosts known in the art.

For example, the host may have a triplet energy level of at least 2.9 eV, for example, in a range from 2.9 eV to 4.5 eV. Accordingly, energy transfer from the host to the fluorescent emitter, the fluorescent dopant, and/or the fluorescent dopant may be efficiently achieved, such that the organic light-emitting device may have high luminescent efficiency.

For example, the host may include at least one compound selected from a fluorene-containing compound, a carbazole-containing compound, a dibenzofuran-containing compound, a dibenzothiophene-containing compound, an indenocarbazole-containing compound, an indolocarbazole-containing compound, a benzofurocarbazole-containing compound, a benzothienocarbazole-containing compound, an acridine-containing compound, a dihydroacridine-containing compound, a triindolobenzene-containing compound, a pyridine-containing compound, a pyrimidine-containing compound, a triazine-containing compound, a silicon-containing compound, a cyano group-containing compound, a phosphineoxide-containing compound, and a sulfoxide-containing compound, but embodiments of the present disclosure are not limited thereto.

In one or more embodiments, the host may include a compound including at least one carbazole ring and at least one cyano group.

For example, the host may be selected from compounds represented by Formulae 11-1 to 11-3, but embodiments of the present disclosure are not limited thereto:

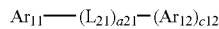

Formula 11-1

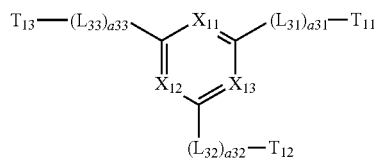

Formula 11-2

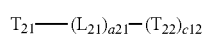

Formula 11-3

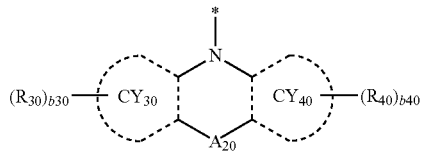

Formula 13

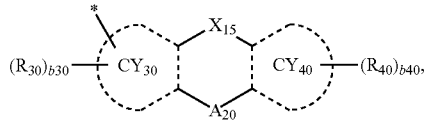

Formula 14 wherein, in Formulae 11-1 to 11-3, 13, and 14, $Ar_{11}$ and $Ar_{12}$ may each independently be selected from groups represented by Formulae 13 and 14, $X_{15}$ may be $N(R_{200})$, O, or S, $X_{11}$ may be N or $C(T_{14})$, $X_{12}$ may be N or $C(T_{15})$, and $X_{13}$ may be N or $C(T_{16})$, wherein at least one of $X_{11}$ to $X_{13}$ may be N, $T_{21}$ and $T_{22}$ may each independently be selected from *-$(L_{21})_{a21}$-Si$(Q_{41})(Q_{42})(Q_{43})$ and *-$(L_{21})_{a21}$-P(=O)$(Q_{51})(Q_{52})$, $L_{21}$ and $L_{31}$ to $L_{33}$ may each independently be selected from:

a single bond, O, S, Si$(Q_{61})(Q_{62})$, a phenylene group, a pyridinylene group, a pyrimidinylene group, a pyrazinylene group, a pyridazinylene group, a triazinylene group, a naphthylene group, a fluorenylene group, a carbazolylene group, a dibenzofuranylene group, and a dibenzothiophenylene group; and a phenylene group, a pyridinylene group, a pyrimidinylene group, a pyrazinylene group, a pyridazinylene group, a triazinylene group, a naphthylene group, a fluorenylene group, a carbazolylene group, a dibenzofuranylene group, and a dibenzothiophenylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, —$CF_3$, —$CF_2H$, —$CFH_2$, a phenyl group, a phenyl group substituted with a cyano group, a biphenyl group, a terphenyl group, a naphthyl group, a pyridinyl group, a pyrimidinyl group, a pyrazinyl group, a pyridazinyl group, a triazinyl group, a fluorenyl group, a carbazolyl group, a dibenzofuranyl group, a dibenzothiophenyl group, and —Si$(Q_{71})(Q_{72})(Q_{73})$, a21 and a31 to a33 may each independently be an integer from 0 to 5, wherein, when a21 is two or more, two or more of groups $L_{21}$ may be identical to or different from each other, when a31 is two or more, two or more of groups $L_{31}$ may be identical to or different from each other, when a32 is two or more, two or more of groups $L_{32}$ may be identical to or different from each other, and when a33 is two or more, two or more of groups $L_{33}$ may be identical to or different from each other, $CY_{30}$ and $CY_{40}$ may each independently be selected from a benzene group, a naphthalene group, a fluorene group, a carbazole group, a benzocarbazole group, an indolocarbazole group, a dibenzofuran group, and a dibenzothiophene group, A$_{20}$ may be selected from:

a single bond, a $C_1$-$C_4$ alkylene group, and a $C_2$-$C_4$ alkenylene group; and a $C_1$-$C_4$ alkylene group and a $C_2$-$C_4$ alkenylene group, each substituted with at least one selected from:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a biphenyl group, a terphenyl group, a naphthyl group, a pyridinyl group, a pyrimidinyl group, a pyrazinyl group, a pyridazinyl group, a triazinyl group, a fluorenyl group, a carbazolyl group, a dibenzofuranyl group, a dibenzothiophenyl group, and —Si(Q$_{81}$)(Q$_{82}$)(Q$_{83}$), $T_{11}$ to $T_{16}$, $R_{200}$, $R_{30}$, and $R_{40}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, and —Si(Q$_{91}$)(Q$_{92}$)(Q$_{93}$), b30 and b40 may each independently be an integer from 0 to 10, c12 may be 0, 1, 2, or 3, \* indicates a binding site to a neighboring atom, at least one substitute selected from the substituted $C_1$-$C_{60}$ alkyl group, the substituted $C_2$-$C_{60}$ alkenyl group, the substituted $C_2$-$C_{60}$ alkynyl group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from deuterium, —F, —Br, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si(Q$_{101}$)(Q$_{102}$)(Q$_{103}$), and Q$_{41}$ to Q$_{43}$, Q$_{51}$ to Q$_{52}$, Q$_{61}$ to Q$_{62}$, Q$_{71}$ to Q$_{73}$, Q$_{81}$ to Q$_{83}$, Q$_{91}$ to Q$_{93}$, and Q$_{101}$ to Q$_{103}$ may each independently be selected from hydrogen, deuterium, a $C_1$-$C_{60}$ alkyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

For example, the host may include at least one compound selected from Compounds H1 to H19, but embodiments of the present disclosure are not limited thereto:

H1

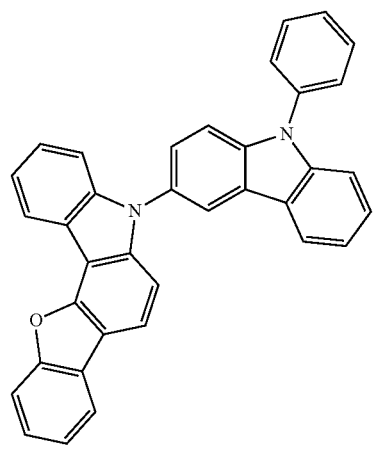

H2

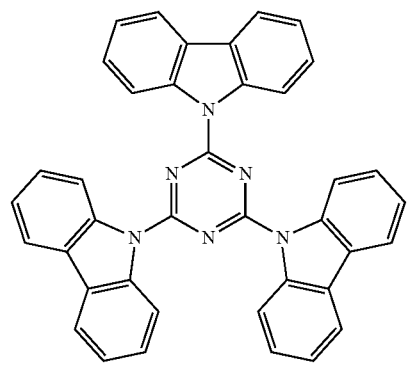

H3

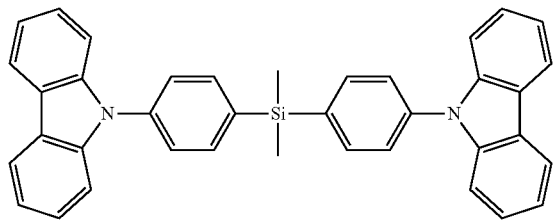

H4

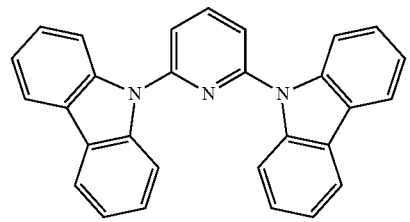

-continued
H5
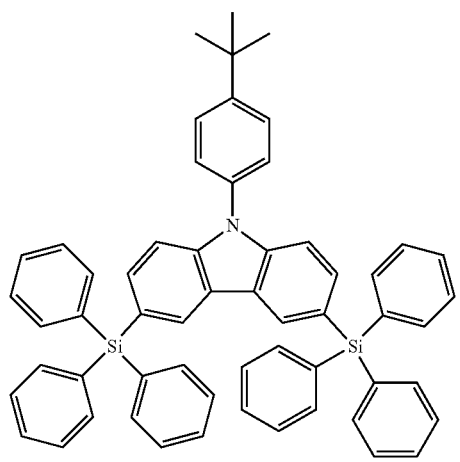
H6
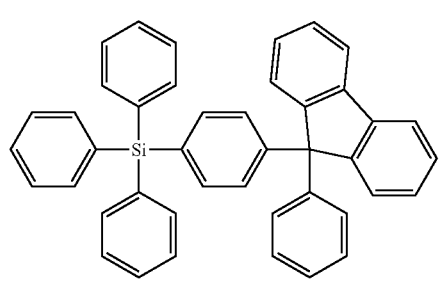
H7
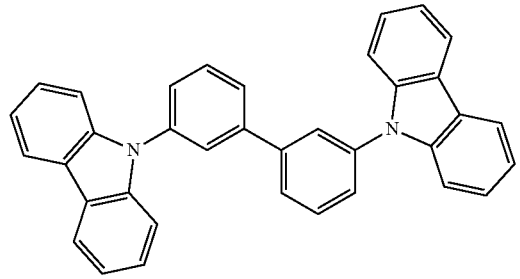
H8
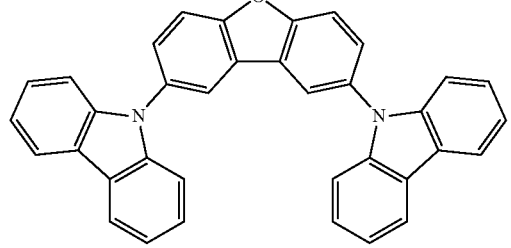
-continued
H9
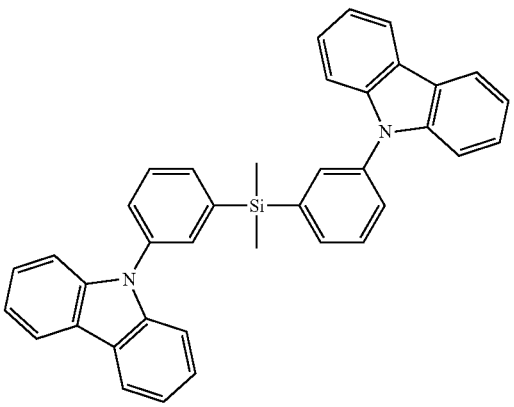
H10
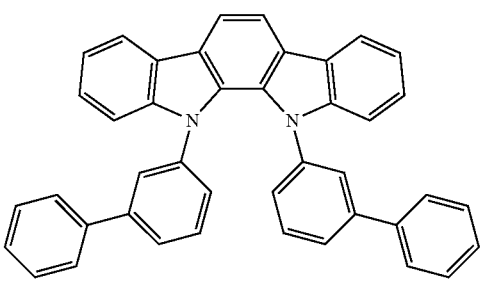
H11
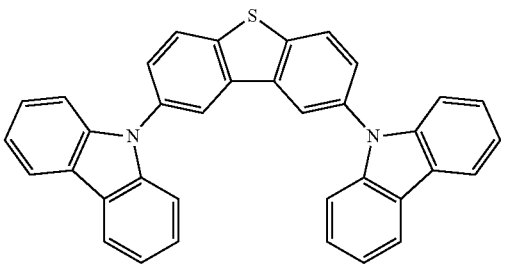
H12
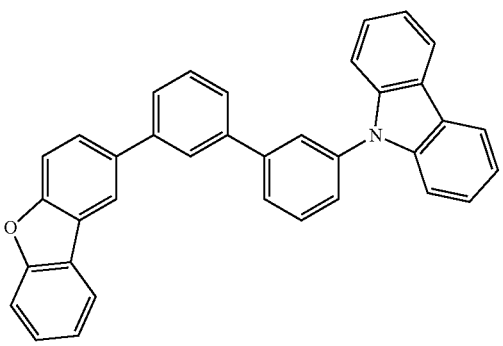

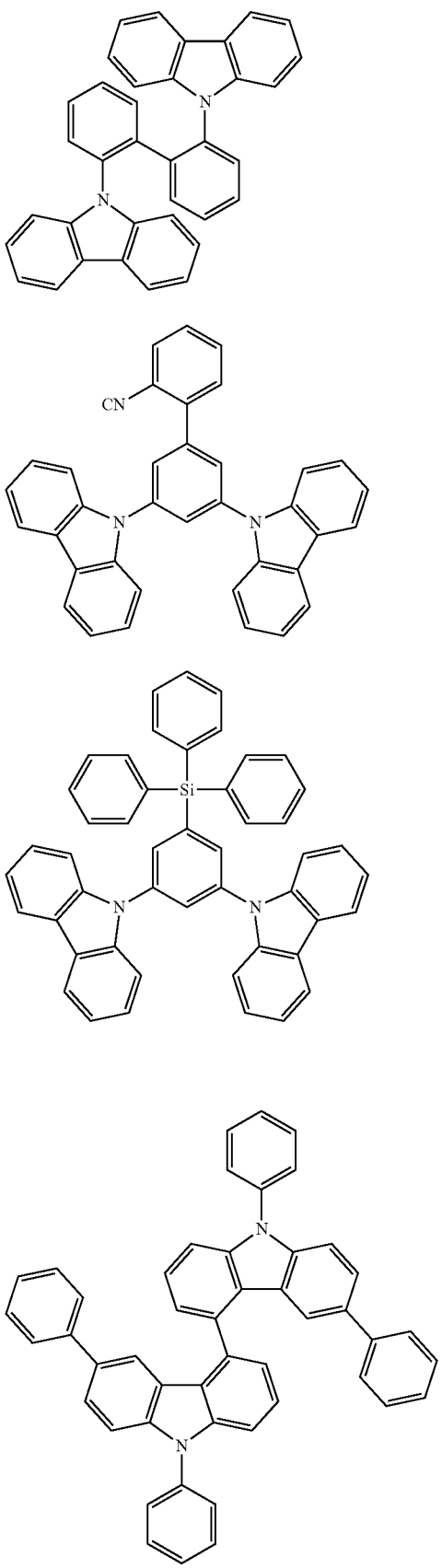
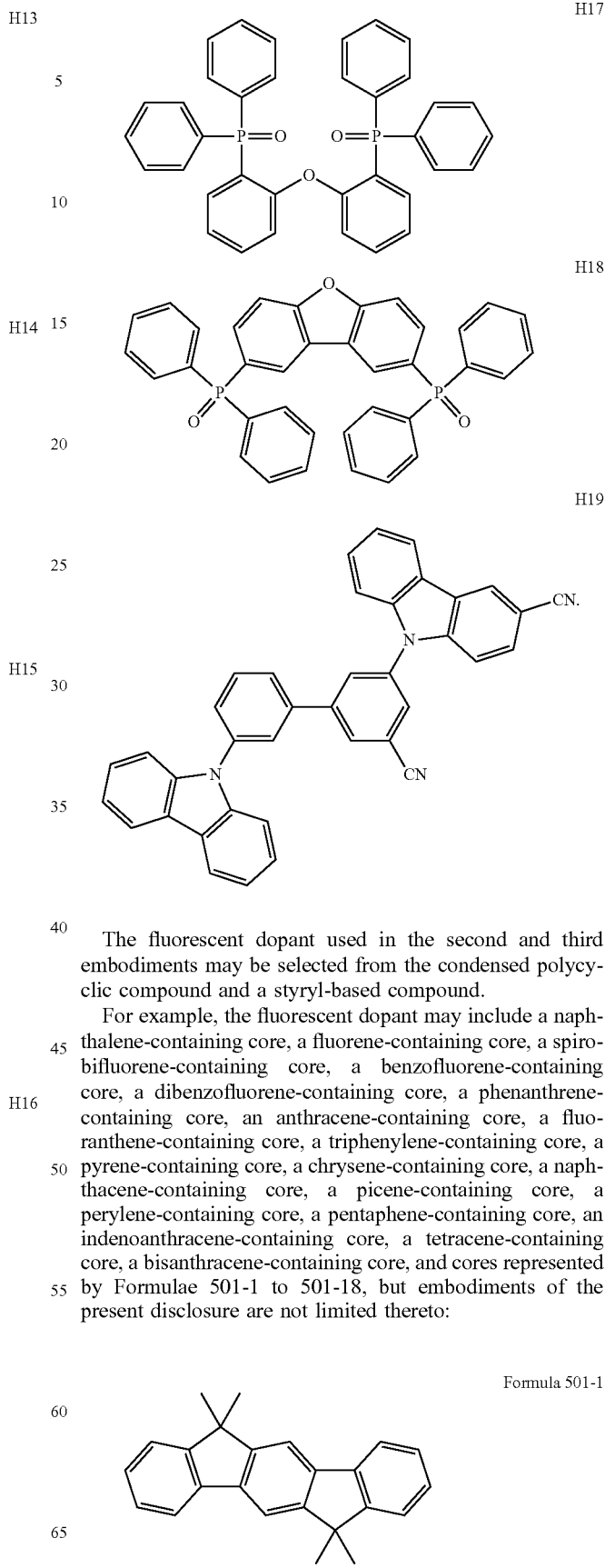

The fluorescent dopant used in the second and third embodiments may be selected from the condensed polycyclic compound and a styryl-based compound.

For example, the fluorescent dopant may include a naphthalene-containing core, a fluorene-containing core, a spirobifluorene-containing core, a benzofluorene-containing core, a dibenzofluorene-containing core, a phenanthrene-containing core, an anthracene-containing core, a fluoranthene-containing core, a triphenylene-containing core, a pyrene-containing core, a chrysene-containing core, a naphthacene-containing core, a picene-containing core, a perylene-containing core, a pentaphene-containing core, an indenoanthracene-containing core, a tetracene-containing core, a bisanthracene-containing core, and cores represented by Formulae 501-1 to 501-18, but embodiments of the present disclosure are not limited thereto:

Formula 501-1

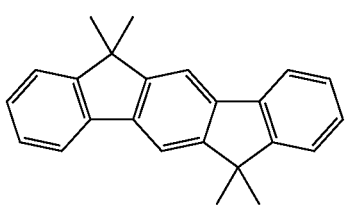

Formula 501-2
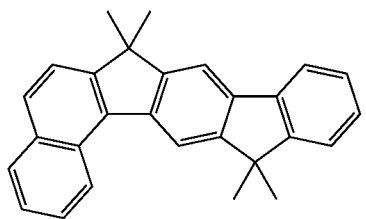
Formula 501-3
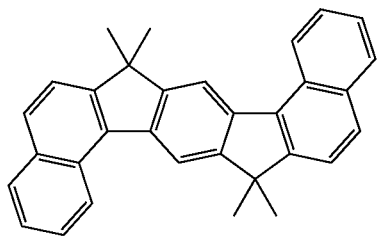
Formula 501-4
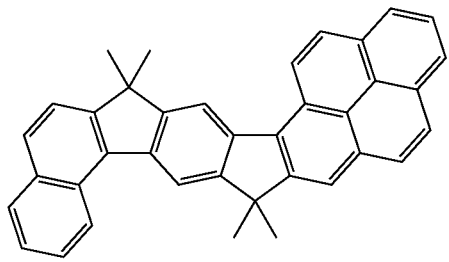
Formula 501-5
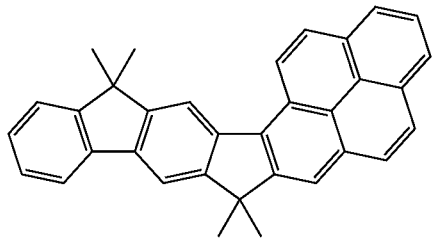
Formula 501-6
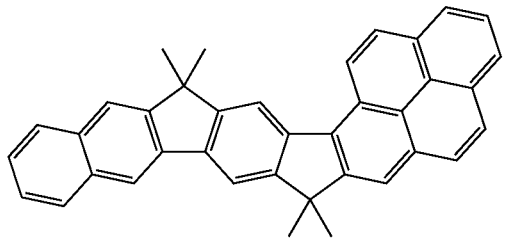
Formula 501-7
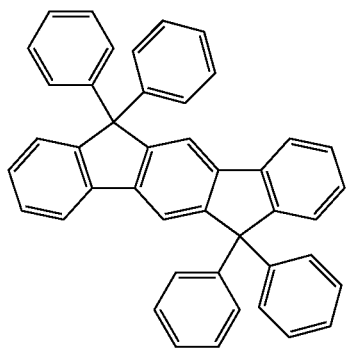
Formula 501-8
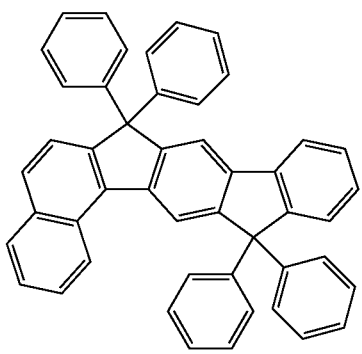
Formula 501-9
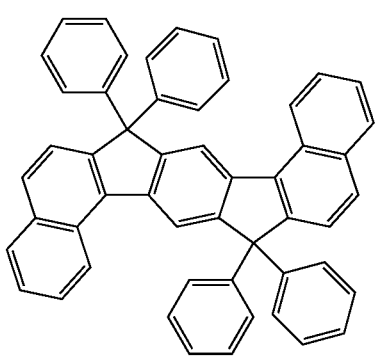
Formula 501-10
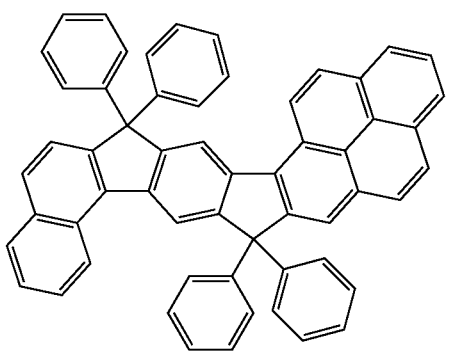
Formula 501-11
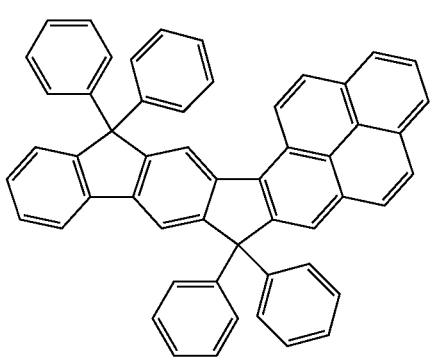

-continued

Formula 501-12
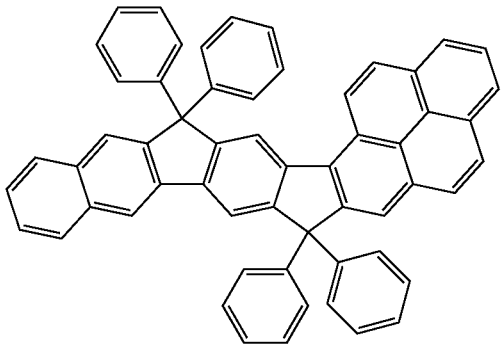

Formula 501-13
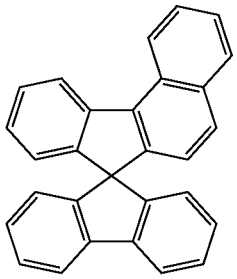

Formula 501-14
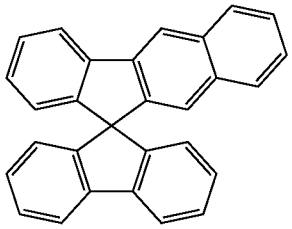

Formula 501-15
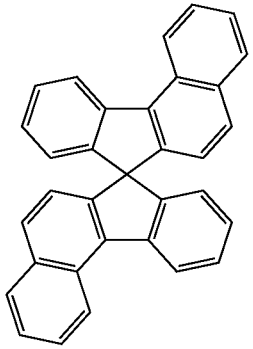

Formula 501-16
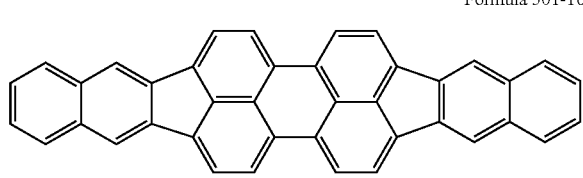

Formula 501-17
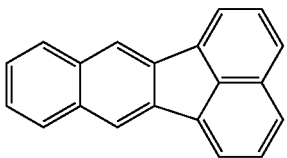

-continued

Formula 501-18
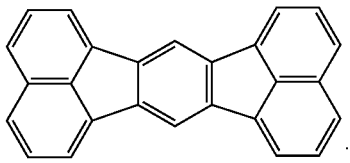

For example, the fluorescent dopant may be selected from a styryl-amine-based compound and a styryl-carbazole-based compound, but embodiments of the present disclosure are not limited thereto.

For example, the fluorescent dopant may be selected from a compound represented by Formula 501:

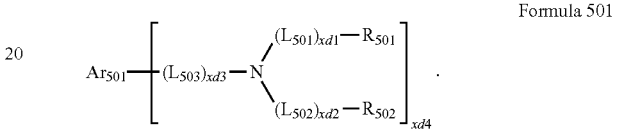

Formula 501

In Formula 501,
$Ar_{501}$ may be selected from:

a naphthalene group, a fluorene group, a spiro-bifluorene group, a benzofluorene group, a dibenzofluorene group, a phenanthrene group, an anthracene group, a fluoranthene group, a triphenylene group, a pyrene group, a chrysene group, a naphthacene group, a picene group, a perylene group, a pentaphene group, an indenoanthracene group, a tetracene group, a bisanthracene group, and groups represented by Formulae 501-1 to 501-18; and a naphthalene group, a fluorene group, a spiro-bifluorene group, a benzofluorene group, a dibenzofluorene group, a phenanthrene group, an anthracene group, a fluoranthene group, a triphenylene group, a pyrene group, a chrysene group, a naphthacene group, a picene group, a perylene group, a pentaphene group, an indenoanthracene group, a tetracene group, a bisanthracene group, and groups represented by Formulae 501-1 to 501-18, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{501}$)($Q_{502}$)($Q_{503}$) (wherein $Q_{501}$ to $Q_{503}$ may each independently be selected from hydrogen, a $C_1$-$C_{60}$ alkyl group, a $C_1$-$C_{60}$ alkoxy group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group), $L_{501}$ to $L_{503}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, $R_{501}$ and $R_{502}$ may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazole group, a triazinyl group, a dibenzofuranyl group, and a dibenzothiophenyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group, xd1 to xd3 may each independently be selected from 0, 1, 2, and 3; and xd4 may be selected from 0, 1, 2, 3, 4, 5, and 6.

For example, in Formula 501, $Ar_{501}$ may be selected from:

a naphthalene group, a fluorene group, a spiro-bifluorene group, a benzofluorene group, a dibenzofluorene group, a phenanthrene group, an anthracene group, a fluoranthene group, a triphenylene group, a pyrene group, a chrysene group, a naphthacene group, a picene group, a perylene group, a pentaphene group, an indenoanthracene group, a tetracene group, a bisanthracene group, and compounds represented by Formulae 501-1 to 501-18; and a naphthalene group, a fluorene group, a spiro-bifluorene group, a benzofluorene group, a dibenzofluorene group, a phenanthrene group, an anthracene group, a fluoranthene group, a triphenylene group, a pyrene group, a chrysene group, a naphthacene group, a picene group, a perylene group, a pentaphene group, an indenoanthracene group, a tetracene group, a bisanthracene group, and groups represented by Formulae 501-1 to 501-18, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a dibenzofuranyl group, a dibenzothiophenyl group, a carbazolyl group, a pyridinyl group, a pyrimidinyl group, a triazinyl group, a quinolinyl group, an isoquinolinyl group, and —Si($Q_{501}$)($Q_{502}$)($Q_{503}$) (wherein $Q_{501}$ to $Q_{503}$ may each independently be selected from hydrogen, a $C_1$-$C_{20}$ alkyl group, a $C_1$-$C_{20}$ alkoxy group, a phenyl group, a biphenyl group, a terphenyl group, and a naphthyl group), $L_{501}$ to $L_{503}$ may be understood by referring to the description provided herein, xd1 to xd3 may each independently be selected from 0, 1, and 2 and, xd4 may be selected from 0, 1, 2, and 3, but embodiments of the present disclosure are not limited thereto.

For example, the fluorescent dopant may include a compound represented by one of Formulae 502-1 to 502-5:

Formula 502-1

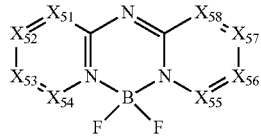

Formula 502-2

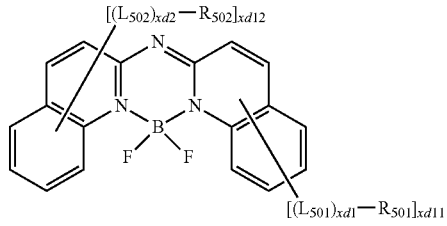

Formula 502-3

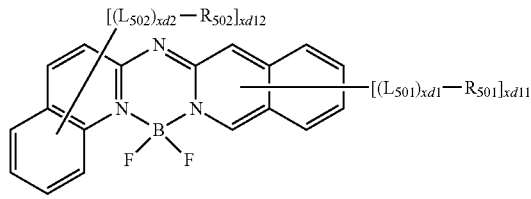

Formula 502-4

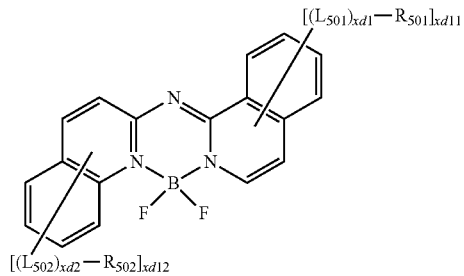

-continued

Formula 502-5

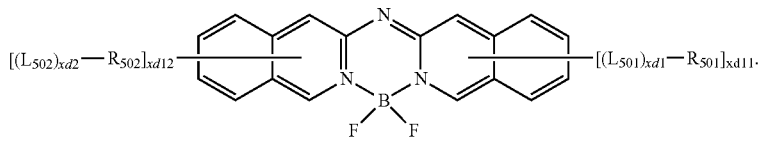

In Formulae 502-1 to 502-5, $X_{51}$ may be N or C-$[(L_{501})_{xd1}$-$R_{501}]$, $X_{52}$ may be N or C-$[(L_{502})_{xd2}$-$R_{502}]$, $X_{53}$ may be N or C-$[(L_{503})_{xd3}$-$R_{503}]$, $X_{54}$ may be N or C-$[(L_{504})_{xd4}$-$R_{504}]$, $X_{55}$ may be N or C-$[(L_{505})_{xd5}$-$R_{505}]$, $X_{56}$ may be N or C-$[(L_{506})_{xd6}$-$R_{506}]$, $X_{57}$ may be N or C-$[(L_{507})_{xd7}$-$R_{507}]$, and $X_{58}$ may be N or C-$[(L_{508})_{xd8}$-$R_{508}]$, $L_{501}$ to $L_{508}$ may each independently be understood by referring to the description provided herein in connection with $L_{501}$ in Formula 501, xd1 to xd8 may each independently be understood by referring to the description provided herein in connection with xd1 in Formula 501, $R_{501}$ to $R_{508}$ may each independently be selected from:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazole group, a triazinyl group, a dibenzofuranyl group, and a dibenzothiophenyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group, xd11 and xd12 may each independently be an integer from 0 to 5, two selected from $R_{501}$ to $R_{504}$ may optionally be linked to form a saturated or unsaturated ring, and two selected from $R_{505}$ to $R_{508}$ may optionally be linked to form a saturated or unsaturated ring.

The fluorescent dopant may include, for example, at least one compound selected from Compounds FD(1) to FD(16) and FD1 to FD13:

FD(1)

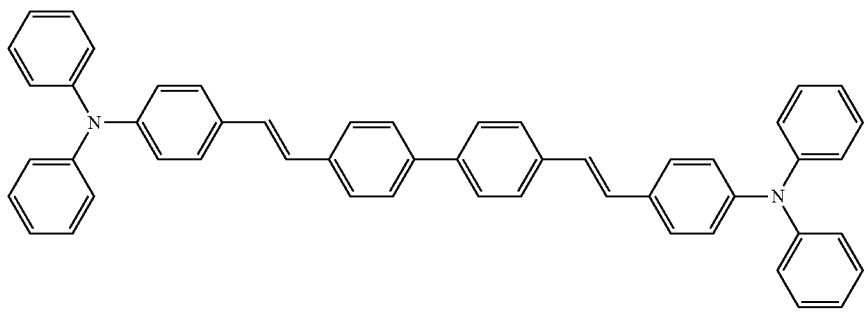

FD(2)

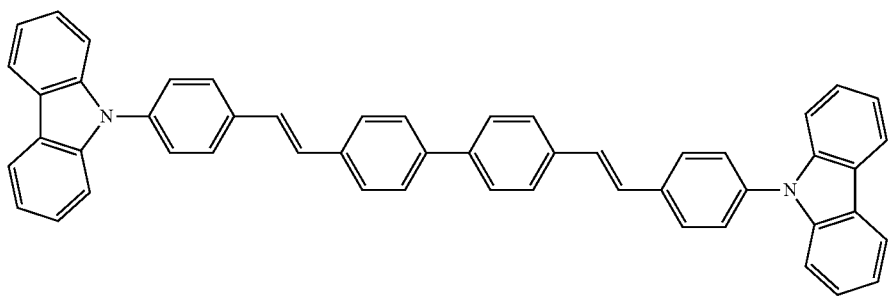

-continued
FD(3)
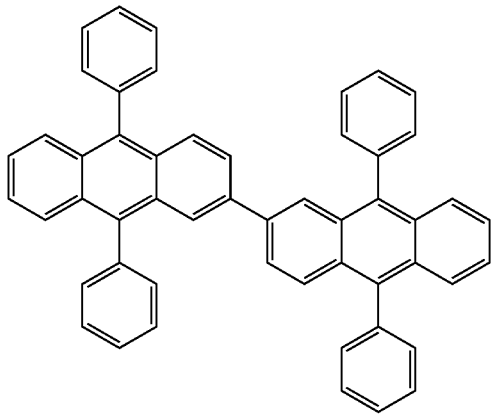
FD(4)
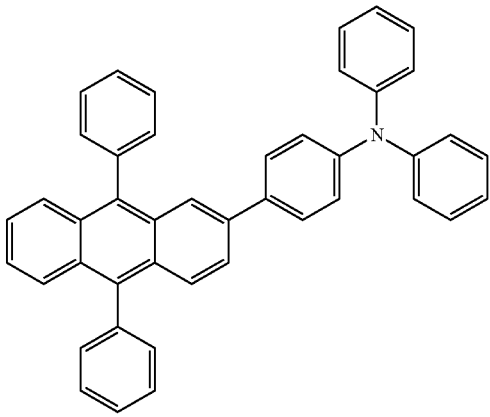
FD(5)
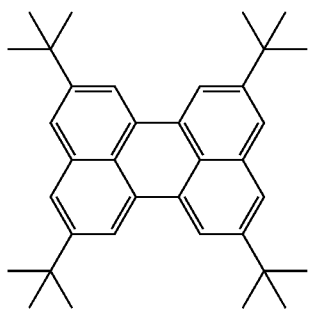
FD(6)
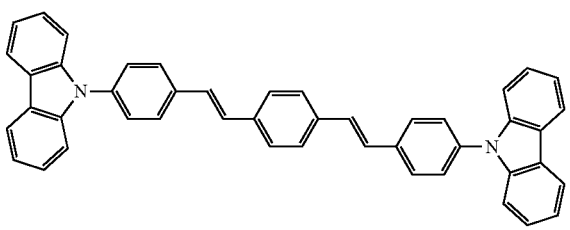
FD(7)
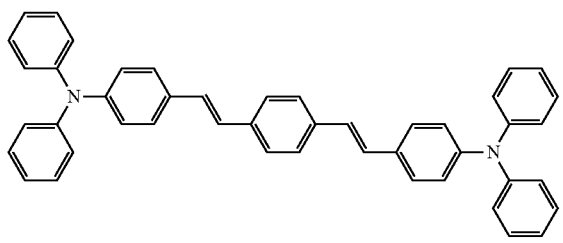
FD(8)
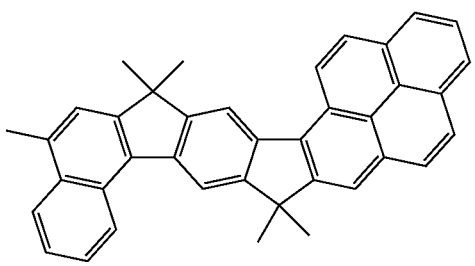
FD(9)
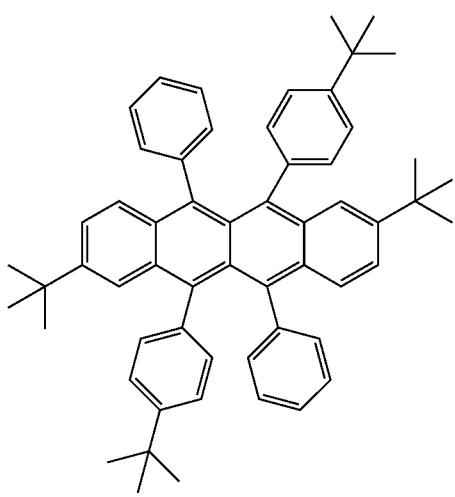
FD(10)
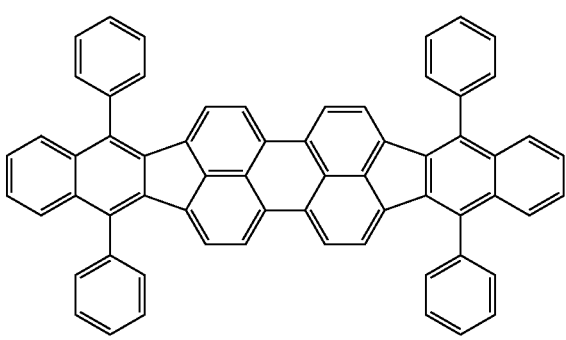

-continued
FD(11)
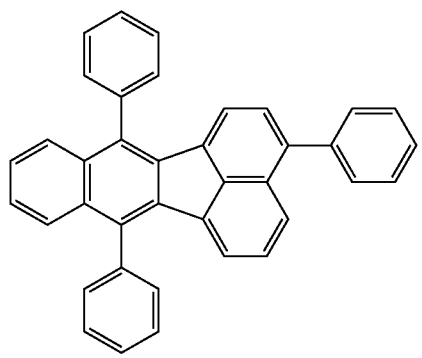
FD(12)
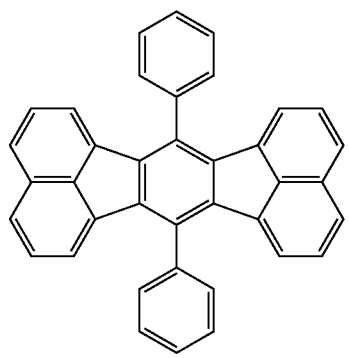
FD(13)
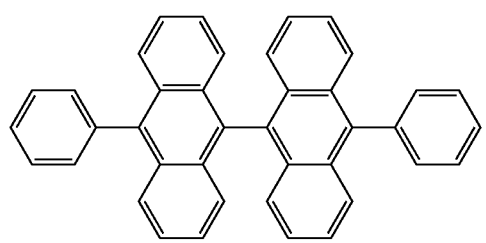
FD(14)
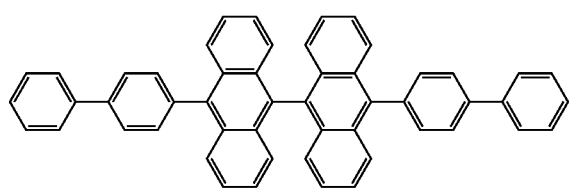
FD(15)
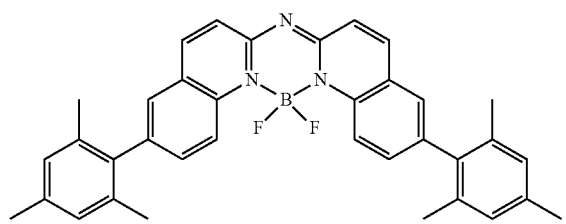
FD(16)
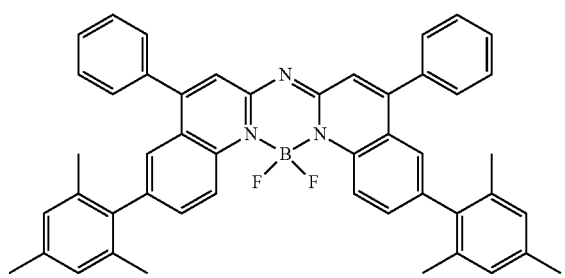
FD1
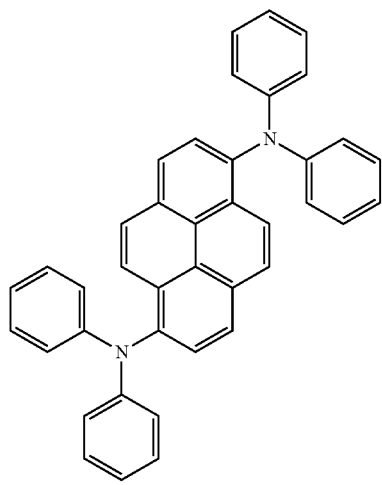
FD2
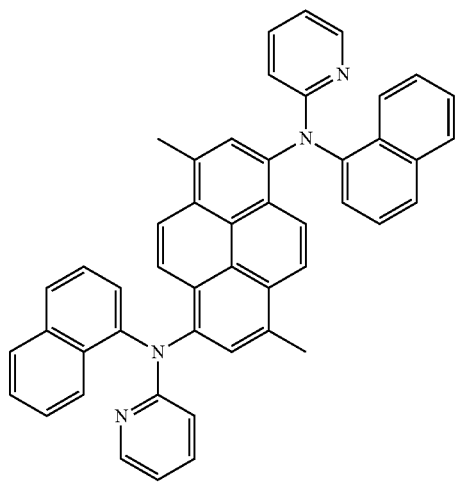

-continued
FD3
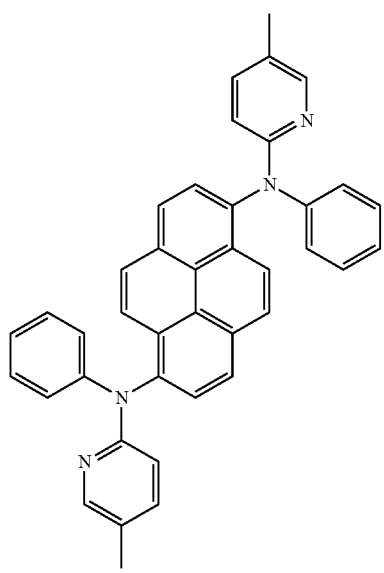
FD4
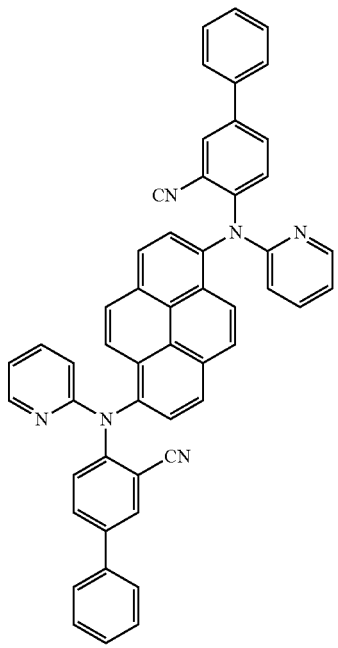
FD5
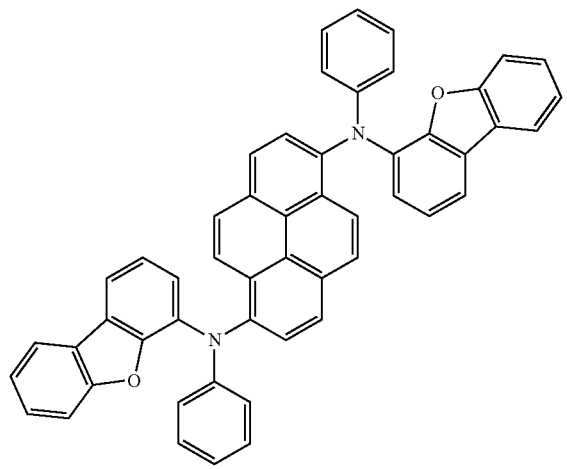
FD6
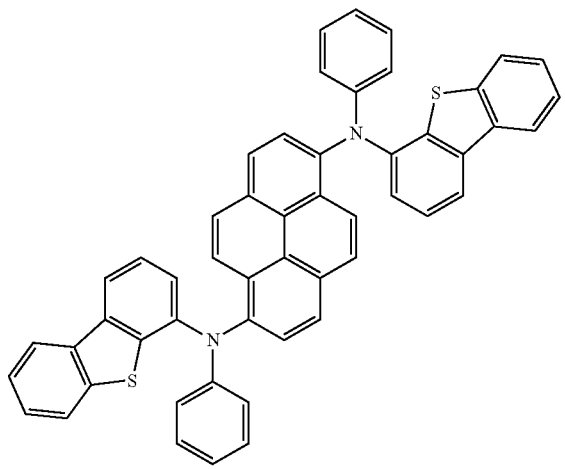
FD7
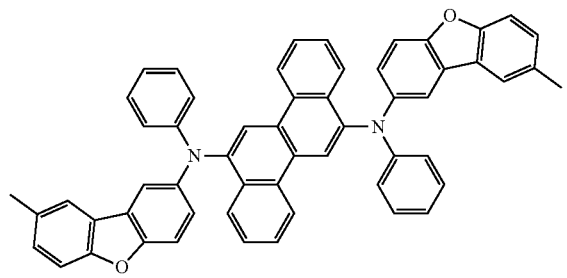
FD8
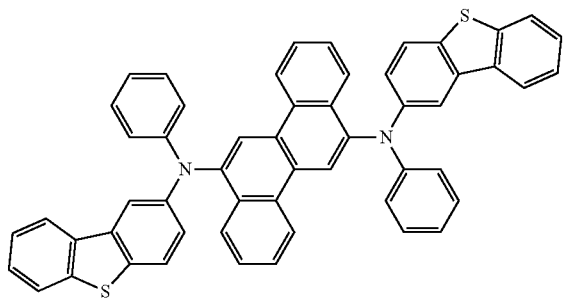

-continued

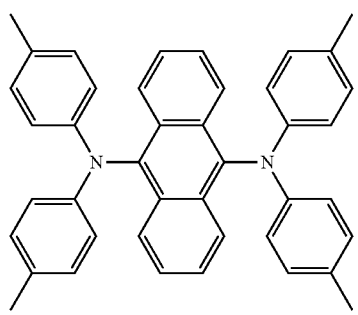
FD9

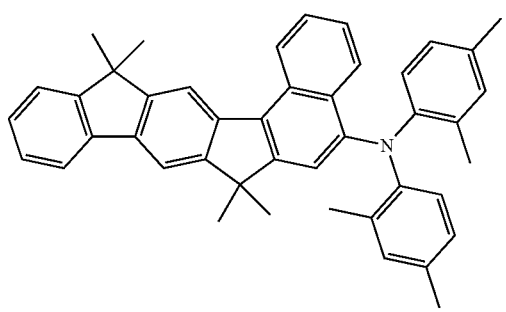
FD10

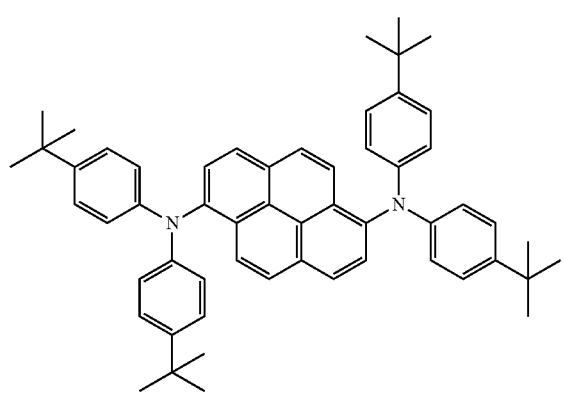
FD11

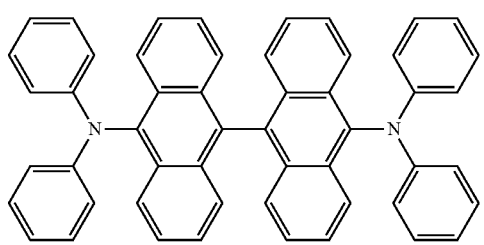
FD12

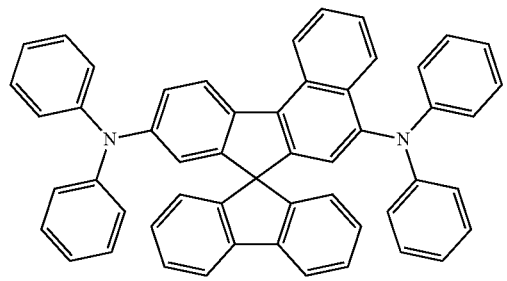
FD13

The FIGURE is a schematic view of an organic light-emitting device 10 according to an embodiment. Hereinafter, the structure of an organic light-emitting device according to an embodiment and a method of manufacturing an organic light-emitting device according to an embodiment will be described in connection with the FIGURE. The organic light-emitting device 10 includes a first electrode 11, an organic layer 15, and a second electrode 19, which are sequentially stacked.

A substrate may be additionally disposed under the first electrode 11 or above the second electrode 19. For use as the substrate, any substrate that is used in general organic light-emitting devices may be used, and the substrate may be a glass substrate or a transparent plastic substrate, each having excellent mechanical strength, thermal stability, transparency, surface smoothness, ease of handling, and water resistance.

The first electrode 11 may be formed by depositing or sputtering a material for forming the first electrode 11 on the substrate. The first electrode 11 may be an anode. The material for forming the first electrode 11 may be selected from materials with a high work function to facilitate hole injection. The first electrode 11 may be a reflective electrode, a semi-transmissive electrode, or a transmissive electrode.

The material for forming the first electrode may be, for example, indium tin oxide (ITO), indium zinc oxide (IZO), tin oxide ($SnO_2$), and zinc oxide (ZnO). In one or more embodiments, magnesium (Mg), aluminum (Al), aluminum-lithium (Al—Li), calcium (Ca), magnesium-indium (Mg—In), or magnesium-silver (Mg—Ag) may be used as the material for forming the first electrode.

The first electrode 11 may have a single-layered structure or a multi-layered structure including two or more layers. For example, the first electrode 11 may have a three-layered structure of ITO/Ag/ITO, but the structure of the first electrode 110 is not limited thereto.

The organic layer 15 is disposed on the first electrode 11.

The organic layer 15 may include a hole transport region, an emission layer, and an electron transport region.

The hole transport region may be disposed between the first electrode 11 and the emission layer.

The hole transport region may include at least one selected from a hole injection layer, a hole transport layer, an electron blocking layer, and a buffer layer.

The hole transport region may include only either a hole injection layer or a hole transport layer. In one or more embodiments, the hole transport region may have a hole injection layer/hole transport layer structure or a hole injection layer/hole transport layer/electron blocking layer structure, which are sequentially stacked in this stated order from the first electrode 11.

A hole injection layer may be formed on the first electrode 11 by using one or more suitable methods selected from vacuum deposition, spin coating, casting, or Langmuir-Blodgett (LB) deposition.

When the hole injection layer is formed by vacuum deposition, the deposition conditions may vary according to a compound that is used to form the hole injection layer, and the structure and thermal characteristics of the hole injection layer. For example, the deposition conditions may include a deposition temperature of about 100° C. to about 500° C., a vacuum pressure of about $10^{-8}$ torr to about $10^{-3}$ torr, and a deposition rate of about 0.01 Angstroms per second (Å/sec) to about 100 Å/sec, but embodiments of the present disclosure are not limited thereto.

When the hole injection layer is formed using spin coating, coating conditions may vary according to the material used to form the hole injection layer, and the structure and thermal properties of the hole injection layer. For example, a coating speed may be from about 2,000 revolutions per minute (rpm) to about 5,000 rpm, and a temperature at which a heat treatment is performed to remove a solvent after coating may be from about 80° C. to about 200° C. However, the coating conditions are not limited thereto.

Conditions for forming a hole transport layer and an electron blocking layer may be understood by referring to conditions for forming the hole injection layer.

The hole transport region may include, for example, at least one selected from m-MTDATA, TDATA, 2-TNATA, NPB, β-NPB, TPD, spiro-TPD, spiro-NPB, methylated-NPB, TAPC, HMTPD, 4,4',4"-tris(N-carbazolyl)triphenylamine (TCTA), polyaniline/dodecylbenzene sulfonic acid (PANI/DBSA), poly(3,4-ethylenedioxythiophene)/poly(4-styrene sulfonate) (PEDOT/PSS), polyaniline/camphor sulfonic acid (PANI/CSA), (polyaniline)/poly(4-styrene sulfonate) (PANI/PSS), a compound represented by Formula 201, and a compound represented by Formula 202:

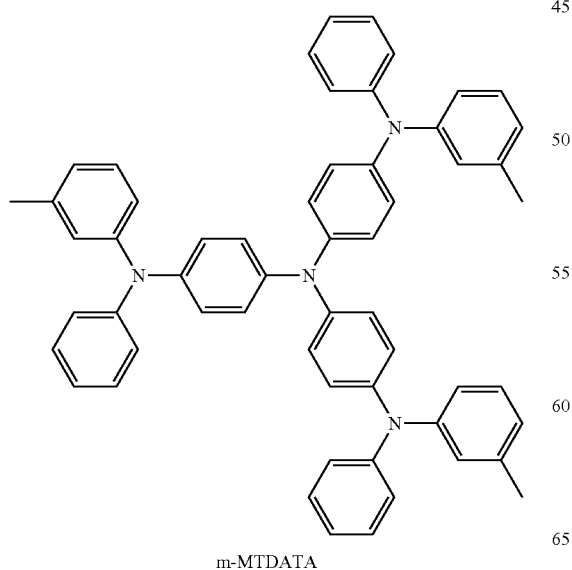

m-MTDATA

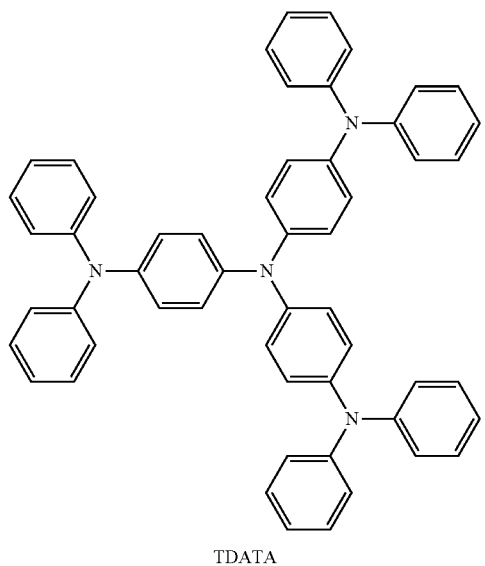

TDATA

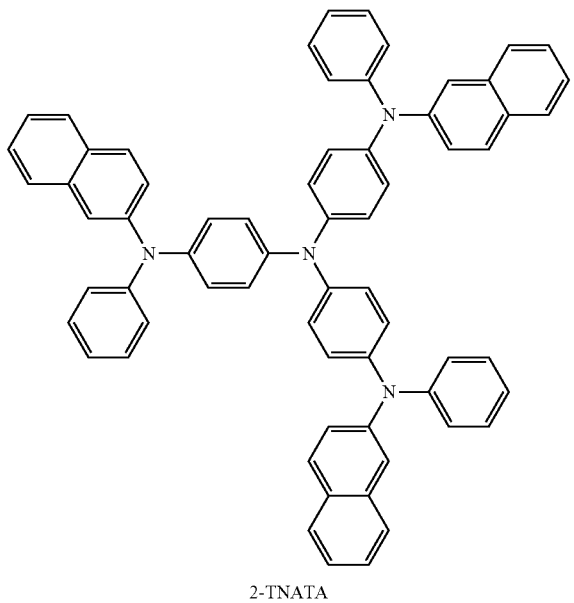

2-TNATA

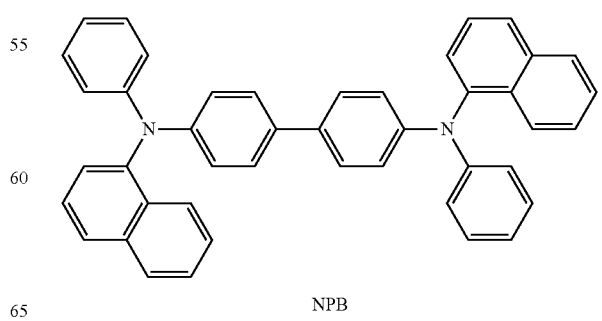

NPB

-continued

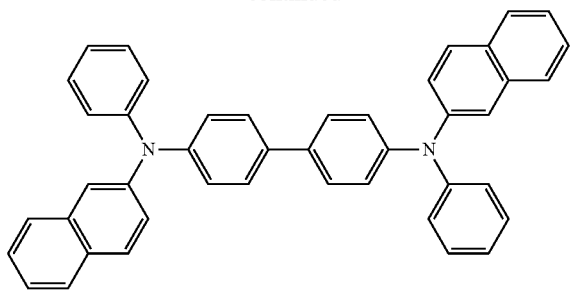

β-NPB

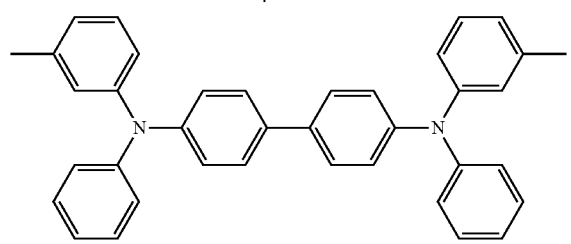

TPD

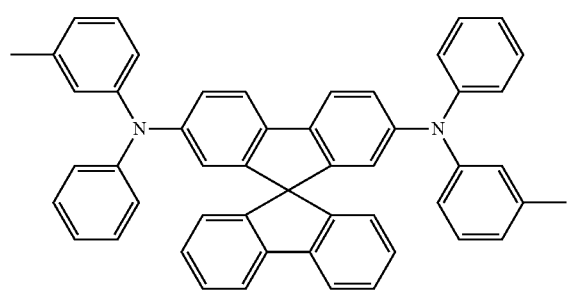

Spiro-TPD

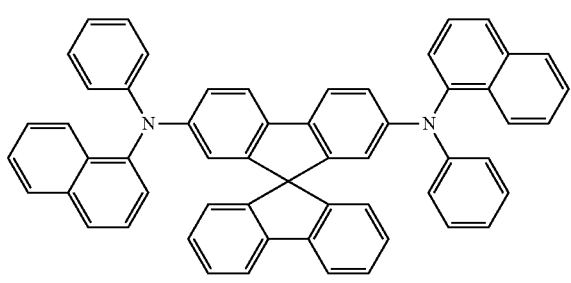

Spiro-NPB

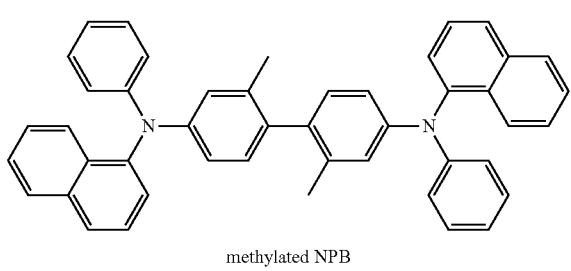

methylated NPB

-continued

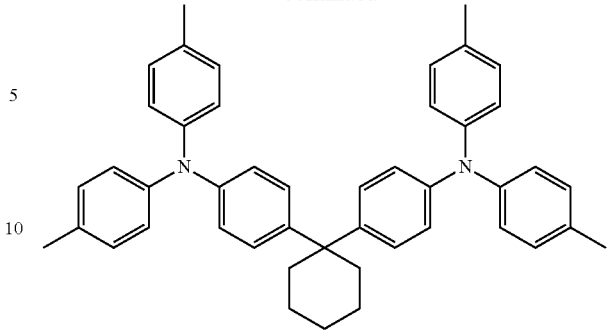

TAPC

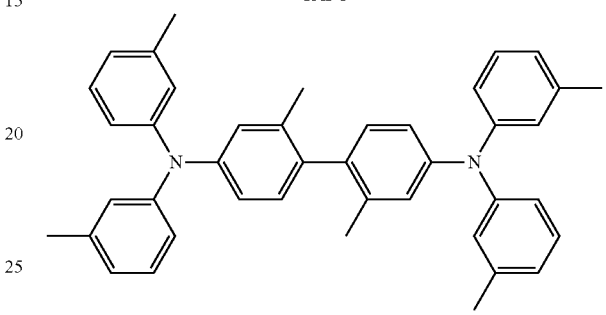

HMTPD

Formula 201

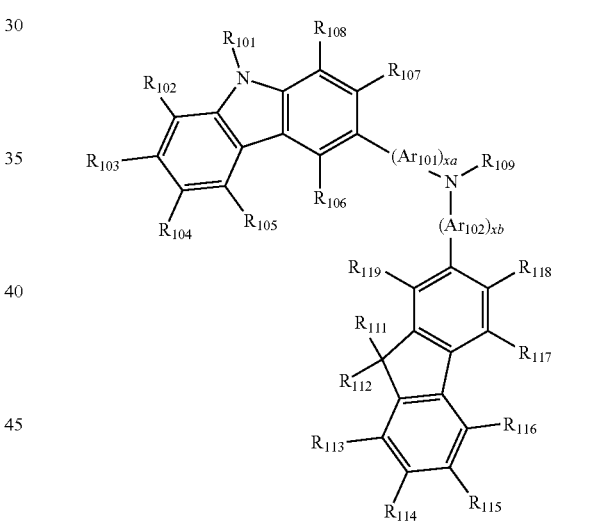

Formula 202

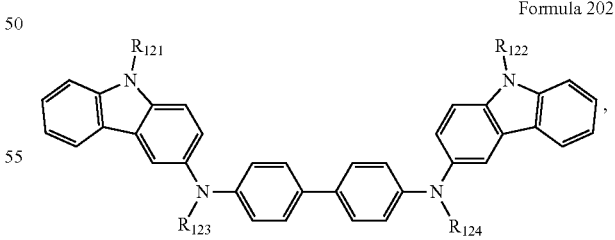

wherein $Ar_{101}$ and $Ar_{102}$ in Formula 201 may each independently be selected from:

a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, and a pentacenylene group; and a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_1$-$C_{10}$ heterocycloalkyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

In Formula 201, xa and xb may each independently be an integer from 0 to 5, or 0, 1, or 2. For example, xa may be 1 and xb may be 0, but xa and xb are not limited thereto.

In Formulae 201 and 202, $R_{101}$ to $R_{108}$, $R_{111}$ to $R_{119}$, and $R_{121}$ to $R_{124}$ may each independently be selected from:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group (for example, a methyl group, an ethyl group, a propyl group, a butyl group, a pentyl group, a hexyl group, and so on), and a $C_1$-$C_{10}$ alkoxy group (for example, a methoxy group, an ethoxy group, a propoxy group, a butoxy group, a pentoxy group, and so on);

a $C_1$-$C_{10}$ alkyl group or a $C_1$-$C_{10}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a naphthyl group, an anthracenyl group, a fluorenyl group, and a pyrenyl group; and a phenyl group, a naphthyl group, an anthracenyl group, a fluorenyl group, and a pyrenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group, but embodiments of the present disclosure are not limited thereto.

In Formula 201, $R_{109}$ may be selected from:

a phenyl group, a naphthyl group, an anthracenyl group, and a pyridinyl group; and a phenyl group, a naphthyl group, an anthracenyl group, and a pyridinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, and a pyridinyl group.

According to an embodiment, the compound represented by Formula 201 may be represented by Formula 201A, but embodiments of the present disclosure are not limited thereto:

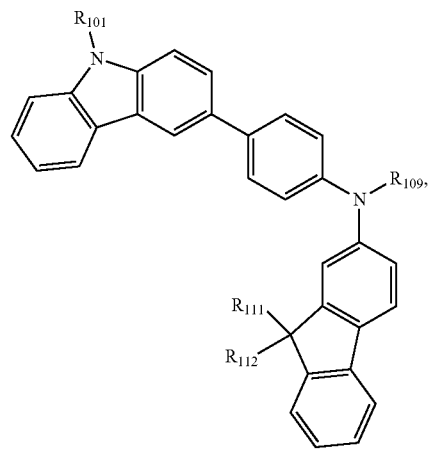

Formula 201A wherein $R_{101}$, $R_{111}$, $R_{112}$, and $R_{109}$ in Formula 201A may be understood by referring to the description provided herein.

For example, the compound represented by Formula 201 and the compound represented by Formula 202 may include Compounds HT1 to HT20 illustrated below, but are not limited thereto:

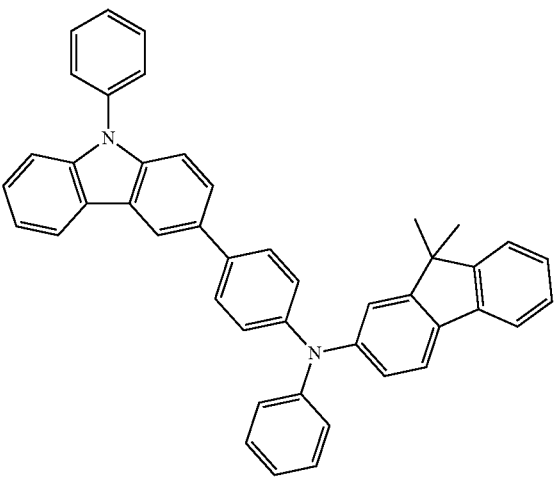

HT1

HT2
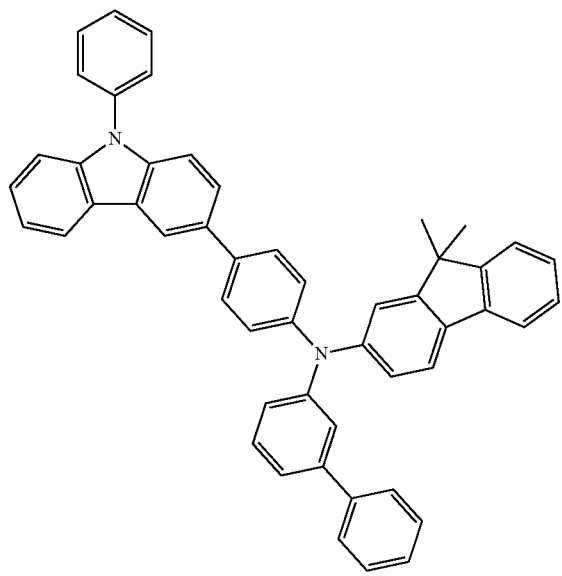
HT4
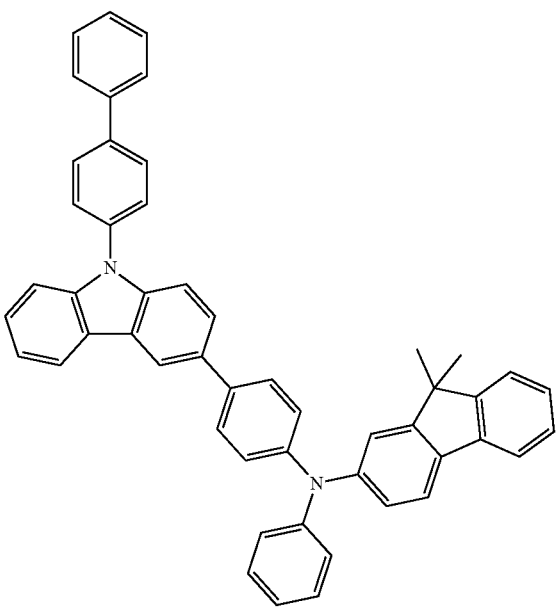
HT3
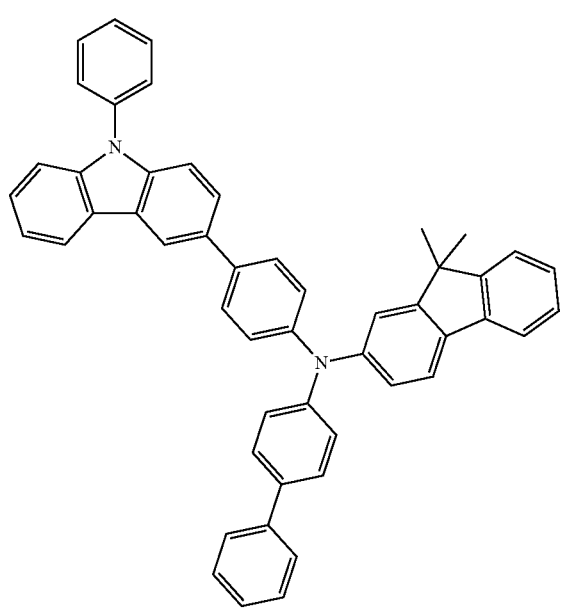
HT5
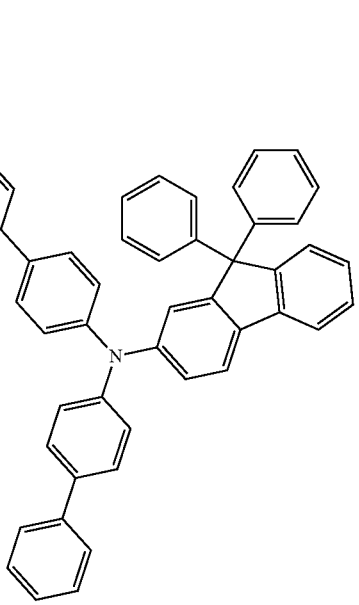

HT6
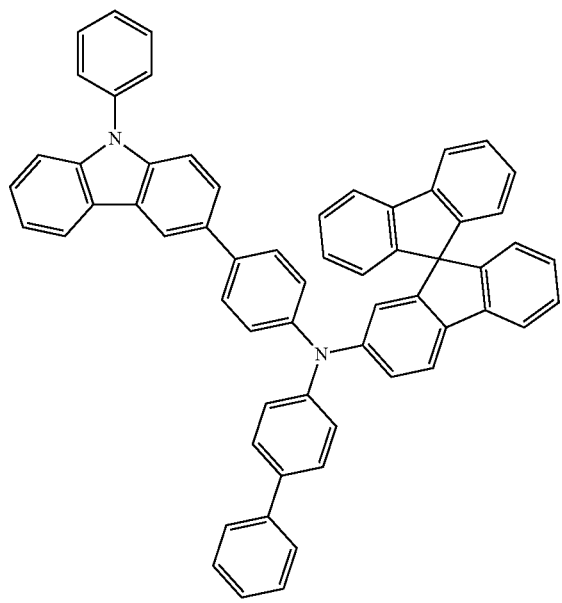
HT8
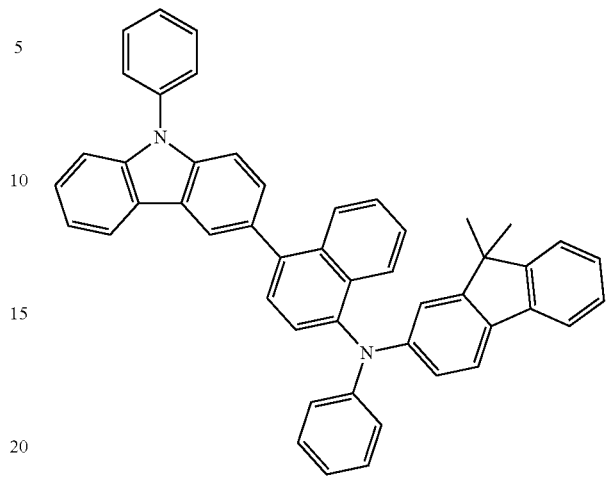
HT9
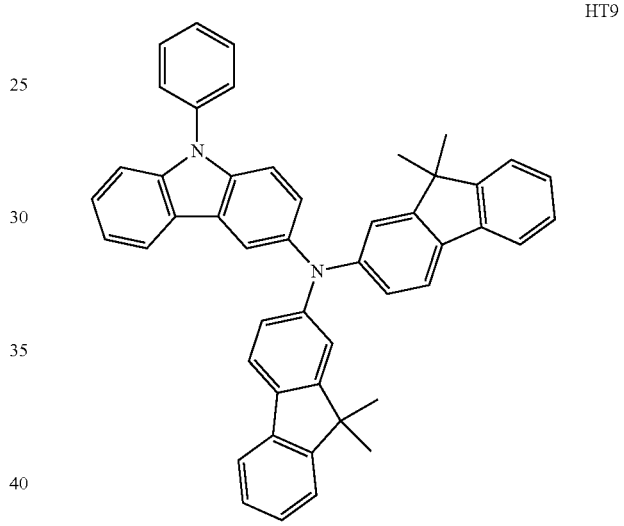
HT7
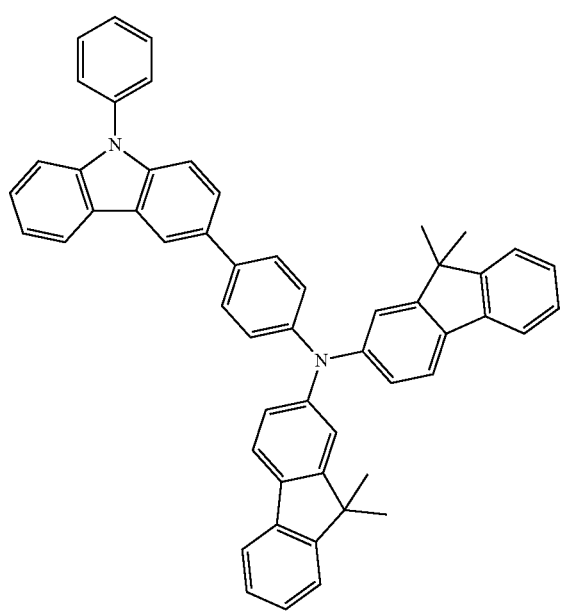
HT10
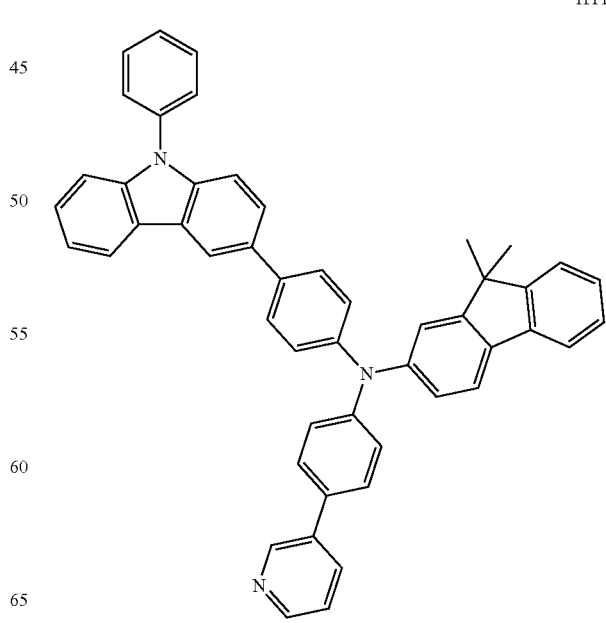

HT11
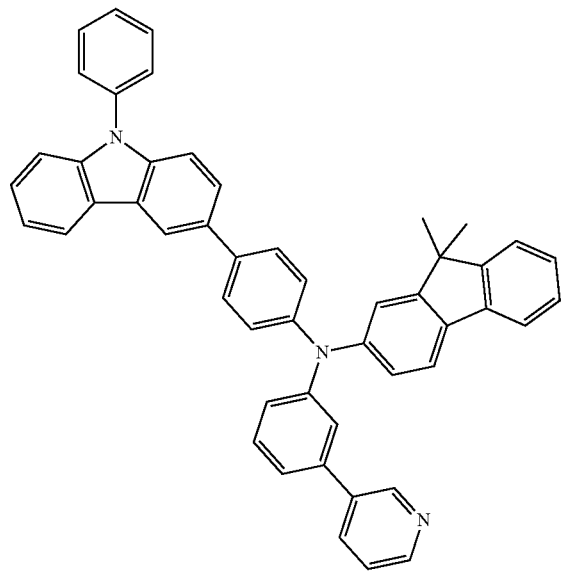
HT12
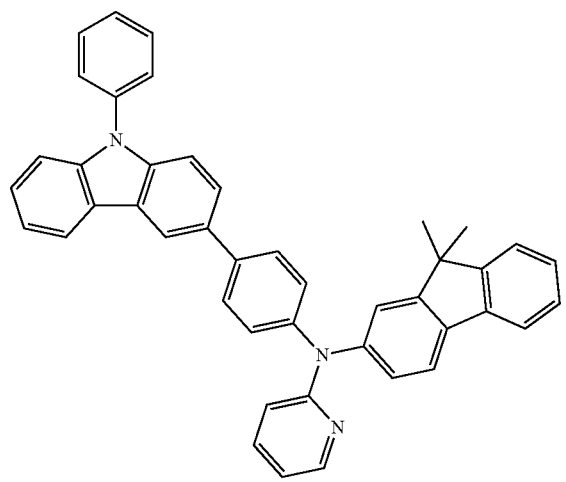
HT13
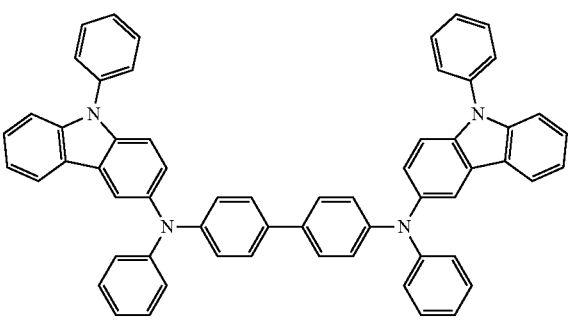
HT14
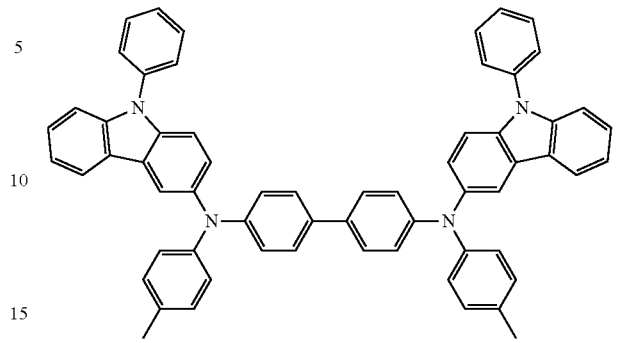
HT15
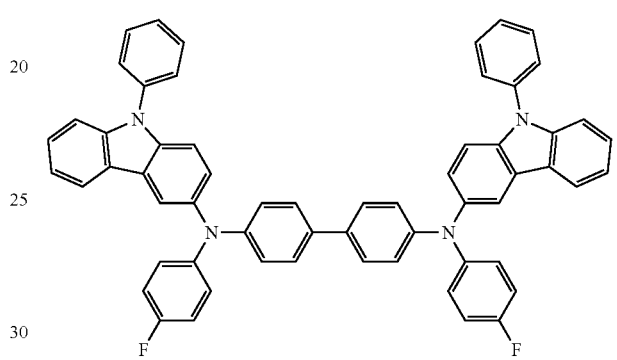
HT16
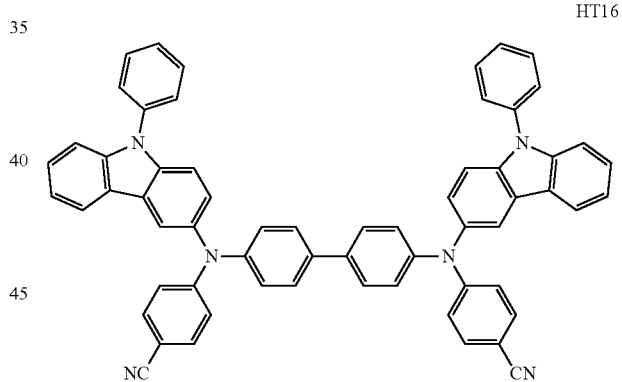
HT17
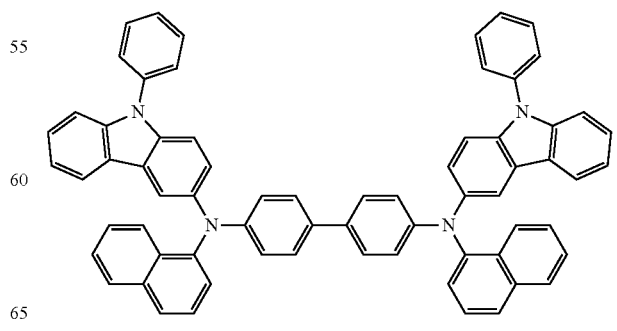

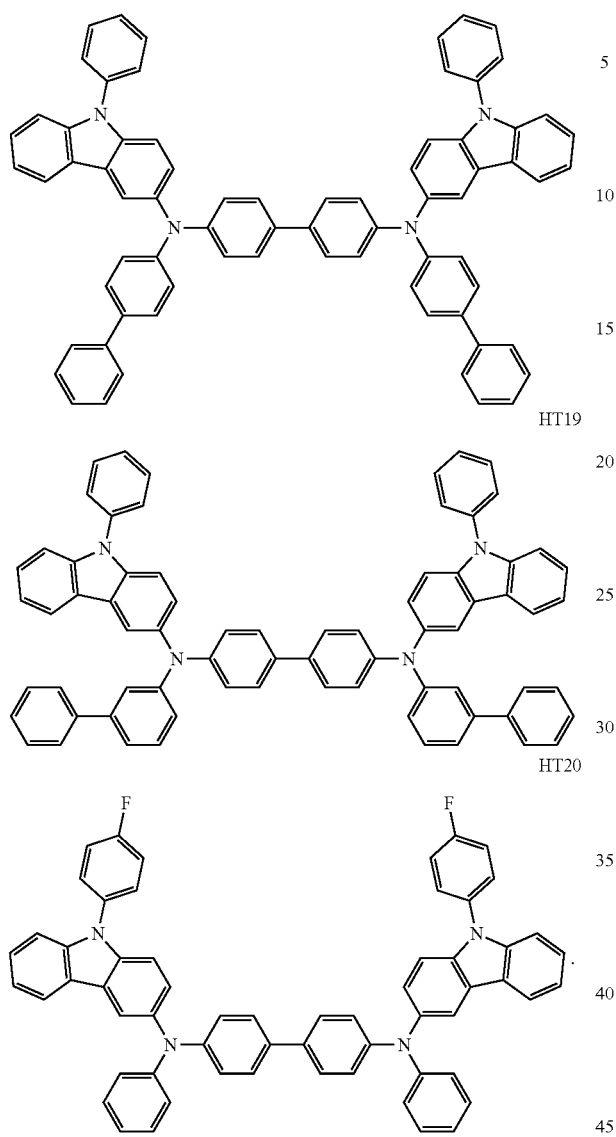

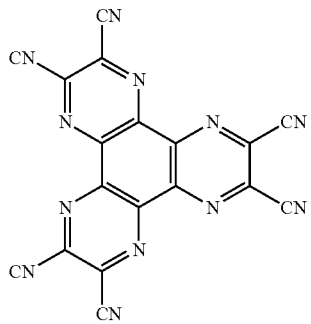

HT-D1

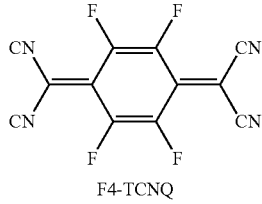

F4-TCNQ derivative, a metal oxide, and a cyano group-containing compound, but embodiments of the present disclosure are not limited thereto. Non-limiting examples of the p-dopant are a quinone derivative, such as tetracyanoquinonedimethane (TCNQ) or 2,3,5,6-tetrafluoro-tetracyano-1,4-benzoquinonedimethane (F4-TCNQ); a metal oxide, such as a tungsten oxide or a molybdenum oxide; and a cyano group-containing compound, such as Compound HT-D1 or HP-1, but are not limited thereto:

Compound HP-1

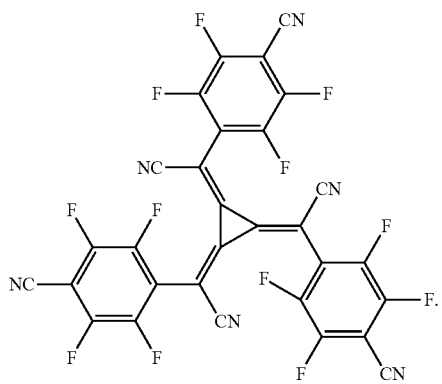

A thickness of the hole transport region may be in a range of about 100 Å to about 10,000 Å, for example, about 100 Å to about 1,000 Å. When the hole transport region includes a hole injection layer and a hole transport layer, the thickness of the hole injection layer may be in a range of about 100 Å to about 10,000 Å, and for example, about 100 Å to about 1,000 Å, and the thickness of the hole transport layer may be in a range of about 50 Å to about 2,000 Å, and for example, about 100 Å to about 1,500 Å. While not wishing to be bound by theory, it is understood that when the thicknesses of the hole transport region, the hole injection layer, and the hole transport layer are within these ranges, satisfactory hole transporting characteristics may be obtained without a substantial increase in driving voltage.

The hole transport region may further include, in addition to these materials, a charge-generation material for the improvement of conductive properties. The charge-generation material may be homogeneously or non-homogeneously dispersed in the hole transport region.

The charge-generation material may be, for example, a p-dopant. The p-dopant may be one selected from a quinone The hole transport region may include a buffer layer.

Also, the buffer layer may compensate for an optical resonance distance according to a wavelength of light emitted from the emission layer, and thus, efficiency of a formed organic light-emitting device may be improved.

The electron transport region may further include an electron blocking layer. The electron blocking layer may include, for example, mCP, but a material therefor is not limited thereto:

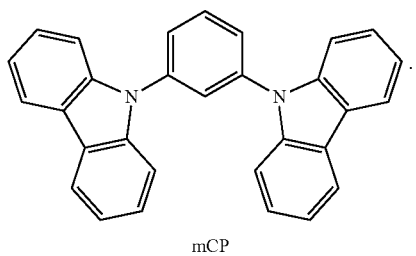 [SMILES: c1cc(-n2c3ccccc3c3ccccc32)cc(-n2c3ccccc3c3ccccc32)c1]

mCP

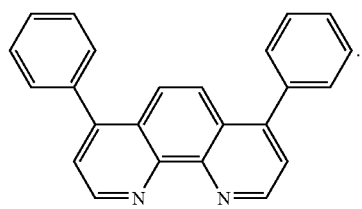

Bphen

Then, an emission layer may be formed on the hole transport region by vacuum deposition, spin coating, casting, LB deposition, or the like. When the emission layer is formed by vacuum deposition or spin coating, the deposition or coating conditions may be similar to those used to form the hole injection layer, although the deposition or coating conditions may vary according to the compound that is used to form the emission layer.

When the organic light-emitting device is a full-color organic light-emitting device, the emission layer may be patterned into a red emission layer, a green emission layer, and a blue emission layer. In one or more embodiments, due to a stacked structure including a red emission layer, a green emission layer, and/or a blue emission layer, the emission layer may emit white light.

The emission layer is the same as described above.

A thickness of the emission layer may be in a range of about 100 Å to about 1,000 Å, for example, about 200 Å to about 600 Å. While not wishing to be bound by theory, it is understood that when the thickness of the emission layer is within this range, excellent light-emission characteristics may be obtained without a substantial increase in driving voltage.

Then, an electron transport region may be disposed on the emission layer.

The electron transport region may include at least one selected from a hole blocking layer, an electron transport layer, and an electron injection layer.

For example, the electron transport region may have a hole blocking layer/electron transport layer/electron injection layer structure or an electron transport layer/electron injection layer structure, but the structure of the electron transport region is not limited thereto. The electron transport layer may have a single-layered structure or a multi-layered structure including two or more different materials.

Conditions for forming the hole blocking layer, the electron transport layer, and the electron injection layer which constitute the electron transport region may be understood by referring to the conditions for forming the hole injection layer.

When the electron transport region includes a hole blocking layer, the hole blocking layer may include, for example, at least one of BCP and Bphen, but may also include other materials:

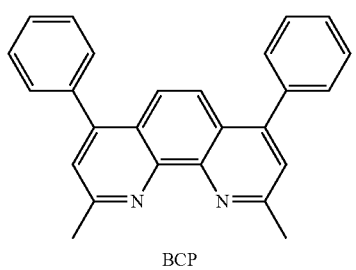

BCP

The hole blocking layer may include a compound selected from the hosts described above. For example, the hole blocking layer may include Compound H19, but embodiments of the present disclosure are not limited thereto.

A thickness of the hole blocking layer may be in a range of about 20 Å to about 1,000 Å, for example, about 30 Å to about 300 Å. While not wishing to be bound by theory, it is understood that when the thickness of the hole blocking layer is within these ranges, the hole blocking layer may have an improved hole blocking ability without a substantial increase in driving voltage.

The electron transport layer may further include at least one selected from BCP, Bphen, Alq$_3$, BAlq, TAZ, and NTAZ:

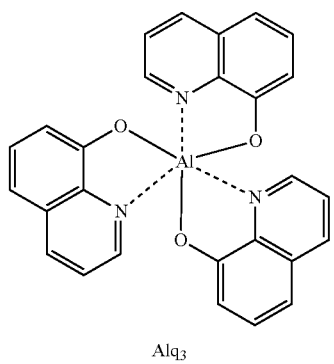

Alq$_3$

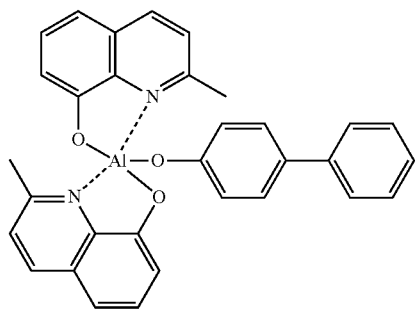

BAlq

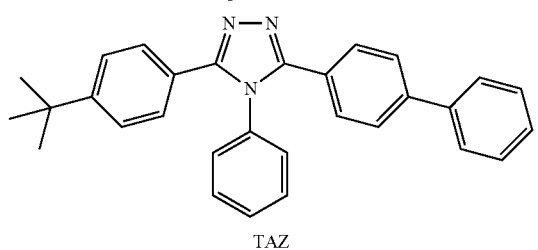

TAZ

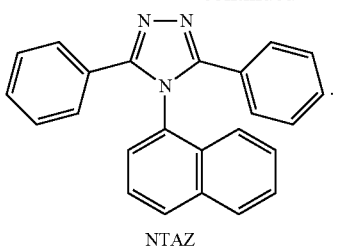

NTAZ

In one or more embodiments, the electron transport layer may include at least one selected from Compounds ET1, ET2, and ET3, but embodiments of the present disclosure are not limited thereto:

ET1
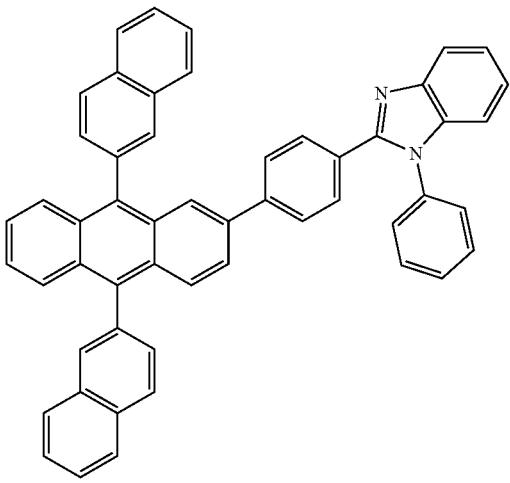

ET2
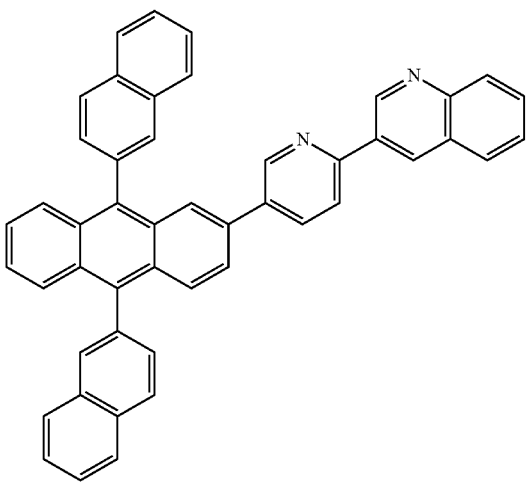

ET3
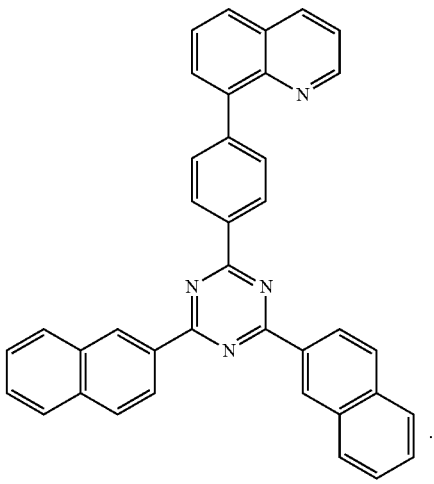

A thickness of the electron transport layer may be in a range of about 100 Å to about 1,000 Å, for example, about 150 Å to about 500 Å. While not wishing to be bound by theory, it is understood that when the thickness of the electron transport layer is within the range described above, the electron transport layer may have satisfactory electron transport characteristics without a substantial increase in driving voltage.

Also, the electron transport layer may further include, in addition to the materials described above, a metal-containing material.

The metal-containing material may include a Li complex. The Li complex may include, for example, Compound ET-D1 (lithium quinolate, LiQ) or ET-D2:

ET-D1
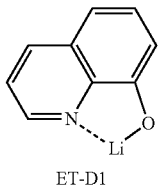

ET-D2
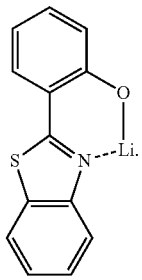

In addition, the electron transport region may include an electron injection layer that promotes injection of electrons from the second electrode 19.

The electron injection layer may include at least one selected from LiF, a NaCl, CsF, $Li_2O$, and BaO.

A thickness of the electron injection layer may be in a range of about 1 Å to about 100 Å, for example, about 3 Å to about 90 Å. While not wishing to be bound by theory, it is understood that when the thickness of the electron injection layer is within the range described above, the electron injection layer may have satisfactory electron injection characteristics without a substantial increase in driving voltage.

The second electrode 19 is disposed on the organic layer 15. The second electrode 19 may be a cathode. A material for forming the second electrode 19 may be selected from metal, an alloy, an electrically conductive compound, and a combination thereof, which have a relatively low work function. For example, lithium (Li), magnesium (Mg), aluminum (Al), aluminum-lithium (Al—Li), calcium (Ca), magnesium-indium (Mg—In), or magnesium-silver (Mg—Ag) may be used as a material for forming the second electrode 19. In one or more embodiments, to manufacture a top-emission-type light-emitting device, a transmissive electrode formed using ITO or IZO may be used as the second electrode 19.

Hereinbefore, the organic light-emitting device has been described with reference to the FIGURE, but embodiments of the present disclosure are not limited thereto.

The term "$C_1$-$C_{60}$ alkyl group" as used herein refers to a linear or branched saturated aliphatic hydrocarbon monovalent group having 1 to 60 carbon atoms, and non-limiting examples thereof include a methyl group, an ethyl group, a propyl group, an iso-butyl group, a sec-butyl group, a tert-butyl group, a pentyl group, an iso-amyl group, and a hexyl group. The term "$C_1$-$C_{60}$ alkylene group" as used herein refers to a divalent group having the same structure as the $C_1$-$C_{60}$ alkyl group.

The term "$C_1$-$C_{60}$ alkoxy group" as used herein refers to a monovalent group represented by —$OA_{101}$ (wherein $A_{101}$ is the $C_1$-$C_{60}$ alkyl group), and non-limiting examples thereof include a methoxy group, an ethoxy group, and an iso-propyloxy group.

The term "$C_2$-$C_{60}$ alkenyl group" as used herein refers to a hydrocarbon group formed by including at least one carbon-carbon double bond in the middle or at the terminus of the $C_2$-$C_{60}$ alkyl group, and examples thereof include an ethenyl group, a propenyl group, and a butenyl group. The term "$C_2$-$C_{60}$ alkenylene group" as used herein refers to a divalent group having the same structure as the $C_2$-$C_{60}$ alkenyl group.

The term "$C_2$-$C_{60}$ alkynyl group" as used herein refers to a hydrocarbon group formed by including at least one carbon-carbon triple bond in the middle or at the terminus of the $C_2$-$C_{60}$ alkyl group, and examples thereof include an ethynyl group, and a propynyl group. The term "$C_2$-$C_{60}$ alkynylene group" as used herein refers to a divalent group having the same structure as the $C_2$-$C_{60}$ alkynyl group.

The term "$C_3$-$C_{10}$ cycloalkyl group" as used herein refers to a monovalent saturated hydrocarbon monocyclic group having 3 to 10 carbon atoms, and non-limiting examples thereof include a cyclopropyl group, a cyclobutyl group, a cyclopentyl group, a cyclohexyl group, and a cycloheptyl group. The term "$C_3$-$C_{10}$ cycloalkylene group" as used herein refers to a divalent group having the same structure as the $C_3$-$C_{10}$ cycloalkyl group.

The term "$C_2$-$C_{10}$ heterocycloalkyl group" as used herein refers to a monovalent saturated monocyclic group having at least one heteroatom selected from N, O, P, Si, and S as a ring-forming atom and 2 to 10 carbon atoms, and non-limiting examples thereof include a tetrahydrofuranyl group and a tetrahydrothiophenyl group. The term "$C_2$-$C_{10}$ heterocycloalkylene group" as used herein refers to a divalent group having the same structure as the $C_2$-$C_{10}$ heterocycloalkyl group.

The term "$C_3$-$C_{10}$ cycloalkenyl group" as used herein refers to a monovalent monocyclic group that has 3 to 10 carbon atoms and at least one carbon-carbon double bond in the ring thereof and no aromaticity, and non-limiting examples thereof include a cyclopentenyl group, a cyclohexenyl group, and a cycloheptenyl group. The term "$C_3$-$C_{10}$ cycloalkenylene group" as used herein refers to a divalent group having the same structure as the $C_3$-$C_{10}$ cycloalkenyl group.

The term "$C_2$-$C_{10}$ heterocycloalkenyl group" as used herein refers to a monovalent monocyclic group that has at least one heteroatom selected from N, O, P, Si, and S as a ring-forming atom, 2 to 10 carbon atoms, and at least one carbon-carbon double bond in its ring. Examples of the $C_2$-$C_{10}$ heterocycloalkenyl group are a 2,3-dihydrofuranyl group and a 2,3-dihydrothiophenyl group. The term "$C_2$-$C_{10}$ heterocycloalkenylene group" as used herein refers to a divalent group having the same structure as the $C_2$-$C_{10}$ heterocycloalkenyl group.

The term "$C_6$-$C_{60}$ aryl group" as used herein refers to a monovalent group having a carbocyclic aromatic system having 6 to 60 carbon atoms, and the term "$C_6$-$C_{60}$ arylene group" as used herein refers to a divalent group having a carbocyclic aromatic system having 6 to 60 carbon atoms. Non-limiting examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

The term "$C_1$-$C_{60}$ heteroaryl group" as used herein refers to a monovalent group having a heterocyclic aromatic system that has at least one heteroatom selected from N, O, P, Si, and S as a ring-forming atom, and 2 to 60 carbon atoms. The term "$C_2$-$C_{60}$ heteroarylene group," as used herein refers to a divalent group having a heterocyclic aromatic system that has at least one heteroatom selected from N, O, P, Si, and S as a ring-forming atom, and 2 to 60 carbon atoms. Non-limiting examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_2$-$C_{60}$ heteroarylene group each include two or more rings, the rings may be fused to each other.

The term "$C_6$-$C_{60}$ aryloxy group" as used herein refers to —$OA_{102}$ (wherein $A_{102}$ is the $C_6$-$C_{60}$ aryl group), and a $C_6$-$C_{60}$ arylthio group used herein indicates —$SA_{103}$ (wherein $A_{103}$ is the $C_6$-$C_{60}$ aryl group).

The term "monovalent non-aromatic condensed polycyclic group" as used herein refers to a monovalent group having two or more rings condensed to each other, only carbon atoms (for example, the number of carbon atoms may be in a range of 8 to 60) as ring-forming atoms, and no aromaticity in its entire molecular structure. Non-limiting examples of the monovalent non-aromatic condensed polycyclic group include a fluorenyl group. The term "divalent non-aromatic condensed polycyclic group," as used herein, refers to a divalent group having the same structure as the monovalent non-aromatic condensed polycyclic group.

The term "monovalent non-aromatic condensed heteropolycyclic group" as used herein refers to a monovalent group having two or more rings condensed to each other, a heteroatom selected from N, O, P, Si, and S, other than carbon atoms (for example, the number of carbon atoms may be in a range of 2 to 60), as a ring-forming atom, and no aromaticity in its entire molecular structure. Non-limiting examples of the monovalent non-aromatic condensed heteropolycyclic group include a carbazolyl group. The term "divalent non-aromatic condensed heteropolycyclic group" as used herein refers to a divalent group having the same structure as the monovalent non-aromatic condensed heteropolycyclic group.

The term "$C_5$-$C_{60}$ carbocyclic group" as used herein refers to a saturated or unsaturated cyclic group having, as ring-forming atoms, 5 to 60 carbon atoms only. The term "$C_5$-$C_{60}$ carbocyclic group" as used herein refers to a monocyclic group or a polycyclic group, and, according to its chemical structure, may be a monovalent, divalent, trivalent, tetravalent, pentavalent, or hexavalent group.

The term "$C_2$-$C_{60}$ heterocyclic group" as used herein refers to a saturated or unsaturated cyclic group having, as a ring-forming atom, at least one heteroatom selected from N, O, Si, P, and S, other than 2 to 60 carbon atoms. The term "$C_2$-$C_{60}$ heterocyclic group" as used herein refers to a monocyclic group or a polycyclic group, and, according to its chemical structure may be a monovalent, divalent, trivalent, tetravalent, pentavalent, or hexavalent group.

At least one substituent selected from the substituted $C_5$-$C_{60}$ carbocyclic group, the substituted $C_2$-$C_{60}$ heterocyclic group, the substituted π electron-depleted nitrogen-containing $C_2$-$C_{60}$ heterocyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), —B($Q_{16}$)($Q_{17}$), and —P(=O)($Q_{18}$)($Q_{19}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), —B($Q_{26}$)($Q_{27}$), and —P(=O)($Q_{28}$)($Q_{29}$); and —N($Q_{31}$)($Q_{32}$), —Si($Q_{33}$)($Q_{34}$)($Q_{35}$), —B($Q_{36}$)($Q_{37}$), and —P(=O)($Q_{38}$)($Q_{39}$), and $Q_1$ to $Q_9$, $Q_{11}$ to $Q_{19}$, $Q_{21}$ to $Q_{29}$, and $Q_{31}$ to $Q_{39}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with at least one selected from a $C_1$-$C_{60}$ alkyl group and a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

The term "room temperature" as used herein refers to about 25° C.

Hereinafter, a compound and an organic light-emitting device according to embodiments are described in detail with reference to Synthesis Examples and Examples. However, the organic light-emitting device is not limited thereto. The wording "'B' was used instead of 'A'" used in describing the Synthesis Examples means that an amount of 'A' used was identical to an amount of 'B' used, in terms of molar equivalents.

EXAMPLES

Synthesis Example 1: Synthesis of Compound 1

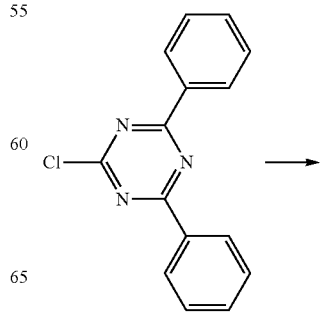

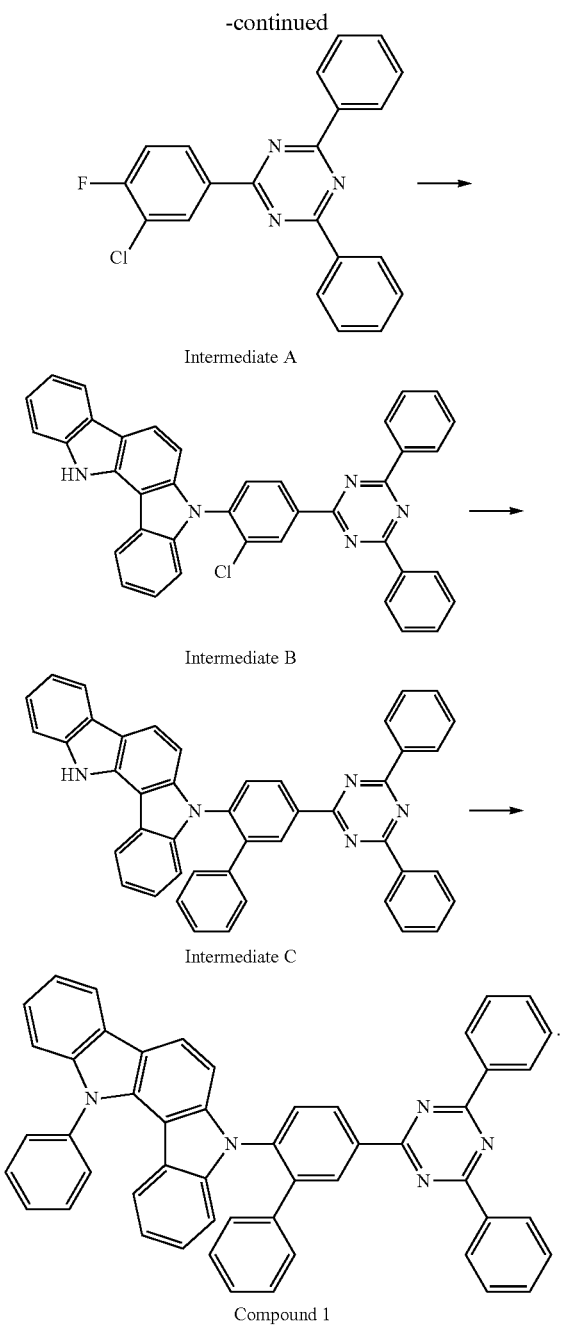

Intermediate A

Intermediate B

Intermediate C

Compound 1

(1) Synthesis of Intermediate A 13.4 grams (g) (50 millimoles, mmol) of 2-chloro-4,6-diphenyl-1,3,5-triazine, 9.59 g (55 mmol) of 3-chloro-4-fluorophenyl)boronic acid, 3.5 g (3 mmol) of tetrakis(triphenylphosphine)palladium (0) (Pd(PPh$_3$)$_4$), and 10.6 g (100 mmol) of sodium carbonate were dissolved in a mixed solution of 100 milliliters (mL) of toluene and 50 mL of water, and the resulting solution was stirred under reflux. When the reaction was complete, the reaction solution was cooled to room temperature. The aqueous solution layer was extracted therefrom, and the remaining product was filtered through silica gel under reduced pressure. The filtrate was purified by silica gel column chromatography and recrystallized with dichloromethane (DCM)/methanol (MeOH) to obtain 14.8 g (yield: 82%) of Intermediate A.

LC-Mass (calculated: 361.80 g/mol, measured: M+1=362 g/mol) (wherein "g/mol" denotes "grams per mole")

(2) Synthesis of Intermediate B 3.61 g (10 mmol) of Intermediate A, 3.61 g (12 mmol) of 5,12-dihydroindolo[3,2-a]carbazole, and 6.5 g (20 mmol) of caesium carbonate were dissolved in 50 mL of DMF, and the resulting solution was stirred under reflux. When the reaction was complete, the reaction solution was cooled to room temperature. The aqueous solution layer was extracted therefrom, and the remaining product was filtered through silica gel under reduced pressure. The filtrate was purified by silica gel column chromatography and recrystallized with DCM/MeOH to obtain 4.7 g (yield: 78%) of Intermediate B.

LC-Mass (calculated: 598.09 g/mol, measured: M+1=599 g/mol)

(3) Synthesis of Intermediate C 4.2 g (7 mmol) of Intermediate B, 1.0 g (8.4 mmol) of phenylboronic acid, 0.05 g (0.2 mmol) of palladium acetate, 6.5 g (0.17 mmol) of S-Phos, and 1.9 g (14 mmol) of potassium carbonate were dissolved in 50 mL of 1,4-dioxane, and the resulting solution was stirred under reflux. When the reaction was complete, the reaction solution was cooled to room temperature. The aqueous solution layer was extracted therefrom, and the remaining product was filtered through silica gel under reduced pressure. The filtrate was purified by silica gel column chromatography and recrystallized with DCM/MeOH to obtain 3.7 g (yield: 83%) of Intermediate C.

LC-Mass (calculated: 639.75 g/mol, measured: M+1=640 g/mol)

(4) Synthesis of Compound 1

3.2 g (5 mmol) of Intermediate C, 1.0 g (6.5 mmol) of bromobenzene, 1.0 g (10 mmol) of sodium tert-butoxide, 0.18 g (0.2 mmol) of tris(dibenzylacetone)dipalladium (0), and 0.16 g (0.8 mmol) of tri-tert-butylphosphine were dissolved in 50 mL of toluene, and the resulting solution was stirred under reflux. When the reaction was complete, the reaction solution was cooled to room temperature. The aqueous solution layer was extracted therefrom, and the remaining product was filtered through silica gel under reduced pressure. The filtrate was purified by silica gel column chromatography and recrystallized with DCM/MeOH to obtain 3.0 g (yield: 85%) of Compound 1.

LC-Mass (calculated: 715.84 g/mol, measured: M+1=716 g/mol)

Synthesis Example 2: Synthesis of Compound 2

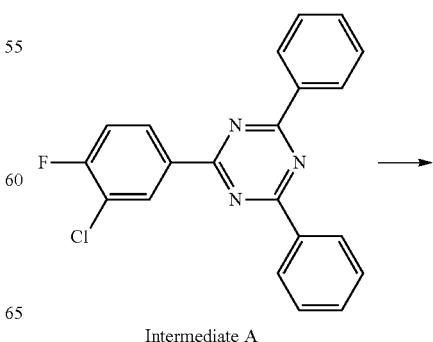

Intermediate A

Synthesis Example 3: Synthesis of Compound 3

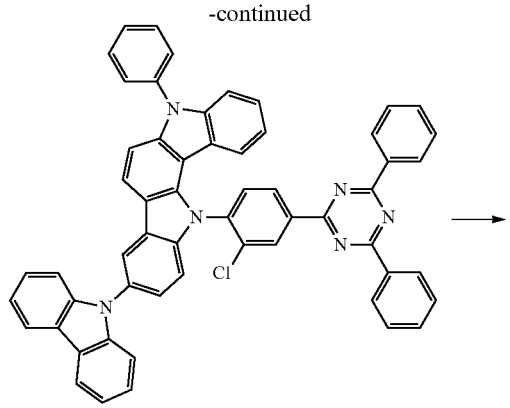

Intermediate D

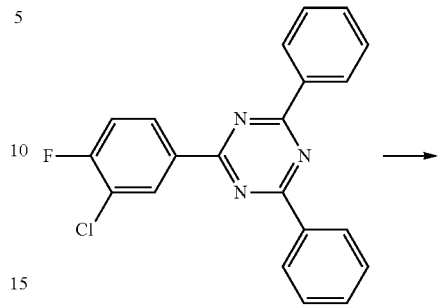

Intermediate A

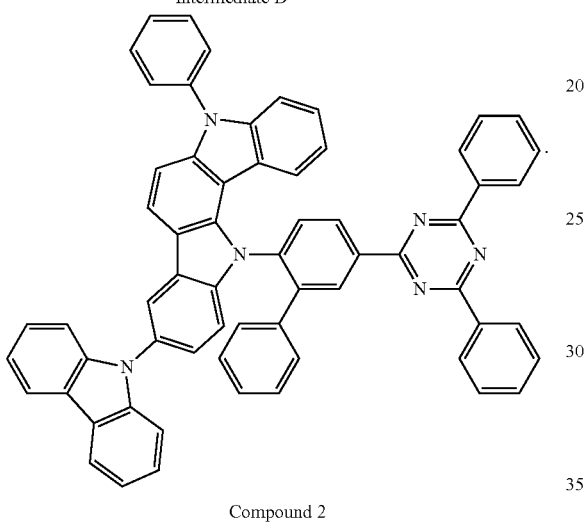

Compound 2

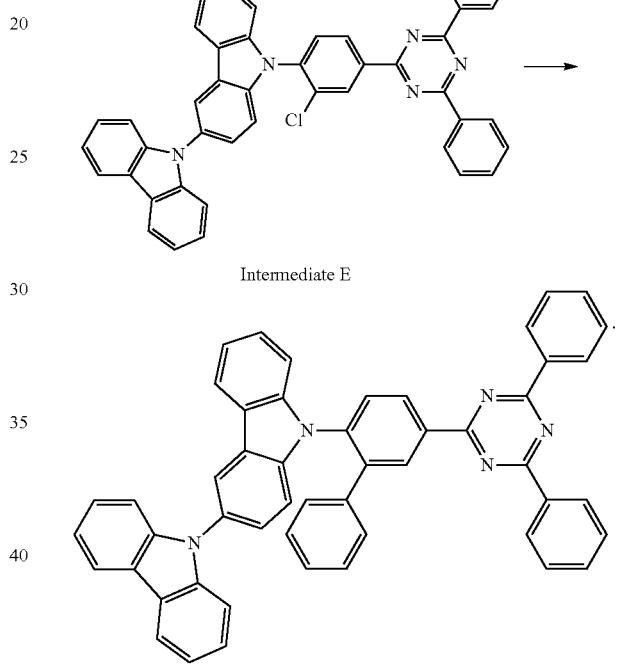

Intermediate E

Compound 3

(1) Synthesis of Intermediate D 3.61 g (10 mmol) of Intermediate A, 6.0 g (12 mmol) of 9-(9H-carbazol-9-yl)-5-phenyl-5,12-dihydroindolo[3,2-a]carbazole, and 6.5 g (20 mmol) of caesium carbonate were dissolved in 50 mL of DMF, and the resulting solution was stirred under reflux. When the reaction was complete, the reaction solution was cooled to room temperature. The aqueous solution layer was extracted therefrom, and the remaining product was filtered through silica gel under reduced pressure. The filtrate was purified by silica gel column chromatography and recrystallized with DCM/MeOH to obtain 6.3 g (yield: 75%) of Intermediate D.

LC-Mass (calculated: 839.38 g/mol, measured: M+1=840 g/mol)

(2) Synthesis of Compound 2

5.9 g (7 mmol) of Intermediate D, 1.0 g (8.4 mmol) of phenylboronic acid, 0.05 g (0.2 mmol) of palladium acetate, 6.5 g (0.17 mmol) of S-Phos, and 1.9 g (14 mmol) of potassium carbonate were dissolved in 70 mL of 1,4-dioxane, and the resulting solution was stirred under reflux. When the reaction was complete, the reaction solution was cooled to room temperature. The aqueous solution layer was extracted therefrom, and the remaining product was filtered through silica gel under reduced pressure. The filtrate was purified by silica gel column chromatography and recrystallized with DCM/MeOH to obtain 4.7 g (yield: 75%) of Compound 2.

LC-Mass (calculated: 881.03 g/mol, measured: M+1=882 g/mol)

(1) Synthesis of Intermediate E 3.61 g (10 mmol) of Intermediate A, 3.1 g (12 mmol) of 9H-3,9'-bicarbazole, and 6.5 g (20 mmol) of caesium carbonate were dissolved in 50 mL of DMF, and the resulting solution was stirred under reflux. When the reaction was complete, the reaction solution was cooled to room temperature. The aqueous solution layer was extracted therefrom, and the remaining product was filtered through silica gel under reduced pressure. The filtrate was purified by silica gel column chromatography and recrystallized with DCM/MeOH to obtain 5.2 g (yield: 77%) of Intermediate E.

LC-Mass (calculated: 674.19 g/mol, measured: M+1=675 g/mol)

(2) Synthesis of Compound 3

4.7 g (7 mmol) of Intermediate E, 1.0 g (8.4 mmol) of phenylboronic acid, 0.05 g (0.2 mmol) of palladium acetate, 6.5 g (0.17 mmol) of S-Phos, and 1.9 g (14 mmol) of potassium carbonate were dissolved in 70 mL of 1,4-dioxane, and the resulting solution was stirred under reflux. When the reaction was complete, the reaction solution was cooled to room temperature. The aqueous solution layer was extracted therefrom, and the remaining product was filtered through silica gel under reduced pressure. The filtrate was purified by silica gel column chromatography and recrystallized with DCM/MeOH to obtain 3.8 g (yield: 76%) of Compound 3.

LC-Mass (calculated: 715.84 g/mol, measured: M+1=716 g/mol)

Evaluation Example 1

According to the methods described in Table 2, photoluminescence (PL) spectra, HOMO levels, LUMO levels, $S_1$ energy levels, $T_1$ energy levels, and $\Delta E_{ST}$ of Compounds 1, 2, 3, A, B, and C were evaluated, and the results are shown in Table 3:

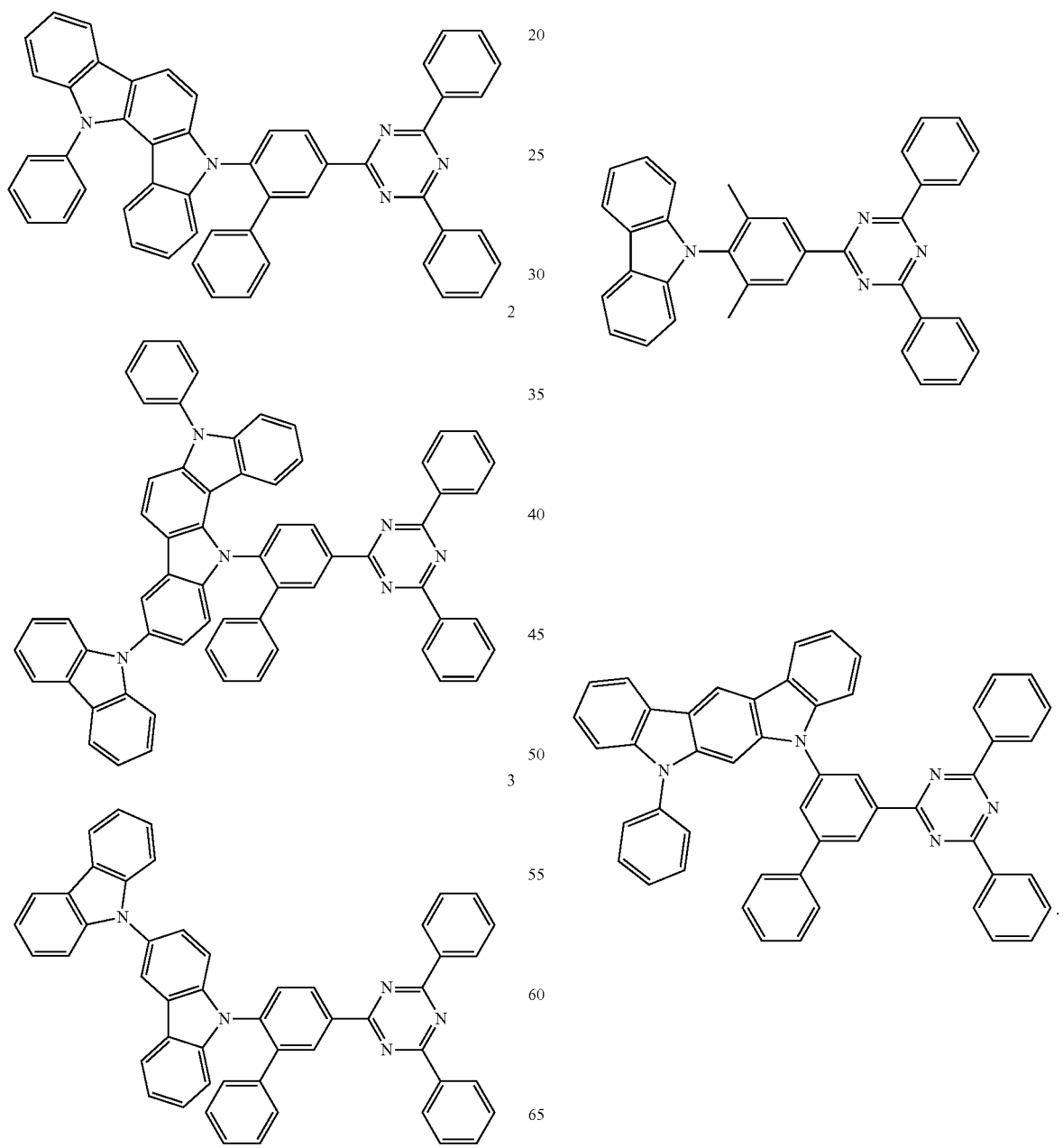

TABLE 2

| | |
|---|---|
| Photoluminescence (PL) spectrum | Each compound was diluted using toluene to have a concentration of $10^{-5}$ molar (M), and a photoluminescence (PL) spectrum thereof was measured using an F7000 spectrofluorometer (manufactured by Hitachi company) equipped with a Xenon lamp (@ 298 Kelvin, K) |
| $S_1$ energy level evaluation | A PL spectrum of a mixture of toluene and each compound (diluted to have a concentration of $1 \times 10^{-4}$M) was measured at room temperature by using a photoluminescence spectrometer, and peaks observed on the photoluminescence spectrum were analyzed to calculate an onset S1 energy level |
| $T_1$ energy level evaluation method | A PL spectrum of a mixture of toluene and each compound (diluted to have a concentration of $1 \times 10^{-4}$M) was loaded into a quartz cell, and the resultant quartz cell was loaded into liquid nitrogen (77K). A PL spectrum thereof was measured by using a device, and the obtained spectrum was compared with a PL spectrum measured at room temperature. Then, peaks observed only at a low temperature were analyzed to calculate an onset T1 energy level |
| $\Delta E_{ST}$ | A difference between the $S_1$ energy level and the $T_1$ energy level of each compound was calculated |

TABLE 3

| Compound No. | HOMO (eV) | LUMO (eV) | $S_1$ energy level (eV) | $T_1$ energy level (eV) | $\Delta E_{ST}$ (eV) | Maximum emission wavelength in PL spectrum (nm) |
|---|---|---|---|---|---|---|
| 1 | −5.39 | −2.52 | 2.91 | 2.84 | 0.07 | 455 |
| 2 | −5.38 | −2.46 | 2.92 | 2.92 | 0.00 | 467 |
| 3 | −5.49 | −2.51 | 3.06 | 2.90 | 0.16 | 457 |
| A | −5.79 | −2.42 | 3.04 | 2.96 | 0.08 | 423 |
| B | −5.83 | −2.45 | 3.07 | 2.99 | 0.08 | 425 |
| C | −5.21 | −2.49 | 2.87 | 2.64 | 0.23 | 497 |

Referring to Table 3, it was confirmed that Compounds 1, 2, and 3 had a deep blue color, and at the same time, were able to emit light, i.e., heat-activated delayed fluorescence.

Evaluation Example 2

Compounds H19 and 1 (15 percent by weight, weight %) were co-deposited on a quartz cell to form Film 1 having a thickness of 100 Angstroms (Å). Using the same method, Films 2, 3, A, B, and C, respectively, were prepared using Compounds 2, 3, A, B, and C, instead of Compound 1. Afterwards, PL quantum yields of Films 1, 2, 3, A, B, and C were measured as being excited at an excitation wavelength of 340 nanometers (nm) under a nitrogen atmosphere by using a C9920-02 measurement system and a PMA-11 analyzer (manufactured by Hamamatsu photonics company), and the results are shown in Table 4:

TABLE 4

| Film No. | Film component | PL quantum yield (%) |
|---|---|---|
| 1 | H19:1 (15 wt %) | 0.74 |
| 2 | H19:2 (15 wt %) | 0.73 |
| 3 | H19:3 (15 wt %) | 0.72 |
| A | H19:A (15 wt %) | 0.69 |
| B | H19:B (15 wt %) | 0.67 |
| C | H19:C (15 wt %) | 0.24 |

Referring to Table 4, it was determined that Films 1 to 3 showed higher PL quantum yields than those of Films A to C.

Example 1

A glass substrate on which an indium tin oxide (ITO) electrode (a first electrode, an anode) having a thickness of 1,500 Å was formed was ultrasonically cleaned with distilled water. Once completed, the glass substrate was sonicated with iso-propyl alcohol, acetone, and methanol in this stated order, dried, and transferred into a plasma cleaning device. The glass substrate was cleaned with oxygen plasma for 5 minutes, and then, transferred into a vacuum deposition device.

Compound HT3 was vacuum deposited on the ITO electrode of the glass substrate to form a first hole injection layer having a thickness of 100 Å. Compound HT-D1 was vacuum-deposited on the first hole injection layer to form a second hole injection layer having a thickness of 100 Å. mCP was deposited on the second hole injection layer to form an electron blocking layer having a thickness of 150 Å, thereby forming a hole transport region.

Compound H19 (host) and Compound 1 (dopant) were co-deposited on the hole transport region at a volume ratio of 85:15 to form an emission layer having a thickness of 300 Å.

Compound ET3 was vacuum-deposited on the emission layer to form an electron transport layer having a thickness of 300 Å, and Compound ET-D1 (Liq) was deposited on the electron transport layer to form an electron injection layer having a thickness of 10 Å. Al was deposited on the electron injection layer to form an AL second electrode (cathode) having a thickness of 1,200 Å, thereby completing the manufacture of an organic light-emitting device:

HT3

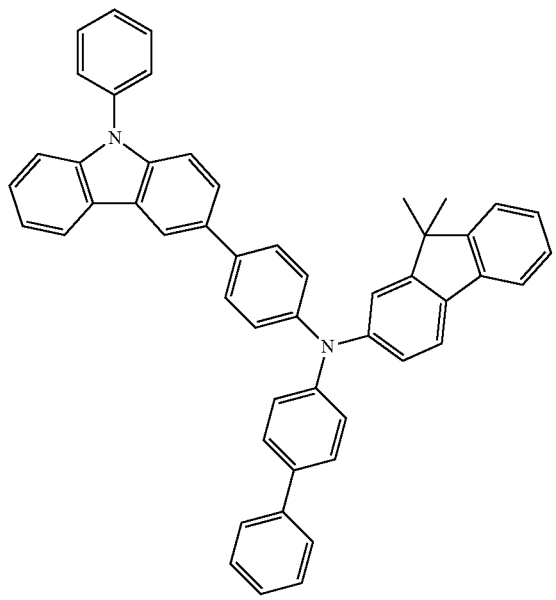

HT-D1

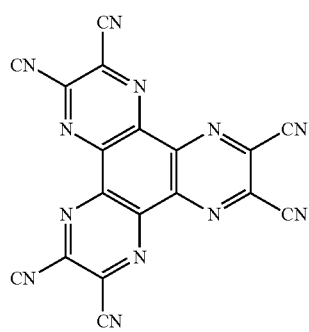

mCP

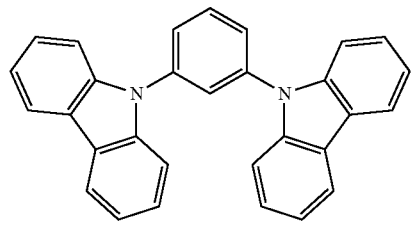

H19

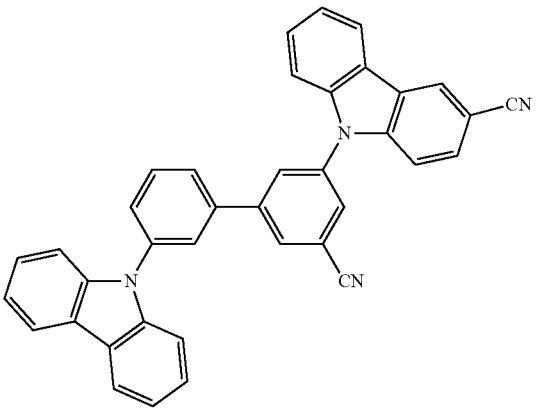

ET3

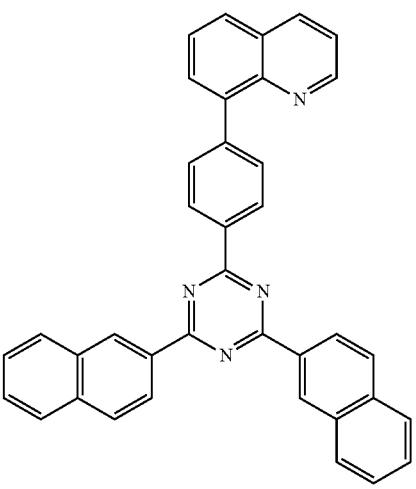

Examples 2 and 3 and Comparative Examples A to C

Organic light-emitting devices were manufactured in the same manner as in Example 1, except that Compounds shown in Table 5 were each used instead of Compound 1 as a dopant, in forming an emission layer.

Evaluation Example 3

The driving voltage, external quantum yield, maximum emission wavelength, and lifespan of the organic light-emitting devices manufactured according to Examples 1 to 3 and Comparative Examples A to C were measured by using a current-voltage meter (Keithley 2400) and a luminance meter (Minolta Cs-1000A) (at 500 candelas per square meter, $cd/m^2$), and the results are shown in Tables 5 and 6. In Table 6, the lifespan data $(T_{95})$(at 500 $cd/m^2$) indicate an amount of time (hours, hr) that had lapsed when luminance was 95% of initial luminance (100%).

TABLE 5

| Example No. | Host | Dopant | Driving voltage (V) | External quantum yield (measured value (%), relative value) |
|---|---|---|---|---|
| Example 1 | Compound H19 | Compound 1 | 3.8 | 21%, 2.63 |
| Example 2 | Compound H19 | Compound 2 | 3.7 | 20%, 2.50 |
| Example 3 | Compound H19 | Compound 3 | 3.9 | 14%, 1.75 |
| Comparative Example A | Compound H19 | Compound A | 4.2 | 8%, 1.00 |
| Comparative Example B | Compound H19 | Compound B | 4.1 | 7%, 0.86 |
| Comparative Example C | Compound H19 | Compound C | 3.9 | 5% 0.63 |

TABLE 6

| Example No. | Host | Dopant | Maximum emission wavelength (nm) | Emission color | $LT_{95}$@500 cd/m² (measured value (%), relative value) |
|---|---|---|---|---|---|
| Example 1 | Compound H19 | Compound 1 | 476 | Blue | 30, 5.66 |
| Example 2 | Compound H19 | Compound 2 | 479 | Blue | 23, 4.33 |
| Example 3 | Compound H19 | Compound 3 | 462 | Blue | 8, 1.51 |
| Comparative Example A | Compound H19 | Compound A | 424 | Blue | 5.3, 1.00 |
| Comparative Example B | Compound H19 | Compound B | 427 | Blue | 1.9, 0.55 |
| Comparative Example C | Compound H19 | Compound C | 494 | Light-blue | 5.2, 0.98 |

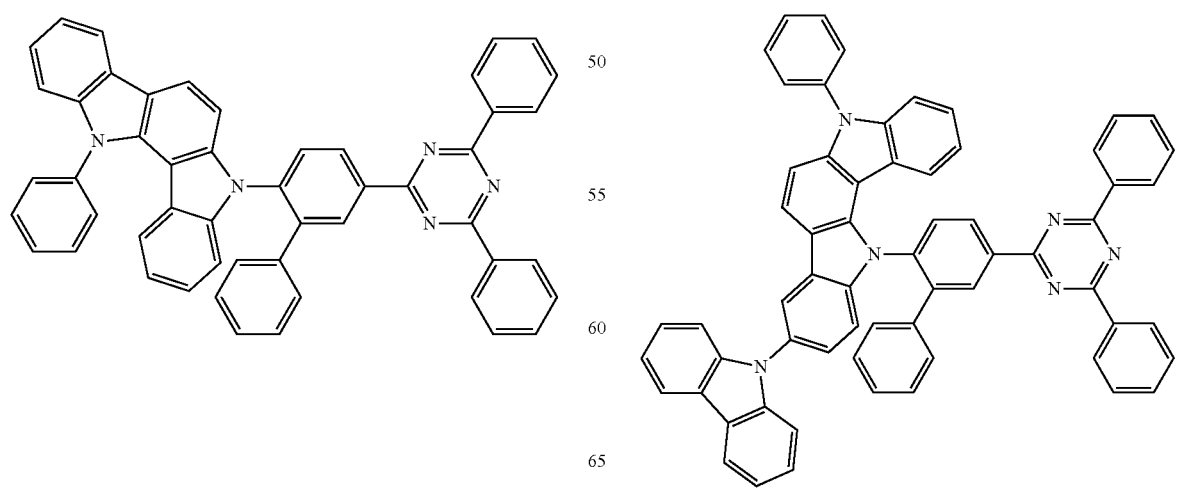

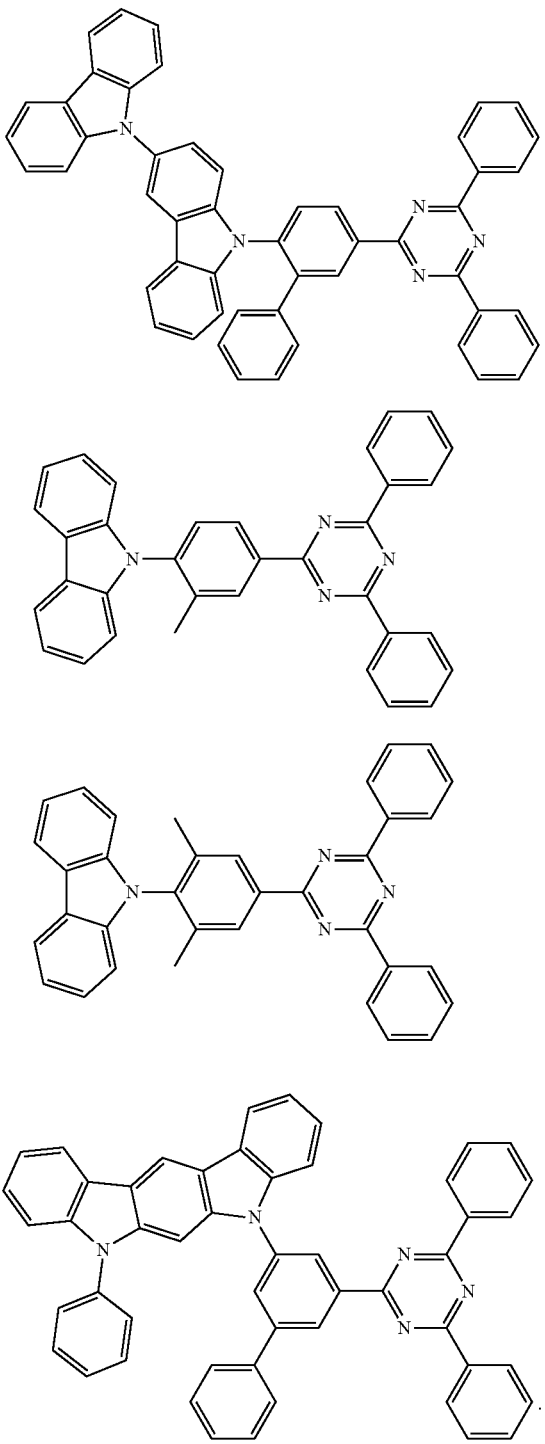

3

5

A

20

25

B 30

35

40

C

45

50

55

Referring to Tables 5 and 6, it was determined that the organic light-emitting devices manufactured according to Examples 1 to 3 had lower driving voltages and better external quantum yields and lifespan characteristics than those of the organic light-emitting devices manufactured according to Comparative Examples A to C, and at the same time, the organic light-emitting devices manufactured according to Examples 1 to 3 also emitted blue light.

As described above, a condensed cyclic compound has excellent delayed fluorescence emission characteristics, and an organic light-emitting device including the condensed cyclic compound has high luminescent efficiency and/or long lifespan.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the FIGURES, it will be understood by those of ordinary skill in the art that various changes in form and details may be made therein without departing from the spirit and scope of the present disclosure as defined by the following claims.

What is claimed is:

1. A condensed cyclic compound represented by Formula 1:

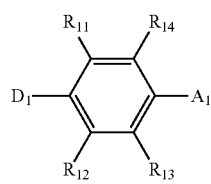

Formula 1

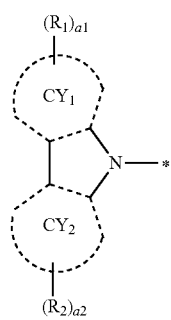

Formula 1-1

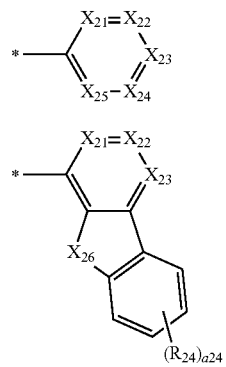

Formula 1-2

Formula 1-3

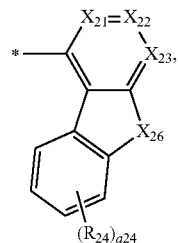

Formula 1-4 wherein $D_1$ in Formula 1 is a group represented by Formula 1-1, $A_1$ in Formula 1 is a group represented by Formula 1-2, 1-3, or 1-4, ring $CY_1$ and ring $CY_2$ in Formula 1-1 are each independently a benzene group, a fluorene group, a carbazole group, a dibenzofuran group, or a dibenzothiophene group, in Formulae 1-2 to 1-4, $X_{21}$ is N or $C(R_{21})$, $X_{22}$ is N or $C(R_{22})$, $X_{23}$ is N or $C(R_{23})$, $X_{24}$ is N or $C(R_{24})$, $X_{25}$ is N or $C(R_{25})$, and $X_{26}$ is O or S, wherein three of $X_{21}$ to $X_{25}$ in Formula 1-2 are each N, two or three of $X_{21}$ to $X_{25}$ in Formula 1-2 are each C(CN), or two of $X_{21}$ to $X_{23}$ in Formulae 1-3 and 1-4 are each N, in Formulae 1 and 1-1 to 1-4, $R_1$, $R_2$, $R_{11}$ to $R_{14}$, and $R_{21}$ to $R_{25}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{10}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_3$-$C_{10}$ heteroaryl group, a substituted or unsubstituted monovalent non-aromatic condensed polycyclic group, a substituted or unsubstituted monovalent non-aromatic condensed heteropolycyclic group, —Si$(Q_1)(Q_2)(Q_3)$, —N$(Q_4)(Q_5)$, and —B$(Q_6)(Q_7)$, wherein at least one of $R_{11}$ to $R_{14}$ are each independently selected from a cyano group, a substituted or unsubstituted $C_3$-$C_{10}$ cycloalkyl group, a substituted or unsubstituted $C_3$-$C_{10}$ cycloalkenyl group, a substituted or unsubstituted $C_6$-$C_{60}$ aryl group, and a substituted or unsubstituted monovalent non-aromatic condensed polycyclic group, a1 and a2 in Formula 1-1 are each independently an integer from 0 to 8, a24 in Formulae 1-3 to 1-4 is an integer from 0 to 4,

* indicates a binding site to a neighboring atom, wherein when $A_1$ in Formula 1 is a group represented by Formula 1-2, one of $R_{11}$ to $R_{12}$ is an unsubstituted phenyl group, and the one of $R_{11}$ and $R_{12}$ that is not an unsubstituted phenyl group, $R_{13}$ and $R_{14}$ are each hydrogen, at least one substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group is selected from:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a 06-060 aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si$(Q_{11})(Q_{12})(Q_{13})$, —N$(Q_{14})(Q_{15})$, and —B$(Q_{16})(Q_{17})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si$(Q_{21})(Q_{22})(Q_{23})$, —N$(Q_{24})(Q_{25})$, and —B$(Q_{26})(Q_{27})$; and —Si$(Q_{31})(Q_{32})(Q_{33})$, —N$(Q_{34})(Q_{35})$, and —B$(Q_{36})(Q_{37})$, and $Q_1$ to $Q_7$, $Q_{11}$ to $Q_{17}$, $Q_{21}$ to $Q_{27}$, and $Q_{31}$ to $Q_{37}$ are each independently selected from hydrogen, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

2. The condensed cyclic compound of claim 1, wherein, in Formula 1-1, ring $CY_1$ is a benzene group, and ring $CY_2$ is a benzene group, a fluorene group, a carbazole group, a dibenzofuran group, or a dibenzothiophene group.

3. The condensed cyclic compound of claim 1, wherein $R_1$ and $R_2$ are each independently selected from:

hydrogen, deuterium, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a furanyl group, a thiophenyl group, an indolyl group, a benzofuranyl group, a benzothiophenyl group, a carbazolyl group, a dibenzofuranyl group, a dibenzothiophenyl group, a benzocarbazolyl group, a naphthobenzofuranyl group, a naphthobenzothiophenyl group, a dibenzocarbazolyl group, a dinaphthofuranyl group, a dinaphthothiophenyl group, an indolocarbazolyl group, an indolodibenzofuranyl group, and an indolodibenzothiophenyl group; and a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a furanyl group, a thiophenyl group, an indolyl group, a benzofuranyl group, a benzothiophenyl group, a carbazolyl group, a dibenzofuranyl group, a dibenzothiophenyl group, a benzocarbazolyl group, a naphthobenzofuranyl group, a naphthobenzothiophenyl group, a dibenzocarbazolyl group, a dinaphthofuranyl group, a dinaphthothiophenyl group, an indolocarbazolyl group, an indolodibenzofuranyl group, and an indolodibenzothiophenyl group, each substituted with at least one selected from deuterium, a $C_1$-$C_{20}$ alkyl group, a $C_1$-$C_{20}$ alkoxy group, a phenyl group, a biphenyl group, a terphenyl group, a naphthyl group, a fluorenyl group, a dimethylfluorenyl group, a diphenylfluorenyl group, a carbazolyl group, a phenylcarbazolyl group, a biphenylcarbazolyl group, a dibenzofuranyl group, and a dibenzothiophenyl group.

4. The condensed cyclic compound of claim 1, wherein $R_{11}$ to $R_{14}$ and $R_{21}$ to $R_{25}$ are each independently selected from:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a pyridinyl group, a pyrimidinyl group, a pyrazinyl group, a pyridazinyl group, and a triazinyl group;

a cyclopentyl group, a cyclohexyl group, a cyclopentenyl group, a cyclohexenyl group, a cycloheptenyl group, a phenyl group, a pentalenyl group, an indenyl group, a naphthyl group, an azulenyl group, a heptalenyl group, an indacenyl group, an acenaphthyl group, a fluorenyl group, a spiro-bifluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzoxazolyl group, a benzimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl roup, a dibenzothiophenyl group, an imidazopyridimidinyl group, and an imidazopyridinyl group; and a cyclopentyl group, a cyclohexyl group, a cyclopentenyl group, a cyclohexenyl group, a cycloheptenyl group, a phenyl group, a pentalenyl group, an indenyl group, a naphthyl group, an azulenyl group, a heptalenyl group, an indacenyl group, an acenaphthyl group, a fluorenyl group, a spiro-bifluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzoxazolyl group, a benzimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, an imidazopyridimidinyl group, and an imidazopyridinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a naphthyl group, an anthracenyl group, a pyrenyl group, a phenanthrenyl group, a fluorenyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group.

5. The condensed cyclic compound of claim 1, wherein $A_1$ in Formula 1 is represented by Formulae 1-3 or 1-4, at least one of $R_{11}$ to $R_{14}$ is selected from:
a cyano group;
a cyclopentyl group, a cyclohexyl group, a cyclopentenyl group, a cyclohexenyl group, a cycloheptenyl group, a phenyl group, a pentalenyl group, an indenyl group, a naphthyl group, an azulenyl group, a heptalenyl group, an indacenyl group, an acenaphthyl group, a fluorenyl group, a spiro-bifluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, and a hexacenyl group; and
a cyclopentyl group, a cyclohexyl group, a cyclopentenyl group, a cyclohexenyl group, a cycloheptenyl group, a phenyl group, a pentalenyl group, an indenyl group, a naphthyl group, an azulenyl group, a heptalenyl group, an indacenyl group, an acenaphthyl group, a fluorenyl group, a spiro-bifluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, and a hexacenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a naphthyl group, an anthracenyl group, a pyrenyl group, a phenanthrenyl group, a fluorenyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group.

6. The condensed cyclic compound of claim 1, wherein $A_1$ in Formula 1 is represented by Formulae 1 -3 or 1 -4, one or two of $R_{11}$ to $R_{14}$ are each independently selected from a cyano group, a substituted or unsubstituted $C_3$-$C_{10}$ cycloalkyl group, a substituted or unsubstituted $C_3$-$C_{10}$ cycloalkenyl group, a substituted or unsubstituted $C_6$-$C_{60}$ aryl group, and a substituted or unsubstituted monovalent non-aromatic condensed polycyclic group, and the others are selected from hydrogen, deuterium, a $C_1$-$C_{20}$ alkyl group, and a $C_1$-$C_{20}$ alkoxy group.

7. The condensed cyclic compound of claim 1, wherein $D_1$ in Formula 1 is selected from groups represented by Formulae 2-1 to 2-7:

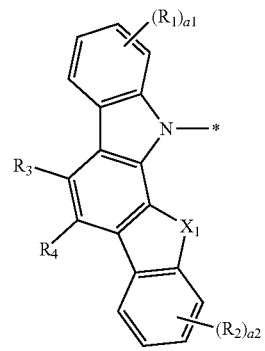

Formula 2-1

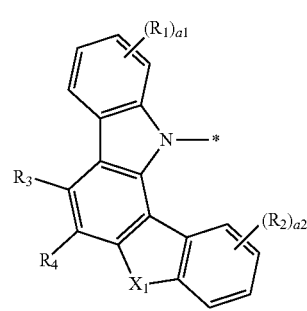

Formula 2-2

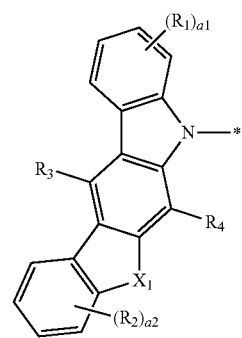

Formula 2-3

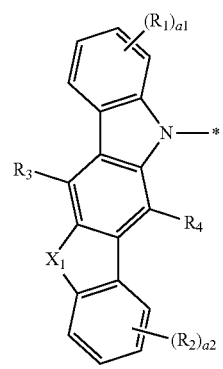

Formula 2-4

Formula 2-5

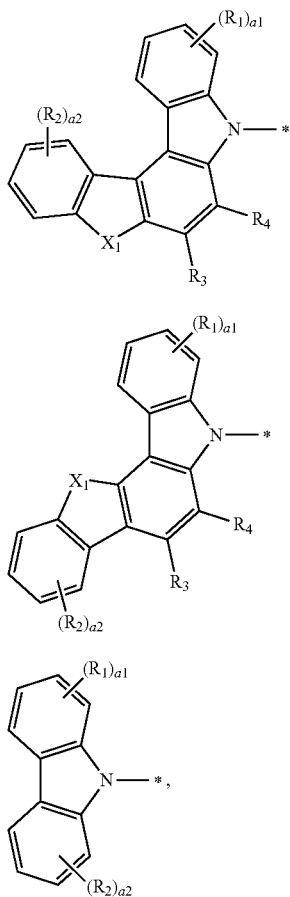

Formula 2-6

Formula 2-7 wherein, in Formulae 2-1 to 2-7,
$X_1$ is $C(R_5)(R_6)$, $N(R_7)$, O, or S,
$R_1$ and $R_2$ are respectively the same as described in claim 1,
$R_3$ to $R_7$ are respectively the same as described in connection with $R_1$,
a1 and a2 are each independently an integer from 0 to 4, and
* indicates a binding site to a neighboring atom.

8. The condensed cyclic compound of claim 1, wherein $A_1$ in Formula 1 is selected from groups represented by Formulae 3-1 and 3-7 to 3-8:

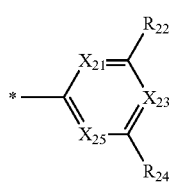

Formula 3-1

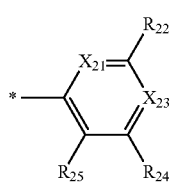

Formula 3-2

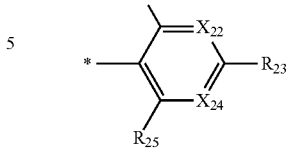

Formula 3-3

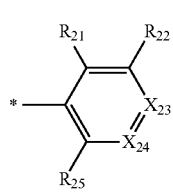

Formula 3-4

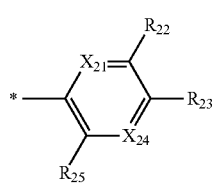

Formula 3-5

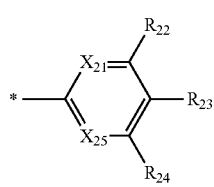

Formula 3-6

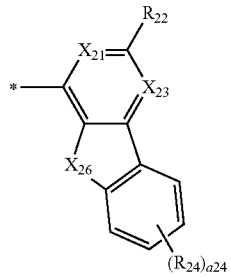

Formula 3-7

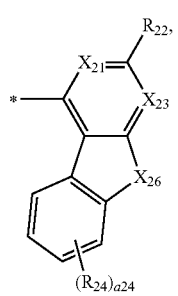

Formula 3-8 wherein, in Formula 3-1, $X_{21}$ to $X_{25}$ are each N,
wherein, in Formulae 3-7 to 3-8, $X_{21}$ to $X_{25}$ are each independently N or C(CN),
wherein in Formulae 3-1 and 3-7 to 3-8, $X_{26}$, $R_{21}$ to $R_{25}$, and a24 are respectively the same as described in claim 1, and * indicates a binding site to a neighboring atom.

9. The condensed cyclic compound of claim 1, wherein the condensed cyclic compound is represented by one of Formulae 1A to 1E:

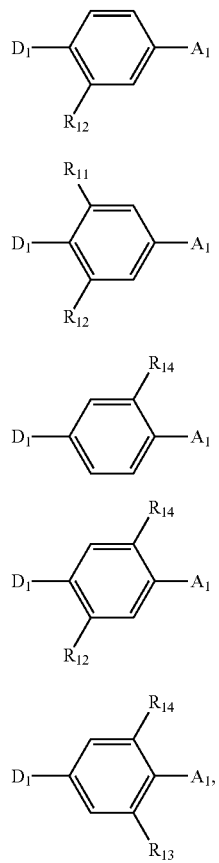

Formula 1A

Formula 1B

Formula 1C

Formula 1D

Formula 1E wherein, in Formulae 1A to 1E,

D$_1$ is the same as described in claim 1,

A$_1$ in Formula 1 is represented by Formulae 1-3 or 1-4, and

R$_{11}$ to R$_{14}$ are each independently selected from a cyano group, a substituted or unsubstituted C$_3$-C$_{10}$ cycloalkyl group, a substituted or unsubstituted C$_3$-C$_{10}$ cycloalkenyl group, a substituted or unsubstituted C$_6$-C$_{60}$ aryl group, and a substituted or unsubstituted monovalent non-aromatic condensed polycyclic group.

10. The condensed cyclic compound of claim 1, wherein the condensed cyclic compound is one of the following Compounds:

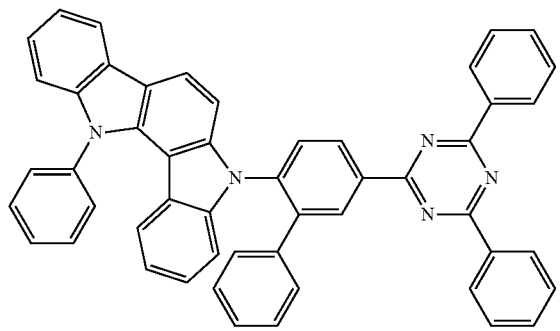

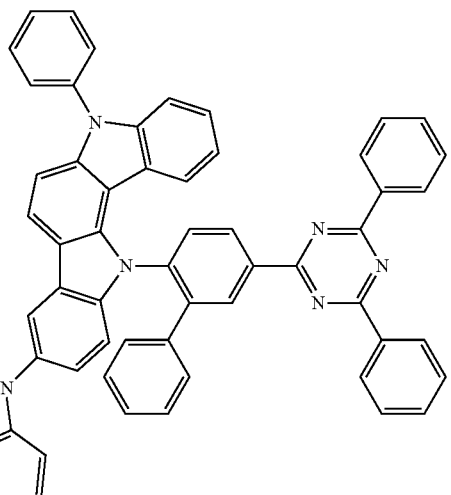

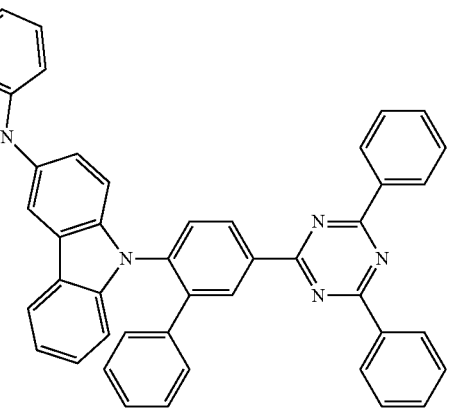

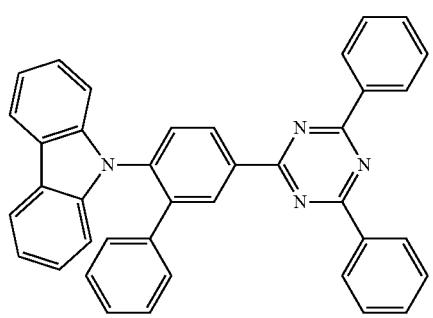

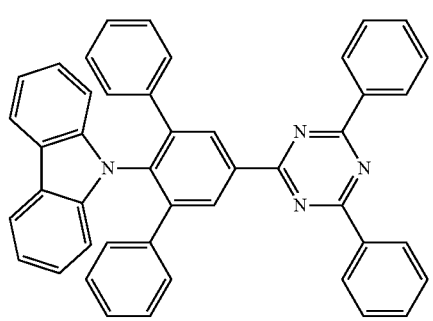

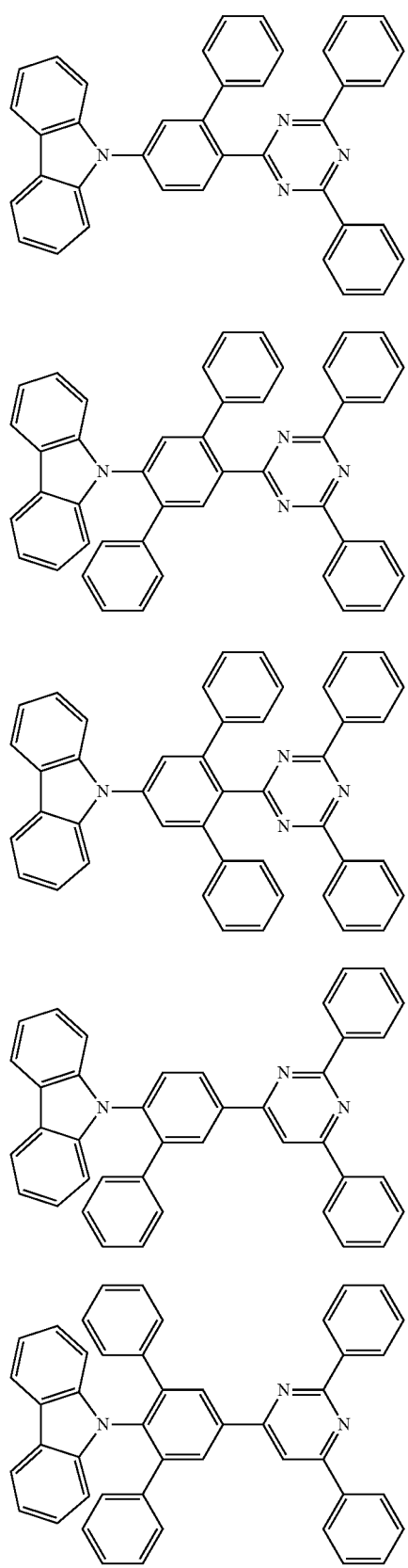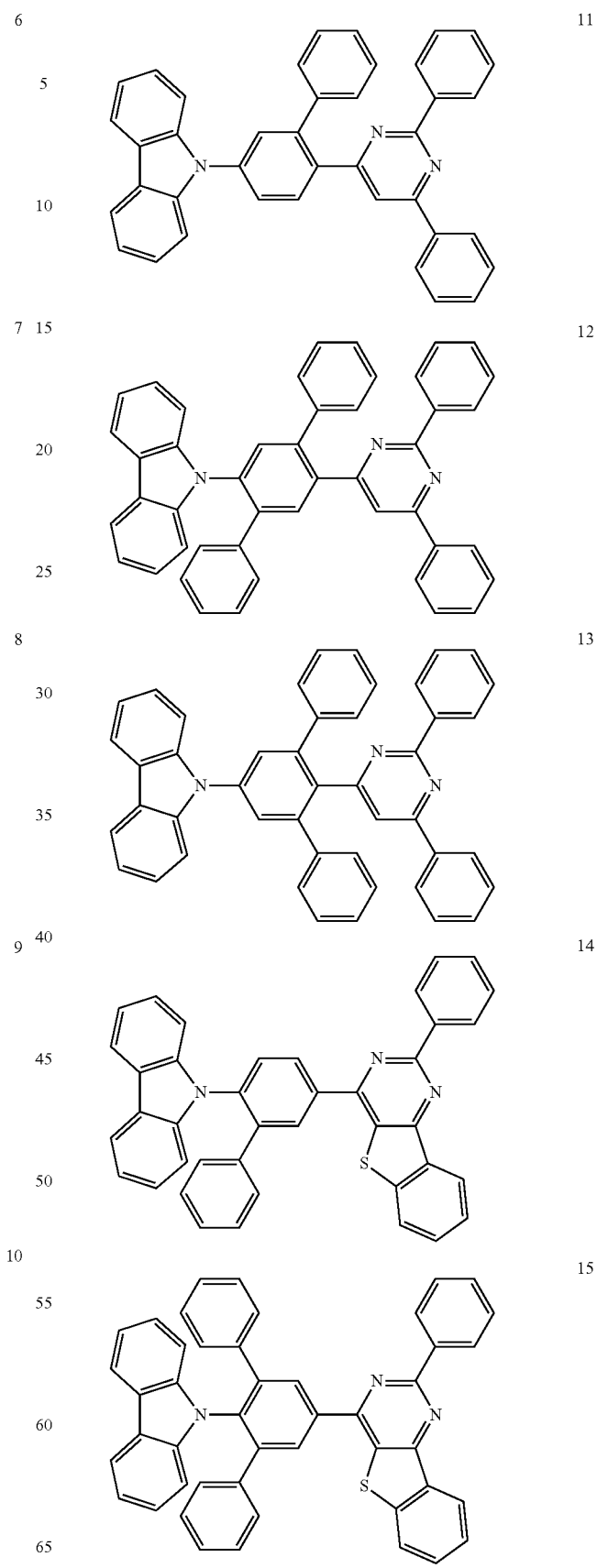

16
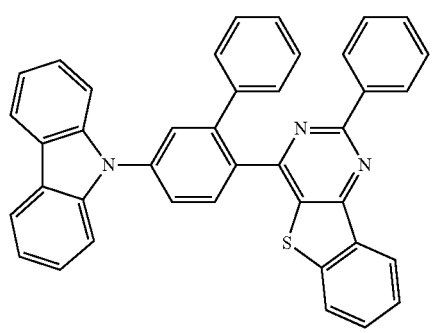
17
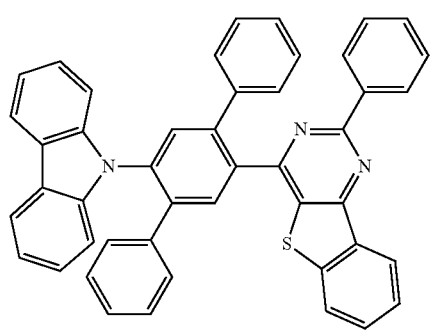
18
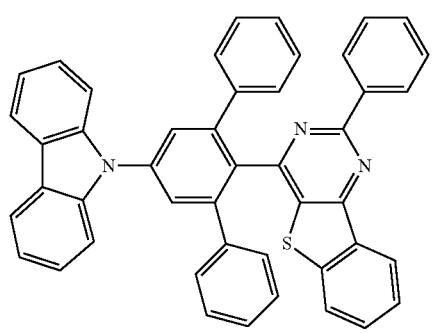
19
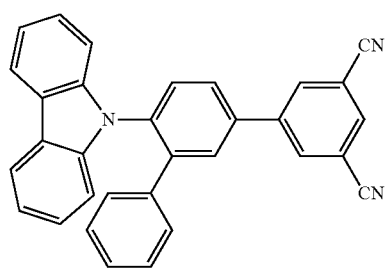
20
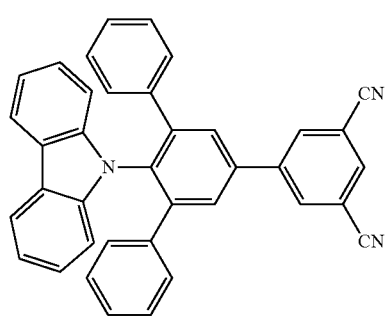
21
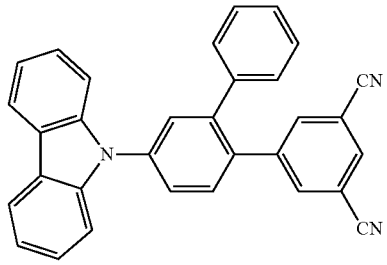
22
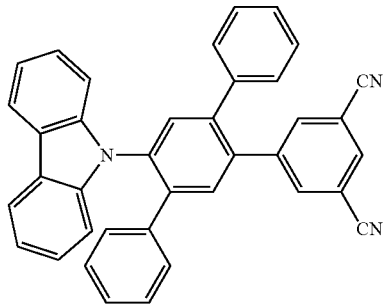
23
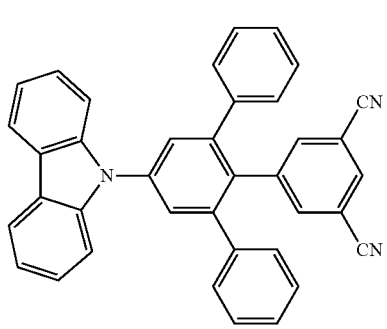
24
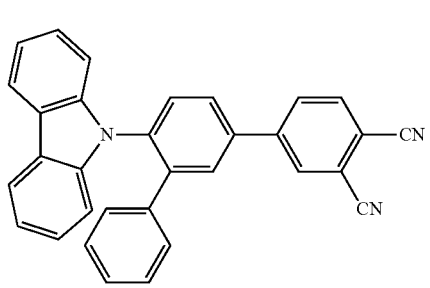
25
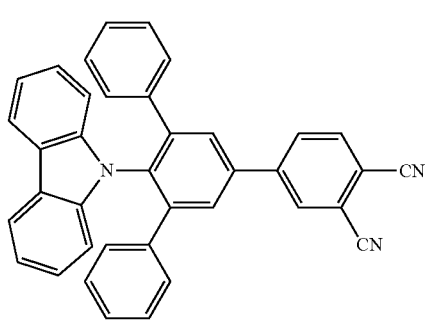

26
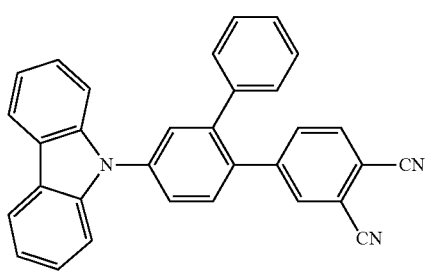
27
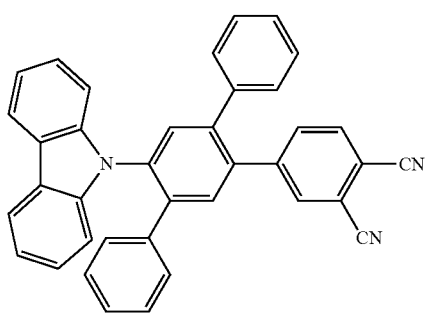
28
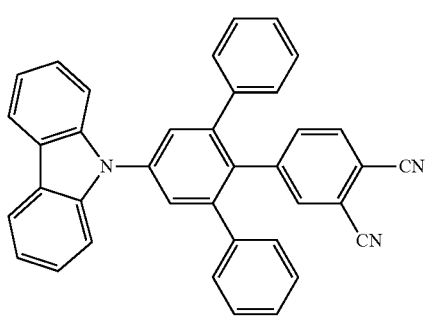
29
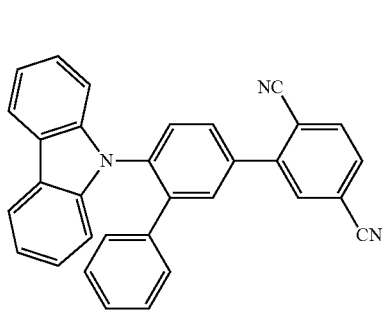
30
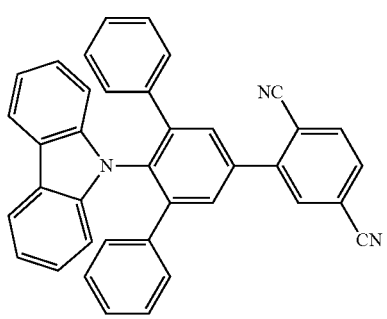
31
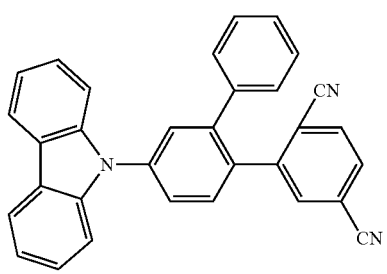
32
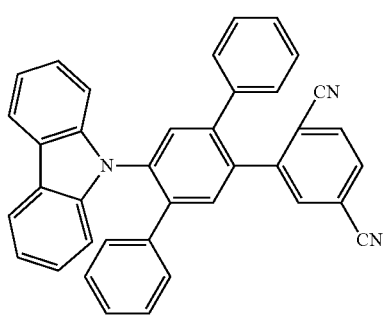
33
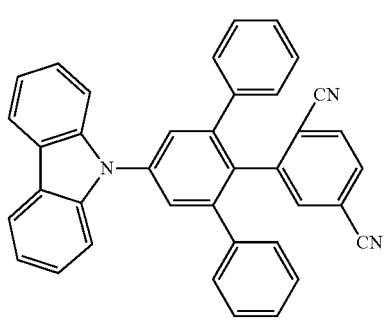
34
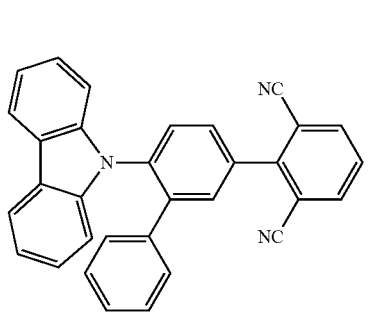
35
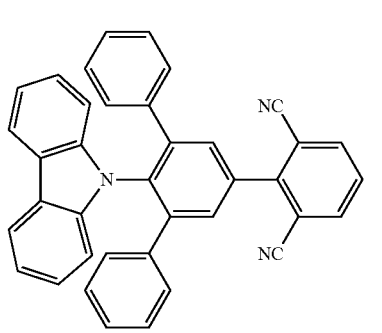

36
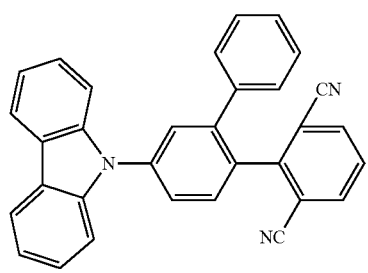
37
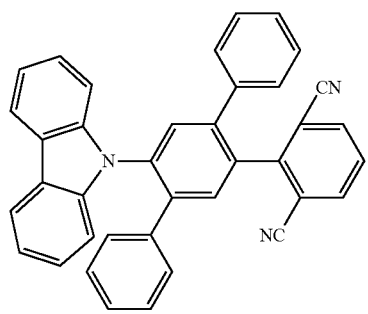
38
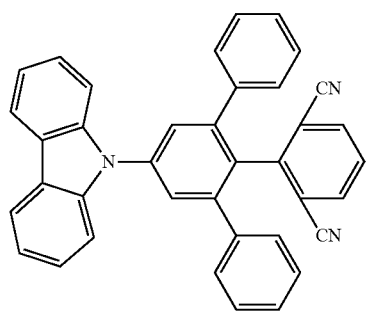
39
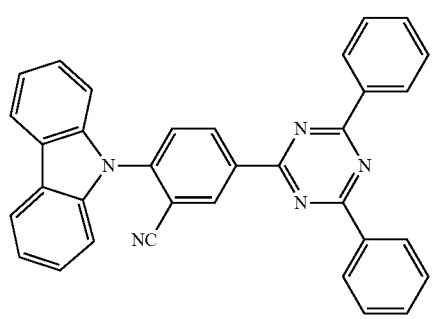
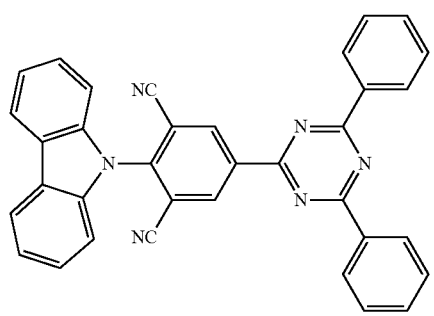
41
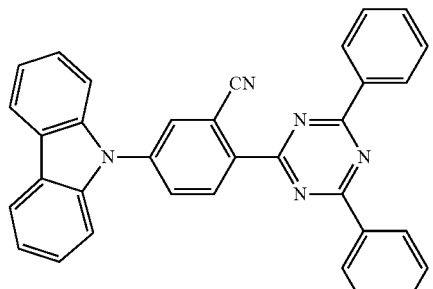
42
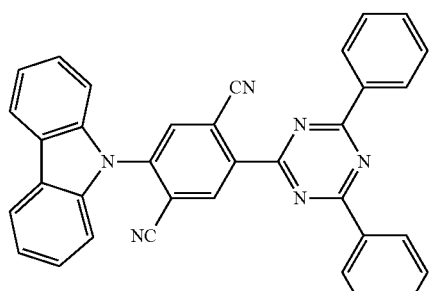
43
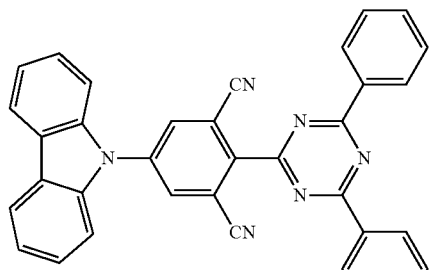
44
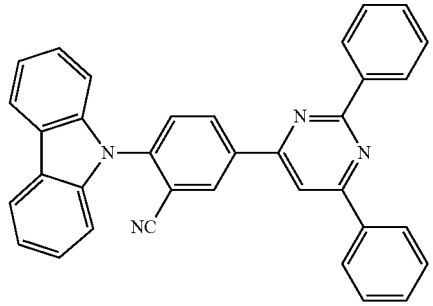
45
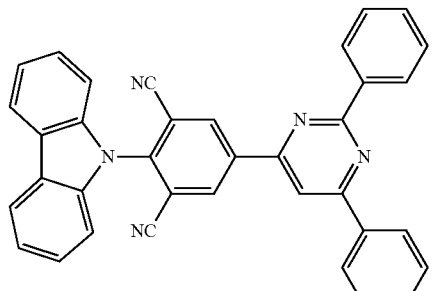

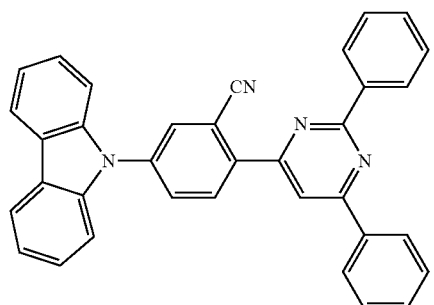
46
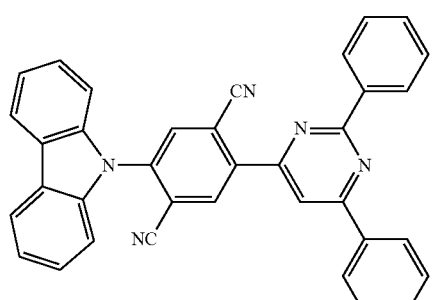
47
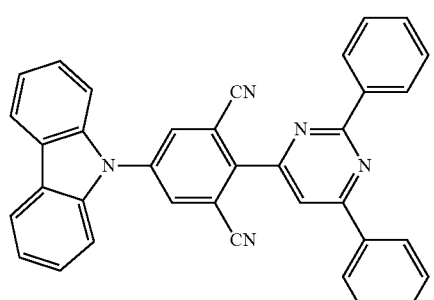
48
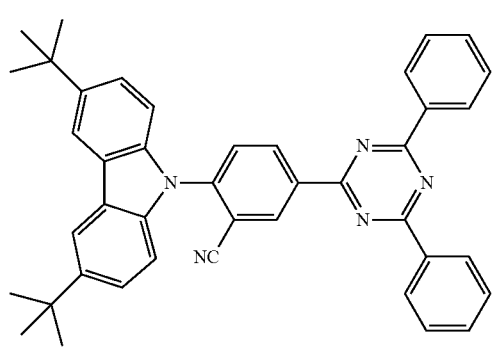
49
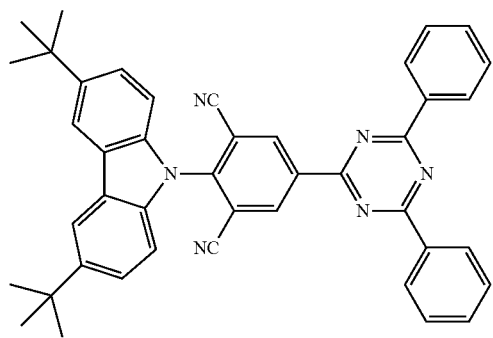
50
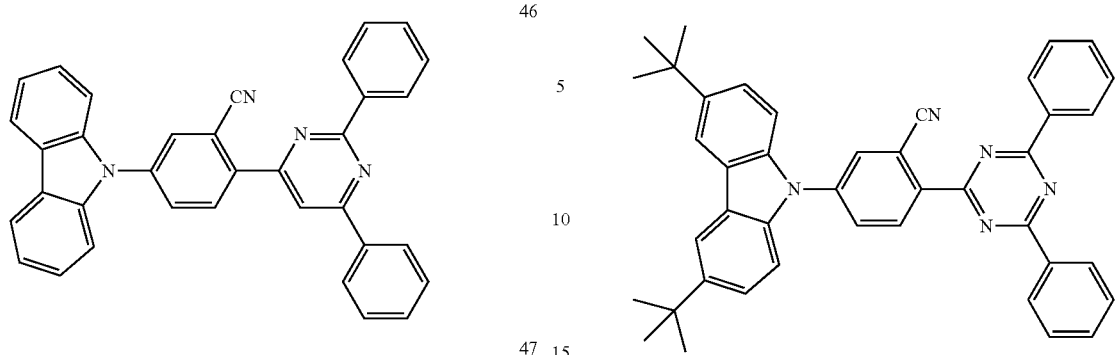
51
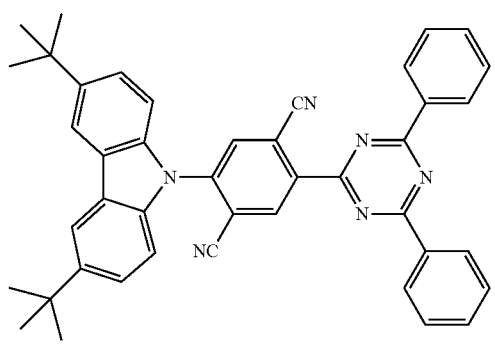
52
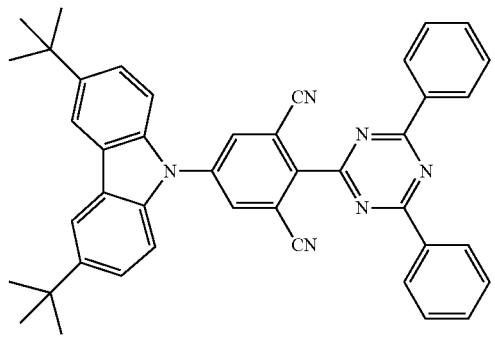
53
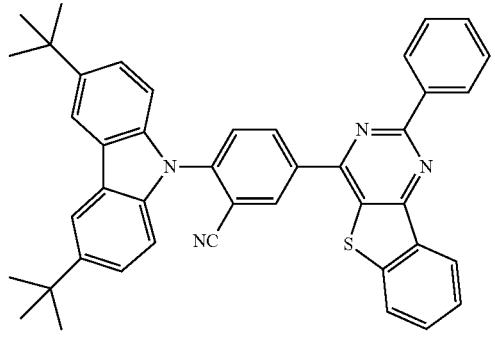
54

187
-continued
55
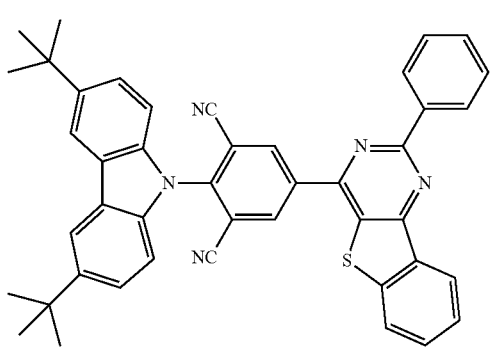
56
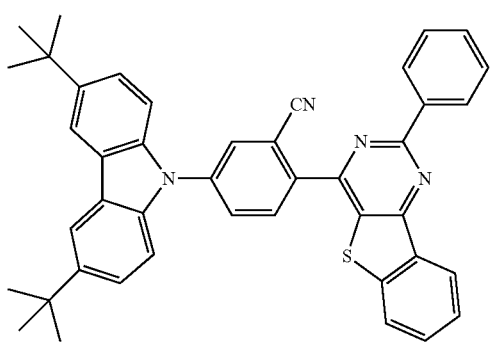
57
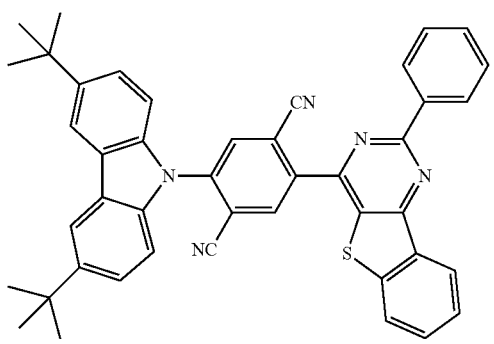
58
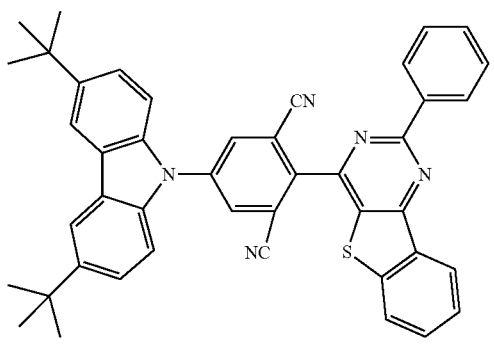
188
-continued
59
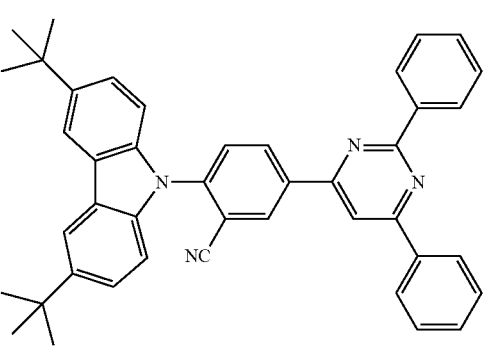
60
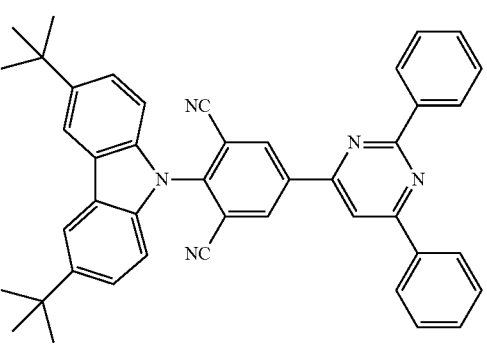
61
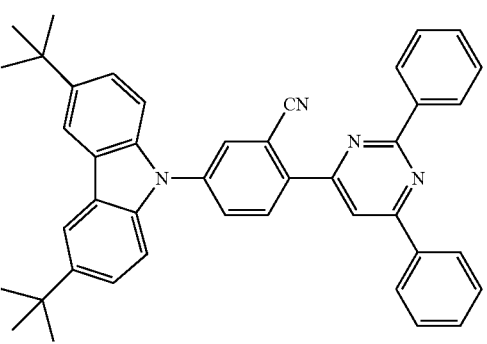
62
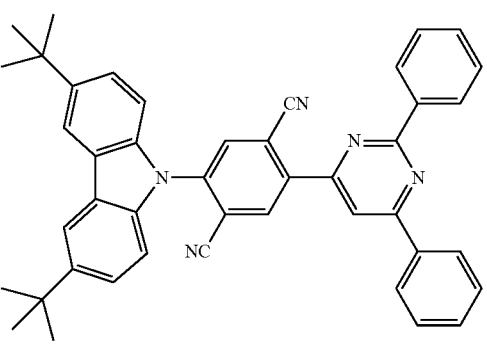

63
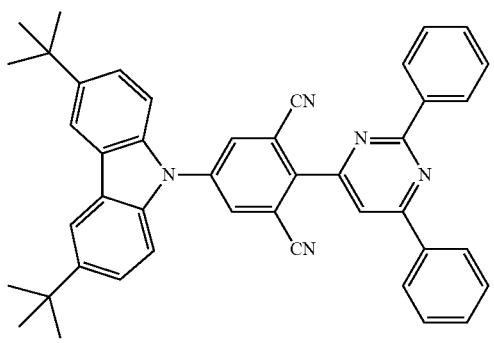
64
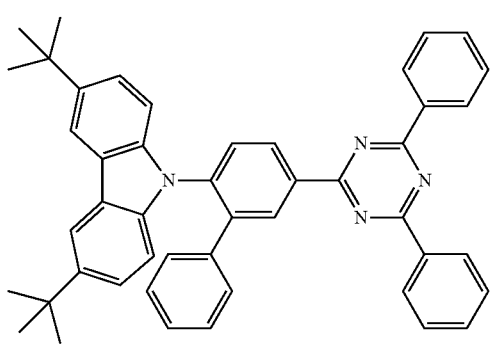
65
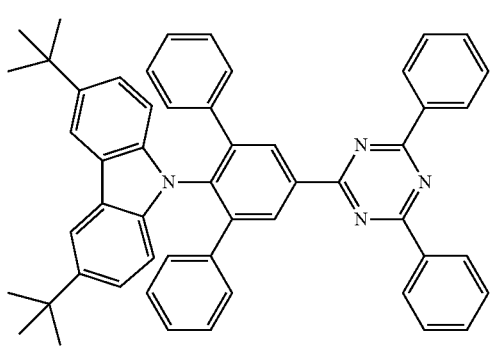
66
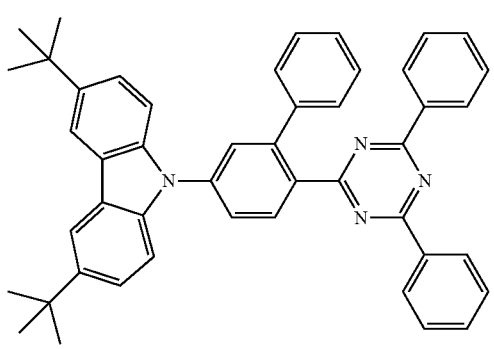
67
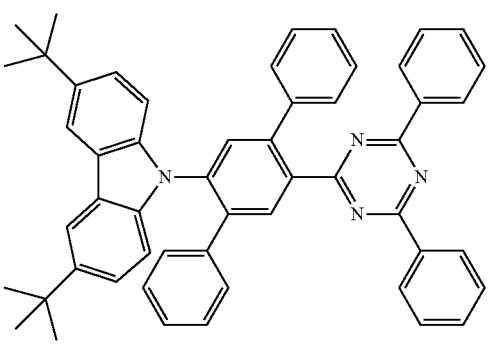
68
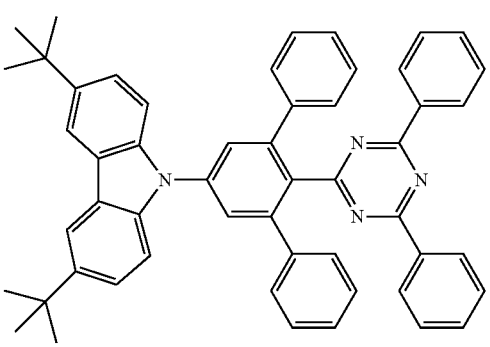
69
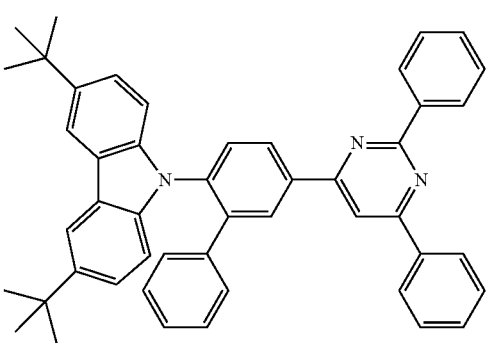
70
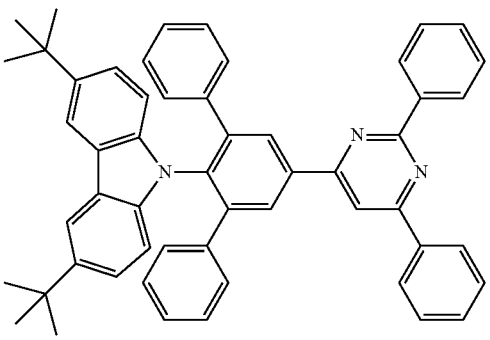

191
-continued
| 71 | 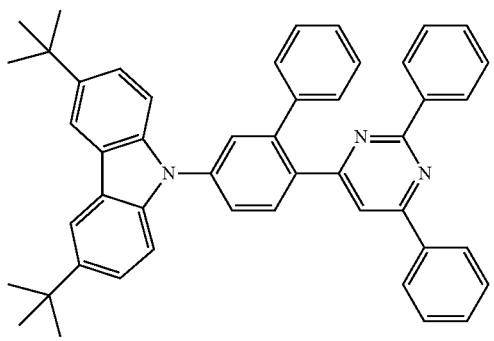 |
| 72 | 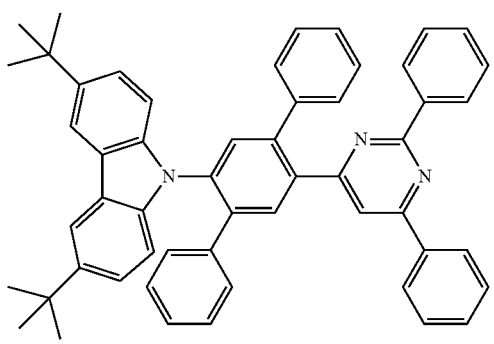 |
| 73 | 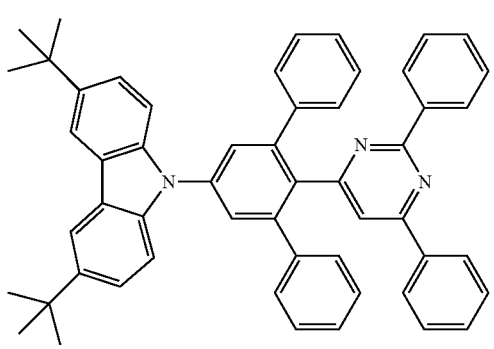 |
| 74 | 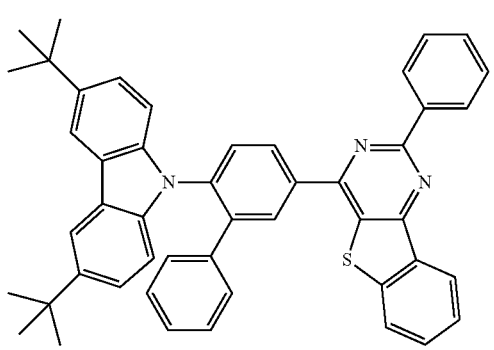 |
192
-continued
| 75 | 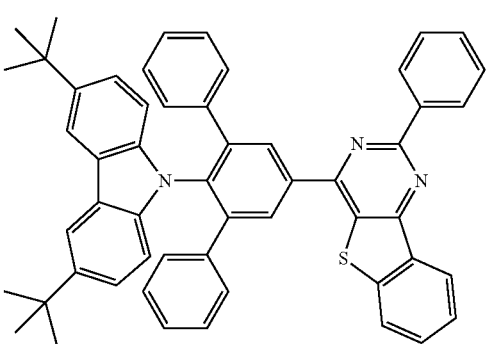 |
| 76 | 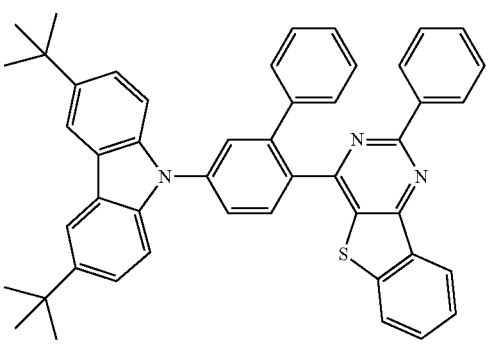 |
| 77 | 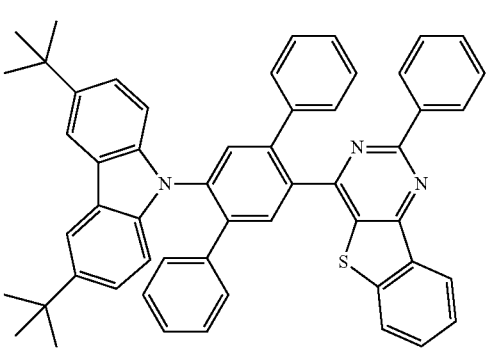 |
| 78 | 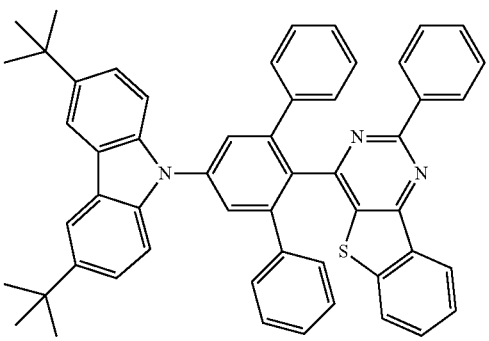 |

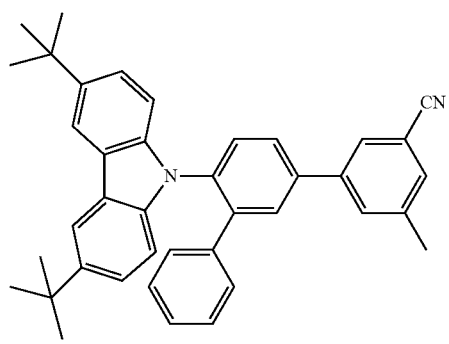
79
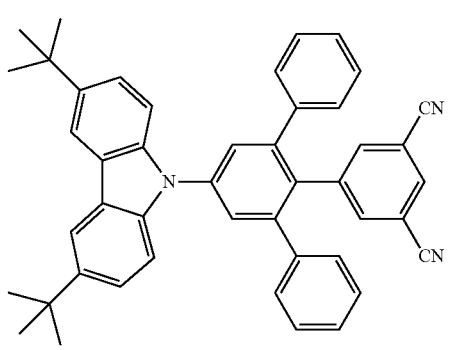
83
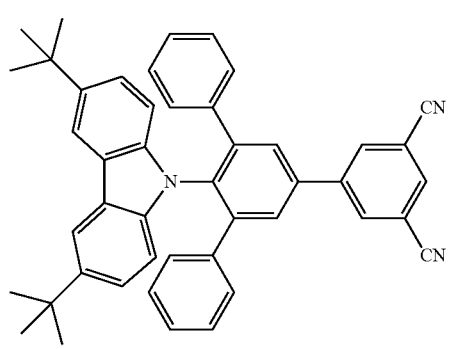
80
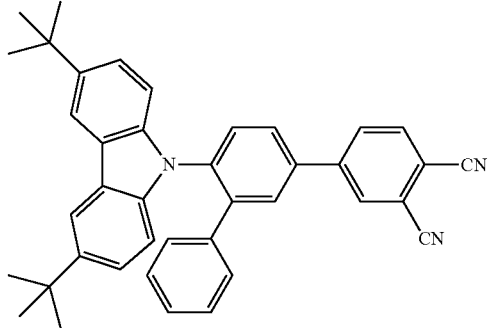
84
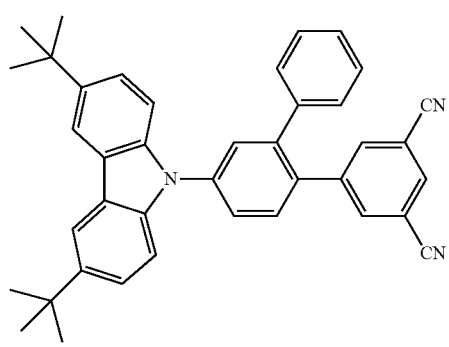
81
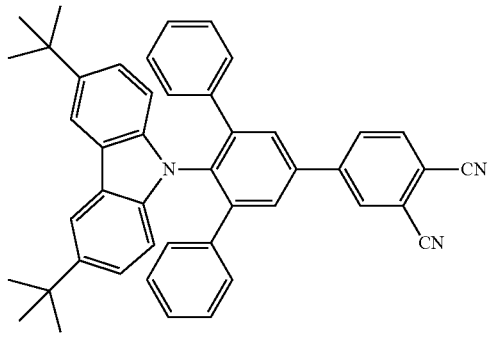
85
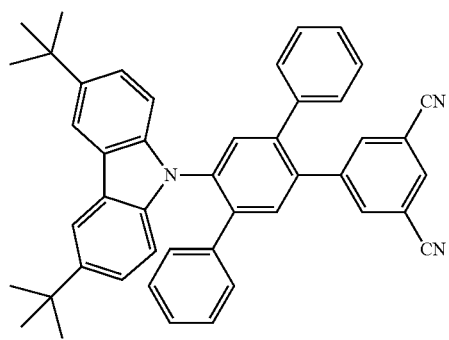
82
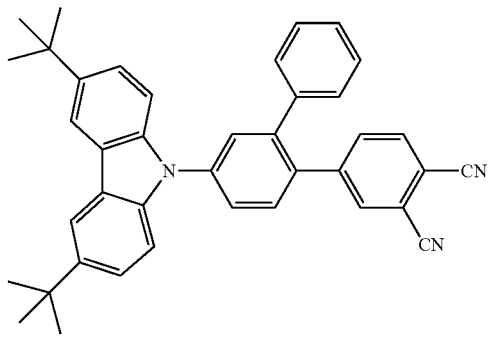
86

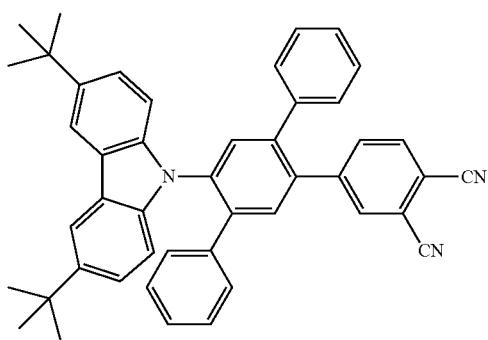
87
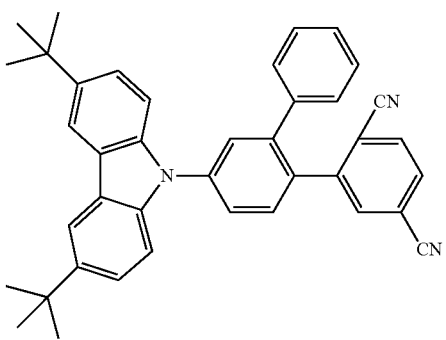
91
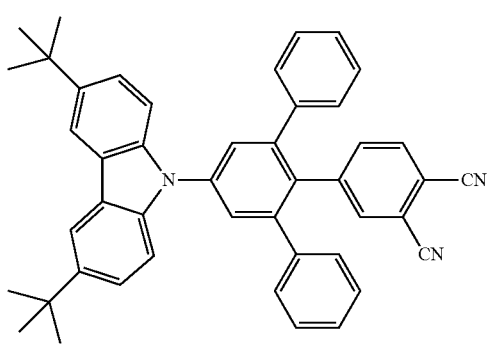
88
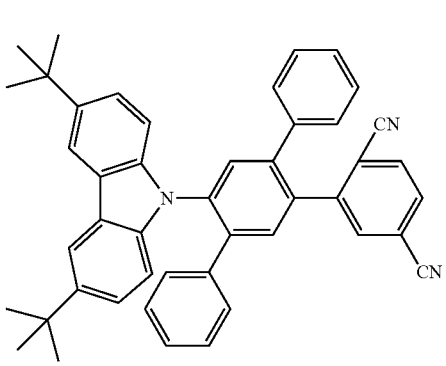
92
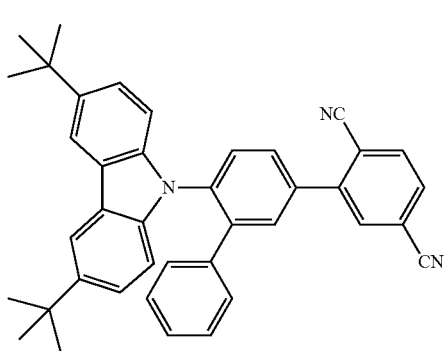
89
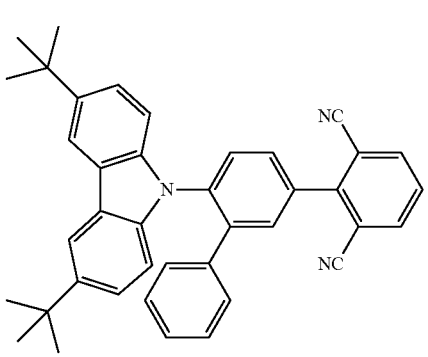
93
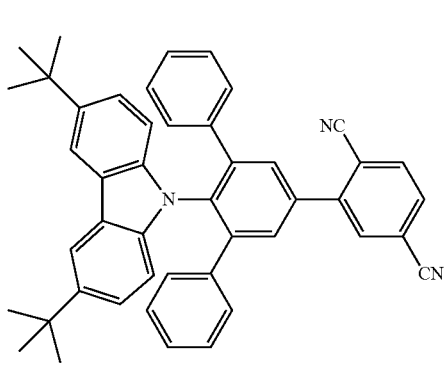
90
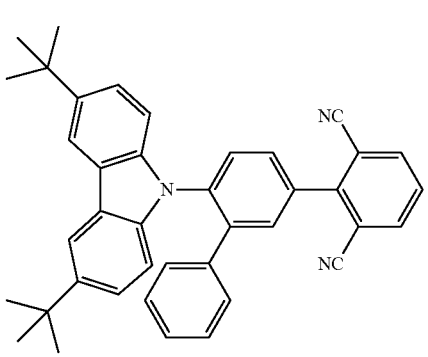
94

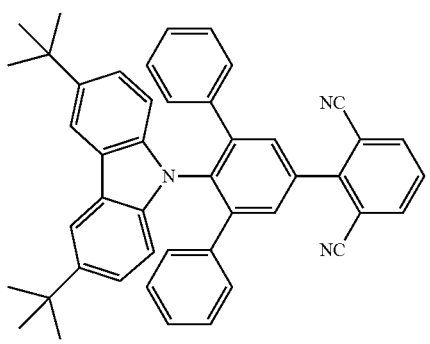
95
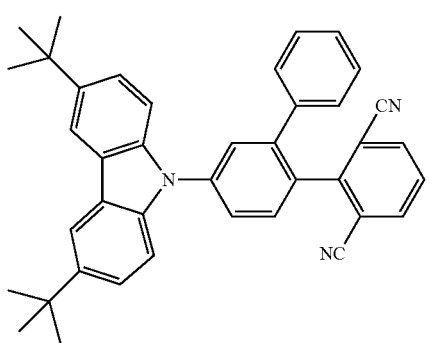
96
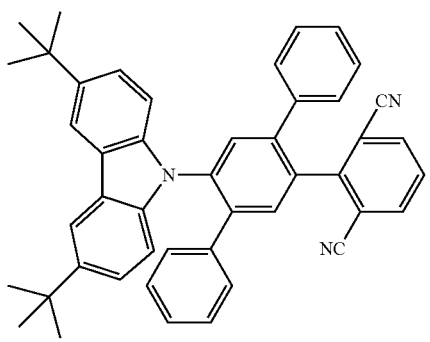
97
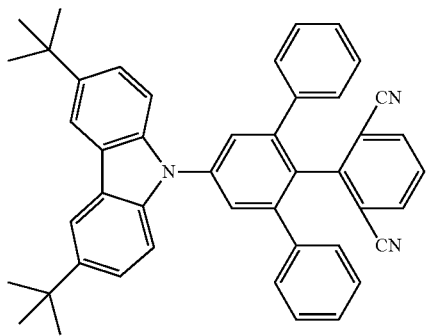
98
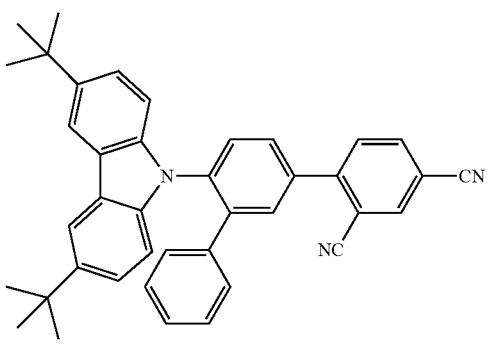
99
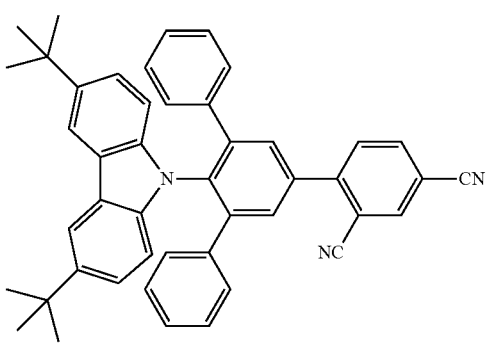
100
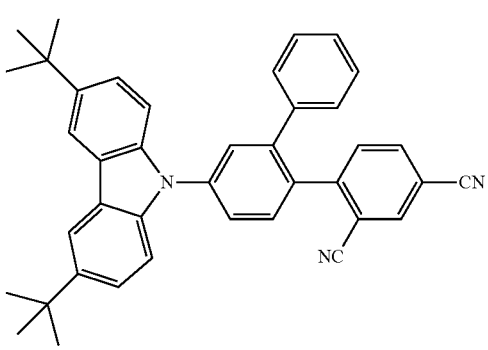
101
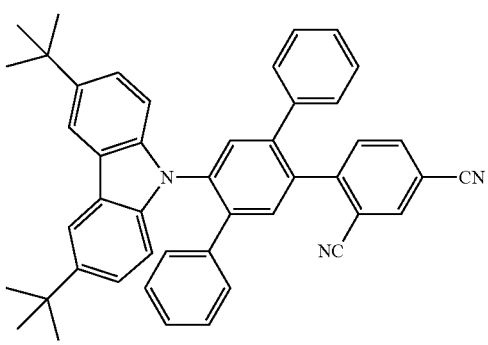
102

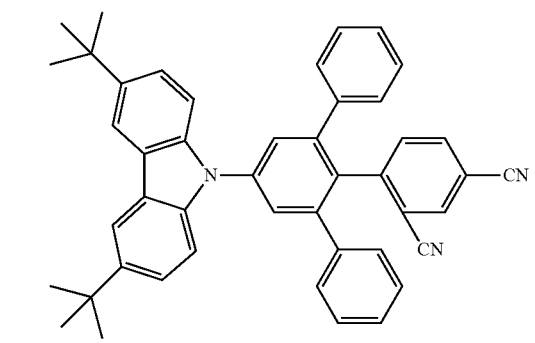
103
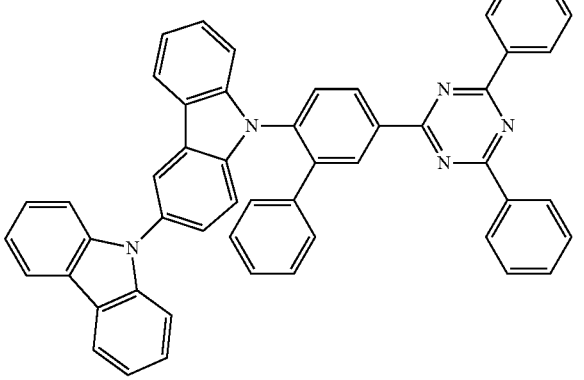
104
105
106
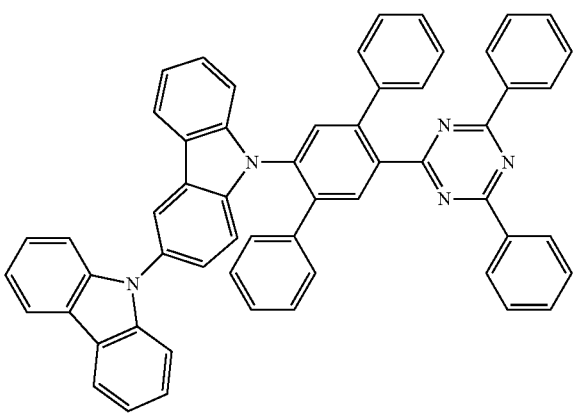
107
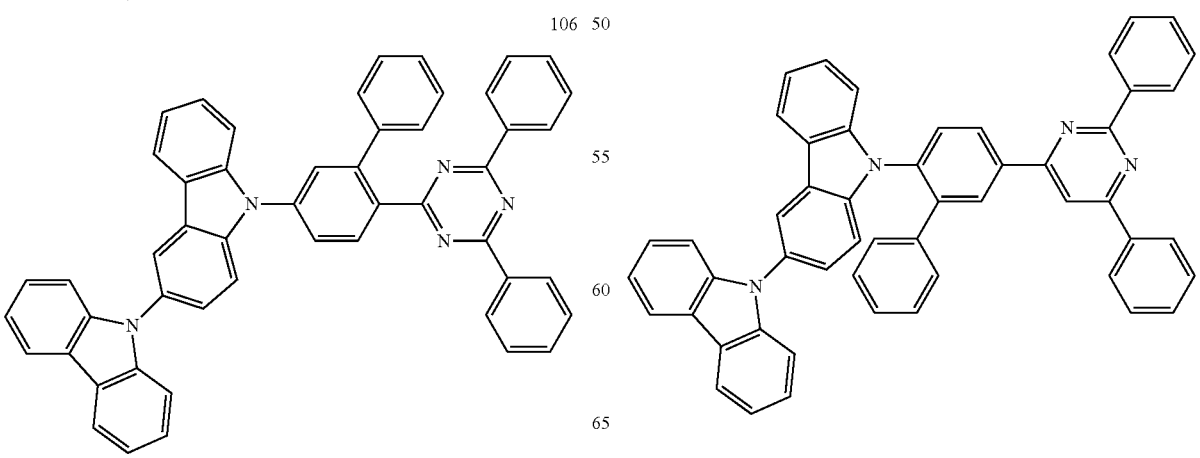
108
109

201
-continued
202
-continued
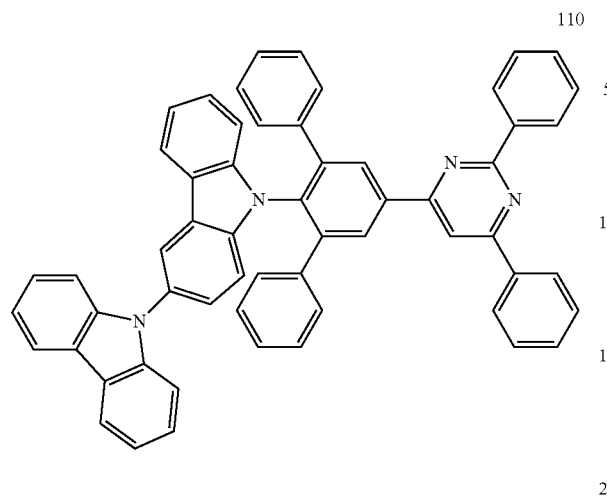
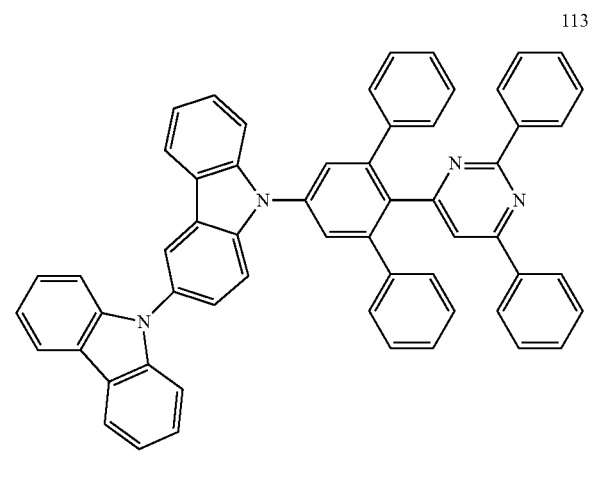
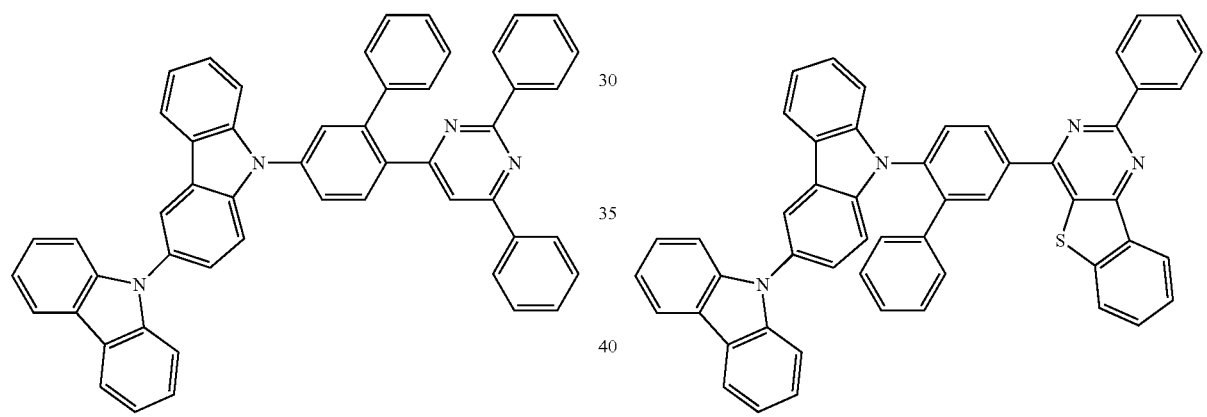
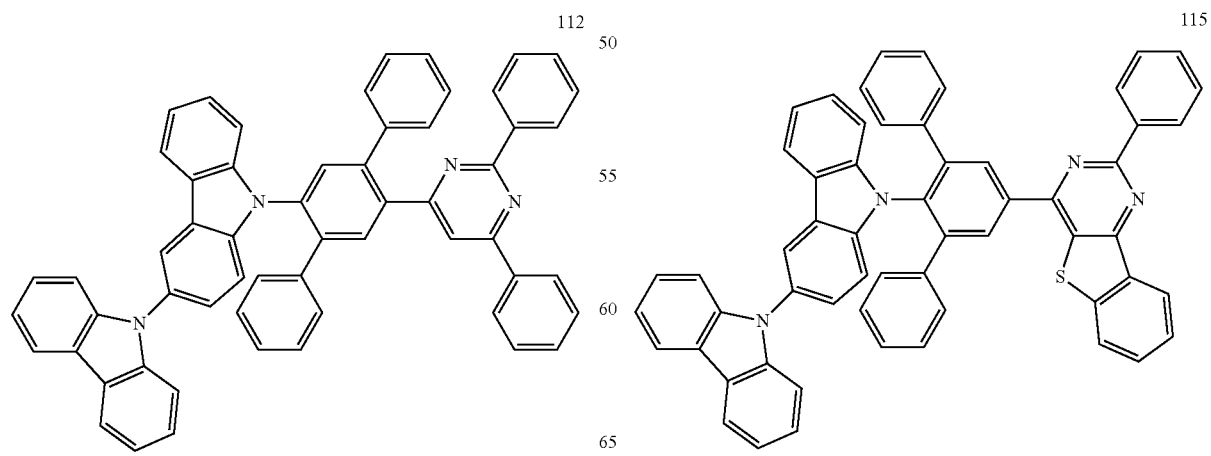

116
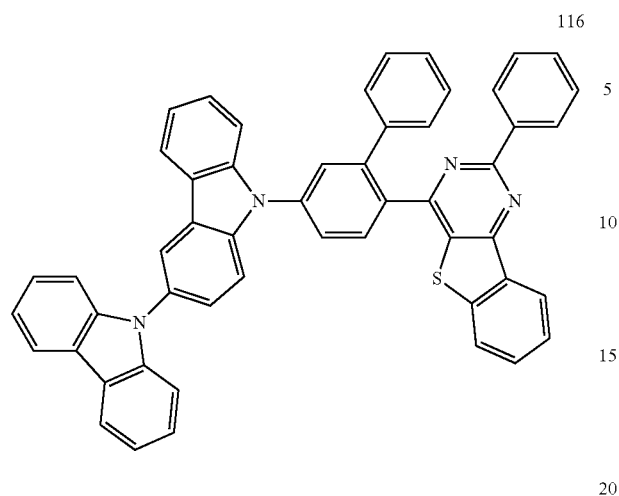
119
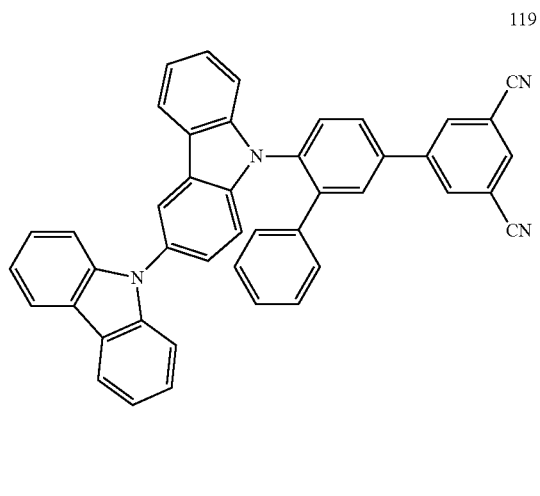
117
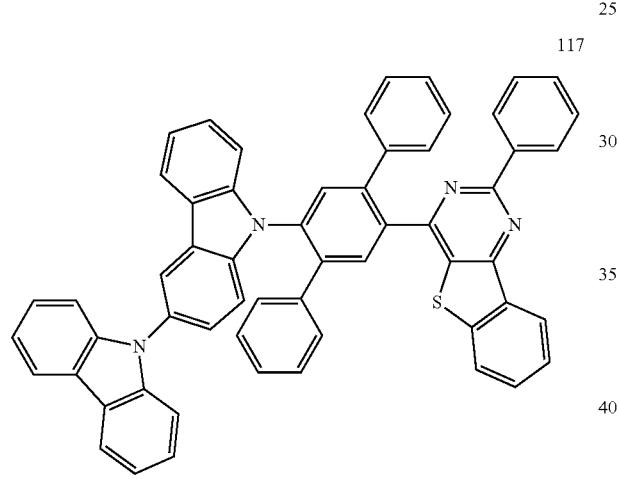
120
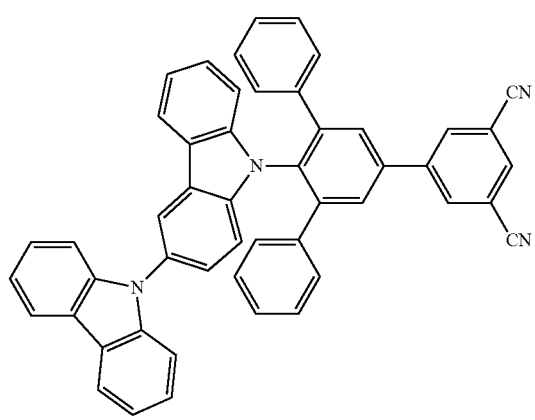
118
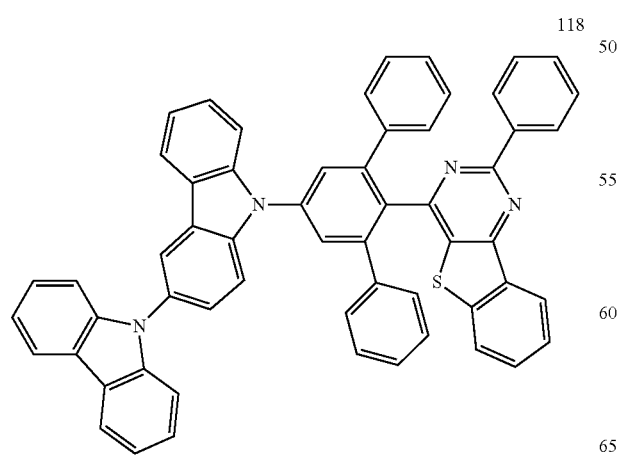
121
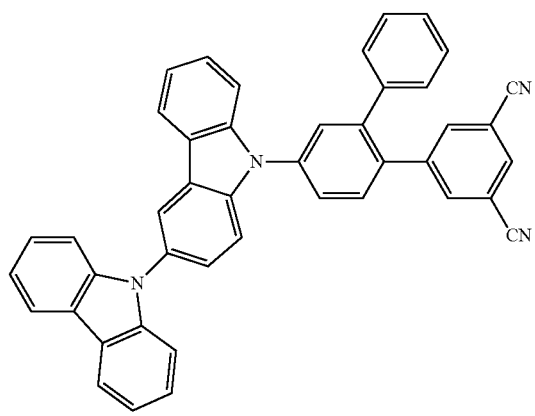

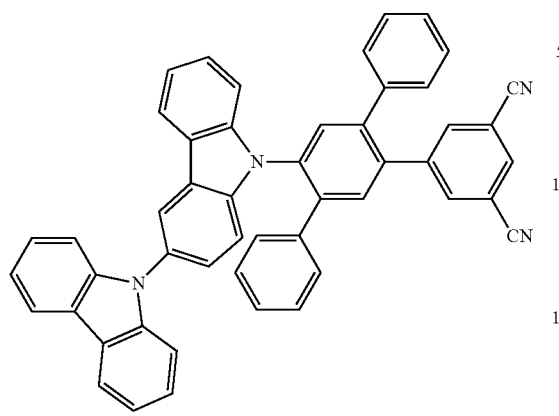
122
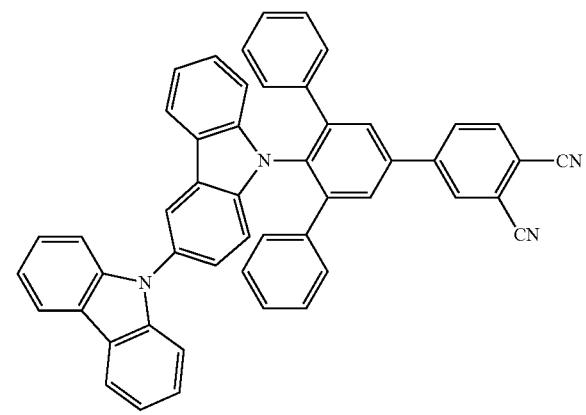
125
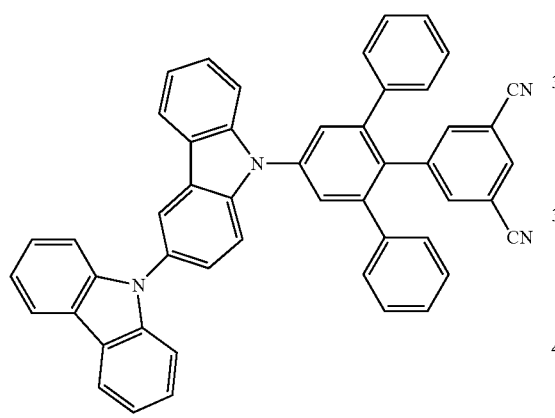
123
126
124
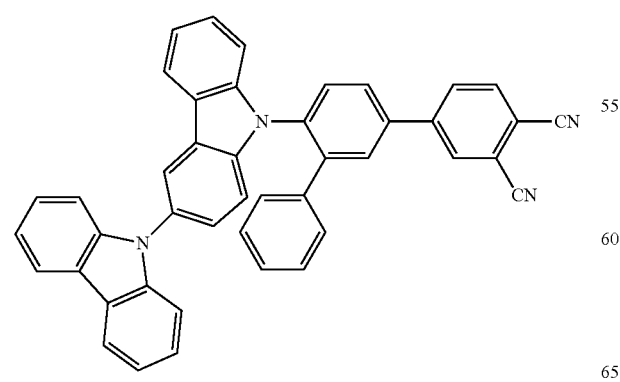
127

128
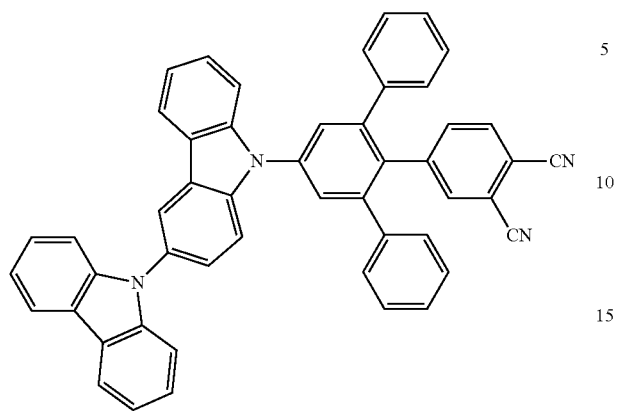
129
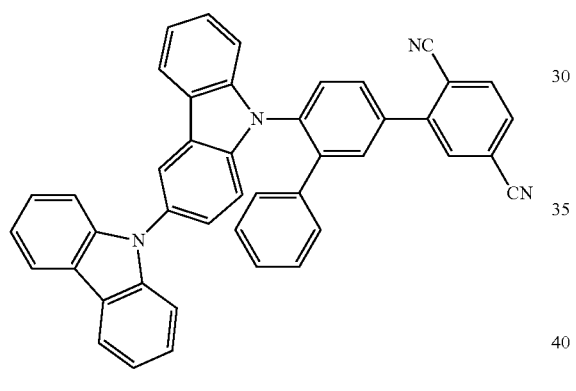
130
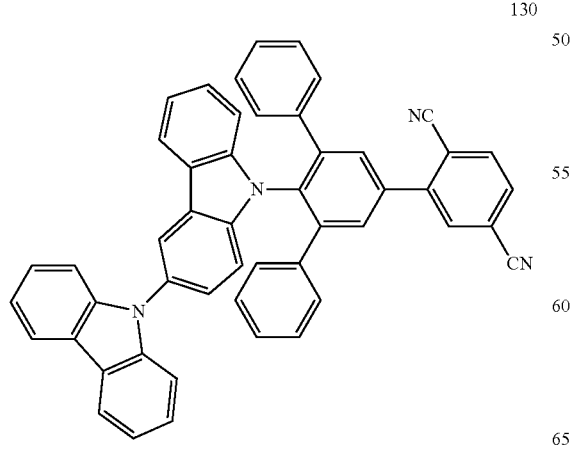
131
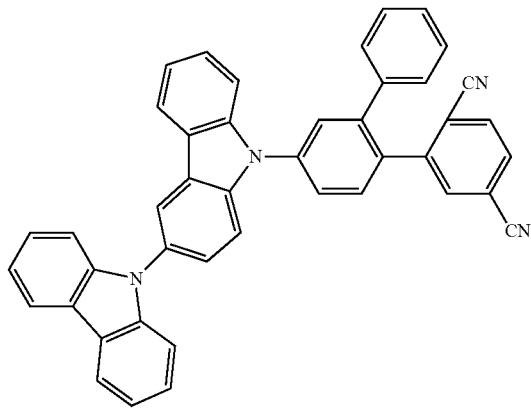
132
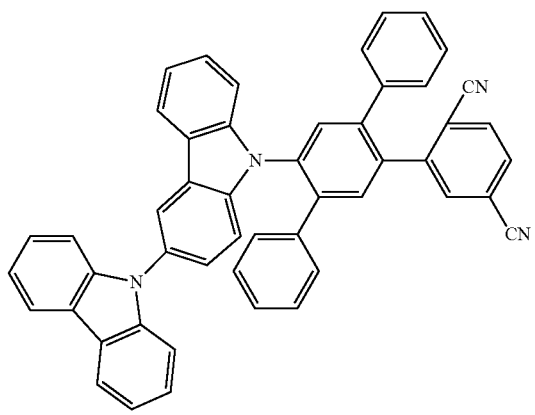
133
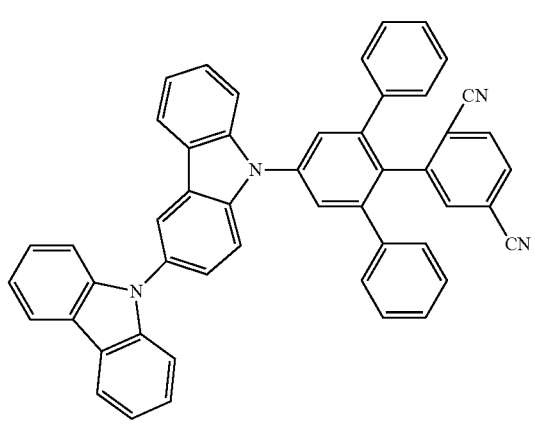

134
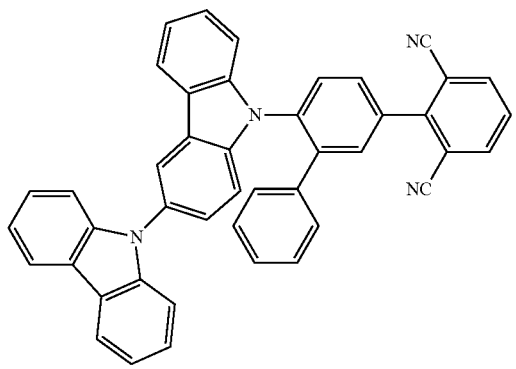
135
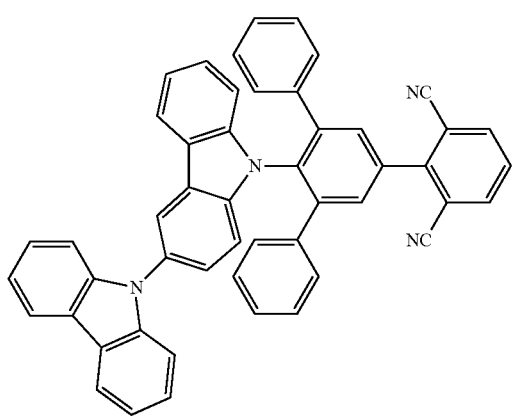
136
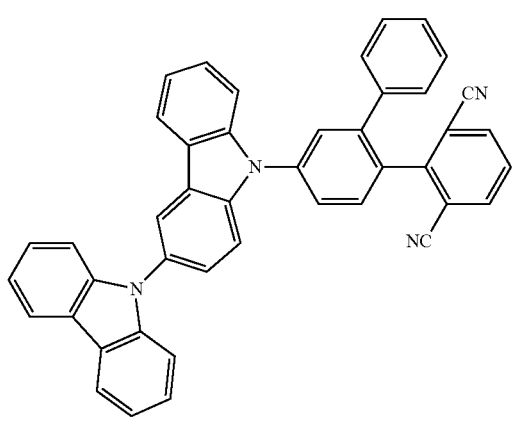
137
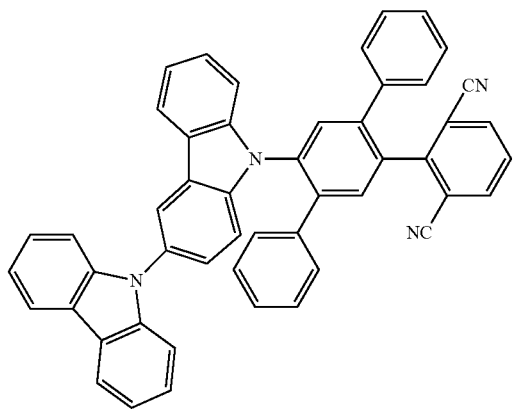
138
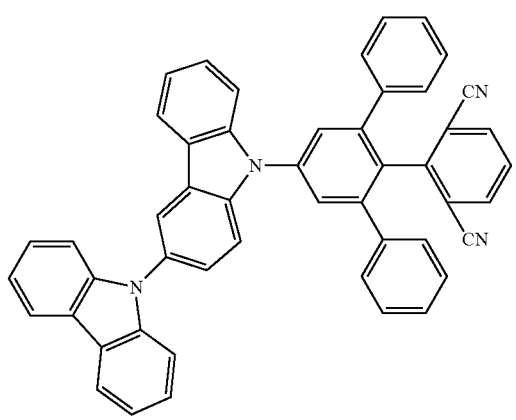
139
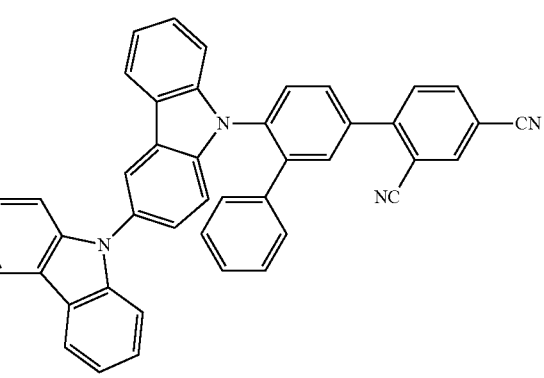

-continued
140
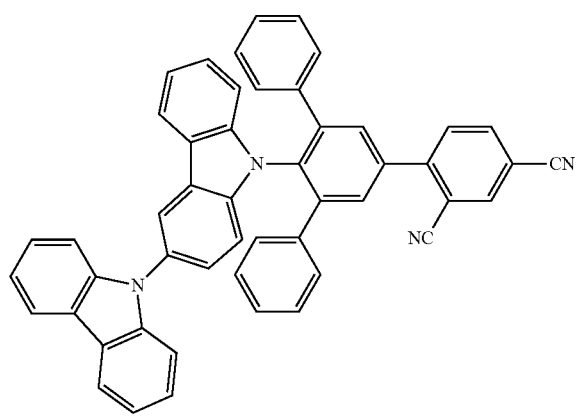
141
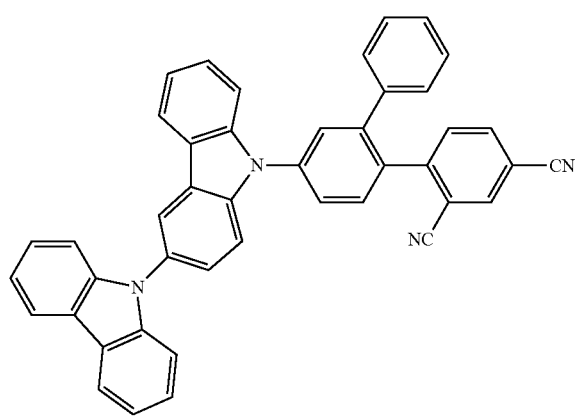
142
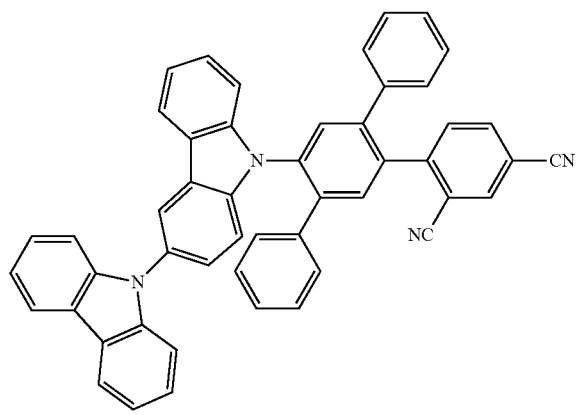
-continued
143
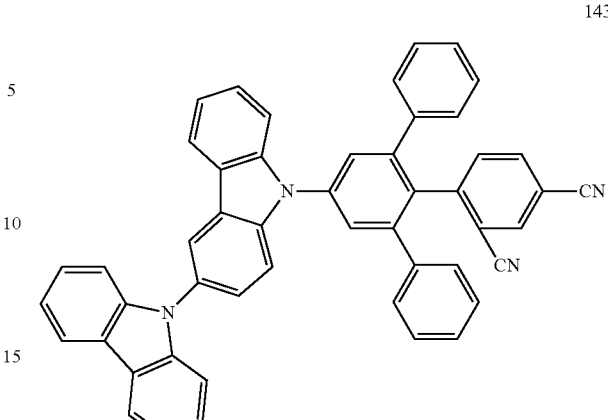
144
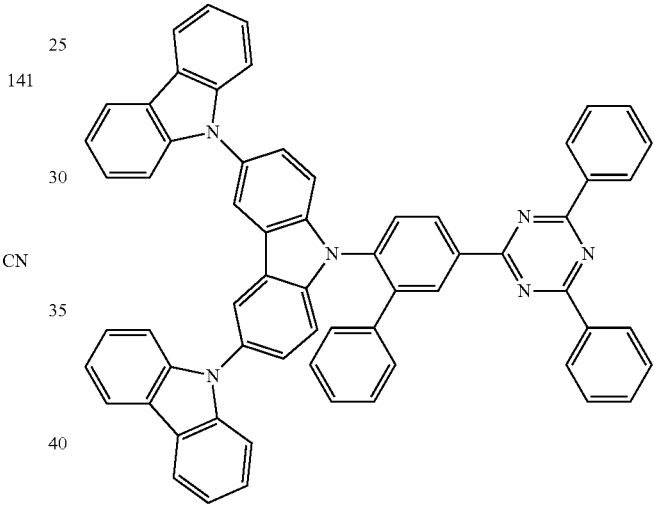
145
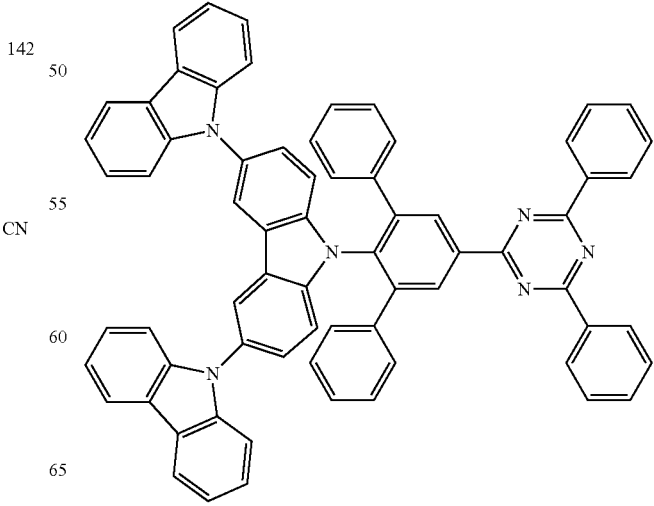

-continued
146
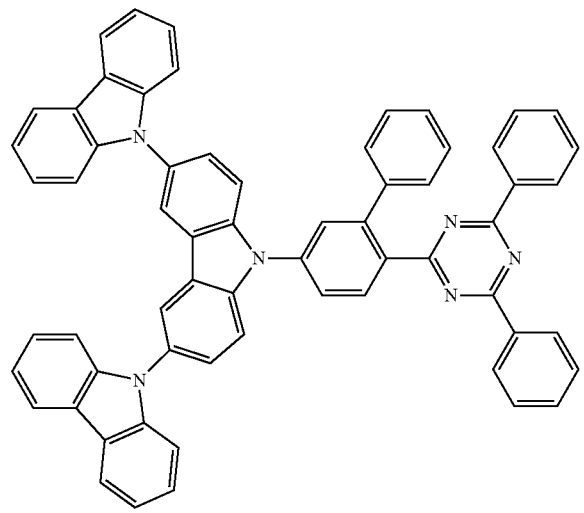
147
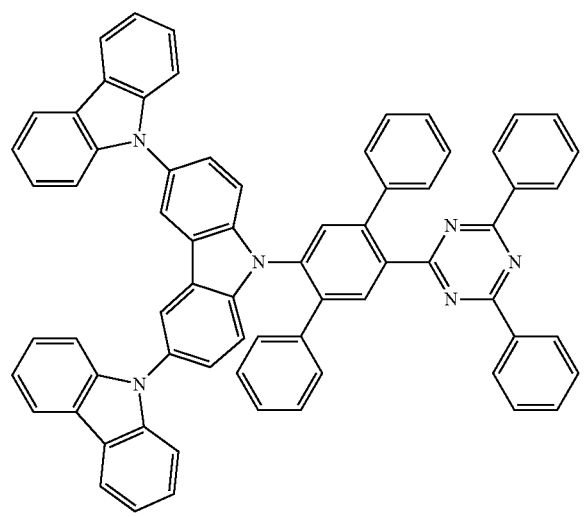
148
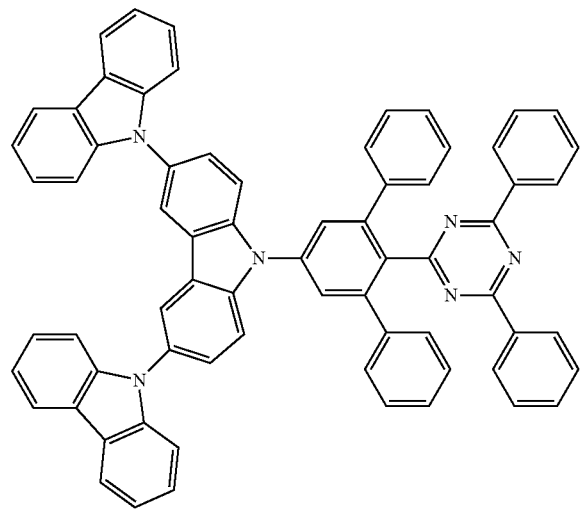
-continued
149
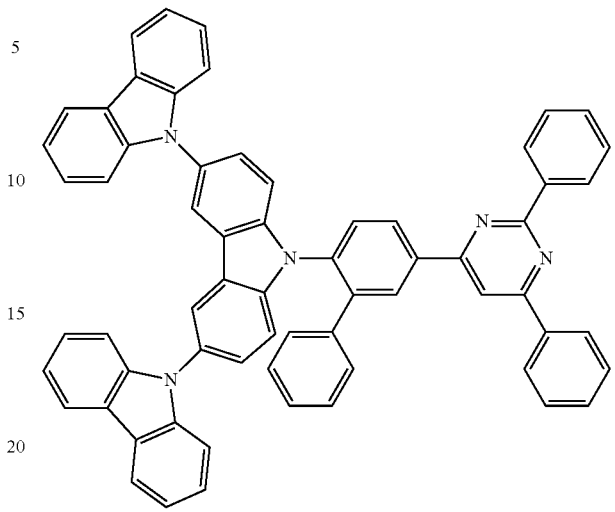
150
151
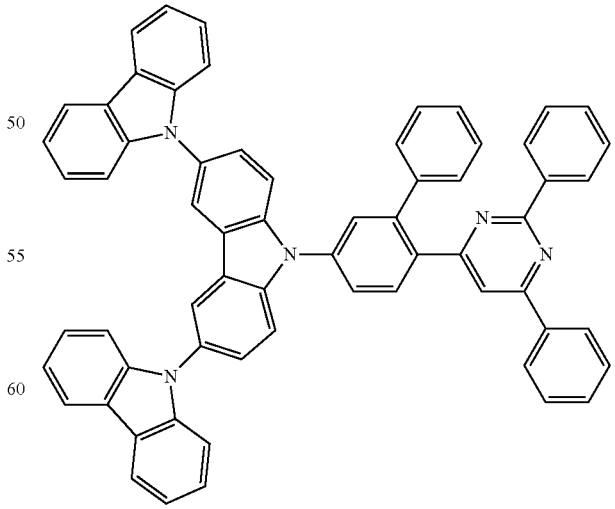

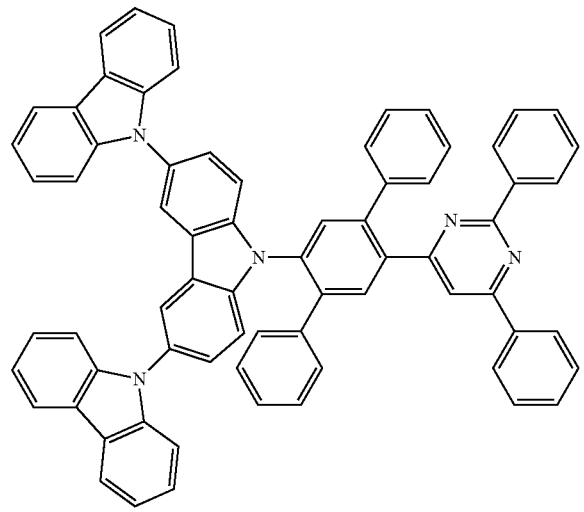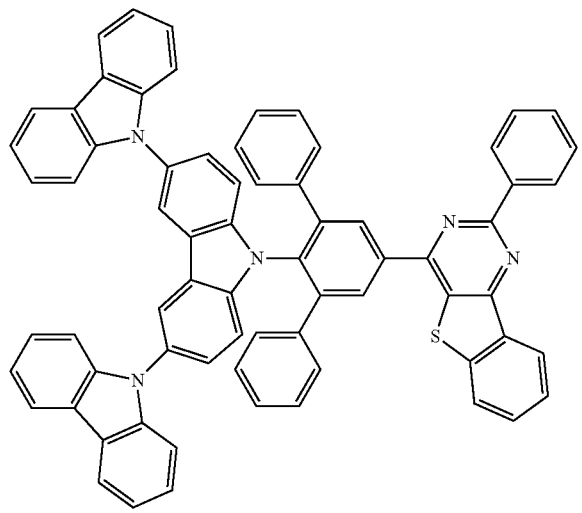

158
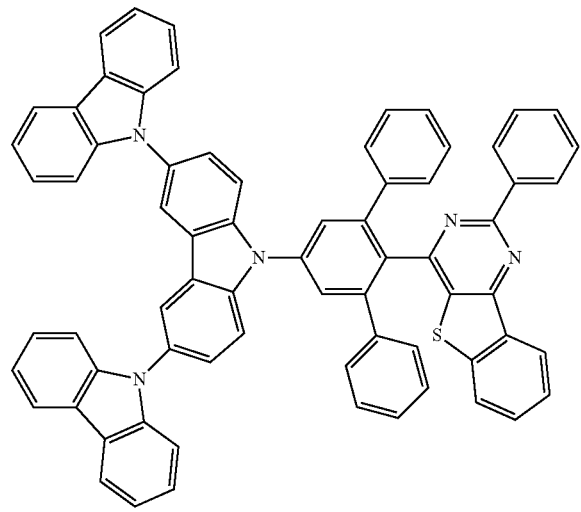
159
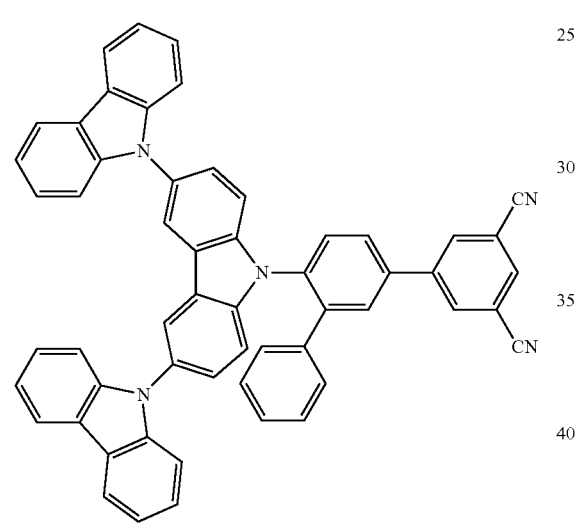
160
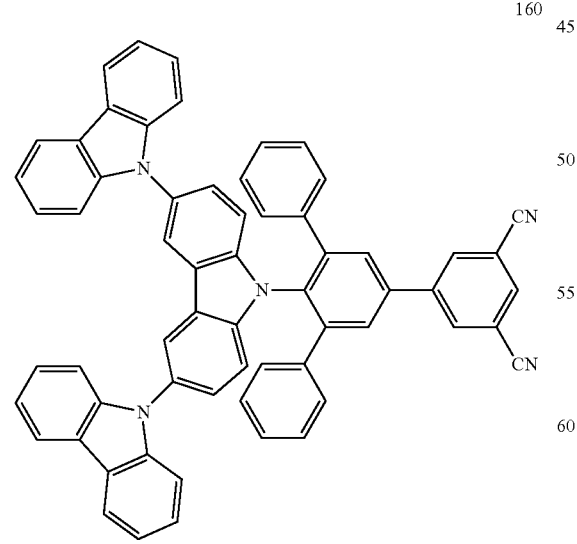
161
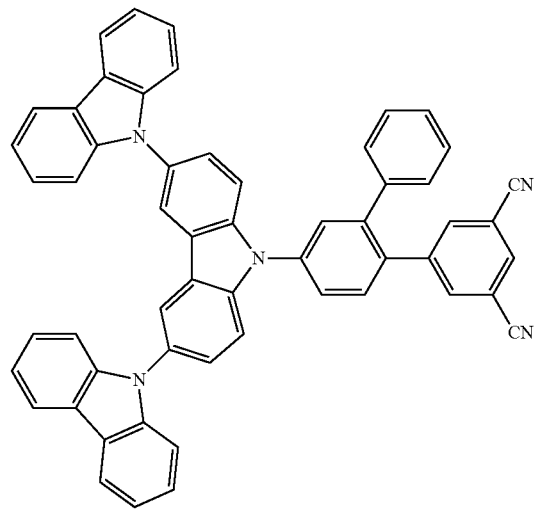
162
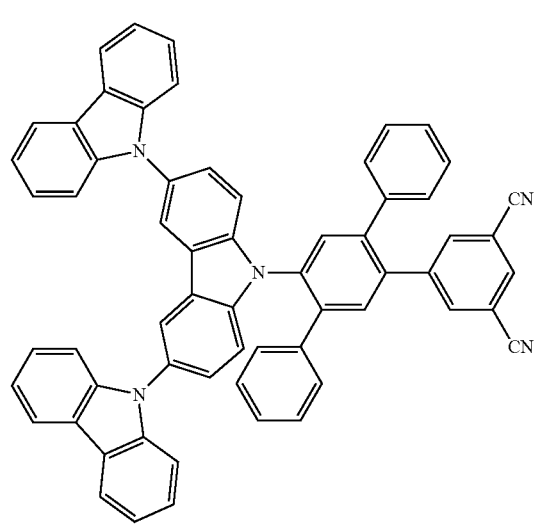
163
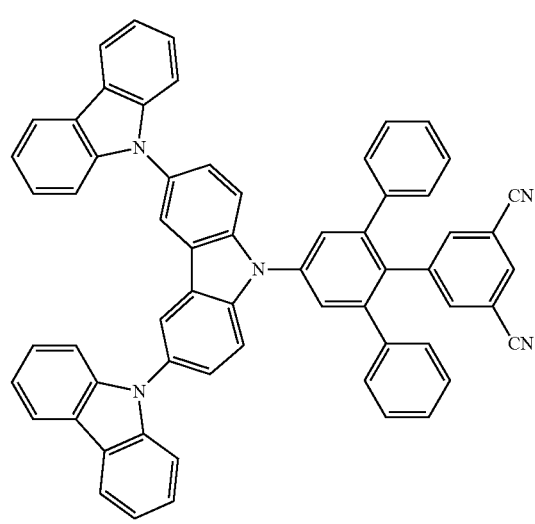

-continued
164
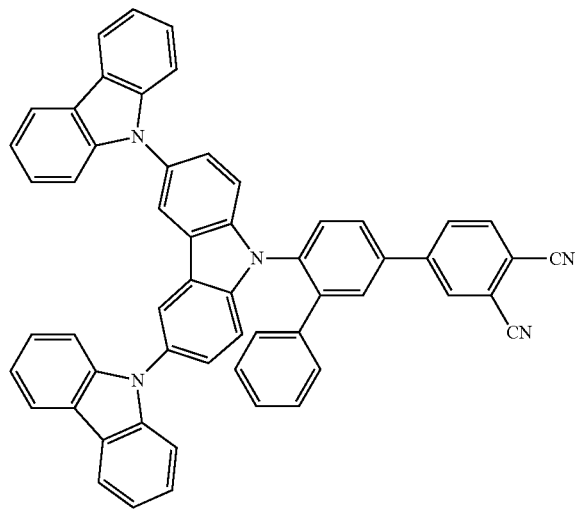
165
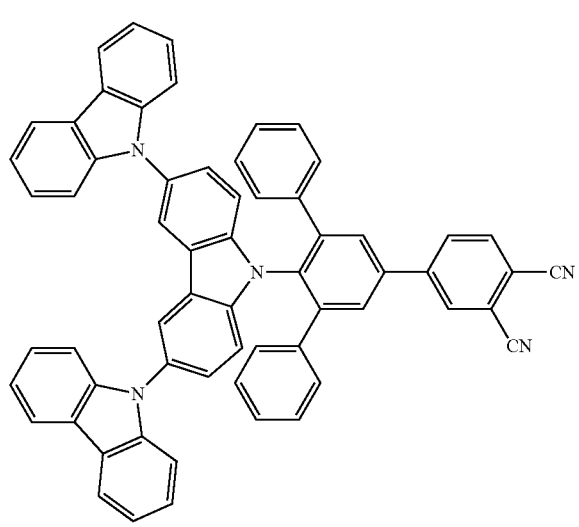
166
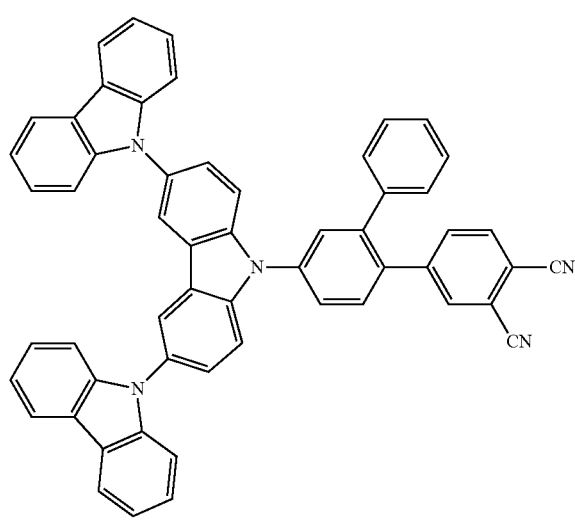
-continued
167
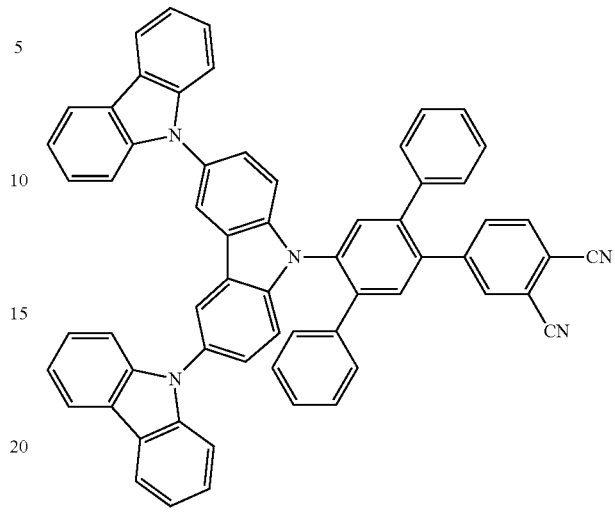
168
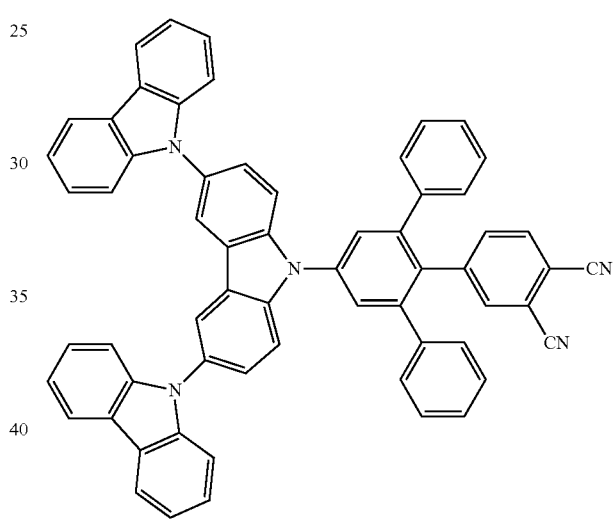
169
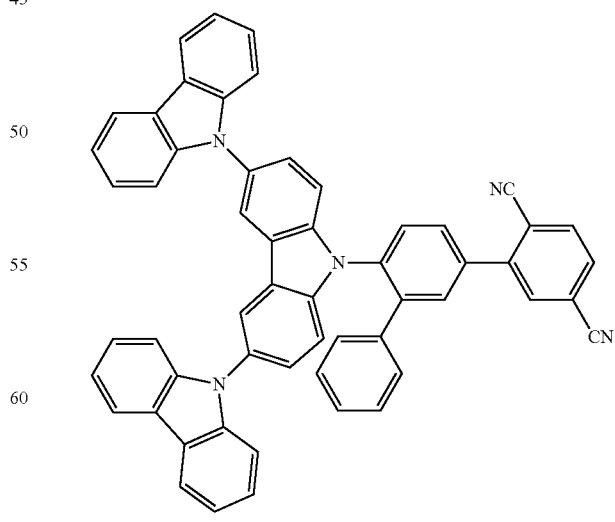

170
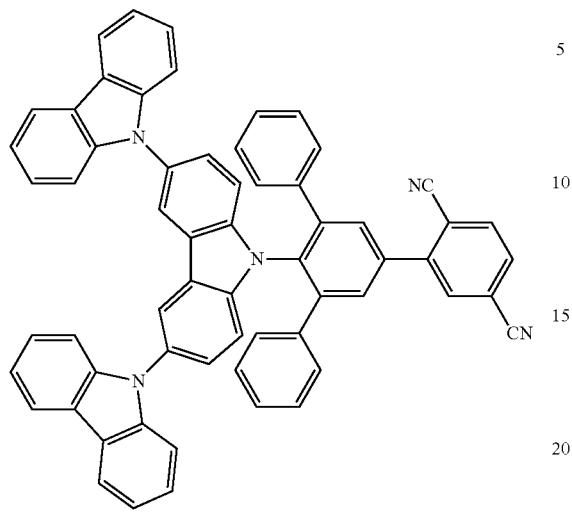
171
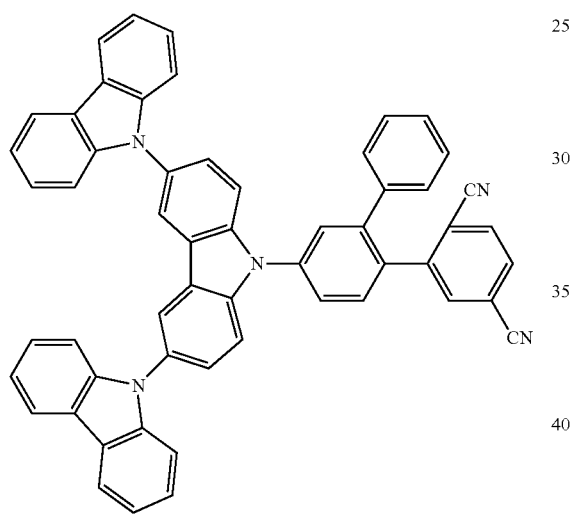
172
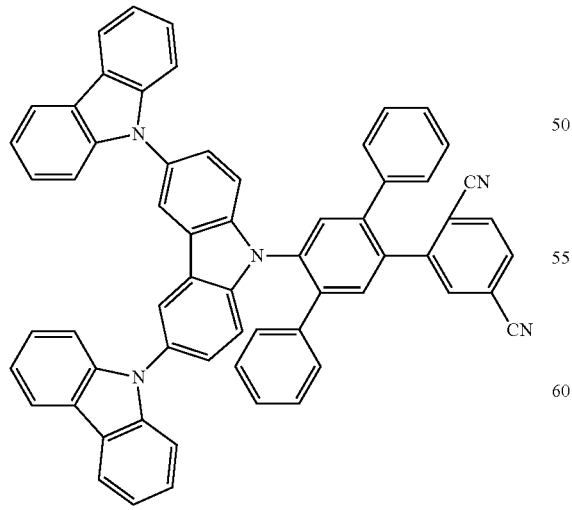
173
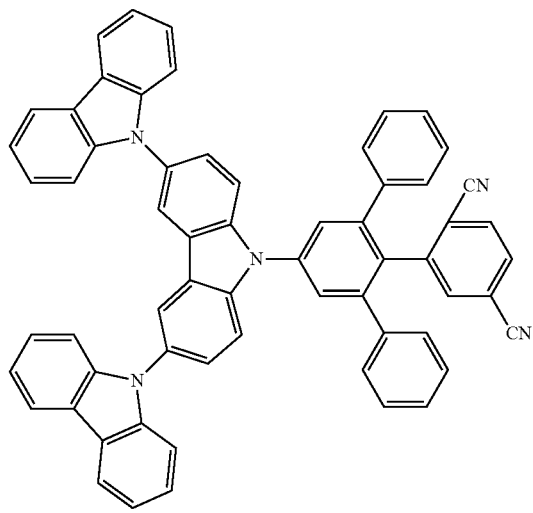
174
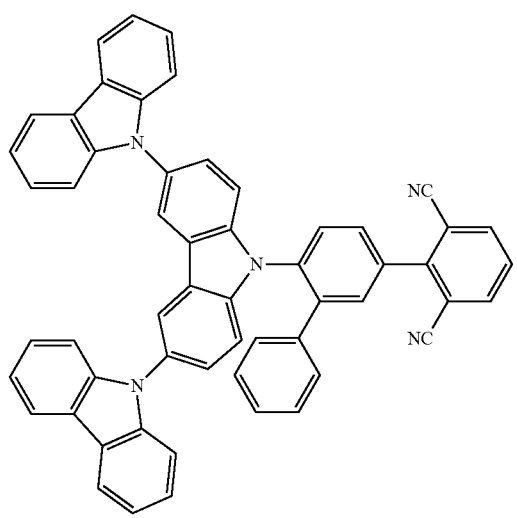
175
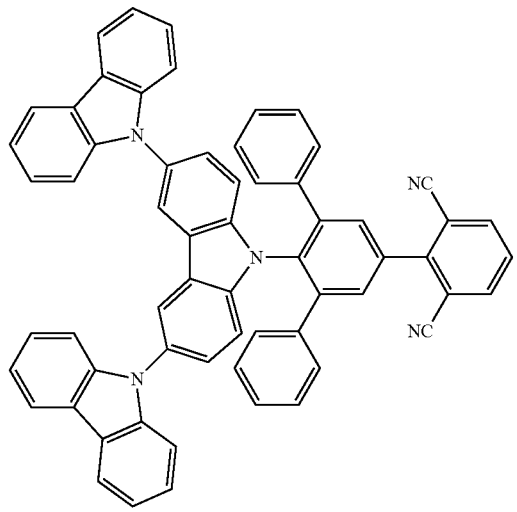

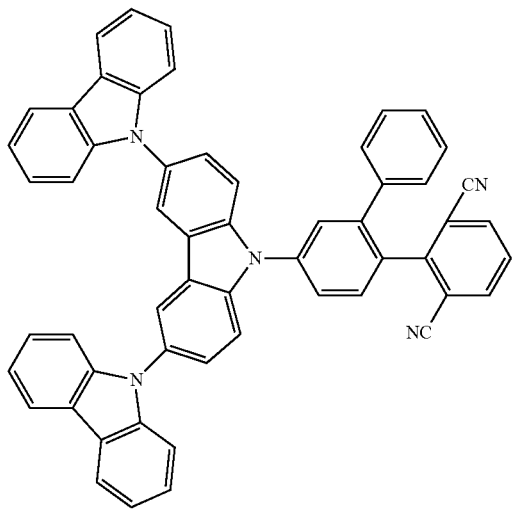
176
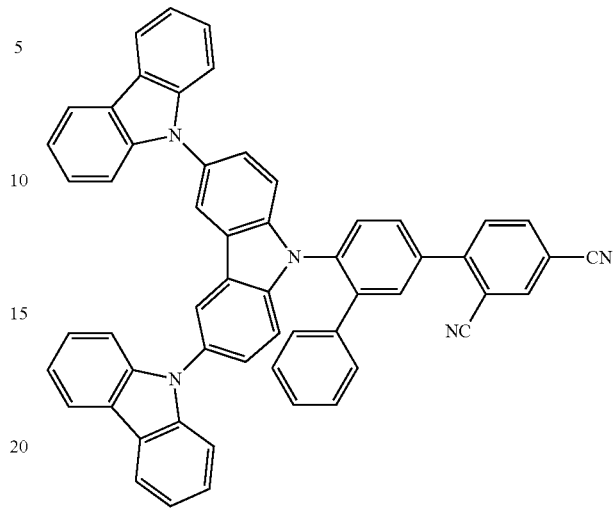
179
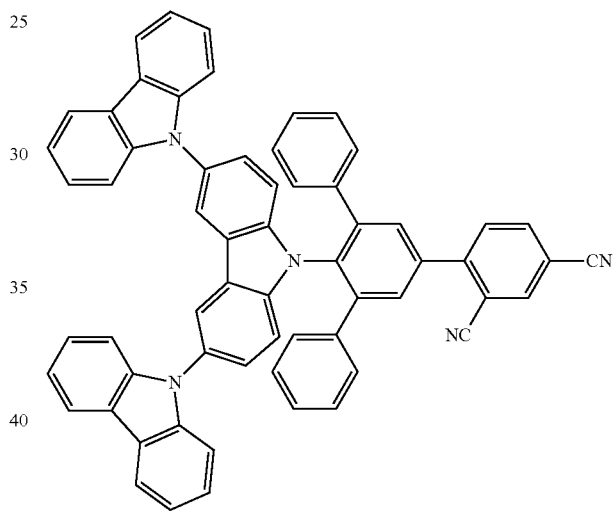
180
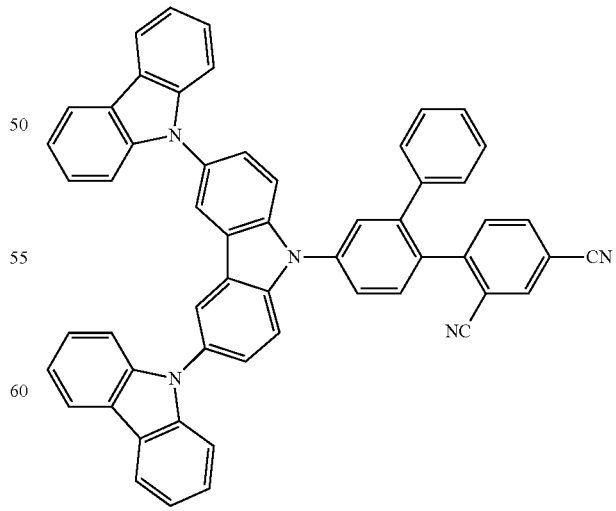
181

182
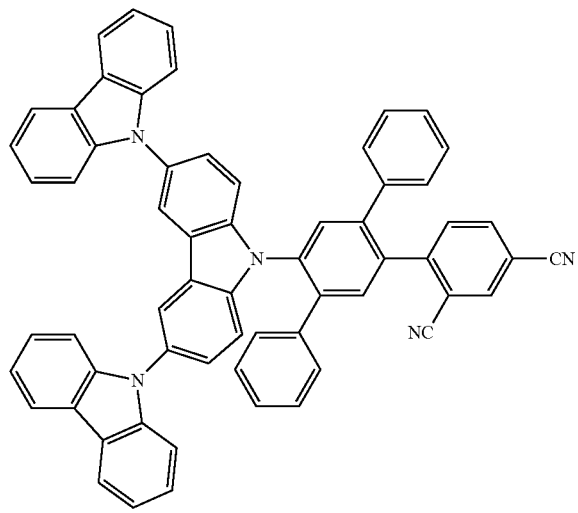
183
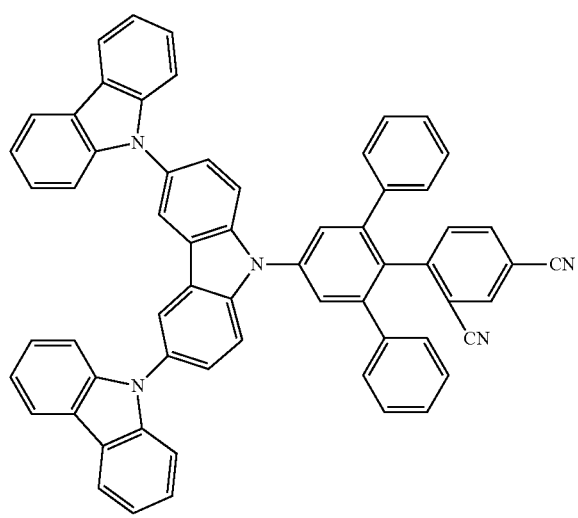
184
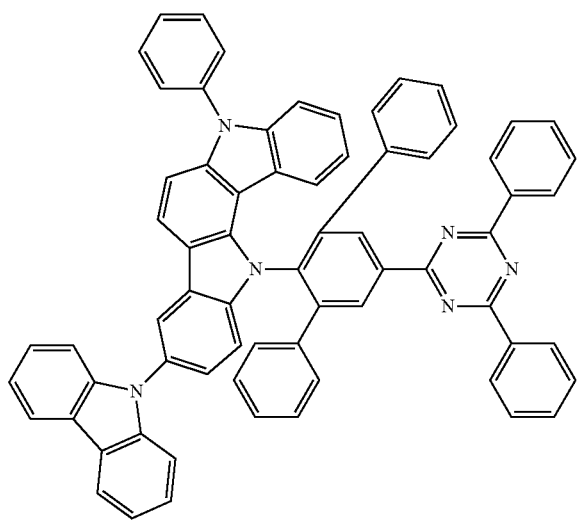
185
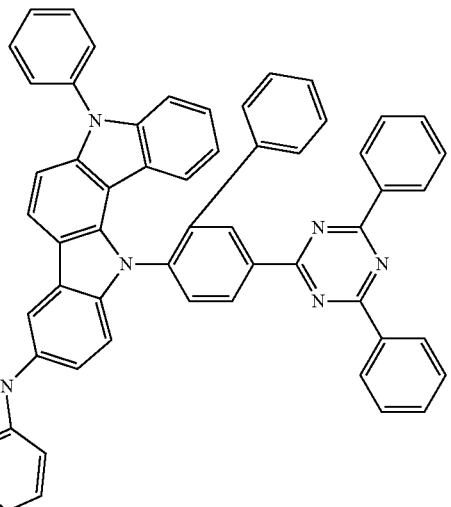
186
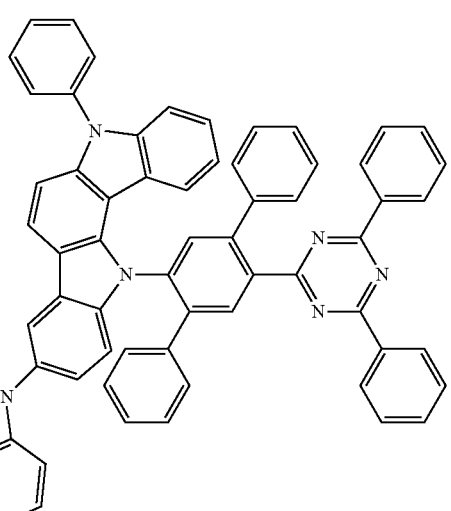
187
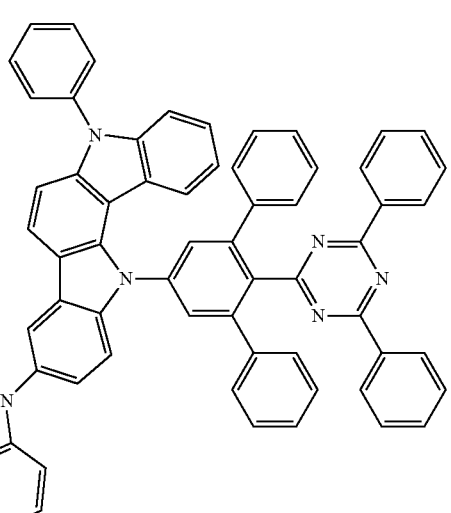

188
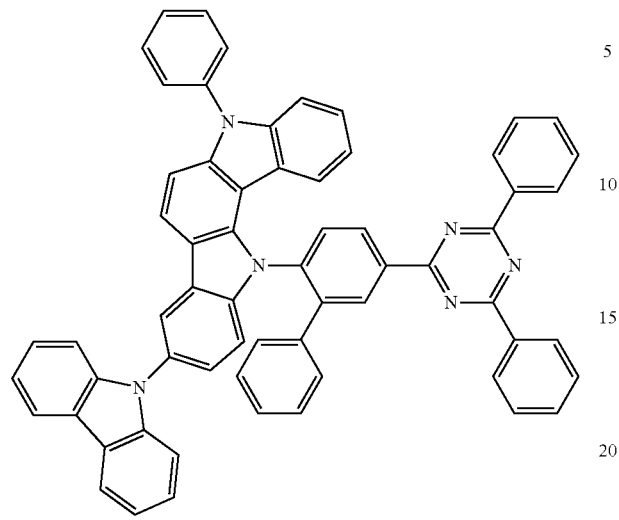
189
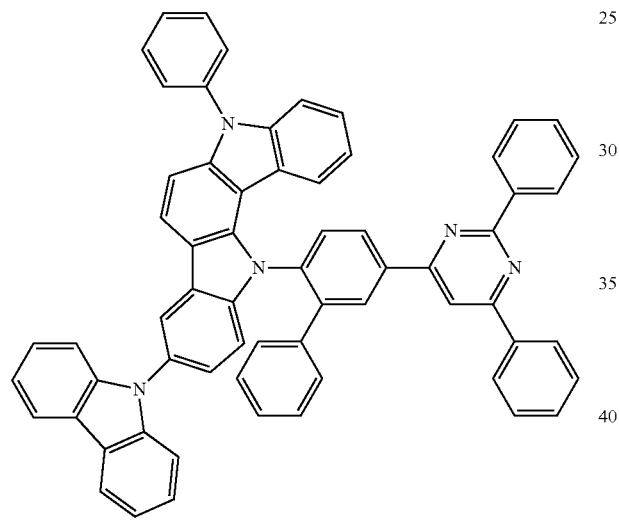
190
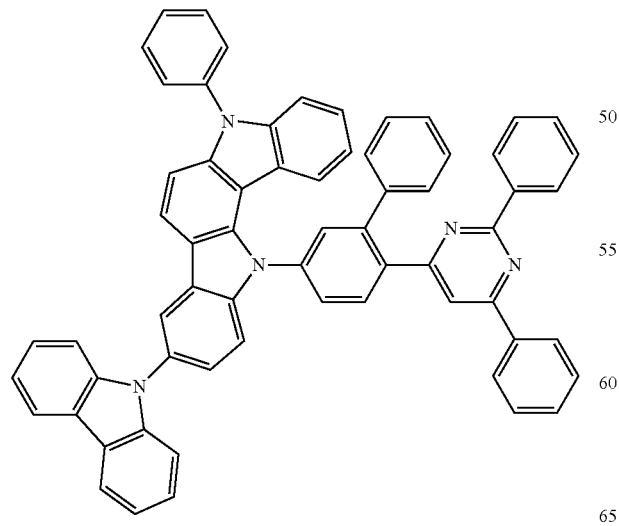
191
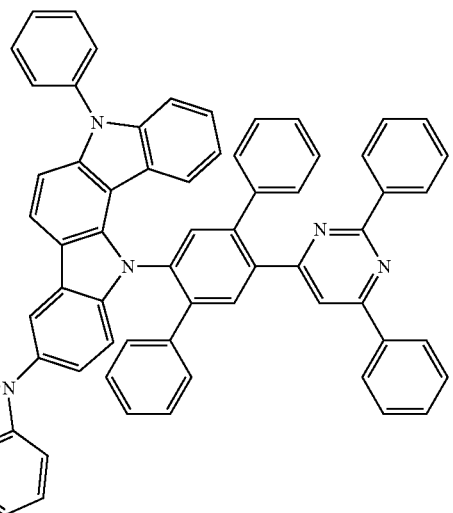
192
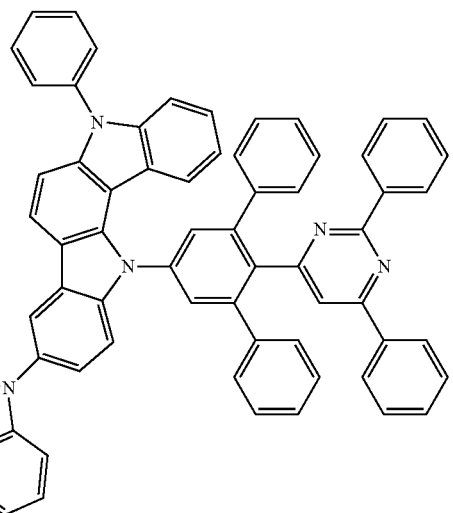
193
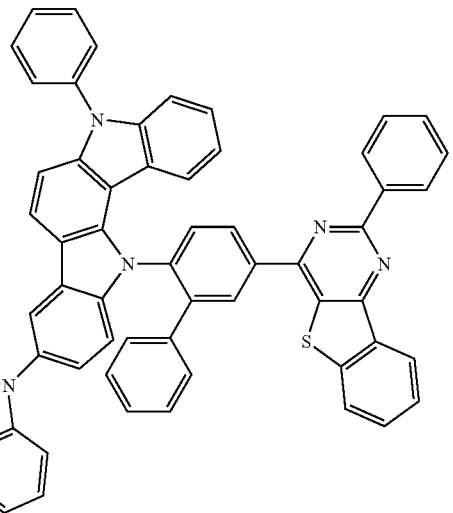

194
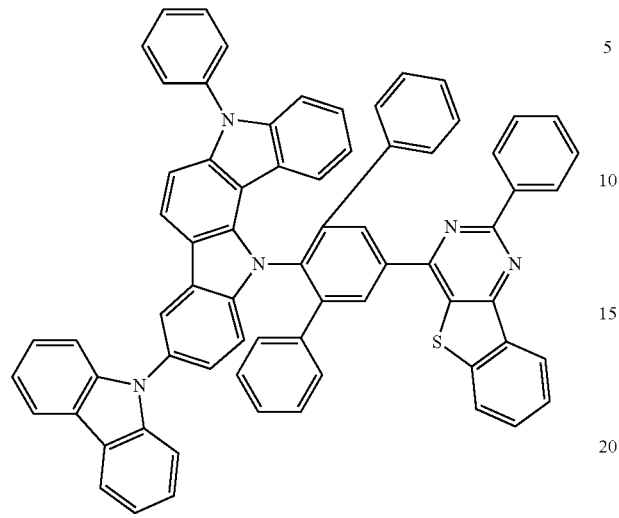
195
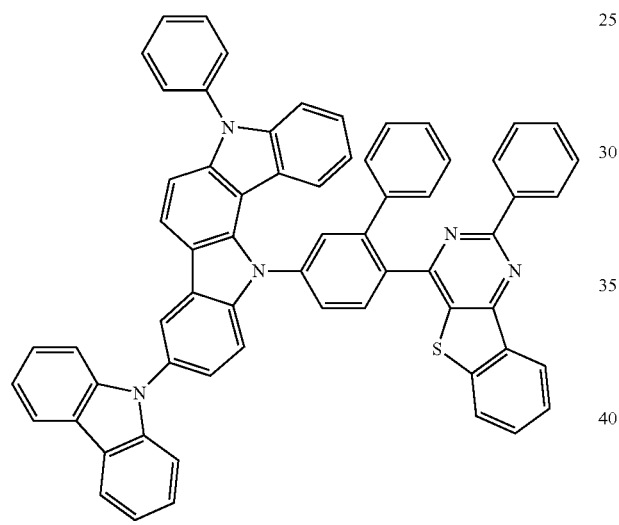
196
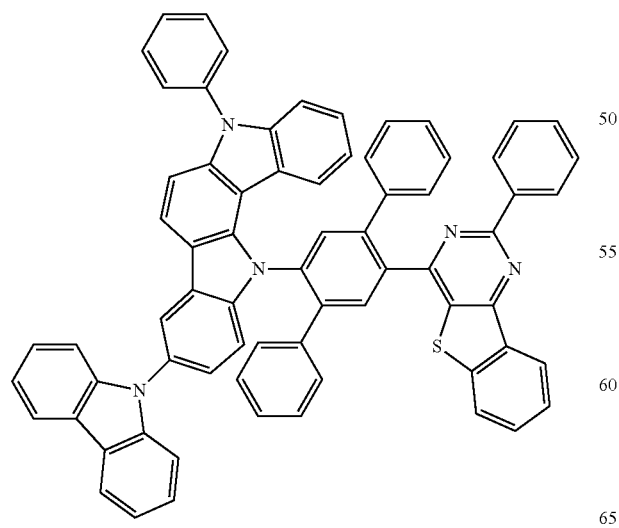
197
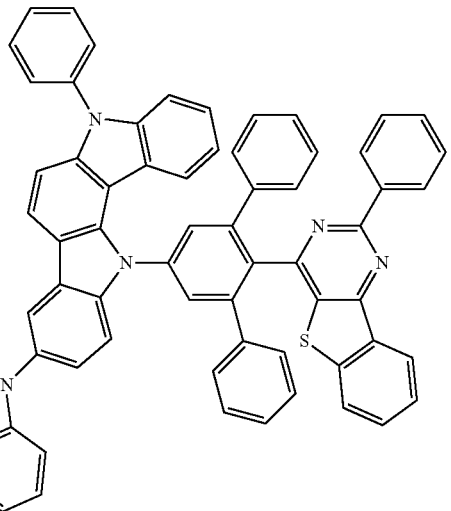
198
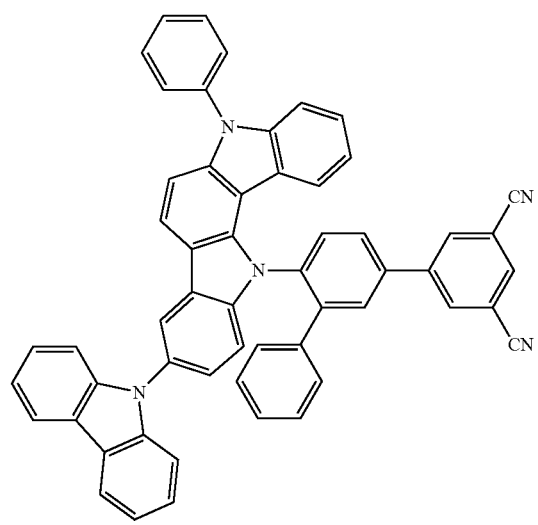
199
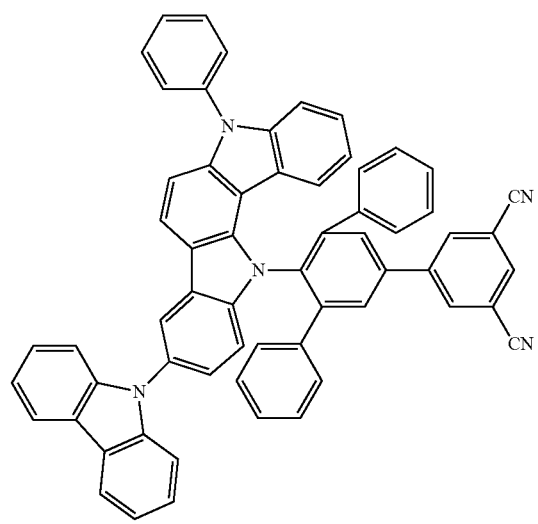

US 10,957,863 B2
200
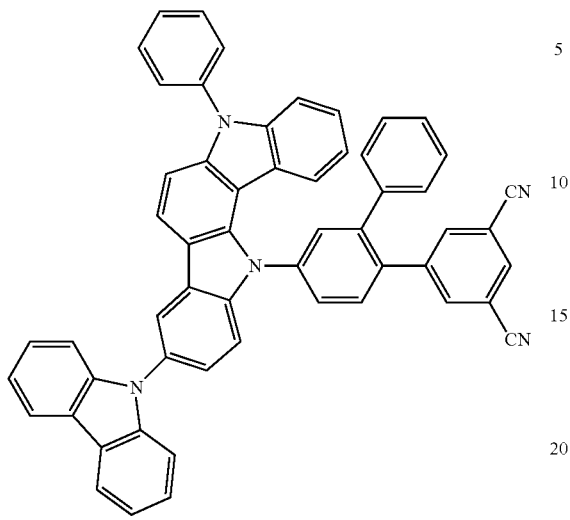
201
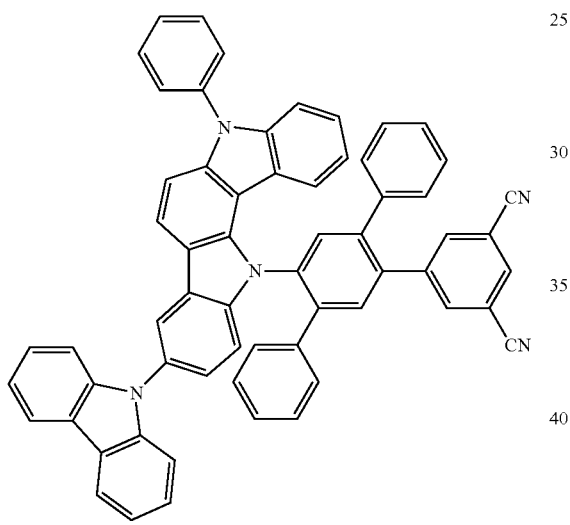
202
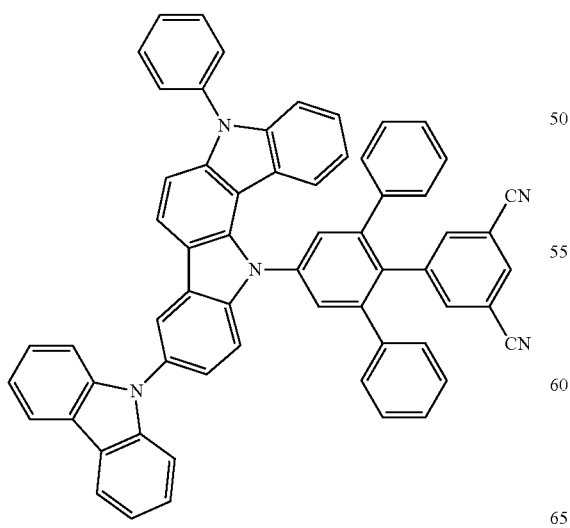
203
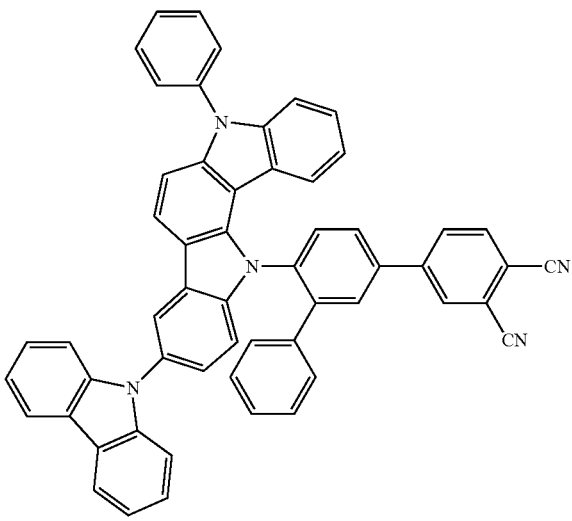
204
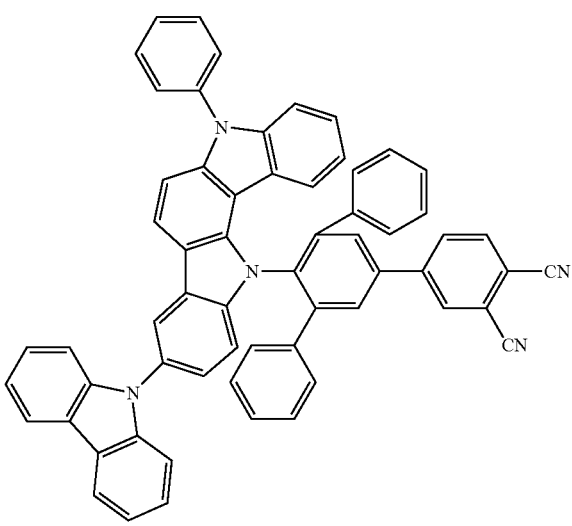
205
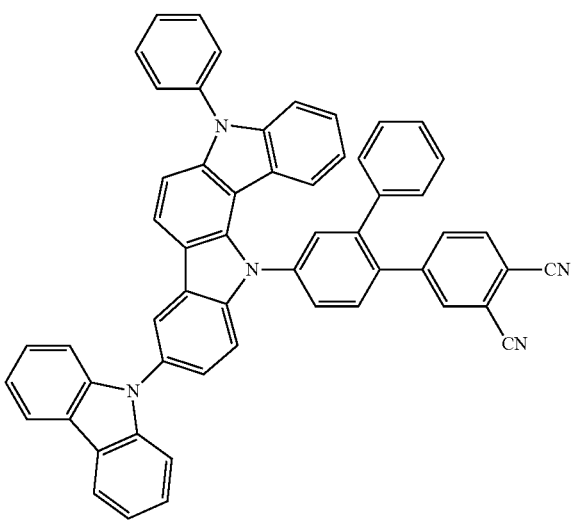

206
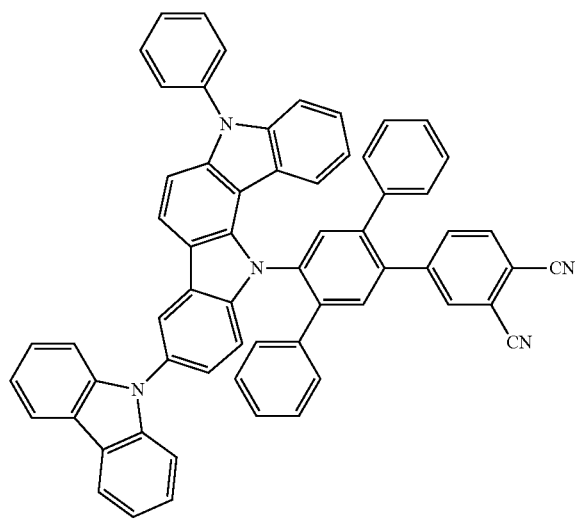
207
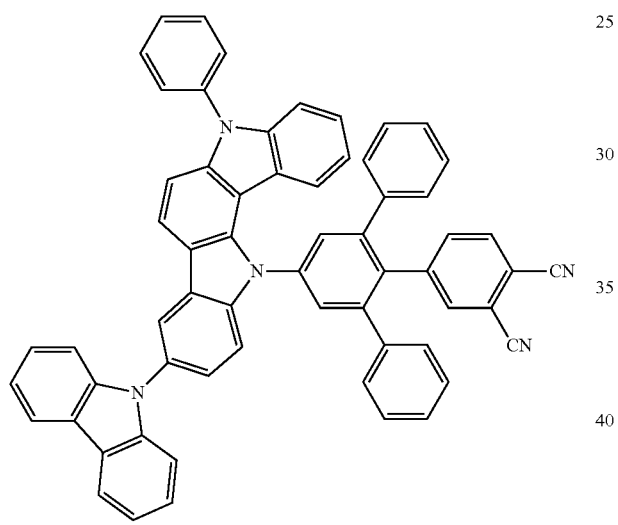
208
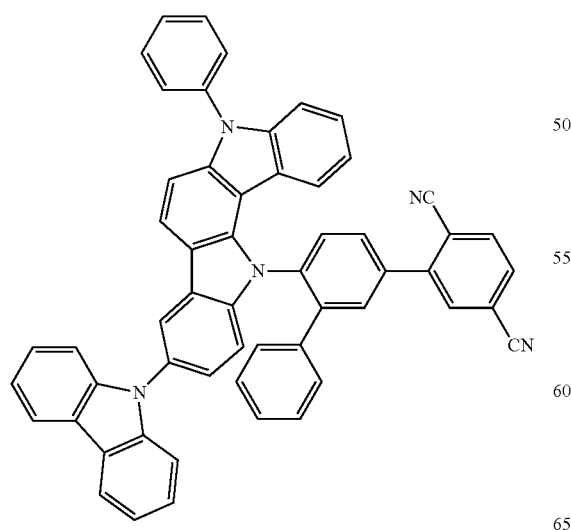
209
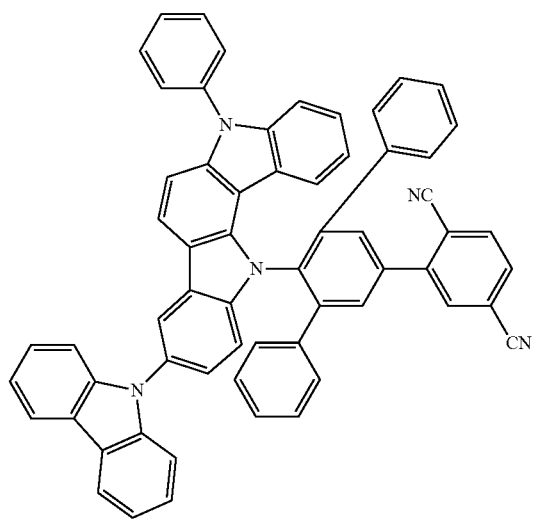
210
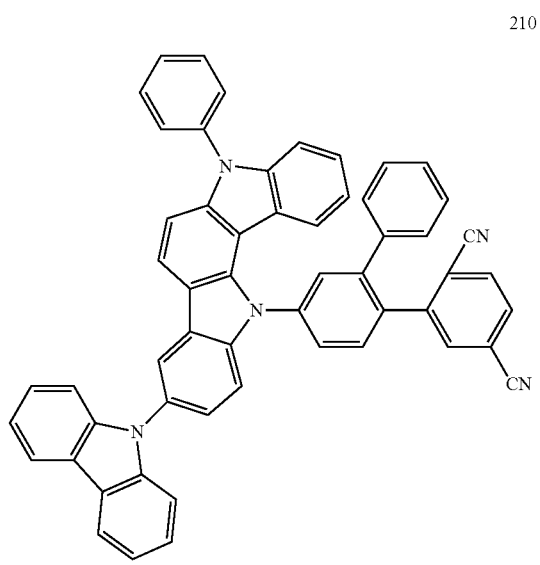
211
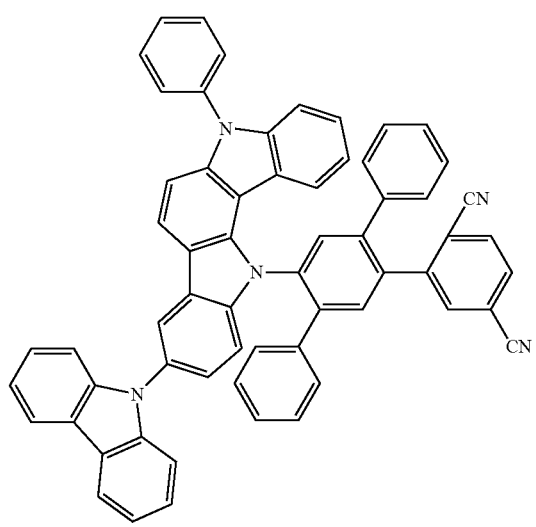

212
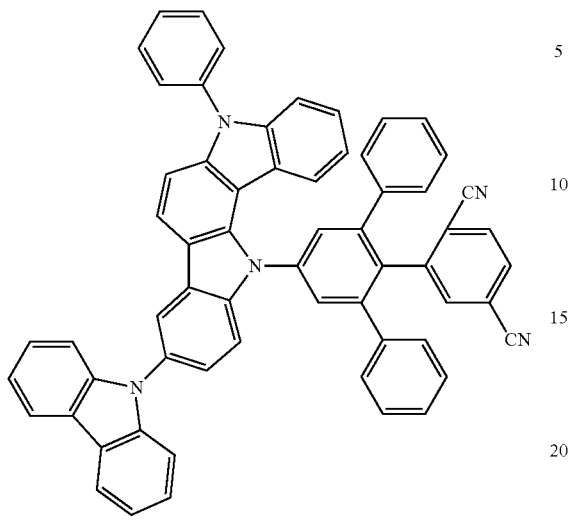
213
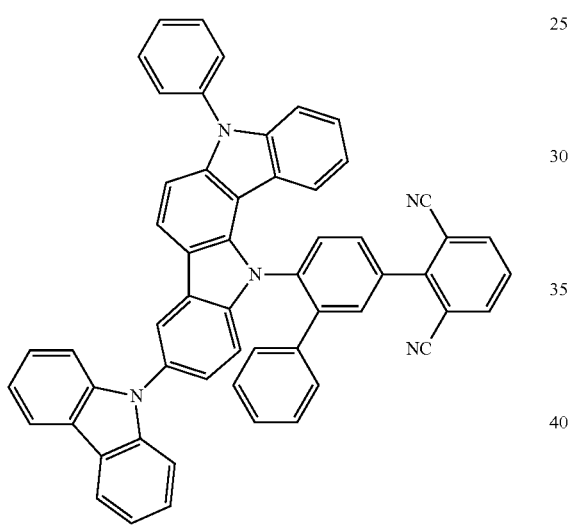
214
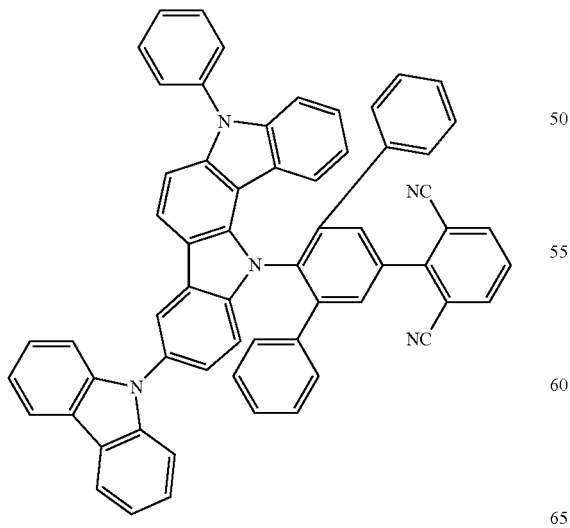
215
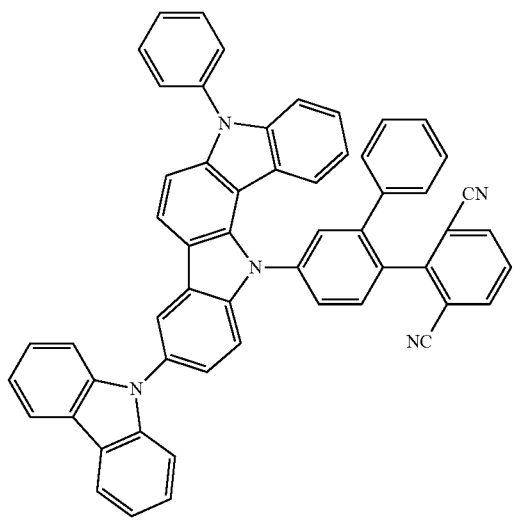
216
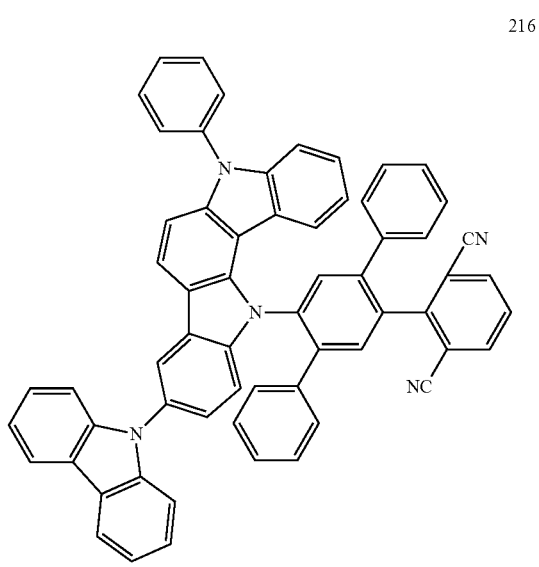
217
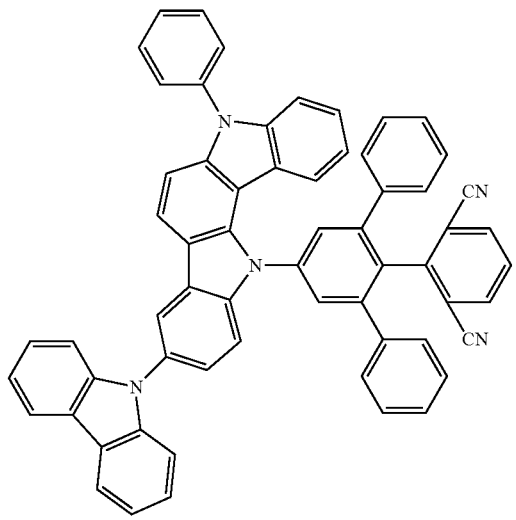

-continued
218
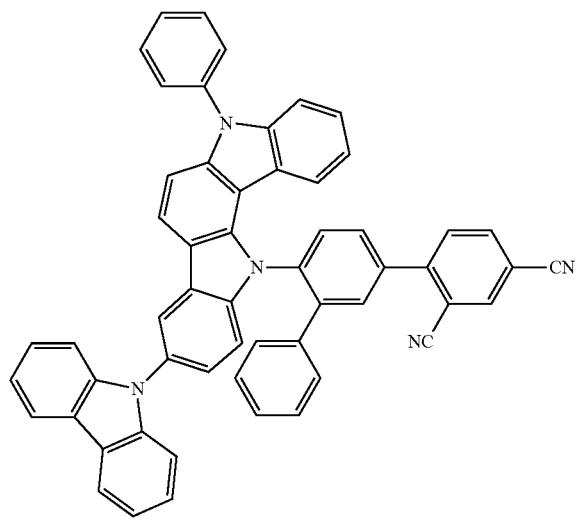
219
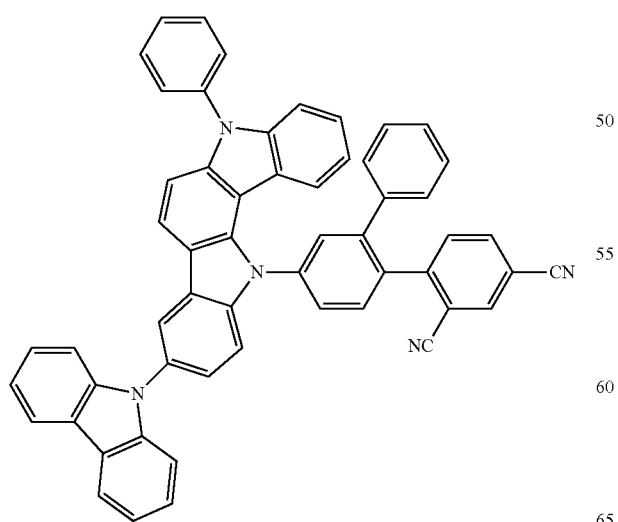
221
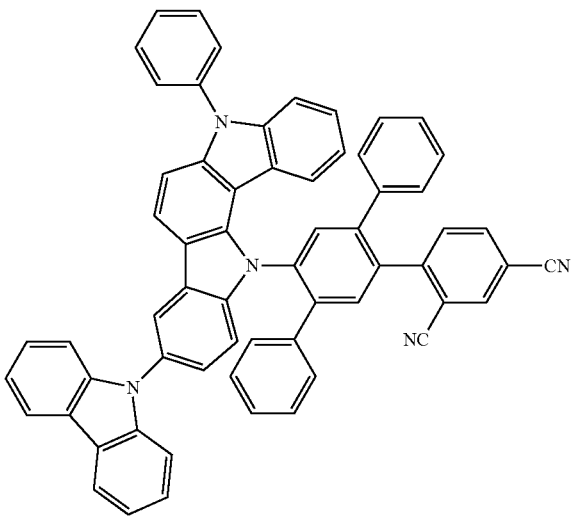
222
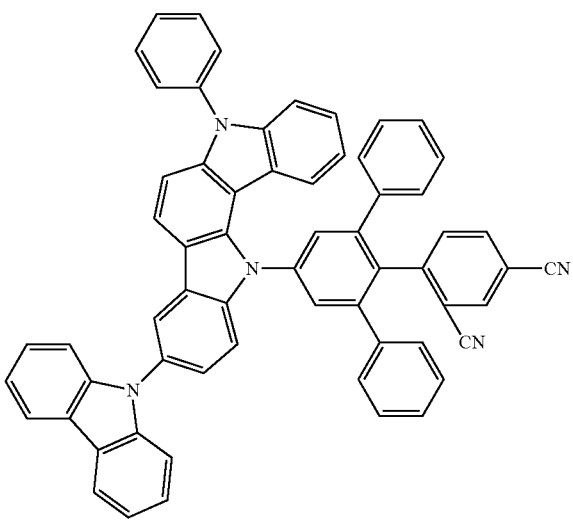
223
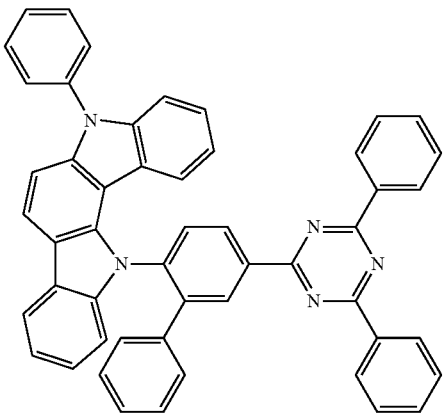

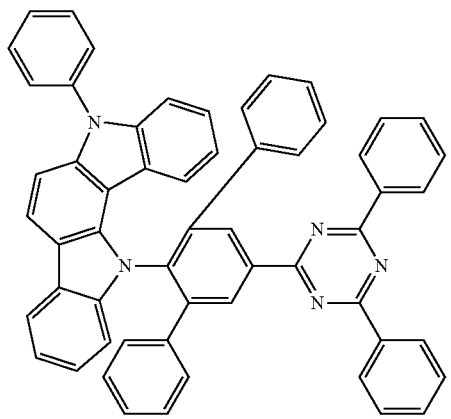
224
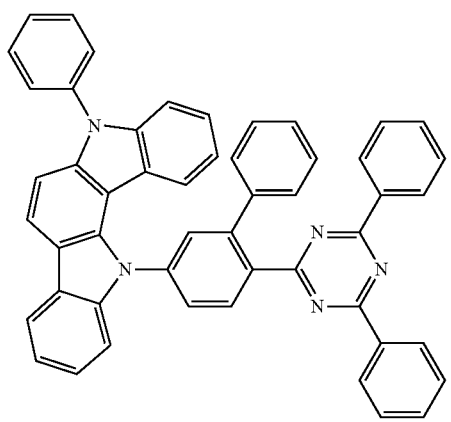
225
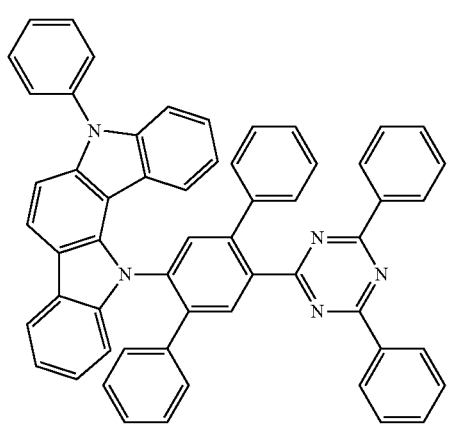
226
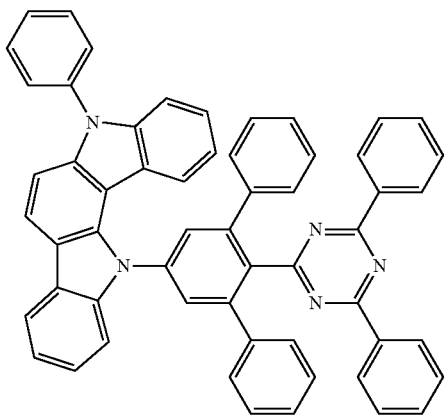
227
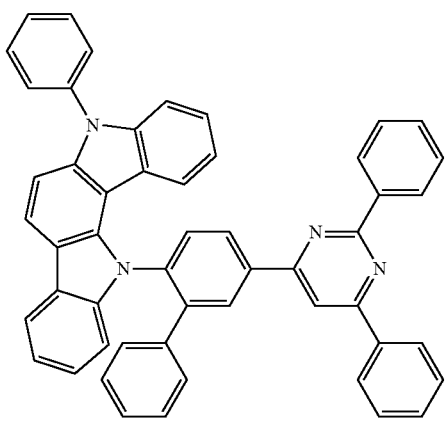
228
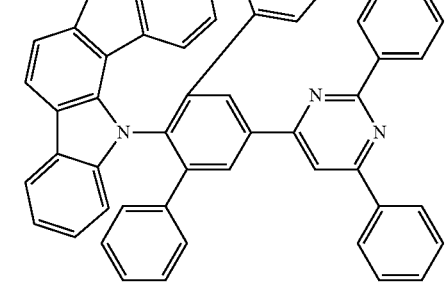
229

230
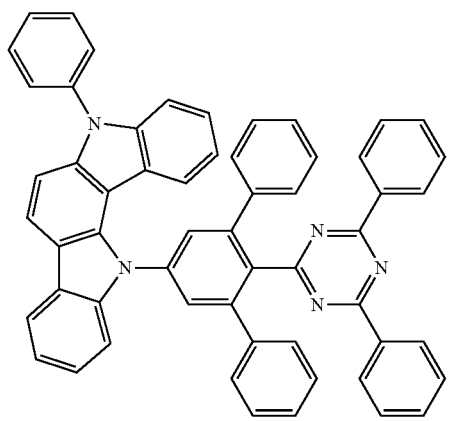
231
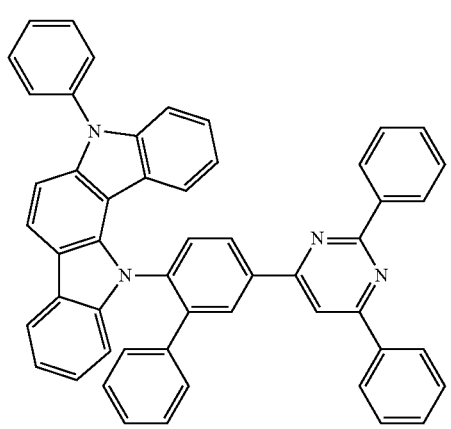
232
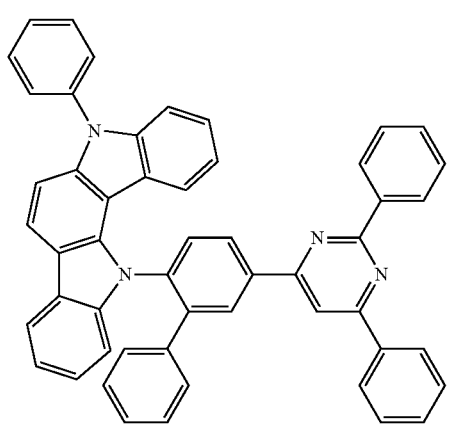
233
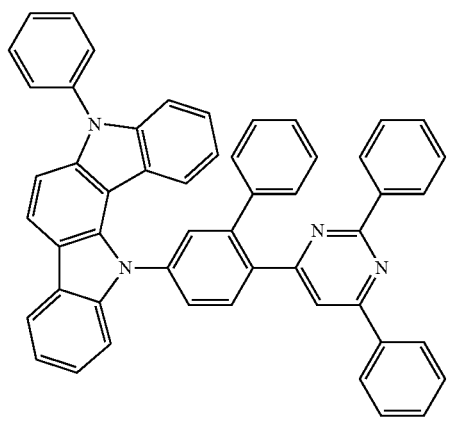
234
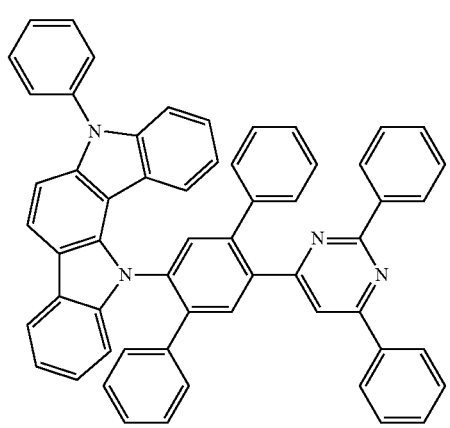
235
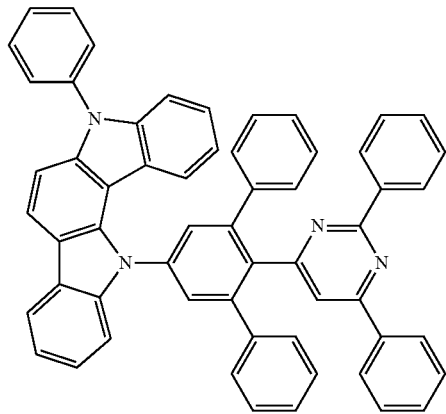

236
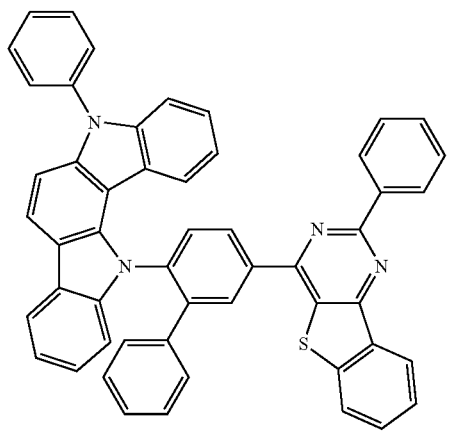
239
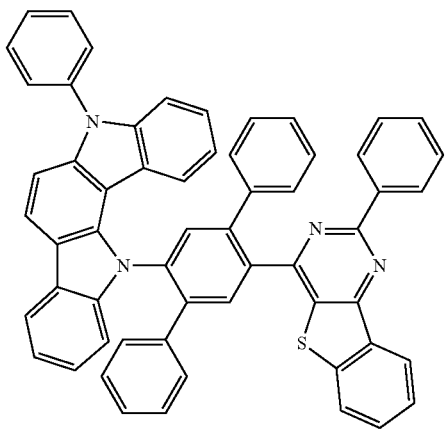
237
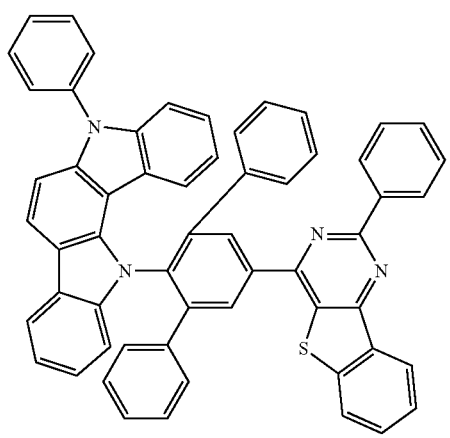
240
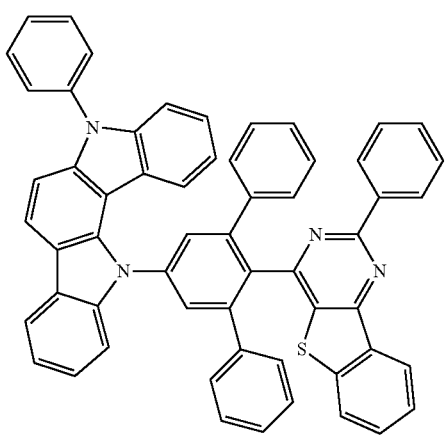
238
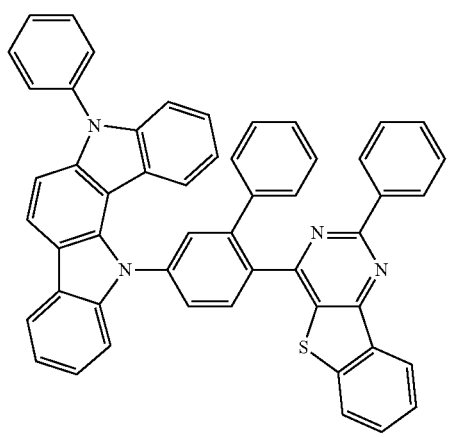
241
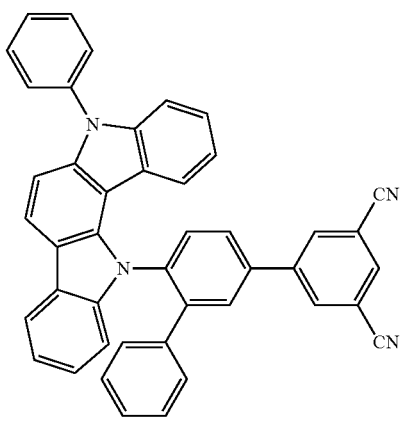

242
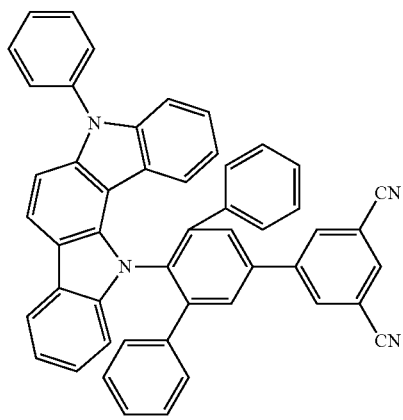
243
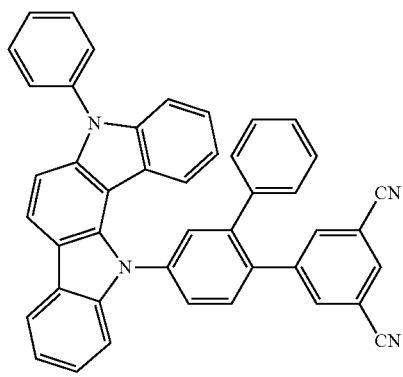
244
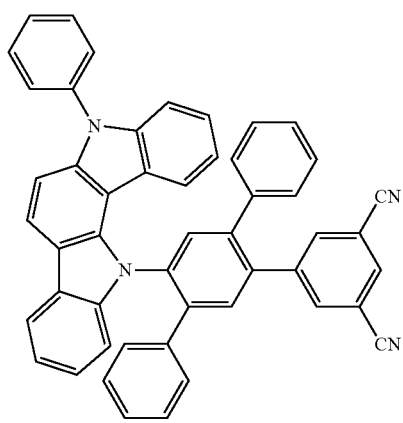
245
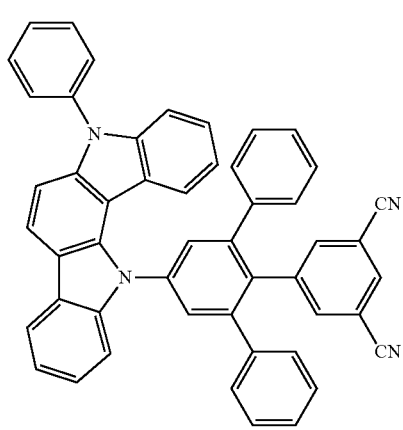
246
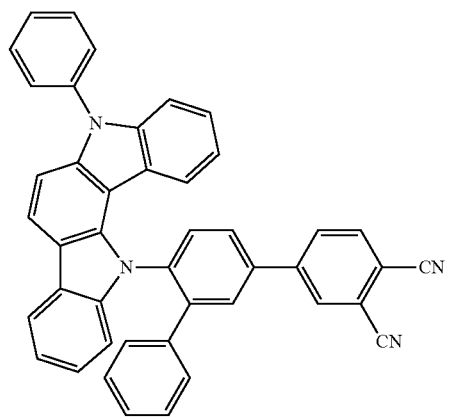
247
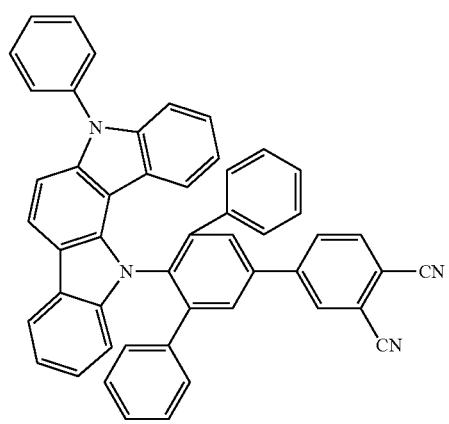
248
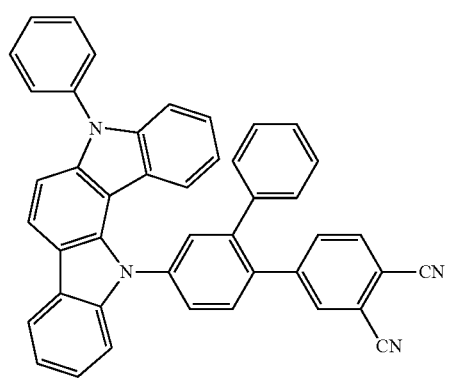
249
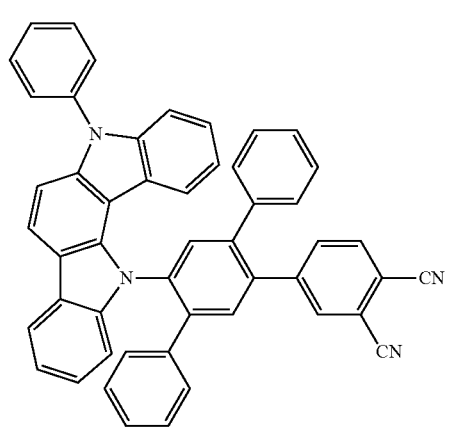

247
-continued
250
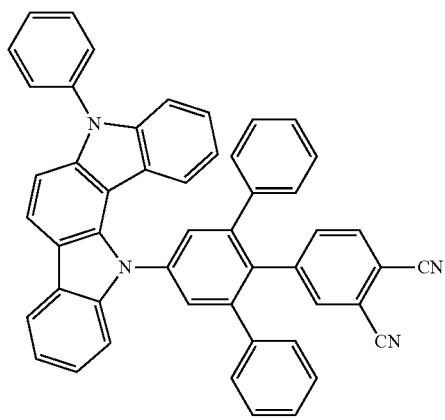
251
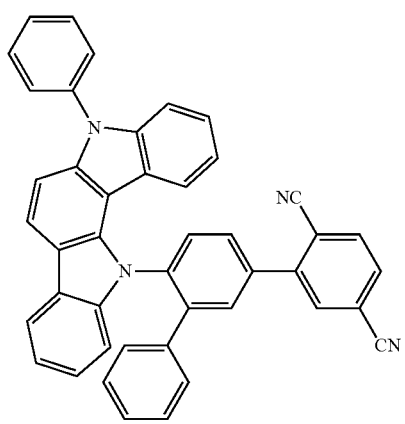
252
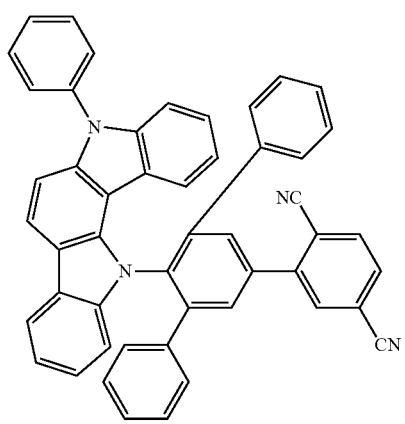
253
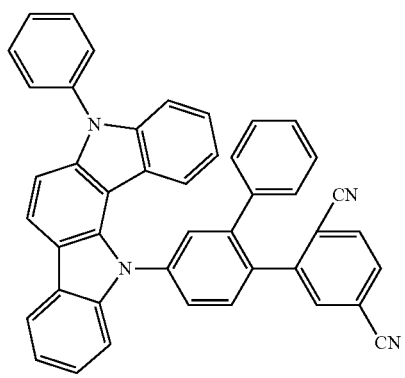
248
-continued
254
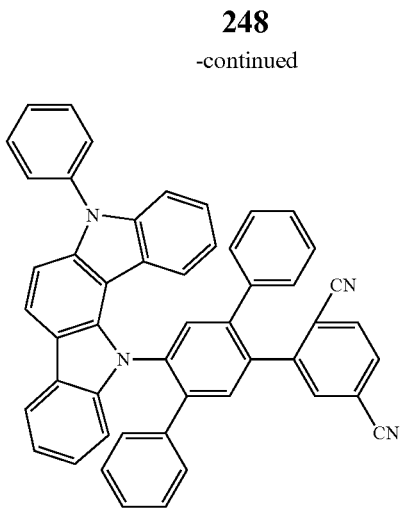
255
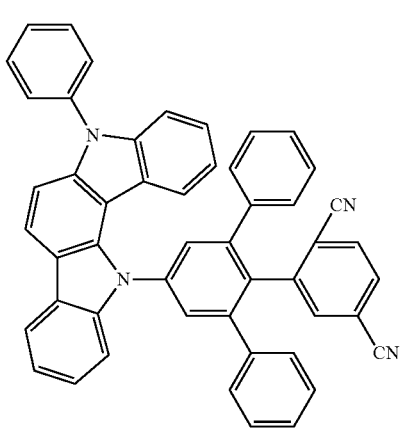
256
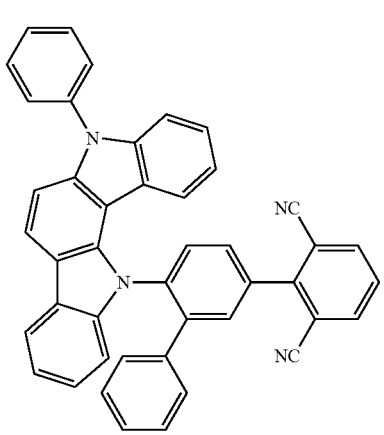

257
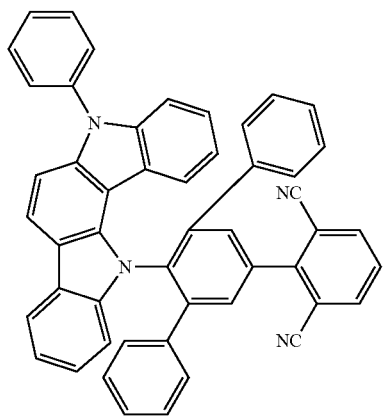
258
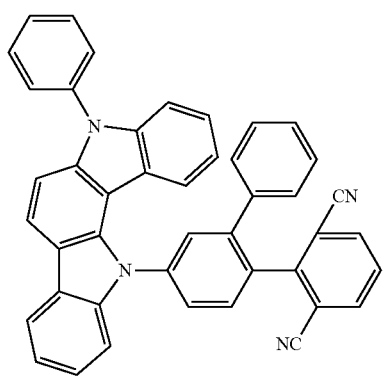
259
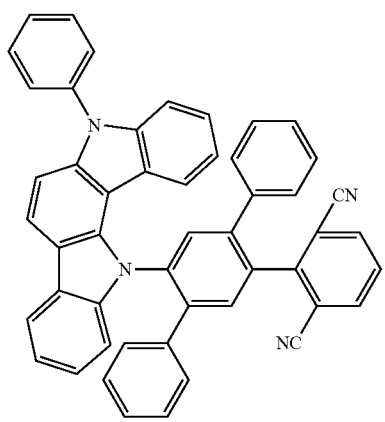
260
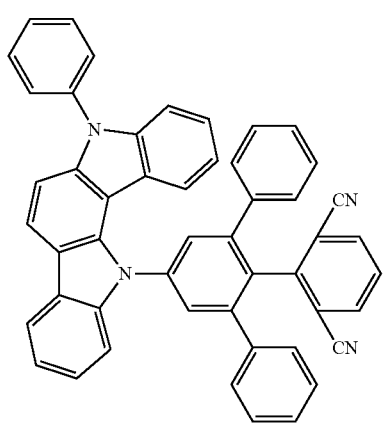
261
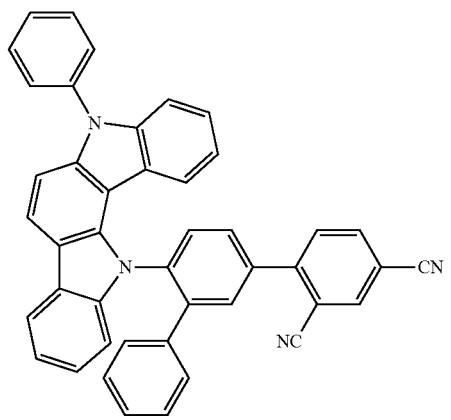
262
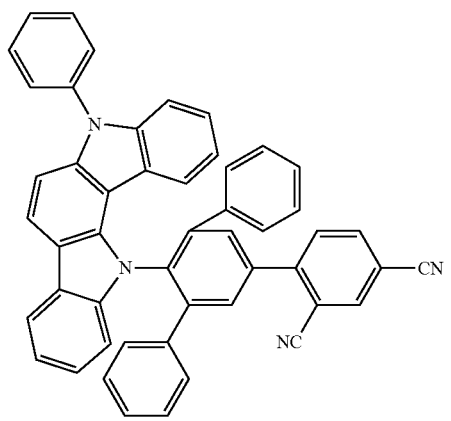
263
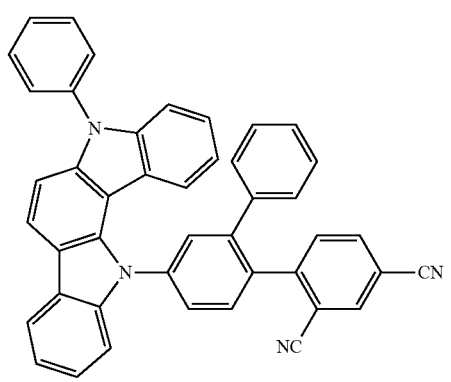
264
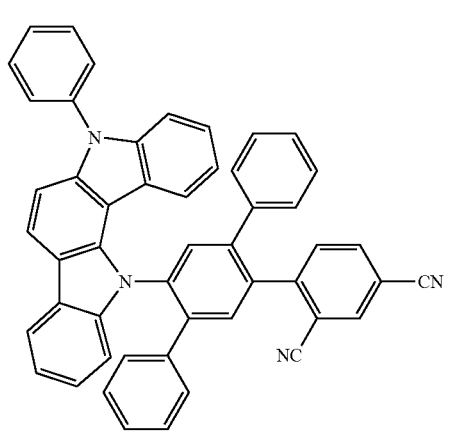

265
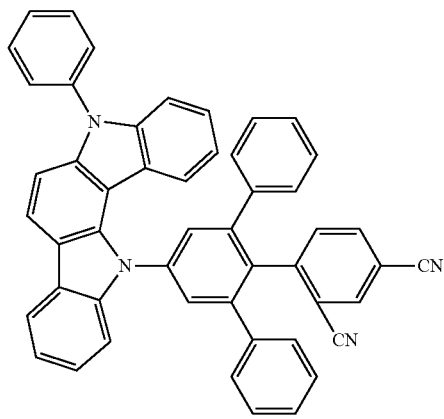
266
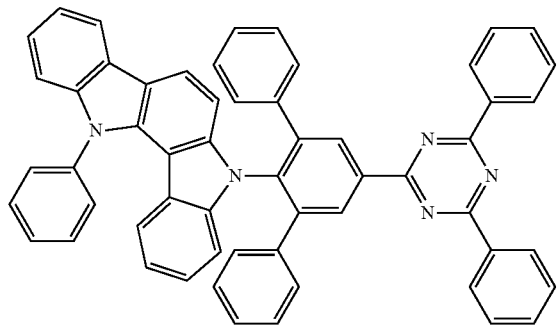
267
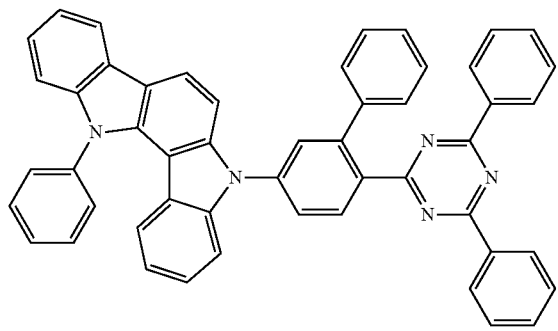
268
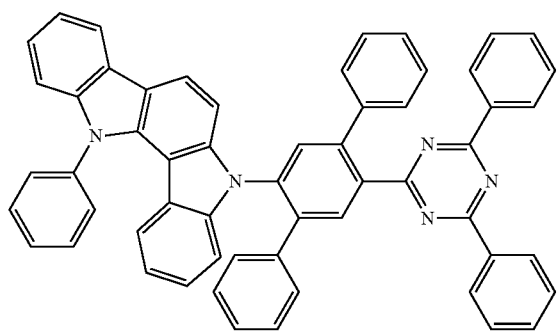
269
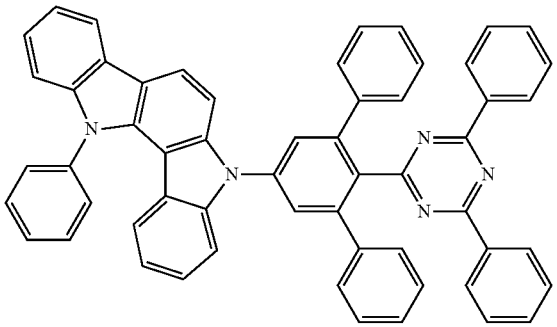
270
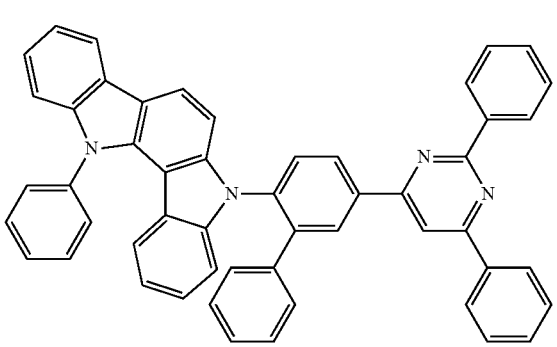
271
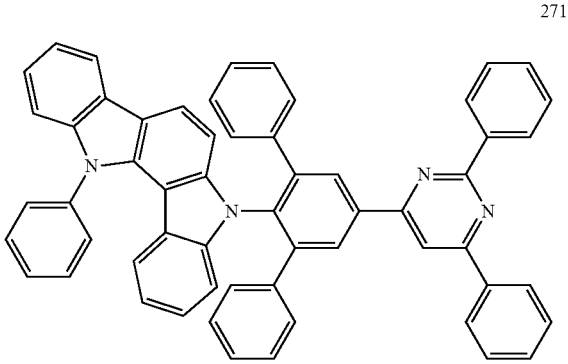
272
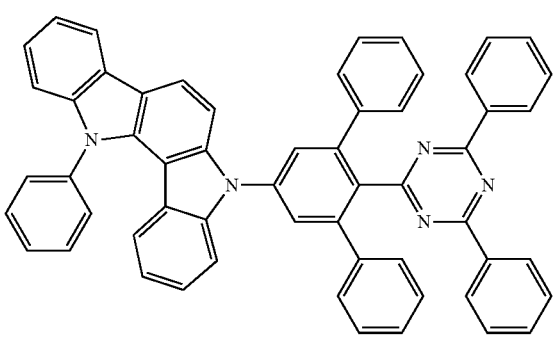

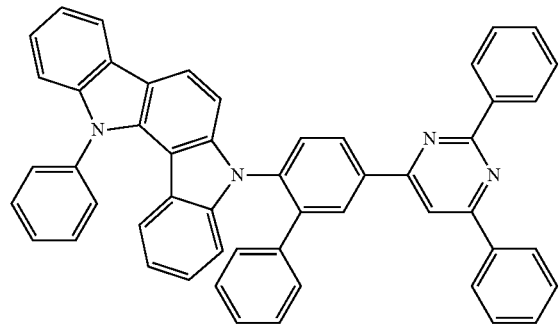
273
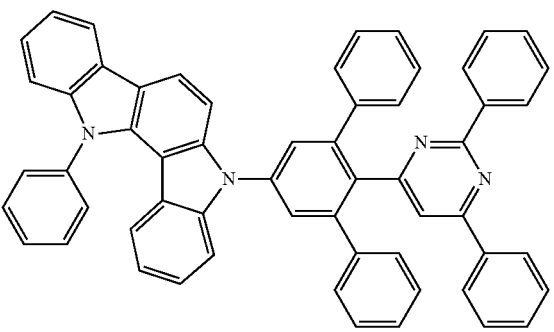
277
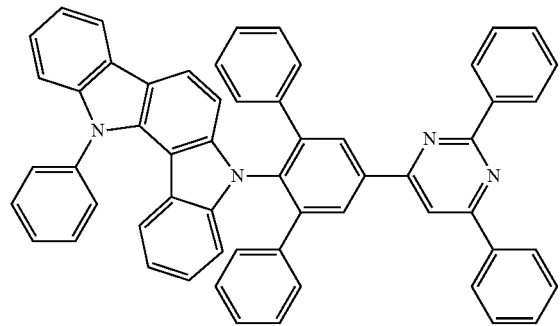
274
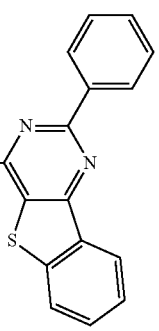
278
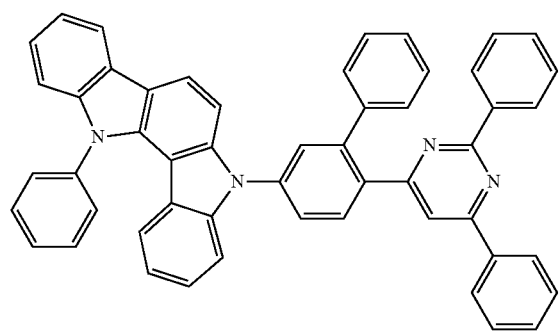
275
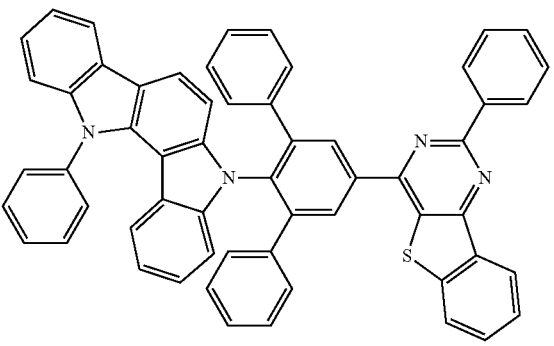
279
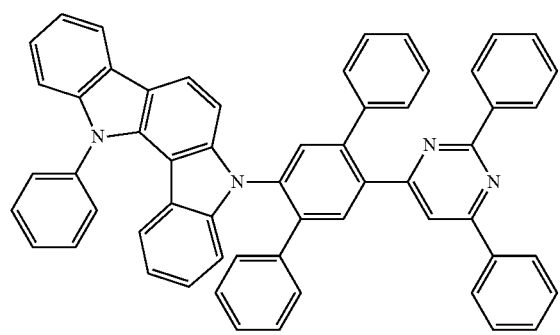
276
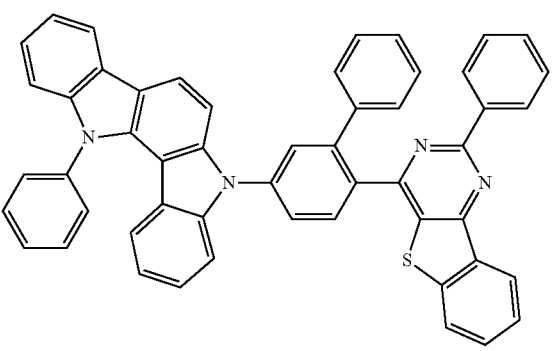
280

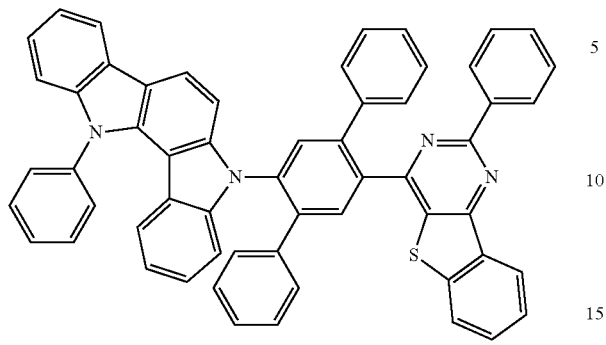
281
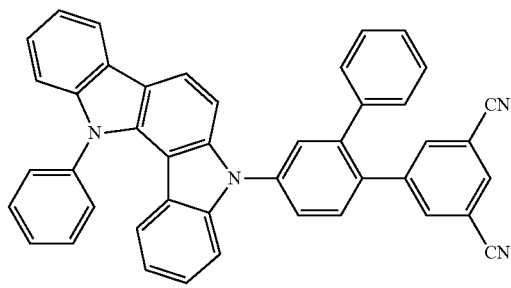
285
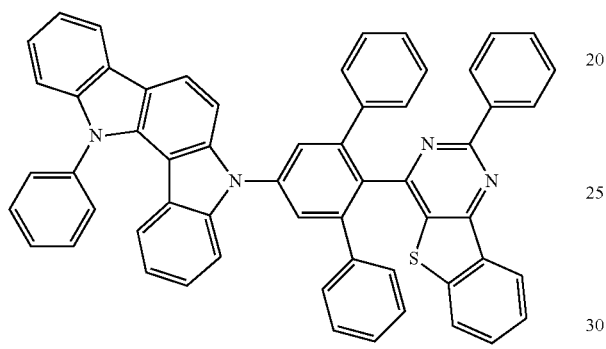
282
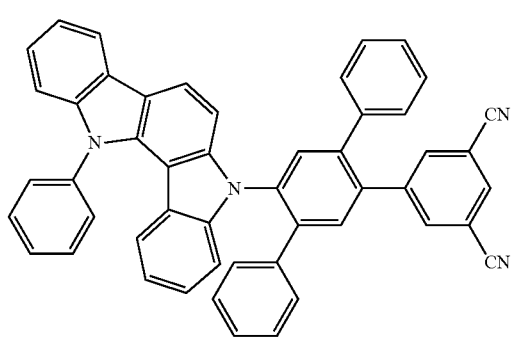
286
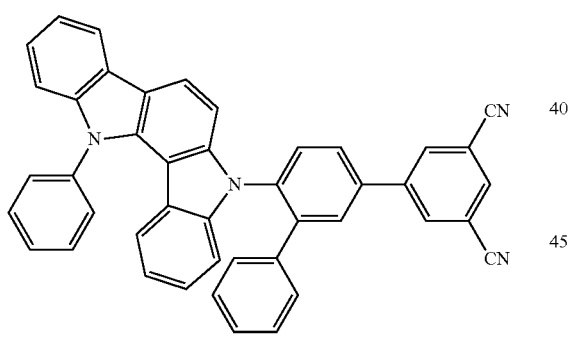
283
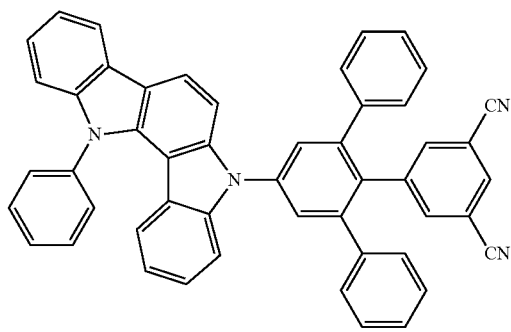
287
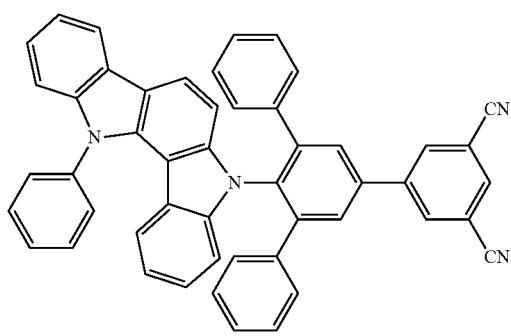
284
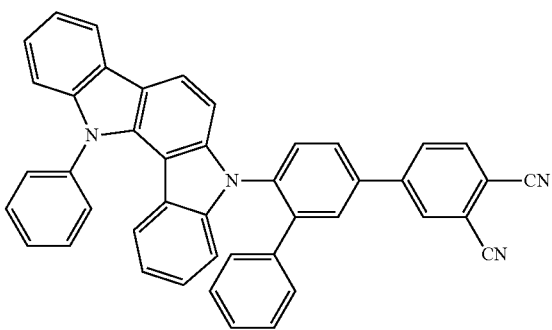
288

289
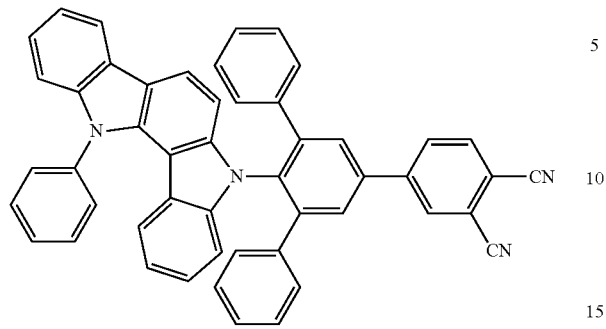
290
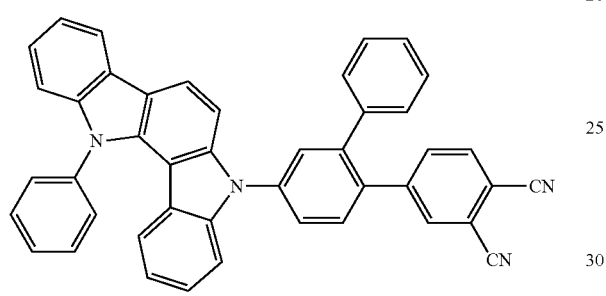
291
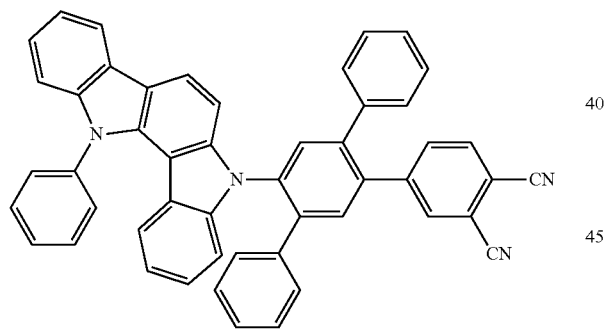
292
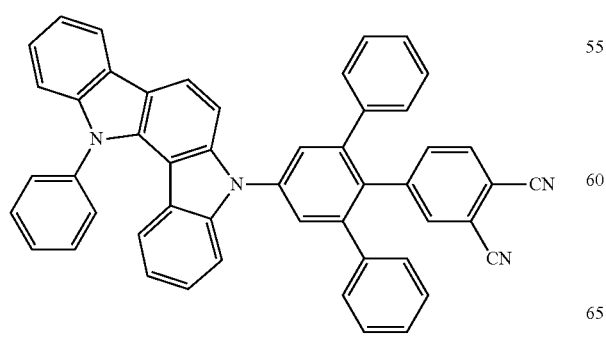
293
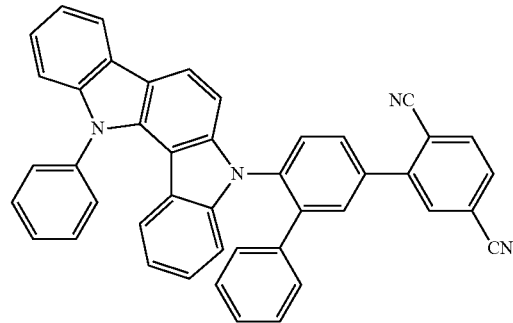
294
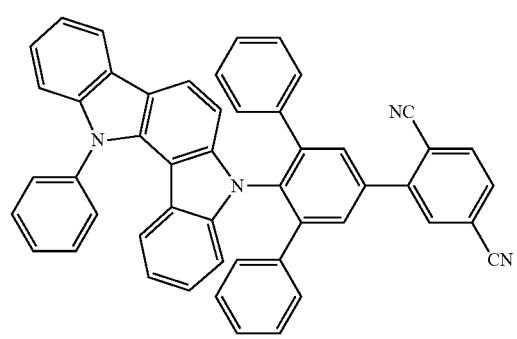
295
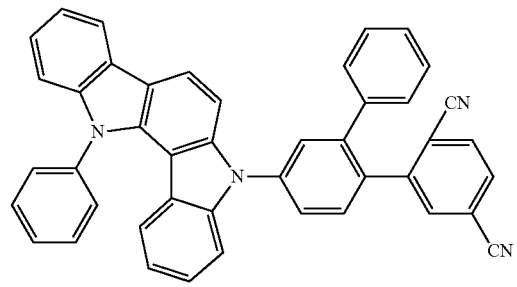
296
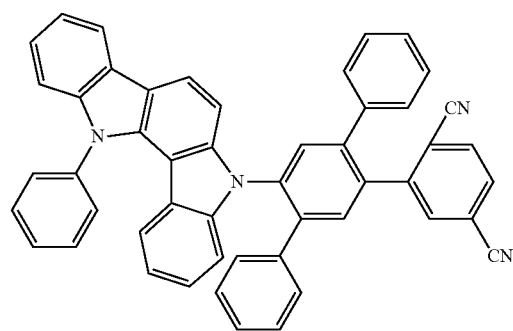

259
-continued
297
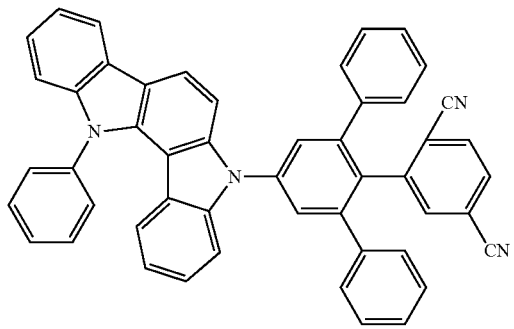
298
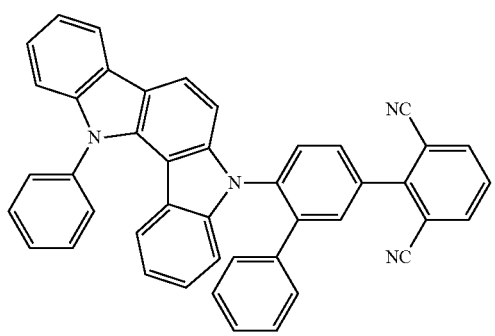
299
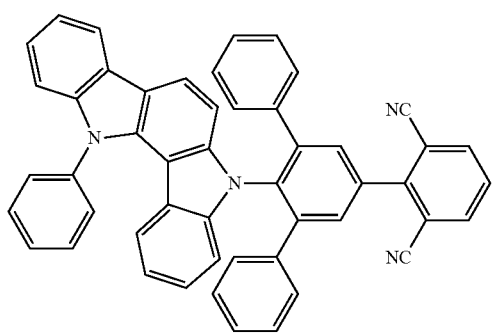
300
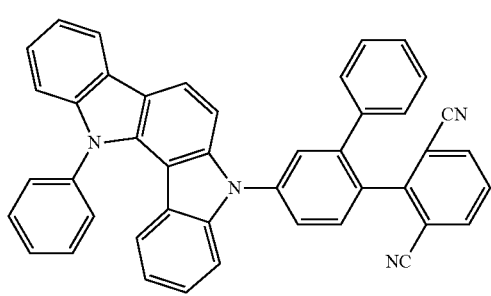
260
-continued
301
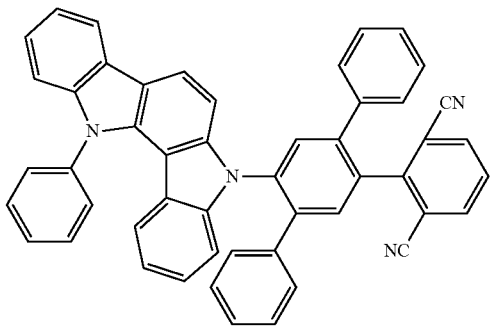
302
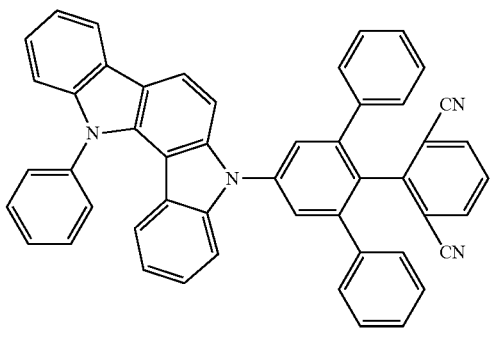
303
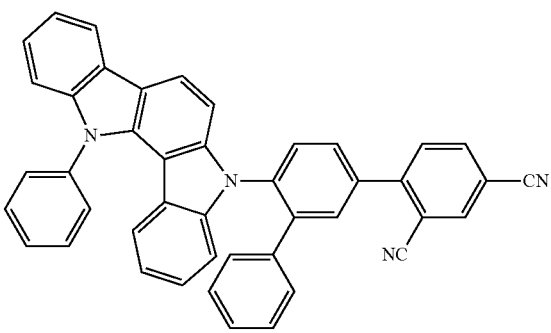
304

-continued

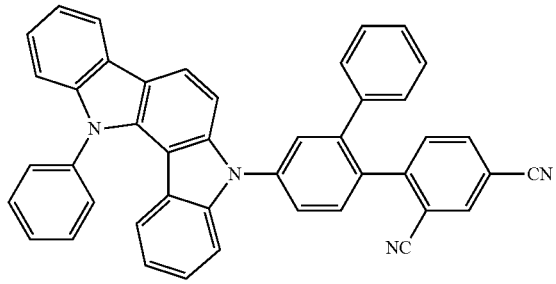

305

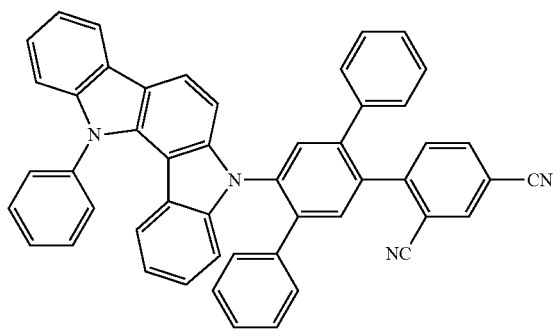

306

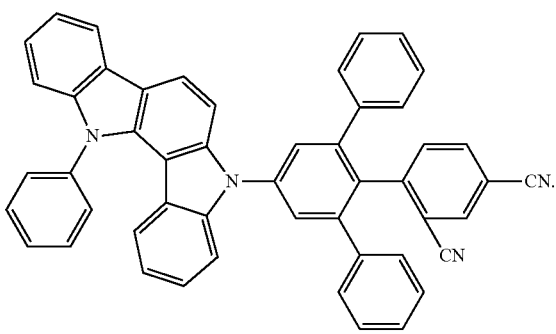

307

11. An organic light-emitting device comprising:
a first electrode;
second electrode; and
an organic layer disposed between the first electrode and the second electrode,
wherein the organic layer comprises an emission layer, and
wherein the organic layer comprises at least one condensed cyclic compound of claim 1.

12. The organic light-emitting device of claim 11, wherein
the first electrode is an anode,
the second electrode is a cathode, and
the organic layer comprises a hole transport region disposed between the first electrode and the emission layer and an electron transport region disposed between the emission layer and the second electrode,
wherein the hole transport region comprises a hole injection layer, a hole transport layer, an electron blocking layer, or any combination thereof, and
wherein the electron transport region comprises a hole blocking layer, an electron transport layer, an electron injection layer, or any combination thereof.

13. An organic light-emitting device comprising:
a first electrode;
second electrode; and
an organic layer disposed between the first electrode and the second electrode,
wherein the organic layer comprises an emission layer,
wherein the emission layer comprises the condensed cyclic compound,
wherein the organic layer comprises at least one condensed cyclic compound of claim 1, and
wherein a ratio of a fluorescent emission component among all emission components emitted from the emission layer is at least 90%.

14. The organic light-emitting device of claim 11, wherein the emission layer does not comprise a phosphorescent compound.

15. The organic light-emitting device of claim 11, wherein
the condensed cyclic compound in the emission layer is a fluorescent emitter, and
among all emission components emitted from the emission layer, a ratio of an emission component of the condensed cyclic compound is at least 80%.

16. The organic light-emitting device of claim 15, wherein the emission layer consists of the condensed cyclic compound only; or
the emission layer further comprises a host.

17. The organic light-emitting device of claim 11, wherein
the emission layer comprises a host and a fluorescent dopant,
the host comprises the condensed cyclic compound, provided that an amount of the host is greater than that of the fluorescent dopant, and
among all emission components emitted from the emission layer, a ratio of an emission component of the condensed cyclic compound is at least 80%.

18. The organic light-emitting device of claim 11, wherein the emission layer comprises a host, an auxiliary dopant, and a fluorescent dopant,
the auxiliary dopant comprises the condensed cyclic compound, and
the emission layer satisfies Equations 1 and 2:

$$E_{T1(HOST)} - E_{T1(AD)} > 0.05 \text{ eV} \qquad \text{Equation 1}$$

$$E_{S1(FD)} - E_{S1(AD)} < 0 \text{ eV}, \qquad \text{Equation 2}$$

wherein, in Equation 1, $E_{T1(HOST)}$ indicates a triplet energy level (expressed in electron volts) of the host, and $E_{T1(AD)}$ indicates a triplet energy level (expressed in electron volts) of the auxiliary dopant,
in Equation 2, $E_{S1(FD)}$ indicates a singlet energy level (expressed in electron volts) of the fluorescent dopant, and $E_{S1(AD)}$ indicates a singlet energy level (expressed in electron volts) of the auxiliary dopant, and
$E_{T1(HOST)}$, $E_{T1(AD)}$, and $E_{S1(FD)}$ are calculated for evaluation according to a density functional theory (DFT) method of a Gaussian program structurally optimized at B3LYP/6-31G(d,p).

* * * * *